United States Patent
Jiang

(10) Patent No.: US 10,179,784 B2
(45) Date of Patent: Jan. 15, 2019

(54) PYRIMIDINE OR PYRIDINE COMPOUNDS, PREPARATION METHOD THEREFOR AND PHARMACEUTICAL USES THEREOF

(71) Applicant: INVENTISBIO SHANGHAI LTD., Shanghai (CN)

(72) Inventor: Yueheng Jiang, Shanghai (CN)

(73) Assignee: InventisBio Shanghai Ltd., Shanghai (CN)

(*) Notice: Subject to any disclaimer, the term of this patent is extended or adjusted under 35 U.S.C. 154(b) by 0 days.

(21) Appl. No.: 15/524,228

(22) PCT Filed: Nov. 5, 2015

(86) PCT No.: PCT/CN2015/093815
§ 371 (c)(1),
(2) Date: May 3, 2017

(87) PCT Pub. No.: WO2016/070816
PCT Pub. Date: May 12, 2016

(65) Prior Publication Data
US 2017/0355696 A1    Dec. 14, 2017

(30) Foreign Application Priority Data

Nov. 5, 2014  (CN) .......................... 2014 1 0619334
Apr. 1, 2015  (CN) .......................... 2015 1 0152615

(51) Int. Cl.
| | |
|---|---|
| C07D 403/04 | (2006.01) |
| C07D 471/04 | (2006.01) |
| C07D 401/14 | (2006.01) |
| C07D 401/04 | (2006.01) |
| C07D 413/04 | (2006.01) |
| C07D 417/04 | (2006.01) |
| A61K 31/437 | (2006.01) |
| A61K 31/506 | (2006.01) |
| C07D 403/14 | (2006.01) |
| C07D 405/14 | (2006.01) |

(52) U.S. Cl.
CPC .......... *C07D 471/04* (2013.01); *A61K 31/437* (2013.01); *A61K 31/506* (2013.01); *C07D 401/04* (2013.01); *C07D 401/14* (2013.01); *C07D 403/04* (2013.01); *C07D 403/14* (2013.01); *C07D 405/14* (2013.01); *C07D 413/04* (2013.01); *C07D 417/04* (2013.01)

(58) Field of Classification Search
CPC .................................................. C07D 403/04
See application file for complete search history.

(56) References Cited

FOREIGN PATENT DOCUMENTS

| | | |
|---|---|---|
| CA | 2959194 A1 | 4/2016 |
| CN | 102363618 A | 2/2012 |
| CN | 103360407 A | 10/2013 |
| CN | 103374000 A | 10/2013 |
| CN | 103501612 A | 1/2014 |
| CN | 103702990 A | 4/2014 |
| CN | 103804303 A | 5/2014 |
| CN | 104140418 A | 11/2014 |
| CN | 104761544 A | 7/2015 |
| CN | 105001208 A | 10/2015 |
| CN | 105085489 A | 11/2015 |
| CN | 105153122 A | 12/2015 |
| CN | 105237515 A | 1/2016 |
| CN | 105254615 A | 1/2016 |
| CN | 105315285 A | 2/2016 |
| CN | 105461695 A | 4/2016 |
| WO | WO 2009/051822 A1 | 4/2009 |
| WO | WO 2011/140338 A1 | 11/2011 |
| WO | WO 2013/014448 A1 | 1/2013 |
| WO | WO 2013/108754 A1 | 7/2013 |
| WO | WO 2013/184766 A1 | 12/2013 |
| WO | WO 2014/081944 A2 | 5/2014 |
| WO | WO 2015/175632 A1 | 11/2015 |
| WO | WO 2015/188777 A1 | 12/2015 |
| WO | WO 2015/195228 A1 | 12/2015 |
| WO | WO 2016/011979 A1 | 1/2016 |
| WO | WO 2016/023422 A1 | 2/2016 |
| WO | WO 2016/029839 A1 | 3/2016 |
| WO | WO 2016/054987 A1 | 4/2016 |
| WO | WO 2016/070816 A1 | 5/2016 |
| WO | WO 2016/094821 A2 | 6/2016 |
| WO | WO 2016/105525 A2 | 6/2016 |
| WO | WO 2017/008761 A1 | 1/2017 |

OTHER PUBLICATIONS

Stella (J. Pharmaceutical Sciences, 2010, 99(12), pp. 4755-4765).*

(Continued)

*Primary Examiner* — Susanna Moore
(74) *Attorney, Agent, or Firm* — Rubin and Rudman LLP

(57) ABSTRACT

The present invention disclosed a class of pyrimidine or pyridine compounds, pharmaceutically acceptable salts, stereoisomers, prodrugs and solvates thereof, preparation method therefor and pharmaceutical compositions and pharmaceutical uses thereof. See e.g., Formula I below. The compounds can inhibit the variants of EGFR (Epidermis Growth Factor Receptor) proteinases, and therefore can inhibit the growth of a variety of tumor cells effectively. The compounds can be used to prepare antitumor drugs, used for the treatment, combined therapy or prevention of various different cancers. The compounds can overcome the drug resistance induced by the existing first-generation EGFR inhibitors such as gefitinib, erlotinib and so on. Particularly, the compounds can be used to prepare drugs for treating or preventing diseases, disturbances, disorders or conditions mediated by epidermis growth factor receptor variants (such as L858R activated mutants, Exon19 deletion activated mutants and T790M resistant mutants).

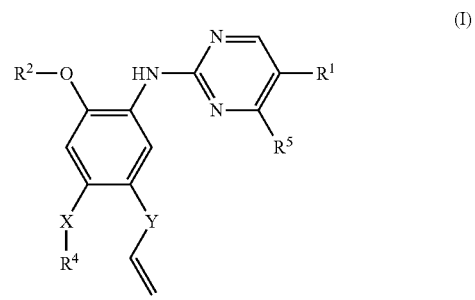

6 Claims, No Drawings

(56) References Cited

OTHER PUBLICATIONS

Roskoski, R., Jr., et al. "The ErbB/HER Receptor Protein-Tyrosine Kinases and Cancer," Biochem. and Biophys. Research Communications, 319:1-11(2004), Elsevier, Netherlands.
Tham Sjin, R.T., "In Vitro and In Vivo Characterization of Irreversible Mutant-Selective EGFR Inhibitors That Are Wild-Type Sparing," Molecular Cancer Therapeutics, 13:1468-1479 (2014) American Association for Cancer Research, Philadelphia, PA.
Lynch, T.J., M.D., et al., "Activating Mutations in the Epidermal Growth Factor Receptor Underlying Responsiveness of Non-Small-Cell Lung Cancer to Gefitinib," The New England Journal of Medicine, 350:2129-2139 (2004), Massachusetts Medical Society, Boston, Massachusetts.
Finlay, R.V.M, et al., "Discovery of a Potent and Selective EGFR Inhibitor (AZD9291) of Both Sensitizing and T790M Resistance Mutations That Spares the Wild Type Form of the Receptor," Journal of Medicinal Chemistry, 57:8249-8267 (2014), American Chemical Society, Washington, D.C.
Jiang, W. et al, "Application of Deuteration in Drug Research," Qilu Pharmaceutical Affairs, 29:682-684 (2010), China Academic Journal Electronic Publishing House, China.
Ciardiello, F., M.D., Ph.D. et al., "EGFR Antagonists in Cancer Treatment," The New England Journal of Medicine, 358:1160-1174 (2008), Massachusetts Medical Society, Boston, Massachusetts.
Paez, J.G., et al., "EGFR Mutations in Lung Cancer: Correlation with Clinical Response to Gefitinib Therapy," Science, 304:1497-1500 (2004), American Association for the Advancement Science, Washington, D.C.
English translation of International Search Report for PCT/CN2015/093815 dated Feb. 3, 2016, WIPO.
Priority document for PCT/CN2015/091189, CN Application No. 201410534203.9, filed Oct. 11, 2014.
Priority document for PCT/CN2015/088015, CN Application No, 201410421609.6, filed Aug. 2014.
Priority document for PCT/CN2015/088015, CN Application No. 201510078497.3, filed Feb. 13, 2015.
Ward, R.A. et al., "Structure-and Reactivity-Based Development of Covalent Inhibitors of the Activating and Gatekeeper Mutant Forms of the Epidermal Growth Receptor (EGFR)," Journal of Medicinal Chemistry, 56:7025-7048 (2013), American Chemical Society, Washington, D.C.
Sullivan, I. et al., "Next-Generation EGFR Tyrosine Kinase Inhibitors for Treating EGFR-Mutant Lung Cancer beyond First Line," Frontiers in Medicine, 3(76):1-13(2017) https://doi.org/10.3389/fmed.2016.00076.
Wang, S. et al., "Third-Generation Inhibitors Targeting EGFR T790M Mutation in Advanced non-Small Cell Lung Cancer," Journal of Hematology & Oncology, 9(34):1-7 (2016), BioMed Central, London, United Kindom.

* cited by examiner

PYRIMIDINE OR PYRIDINE COMPOUNDS, PREPARATION METHOD THEREFOR AND PHARMACEUTICAL USES THEREOF

FIELD OF THE INVENTION

The present invention pertains to the field of pharmaceutical chemistry, and particularly, to pyrimidine or pyridine compounds and pharmaceutically acceptable salts, stereoisomers, prodrugs and solvates thereof; a method for preparing the same; a pharmaceutical composition containing the same and pharmaceutical use of the same. In particular, the present invention relates to pyrimidine or pyridine compounds and pharmaceutically acceptable salts, stereoisomers, prodrugs and solvates thereof a method for preparing the same; a pharmaceutical composition containing the compounds, pharmaceutically acceptable salts, stereoisomers, prodrugs and/or solvates thereof particularly useful polymorphs of the compounds and salts thereof, and a use of the compounds and pharmaceutically acceptable salts, stereoisomers, prodrugs and solvates thereof in the preparation of a medicament for treating diseases mediated by various EGFR forms (e.g. activated mutants and/or resistant mutants).

BACKGROUND

Cancer is becoming the deadliest "killer" to human beings. In recent years, the total number of people died for cancer is close to 2 million each year in China. Although a variety of discovery of treatment pathways and drugs have brought hope for cancer patients, these conventional treatments still have many drawbacks, such as large side effect, poor treatment effect, tumor recurrence, metastasis and so on. There is an urgent need for new treatment techniques to improve the low success rate of cancer treatment. The recent emergence of individualized chemotherapy and targeted therapy has brought new hope to lung cancer treatment. Tumor molecular targeted therapy is a treatment method in which the key molecules that closely relate to the tumor growth will selectively kill the tumor cells through chemical or biological means. Targeted therapy has many characteristics, such as high specificity, high selectivity and mild side effects. When targeted therapy is used in combination with traditional chemotherapy, radiotherapy or tumor immunization, the efficacy can be greatly enhanced and the postoperative recurrence can be reduced. Tumor targeted therapy has rapidly develop in recent years, and becomes the emerging field of cancer treatment and future development trend.

Protein tyrosine kinases (PTKs) are a class of protein enzymes that can catalyze the phenolic hydroxyl phosphorylation on tyrosine residue of a variety of important proteins, thereby activating the biological activity of functional proteins. This reaction process plays a very important role in the intracellular signal transduction pathway, for it regulates a series of physiological and chemical processes such as cell growth, differentiation and death. Protein tyrosine kinase dysfunction can cause a series of diseases in the body. There are many studies showing that the activation of more than half of the original cancer gene and oncogene are associated with protein tyrosine kinase, and protein tyrosine kinase abnormal expression can lead to disorders of cell proliferation regulation, thereby leading to tumor genesis. In addition, tyrosine kinase abnormal expression is also closely associated with tumor invasion and metastasis, tumor neovascularization, tumor resistance to chemotherapy. Tyrosine kinase has become a very important target for the development of antitumor drugs.

Epidermal growth factor receptor (EGFR) is a receptor tyrosine protein kinase, and a transmembrane protein in the ErbB receptor family.

EGFR regulates proliferation, survival, adhesion, migration and differentiation of cells, which is hyperactivated or sustained in a variety of tumor cells, such as lung cancer cells, breast cancer cells, prostate cancer cells and the like. Abnormal activation of EGFR plays a key role in tumor transformation and growth. Blocking activation of EGFR has been clinically proven as one of the effective targeted therapy methods for tumor cell. EGFR was expressed in 50% of NSCLC (non-small cell lung cancer) cases, which makes EGFR and family members thereof a major candidate for targeted therapy. Gefitinib and erlotinib are the first generation of small molecule inhibitors of EGFR, and primarily used as drugs for treating advanced NSCLC. Clinical results show that gefitinib or erlotinib has effect on about 10% of white NSCLC and about 35% of Asian NSCLC patients. The analysis shows that the response rate to EGFR-tyrosine kinase inhibitor (TKI) in most NSCLC patients with EGFR activation mutations was significantly higher than that in EGFR wild type of NSCLC patients.

However, clinical studies have shown that many patients soon (12-14 months) have been resistant to these small molecule inhibitors of EGFR, ie, acquired drug resistance. Gatekeeper residue of T790M mutation is a mutation point in EGFR 20 eon and is one of the major mechanisms leading to drug resistance. Studies on a new generation of inhibitor for these EGFR mutations have recently been very successful. Afatinib is a potent and irreversible double inhibitor of EGFR and human epidermal growth factor receptor 2 (HER2) tyrosine kinases. Other similar multi-target, highly active and irreversible inhibitors, such as canertinib, and dacomitibib are also in later clinical trials. These novel second-generation irreversible inhibitors have a strong inhibitory effect on EGFR with L858R and T790M mutants, and have a significant effect on gefitinib or erlotinib-resistant cancer patients. However, these second-generation EGFR mutant inhibitors also have a strong inhibitory effect on wild-type EGFR (WT-EGFR). Clinical studies have shown that the inhibition of wild-type EGFR can lead to drug toxicity and side effects in most patients, such as rash or diarrhea in the human body.

In order to overcome the toxicity and side effects of the second-generation EGFR inhibitors, it is necessary to reduce the inhibitory effect on wild-type EGFR (WT-EGFR). A new generation (i.e. the third generation) of EGFR inhibitors should remain a strong inhibition against EGFR L858R activated mutants, Exon19 deletion activated mutants and T790M resistant mutants, and show a relatively low inhibitory effect on WT-EGFR and other tyrosine protein kinase receptors. Such compounds can be used not only in the treatment of cancer patients with a resistance to EGFR L858R-activated mutants and Exon19 deletion-activated mutants, but also in the treatment of cancer patients with EGFR-T790M resistant mutants resulting to the resistance against the first-generation EGFR inhibitors such as gefitinib, erlotinib or icotinib. The third-generation EGFR inhibitor, AZD9291, has a beneficial clinical effect, but its major metabolite, AZ5104, has a strong inhibitory effect on wild-type EGFR (WT-EGFR), which is the most probable incentive inducing the most common side effects such as a clinically common rash, diarrhea and the like.

The present invention shows many pyrimidine or pyridine compounds that have a high inhibitory activity against EGFR mutant(s), but only relatively low inhibitory effects on wild-type EGFR. The compounds of the present invention have good physicochemical properties and safety toxicity parameters. Such compounds will have a better effect in the treatment of cancer with EGFR-activated mutants and/or EGFR-resistant mutations.

The present invention relates to certain pyrimidine or pyridine compounds and pharmaceutically acceptable salt thereof; and can be used for the treatment or prevention of the disease or condition mediated by some mutated forms of epidermal growth factor receptors (e.g., L858R activated mutants, Exon19 deletion activated mutants, and T790M resistant mutants). Such compounds and pharmaceutically acceptable salts, stereoisomers, prodrugs and solvates thereof can be used for the treatment or prevention of many different cancers. The present invention also relates to a pharmaceutical composition comprising the compound and a pharmaceutically acceptable salt, stereoisomer, prodrug and solvate thereof; in particular, the useful polymorphs of the compound and salt; the useful intermediates used for preparing the said compounds; and the method for the treating diseases mediated by EGFR in the form of activated and/or resistant mutants by the compounds, pharmaceutically acceptable salts, stereoisomers, prodrugs and solvates thereof.

Therefore, there is an urgent need for a new type of compound, especially a compound with novel skeleton, to solve problems such as poor resistance, poor selectivity and the like. In the following list of documents, the patent or non-patent documents (journals, magazines, manuals and books, etc.) that are closest to patent applications are cited:
1. New England Journal of medicine, 2008, vol. 358, pp. 1160-1174;
2. Chemical and Biophysical Research Communications, 2004, vol. 319, pp. 1-11;
3. Science, 2004, vol. 304, pp. 1497-1500;
4. New England Journal of medicine, 2004, vol. 350, pp. 2129-2139;
5. Molecular Cancer Therapeutics, 2014, vol. 13, pp. 1468-1479;
6. Journal of Medicinal Chemistry, 2014, vol. 57, pp. 8249-8267;
7. WO2013014448A1, corresponding to CN103702990A;
8. WO2013108754A1;
9. CN103374000A;
10. CN103804303A;
11. WO2013184766A1; and
12. WO2009051822A1.

It should be stated that the above-mentioned patent or non-patent documents is only representative documents and are not a complete list of all the relevant literature. The entire disclosure of the above-mentioned patent or non-patent document is hereby incorporated in its entirety for a reference, and in the cases where there is a conflict, the description in the present application document shall prevail.

The current EGFR-TKI does still not solve the clinical problems caused by drug resistance, and the most of existing drugs are EGFR reversible or irreversible inhibitors based on quinazoline or quinolinamine as the basic nucleus, and they are still inevitably brought to the side effects of poor selectivity to EGFR wild-type cells. Therefore, there is an urgent need for a new type of compounds, especially compounds with novel skeletons, so as to solve problems such as poor drug resistance and selectivity.

SUMMARY OF THE INVENTION

It is an object of the present invention to provide a pyrimidine or pyridine compound represented by the following formula (I) and a pharmaceutically acceptable salt, stereoisomer, prodrug molecule or solvate thereof. The compounds can inhibit the variants of epidermal growth factor receptor (EGFR) protein kinases, and therefore can inhibit the growth of a variety of tumor cells effectively. The compounds can be used to prepare antitumor drugs, used for the treatment or prevention of various different cancers. The compounds can overcome the drug resistance induced by the existing Gefitinib, erlotinib and so on. More particularly, the compounds can be used to prepare drugs for treating or preventing diseases, disturbances, disorders or conditions mediated by EGFR variants (such as L858R activated mutants, Exon19 deletion activated mutants and/or T790M resistant mutants).

It is another object of the present invention to provide a method for preparing the above-mentioned compounds.

It is a further object of the present invention to provide a pharmaceutical composition comprising one or more selected from the group consisting of the pyrimidine or pyridine compounds, pharmaceutically acceptable salt, stereoisomer, prodrug molecule and solvate thereof, and one or more pharmaceutical excipients.

It is a further object of the present invention to provide a use of the above-mentioned pyrimidine or pyridine compounds, pharmaceutically acceptable salt, stereoisomer, prodrug molecule and/or solvates thereof, and the above pharmaceutical composition in preparing a drug for treating or preventing diseases, disturbances, disorders or conditions mediated by a variant EGFR, particularly in preparing a drug for treating or preventing one or more cancers.

It is a further object of the present invention to provide a method of treating or preventing a disease, disorder, disorder or condition mediated by a variant EGFR, in particular one or more cancers.

It is a further object of the present invention to provide a combined treatment of cancer, that is to say, a method for treating cancer by using one or more of selected from the above pyrimidine or pyridine compounds, pharmaceutically acceptable salt, stereoisomer, prodrug molecule and solvates thereof; or the pharmaceutical composition according to the present invention in combination with conventional surgery, radiotherapy, chemotherapy or tumor immunotherapy.

It is the first aspect of the invention to provide a compound of formula (I) or a pharmaceutically acceptable salt, stereoisomer, prodrug molecule or solvate thereof:

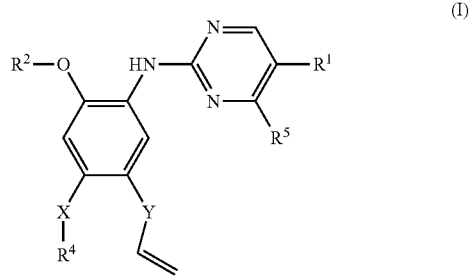

wherein,
$R^1$ is hydrogen, deuterium, halogen or cyano;
$R^2$ is a C1-C6 alkyl, $CD_3$, or halogen-substituted C1-C6 alkyl;
X is $NR^3$ or O;
Y is $NHC(=O)$ or $NHS(=O)_2$, and the nitrogen in said $NHC(=O)$ or $NHS(=O)_2$ is bonded to the benzene ring in formula (I);
$R^3$ is a C1-C6 alkyl, C1-C6 alkoxy, $CD_3$, C1-C6 alkoxy C1-C6 alkyl;

R⁴ is a C1-C3 alkyl, unsubstituted or substituted with 1-3 substituents, wherein said substituent is a C1-C3 alkyl, CD₃, C1-C3 alkoxy, methanesulfonyl, NR⁷R⁸ or a 3- to 6-membered heterocyclic group containing 1 to 2 heteroatoms selected from N and O, unsubstituted or substituted with hydroxy or C1-C3 alkyl;

or, R³ and R⁴, together with the nitrogen atom to which they are bonded, form a 4-6 membered heterocyclic ring containing 1 to 4 nitrogen or oxygen and having one or more substituents, and the substituent is amino, dimethylamino, C1-C3 alkoxy, or a 4- to 6-membered heterocyclic group containing 1 to 2 heteroatoms selected from N and O, unsubstituted or substituted with C1-C3 alkyl;

R⁵ is a fused ring formed by two rings, and the fused ring formed by two rings is optionally substituted with 1-3 substituents, wherein the two rings forming the fused ring are each independently benzene, a 5-7-membered heterocyclic ring or a 5-7-membered heteroaromatic ring, wherein the 5-7 membered heterocyclic or 5-7 membered heteroaromatic ring contains 1-4 heteroatoms selected from S, N or O, and the substituent is oxo group (=O) or R6, R⁶ is hydrogen, C1-C3 alkyl (e.g., methyl, ethyl, n-propyl, isopropyl), CD₃, C1-C3 alkylsulfonyl, C3-C6 cycloalkyl (e.g., C3-C4 cycloalkyl), 4-6 membered heterocyclyl, 4-6 membered heteroaryl, or halogen-substituted C1-C3 alkyl (e.g., a fluorine-substituted C2-C3 alkyl), wherein the 4-6 membered heterocyclyl or 4-6 membered heteroaryl contains 1 to 3 heteroatoms selected from N, O and S and is optionally substituted with C1-C2 alkyl;

R⁷ and R⁸ are each independently C1-C3 alkyl, CD₃, C1-C3 alkoxy or C3-C5 cycloalkyl;

and when R¹ is hydrogen, R² is methyl, X is NCH₃, Y is NHC(=O), R⁴ is dimethylaminoethyl, R⁵ cannot be

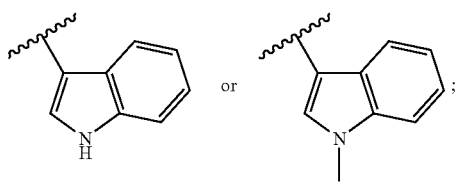 [SMILES: *c1c[nH]c2ccccc12 ; *c1cn(C)c2ccccc12]

or when R¹ is hydrogen, R² is methyl, X is NR₃, Y is NHC(=O), R³ is methyl, R⁴ is dimethylaminoethyl, R5 is

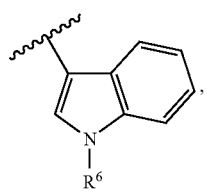

R⁶ is methyl, no hydrogen in any one of R¹, R², R³, R⁴ and R⁶ can be substituted by deuterium.

In one preferred embodiment of the present application,

R¹ is hydrogen, deuterium, fluorine, chlorine or cyano;

R² is a C1-C3 alkyl, CD₃, or C1-C3 alkyl substituted with 1 to 3 fluorines or chlorines;

X is NR³ or O;

R³ is a C1-C3 alkyl, CD₃, or C1-C3 alkoxyC1-C3alkyl; Y is NHC(=O) or NHS(=O)₂;

R⁴ is selected from the following groups:

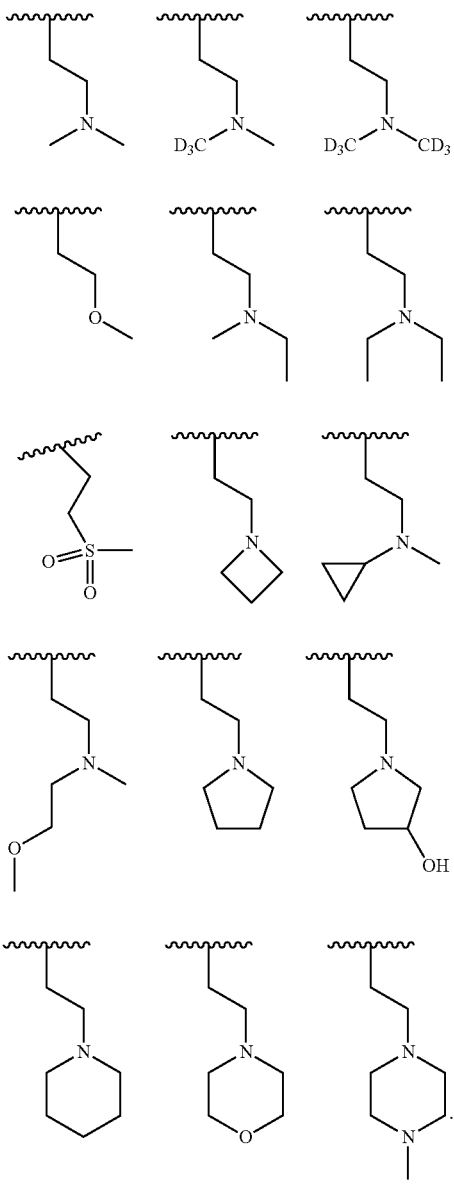

Or, when X is NR³, R³ and R⁴, together with the nitrogen atom to which they are bonded, form a nitrogen-containing heterocyclic ring with substituent(s), and the nitrogen-containing heterocyclic ring with substituent(s) is selected from the following heterocyclic groups

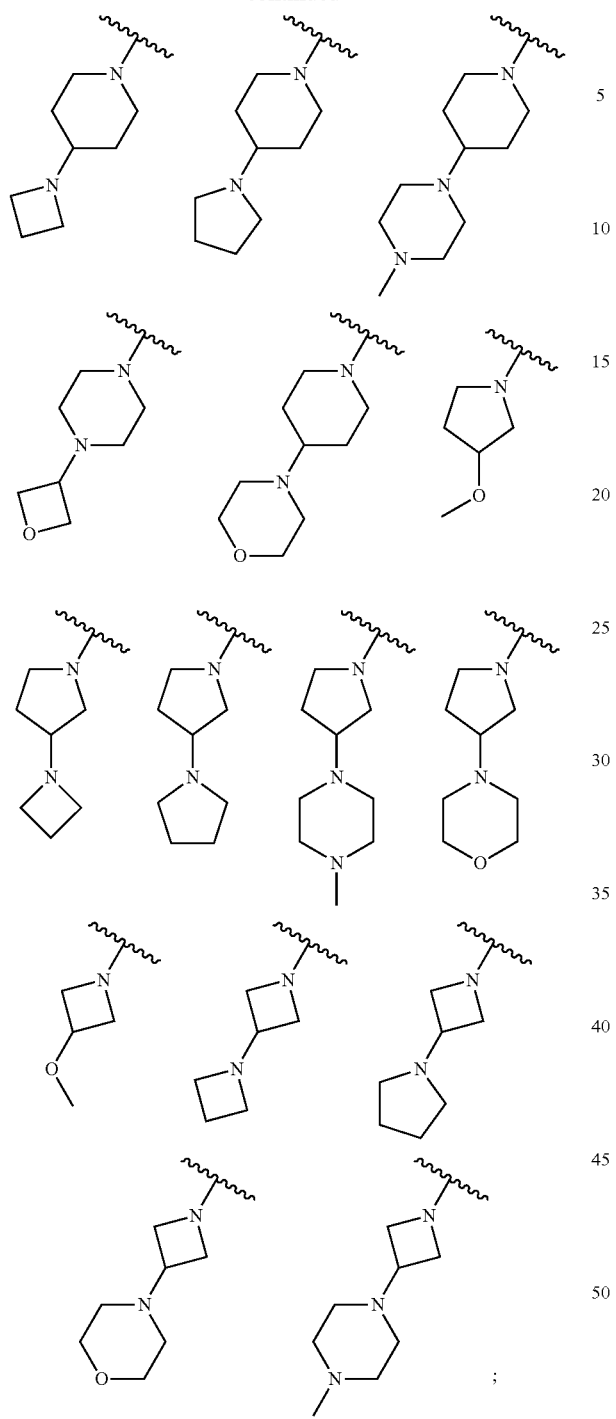
$R^5$ is a group selected from the following groups:
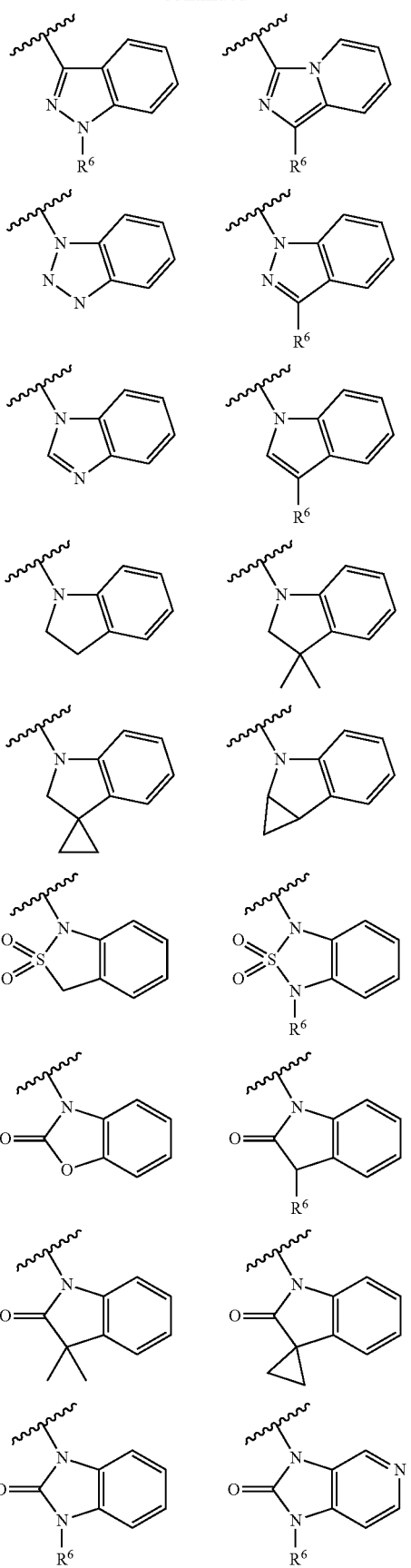

-continued

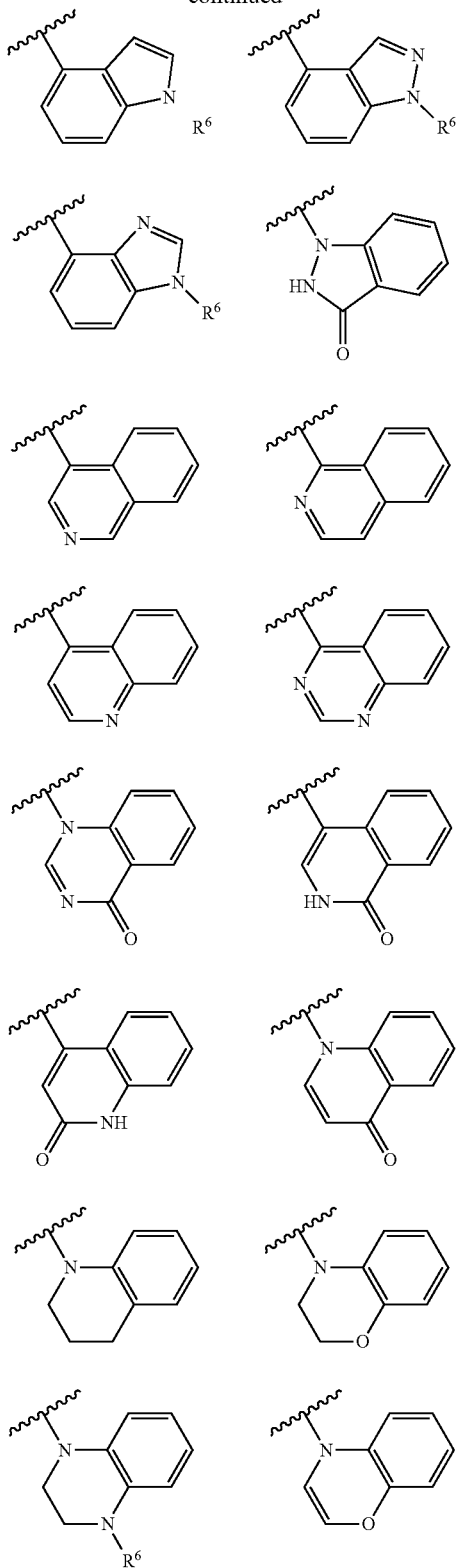

$R^6$ is hydrogen, methyl, $CD_3$, ethyl, isopropyl, methylsulfonyl, C3-C6 cycloalkyl (e.g., C3-C4 cycloalkyl, cyclopropyl), or fluorine-substituted C1-C3 alkyl (e.g., 2,2-difluoroethyl, 2,2,2-trifluoroethyl); preferably, R6 is selected from hydrogen, methyl, $CD_3$, ethyl or methylsulfonyl;

and when $R^1$ is hydrogen, $R^2$ is methyl, X is $NCH_3$, Y is NHC(=O), $R^4$ is dimethylaminoethyl, R5 cannot be

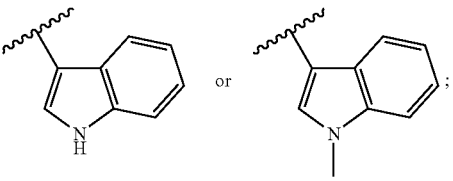 [SMILES: *c1c[nH]c2ccccc12 ; *c1cn(C)c2ccccc12]

when $R^1$ is hydrogen, $R^2$ is methyl, X is $NR_3$, Y is NHC(=O), $R^3$ is methyl, $R^4$ is dimethylaminoethyl, $R^5$ is

$R^6$ is methyl, no hydrogen in any of the groups of $R^1$, $R^2$, $R^3$, $R^4$, $R^6$ can be substituted by deuterium.

In another preferred embodiment of the present application, $R^1$ is hydrogen, $R^2$ is methyl or $CD_3$, X is $NR^3$, $R^3$ is $CH_3$, $CD_3$, ethyl or methoxyethyl, Y is NHC(=O) or NHS(=O)$_2$, $R^4$ is dimethylaminoethyl, $R^5$ is selected from the following groups:

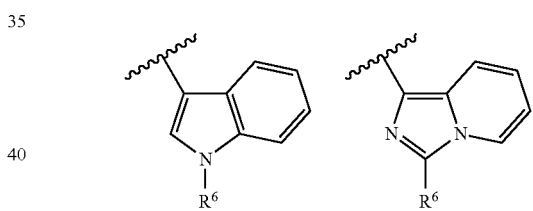

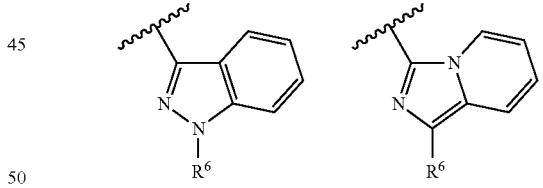


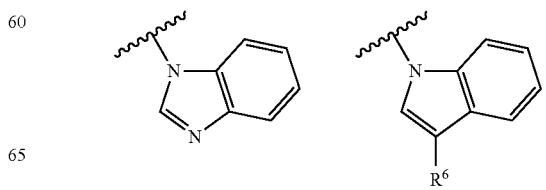

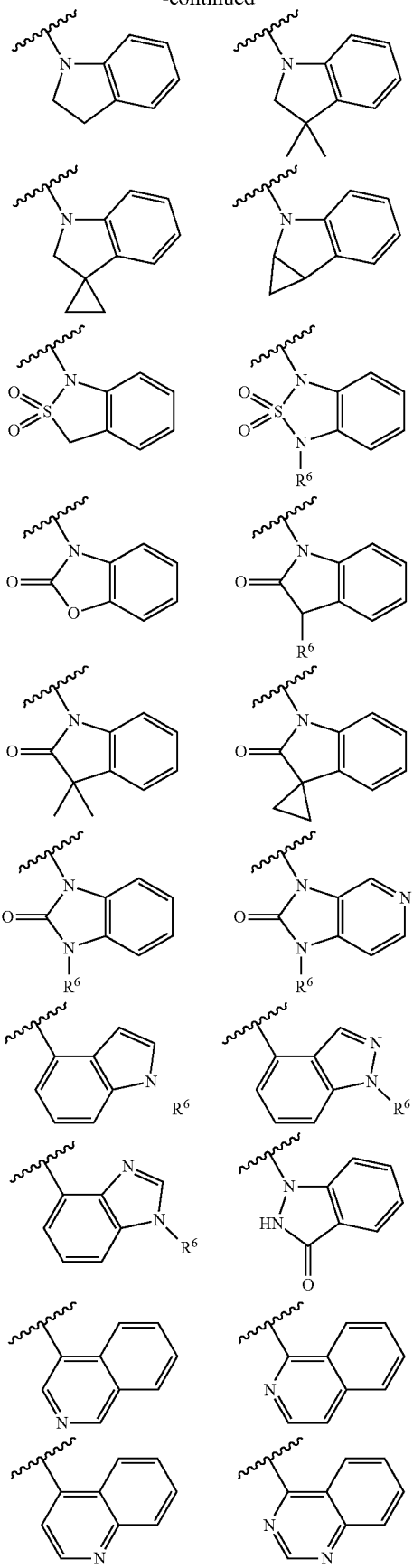

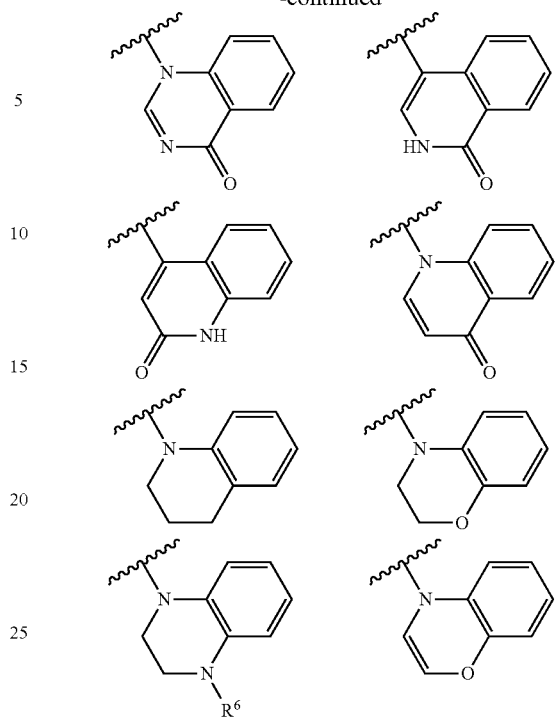

wherein $R^6$ is hydrogen, methyl, $CD_3$, ethyl, isopropyl, methylsulfonyl, C3-C6 cycloalkyl (e.g., C3-C4 cycloalkyl, cyclopropyl), or fluorine-substituted C1-C3 alkyl (e.g., 2,2-difluoroethyl, 2,2,2-trifluoroethyl); preferably, $R^6$ is hydrogen, methyl, $CD_3$, ethyl, or methylsulfonyl;

In another preferred embodiment of the present application, $R^1$ is hydrogen, $R^2$ is methyl or $CD_3$, X is $NR^3$, $R^3$ is $CH_3$, $CD_3$, ethyl or methoxyethyl, Y is NHC(=O) or $NHS(=O)_2$, $R^4$ is dimethylaminoethyl, $R^5$ is selected from the following groups:

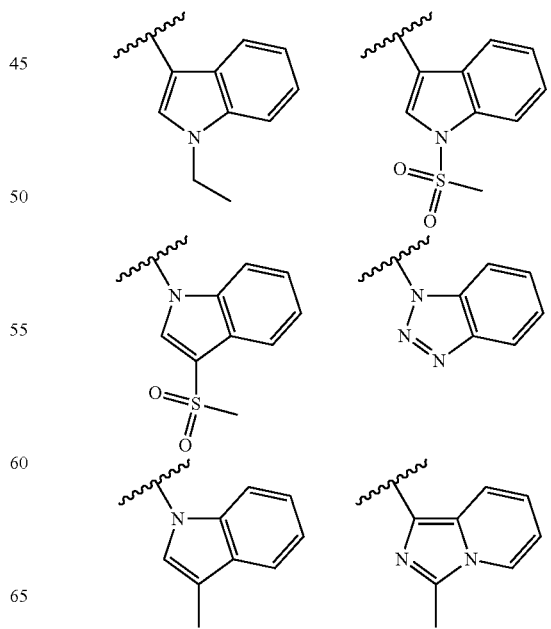

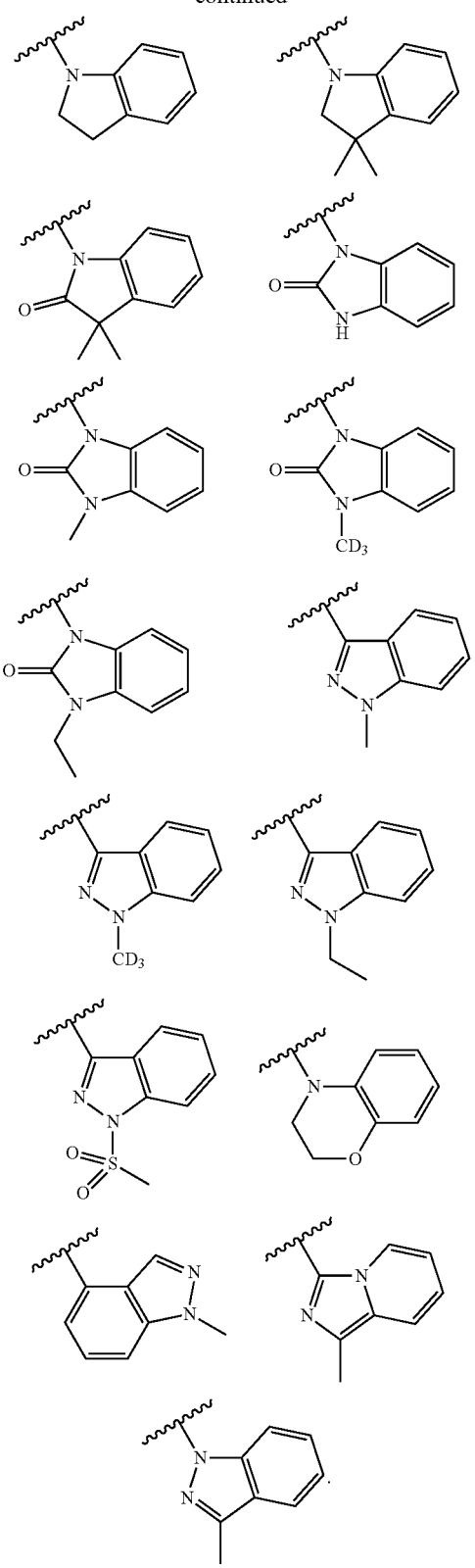
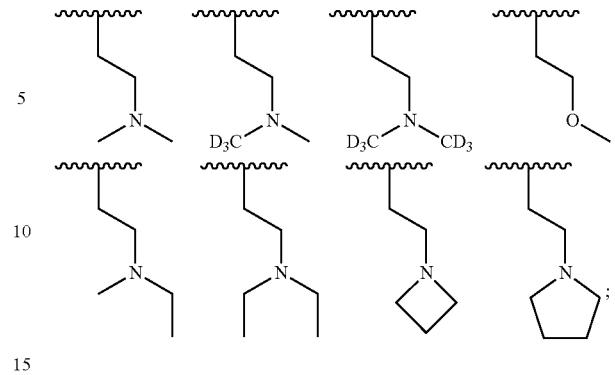
$R^5$ is a group selected from the following groups:
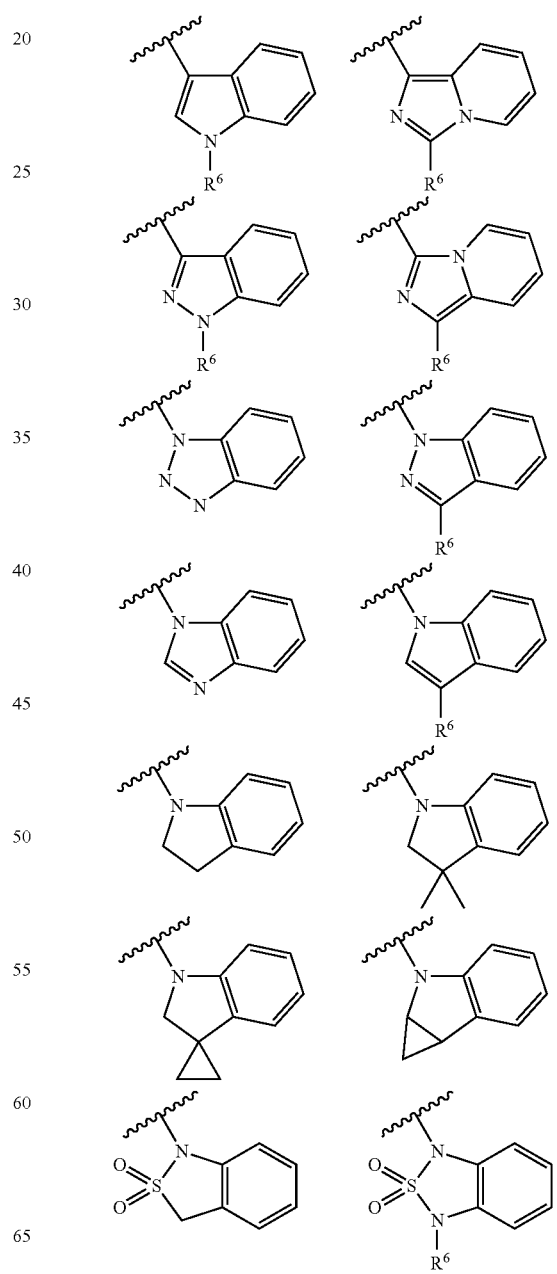
In another preferred embodiment of the present application, $R^1$ is hydrogen; $R^2$ is a methyl or $CD_3$, X is $NR^3$, $R^3$ is $CD_3$ or ethyl; Y is NHC(=O) or NHS(=O)$_2$; $R^4$ is selected from the following groups:

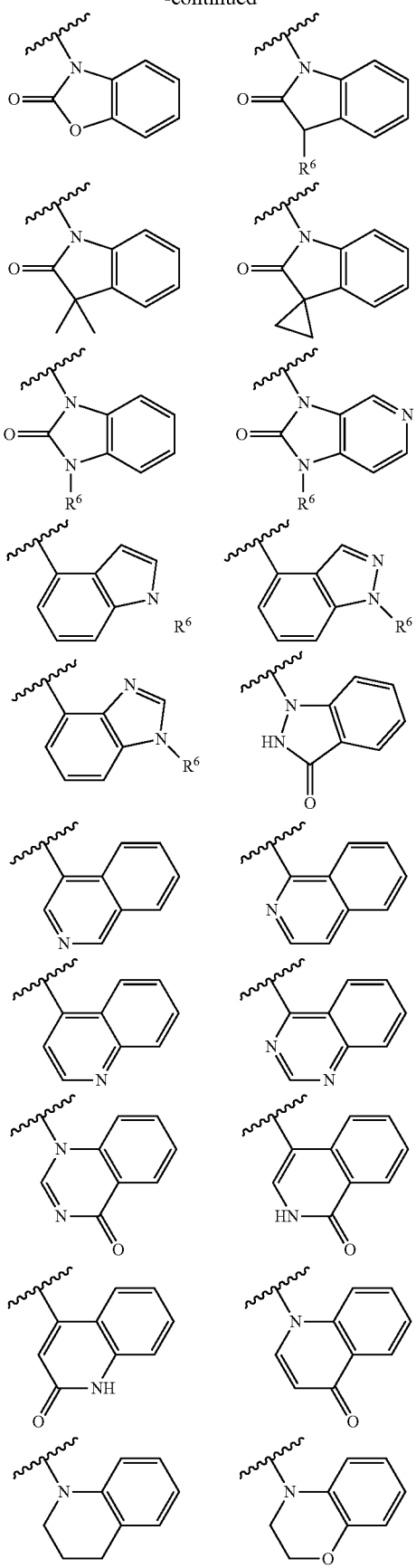

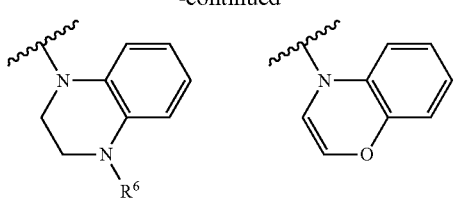

wherein $R^6$ is hydrogen, methyl, $CD_3$, ethyl, isopropyl, methylsulfonyl, C3-C6 cycloalkyl (e.g., C3-C4 cycloalkyl, cyclopropyl), or fluorine-substituted C1-C3 alkyl (e.g., 2,2-difluoroethyl, 2,2,2-trifluoroethyl); preferably, $R^6$ is hydrogen, methyl, $CD_3$, ethyl, or methylsulfonyl.

In another preferred embodiment of the present application, $R^1$ is hydrogen; $R^2$ is a methyl or $CD_3$, X is $NR^3$, $R^3$ is $CD_3$ or ethyl; Y is NHC(=O) or NHS(=O)$_2$; $R^4$ is selected from the following groups:

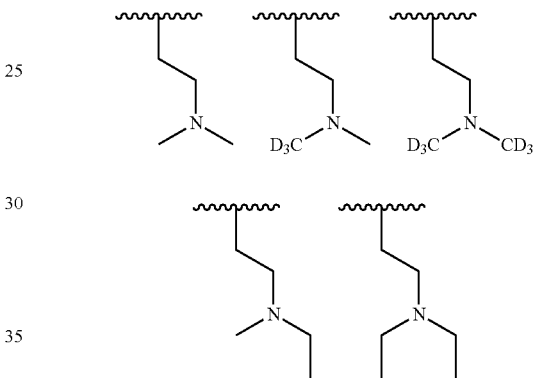

$R^5$ is a group selected from the following groups:

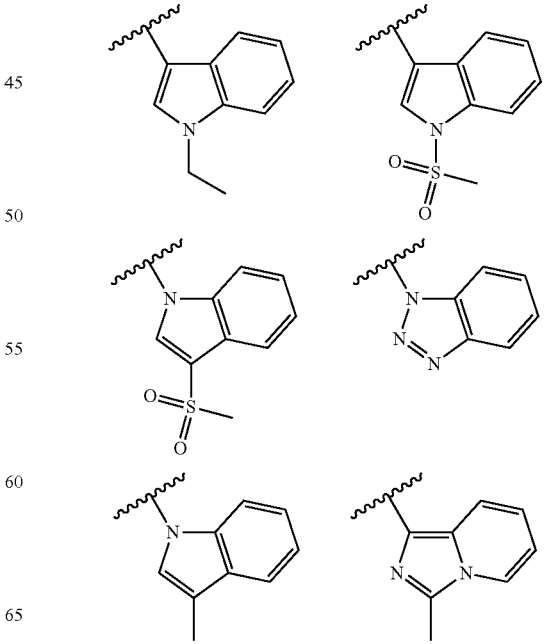

-continued
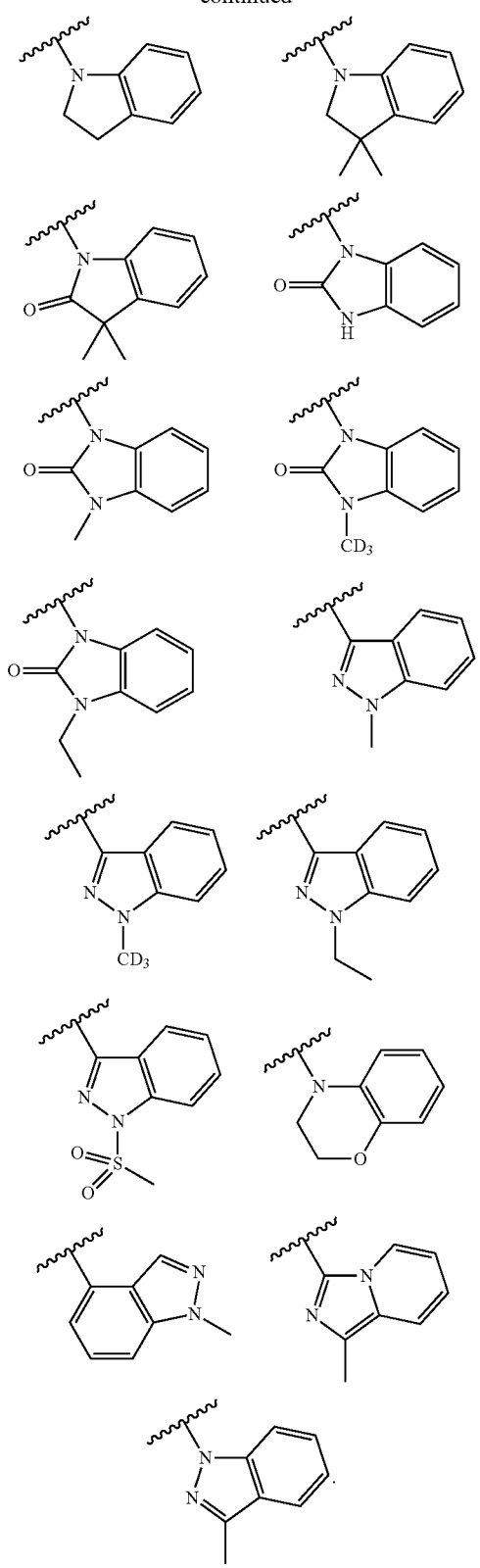
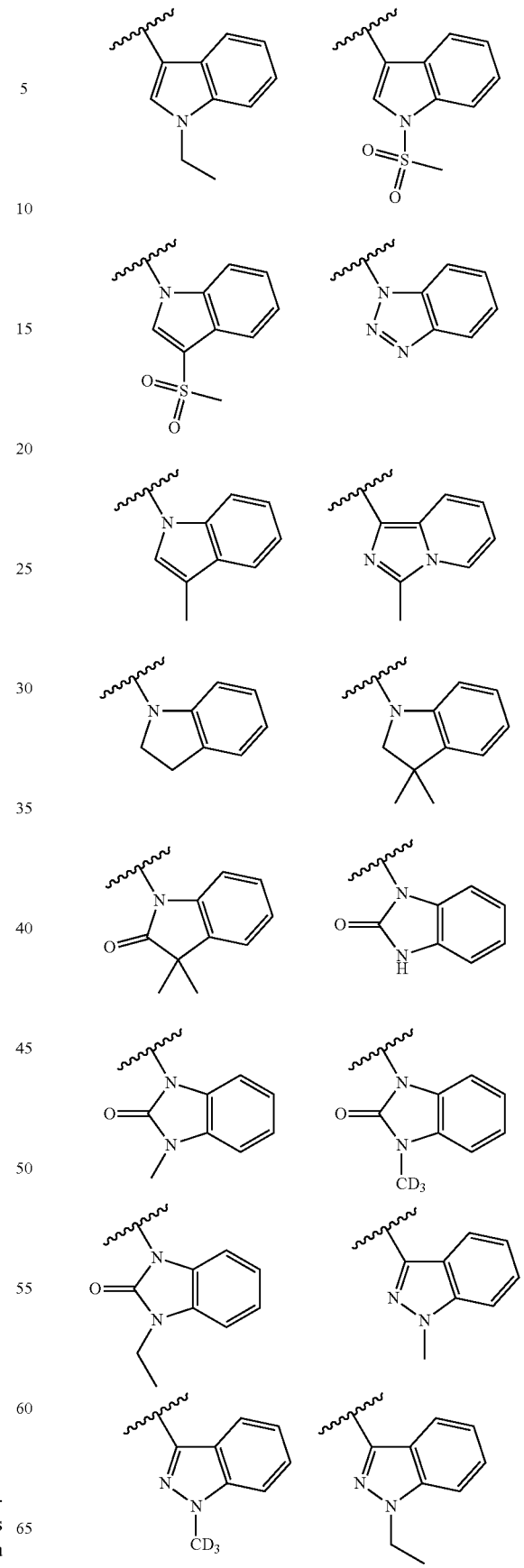
In another preferred embodiment of the present application, $R^1$ is hydrogen; $R^2$ is a methyl, X is $NCH_3$; Y is $NHC(O)$ or $NHS(=O)_2$; $R^4$ is dimethylaminoethyl, $R^5$ is a group selected from the following groups:

-continued
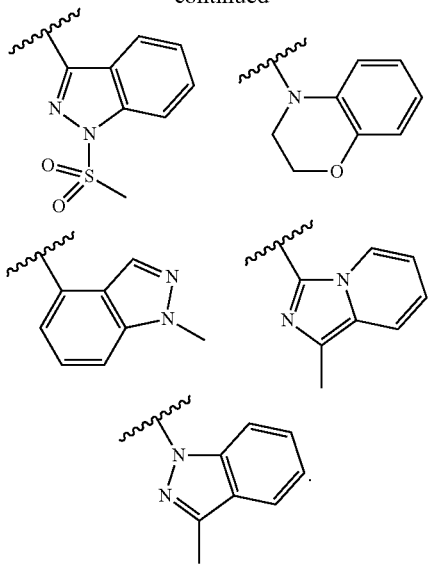
In a most preferred embodiment of the present application, the compound of formula (I) is selected from:
1
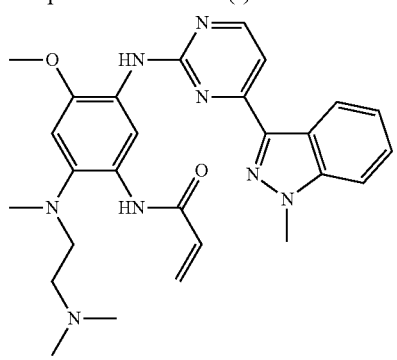
2
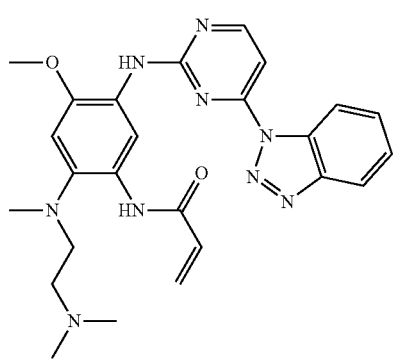
3
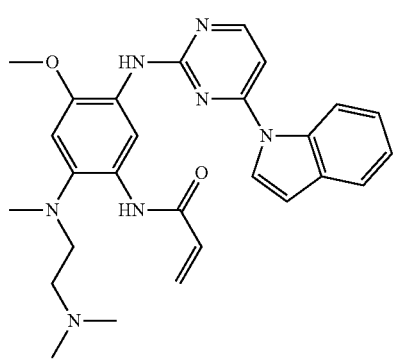
-continued
4
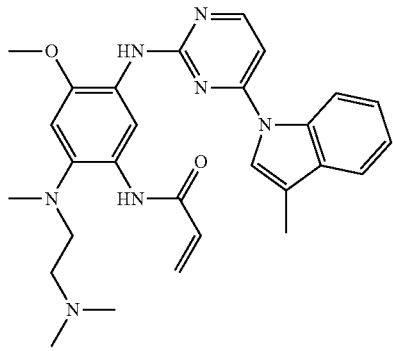
5
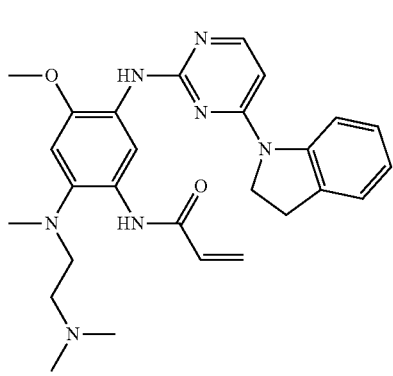
6
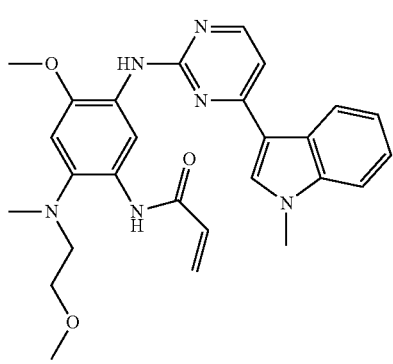
7
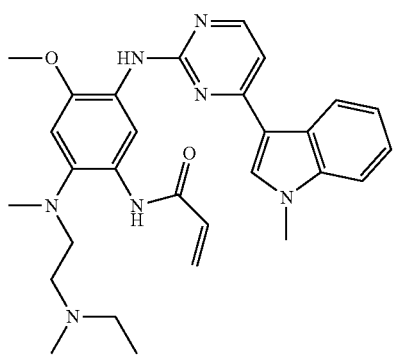

-continued
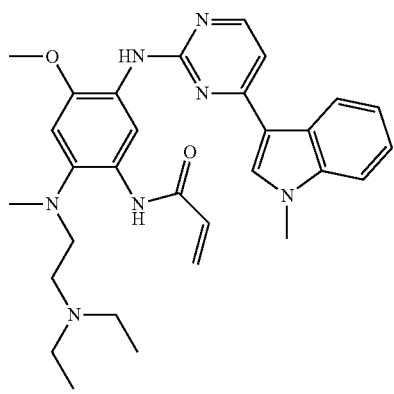
8
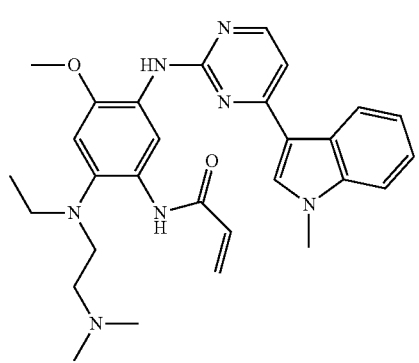
9
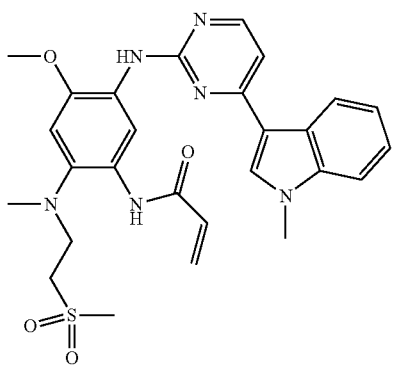
10
-continued
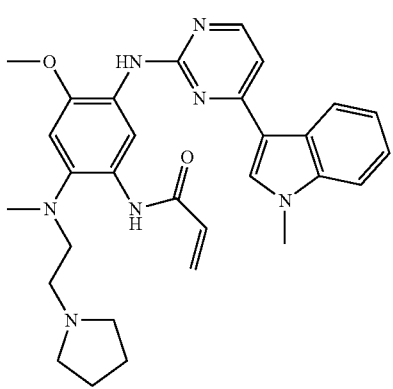
12
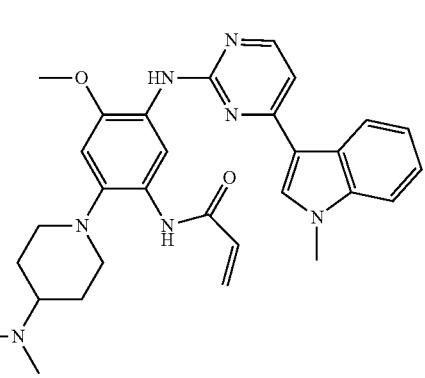
13
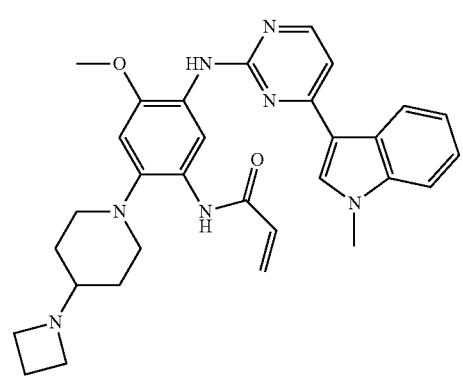
14
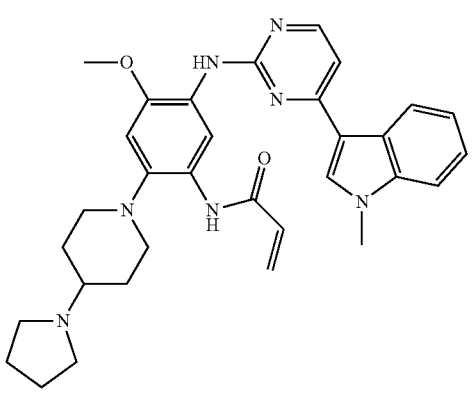
15

-continued
16
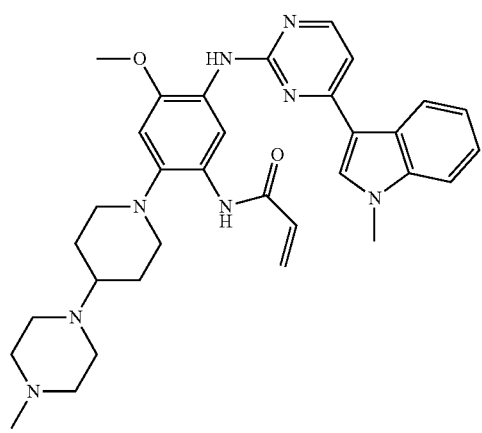
17
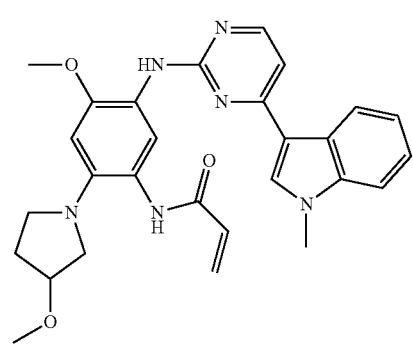
18
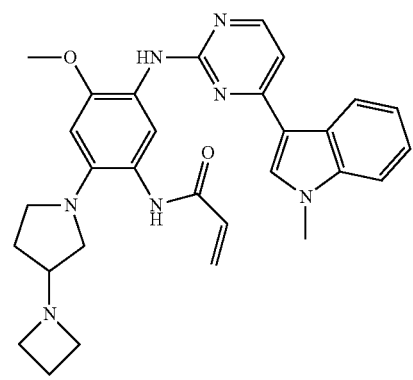
19
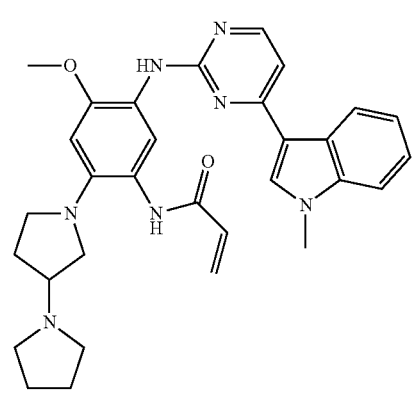
-continued
20
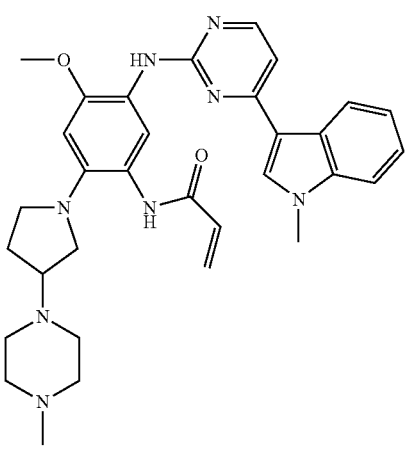
21
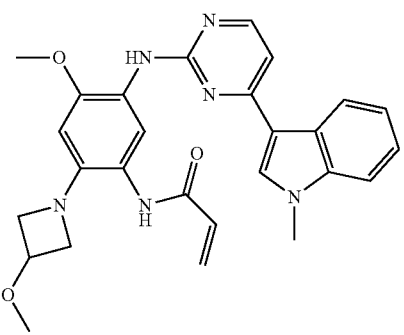
22
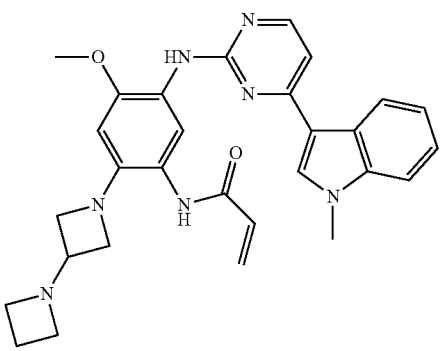
23
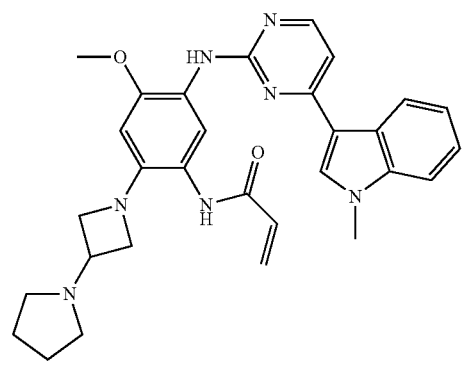

24
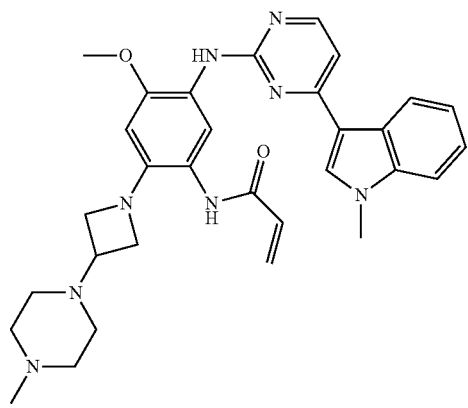
25
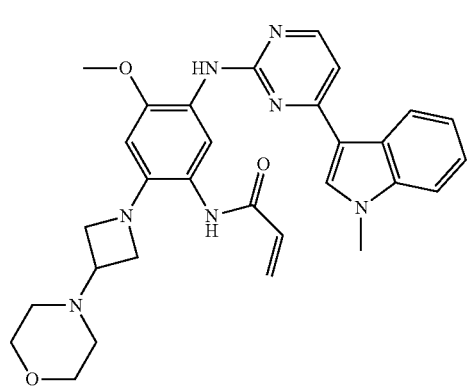
26
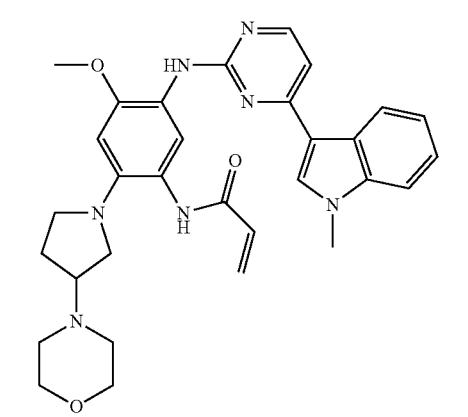
27
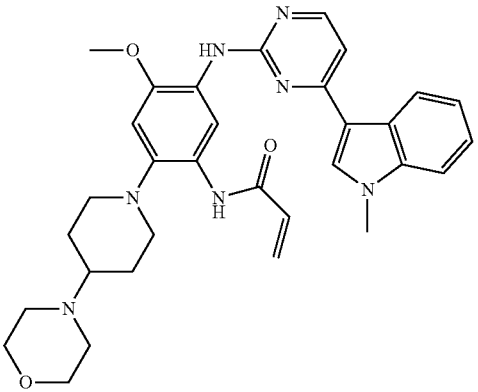
28
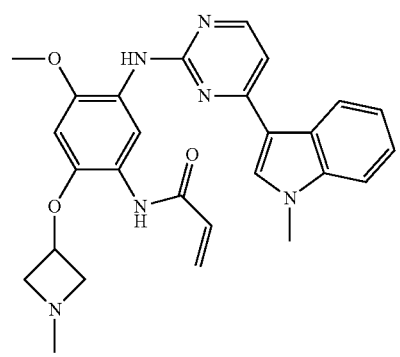
29
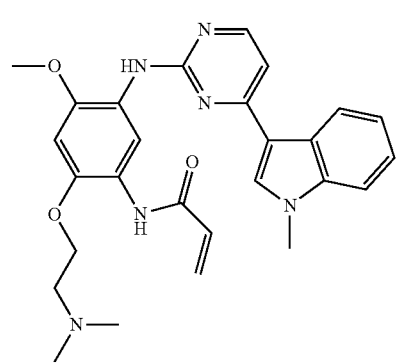
30
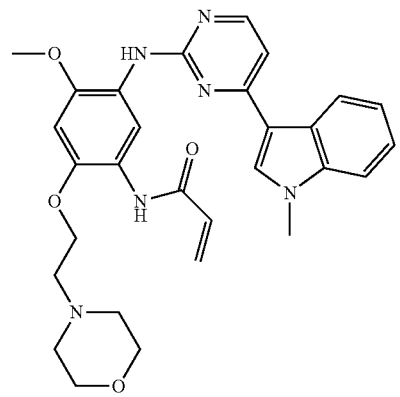
31
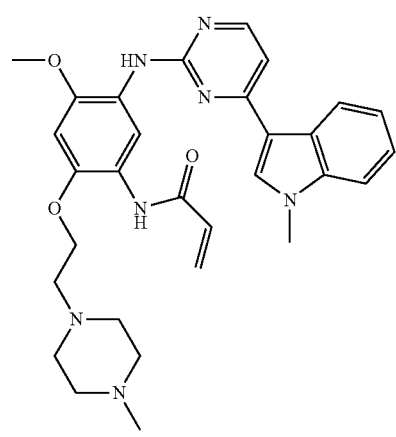

32 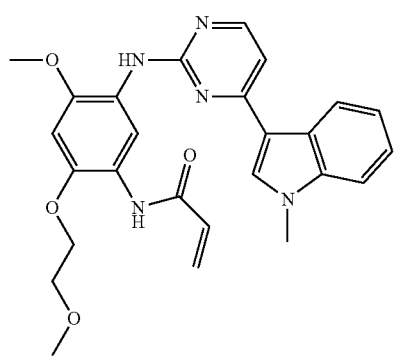
33 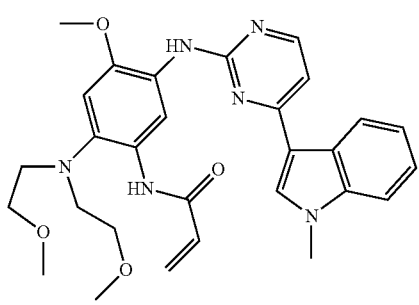
34 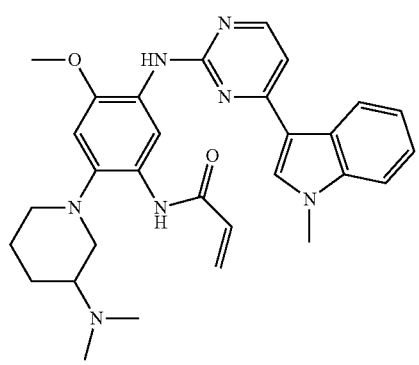
35 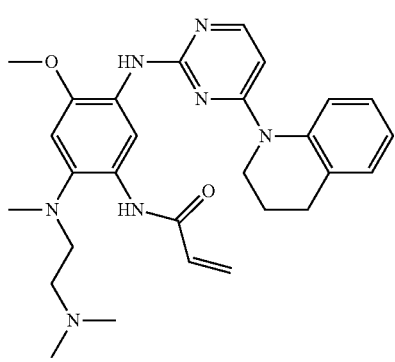
36 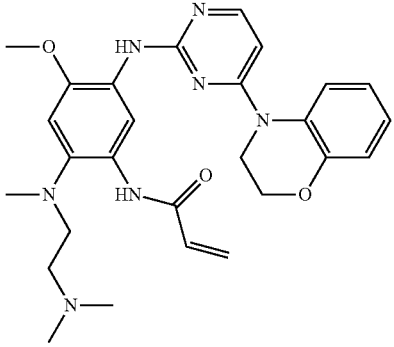
37 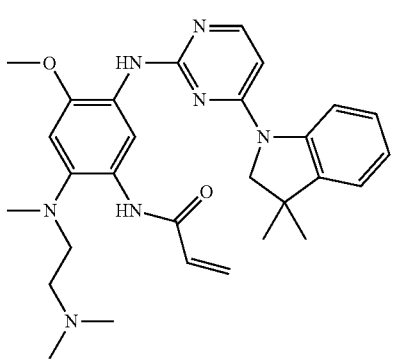
38 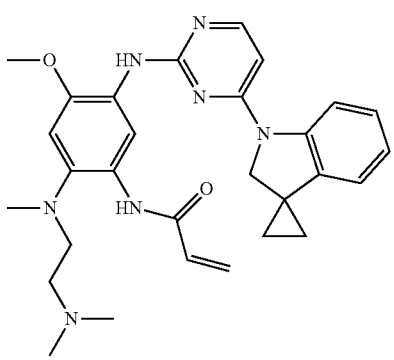
39 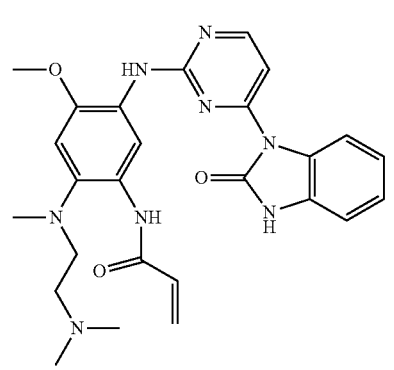

-continued
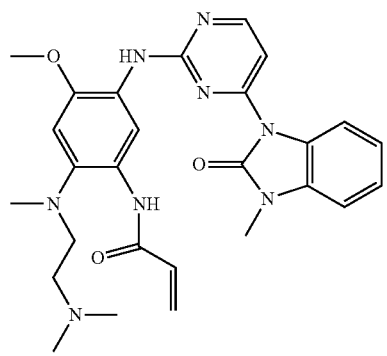
40
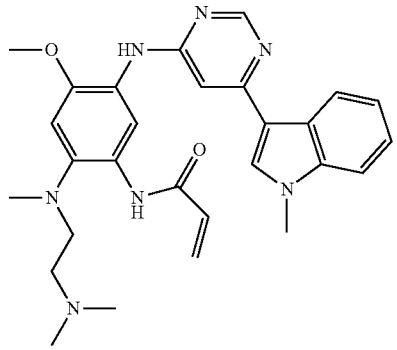
44
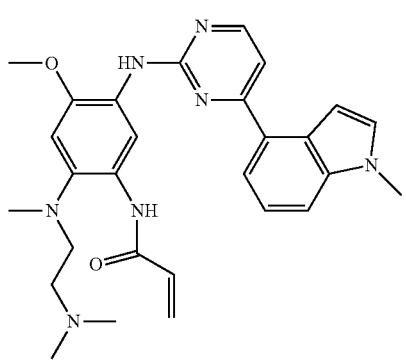
41
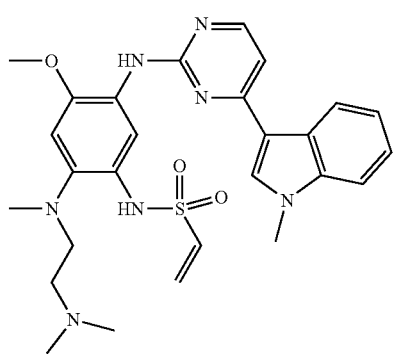
45
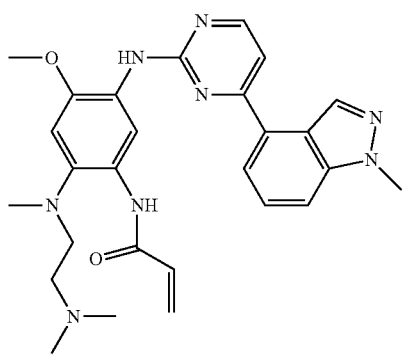
42
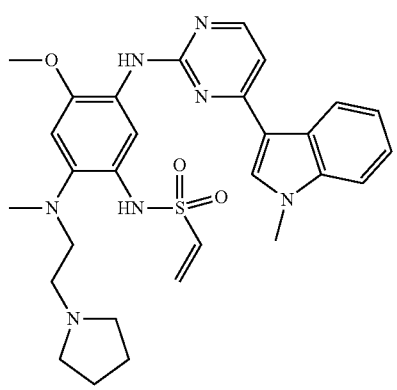
46
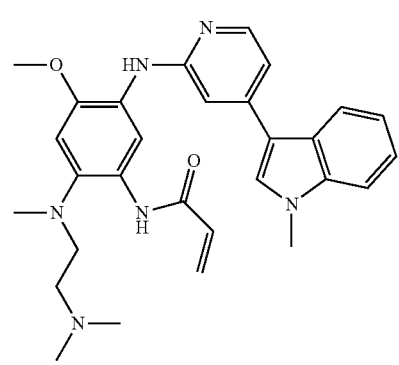
43
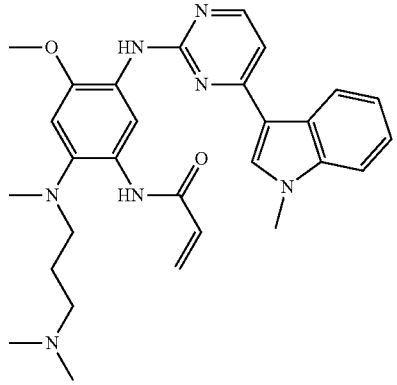
47

48 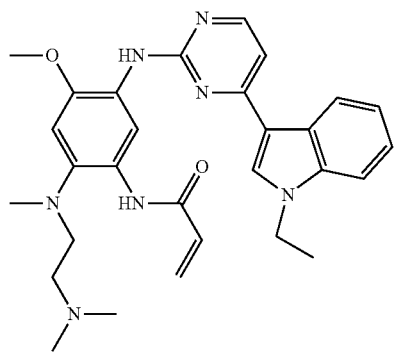
49 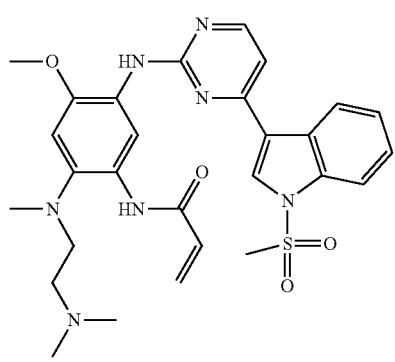
50 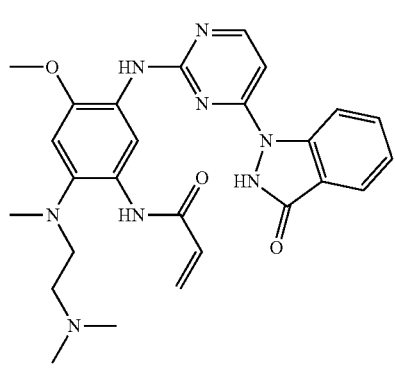
51 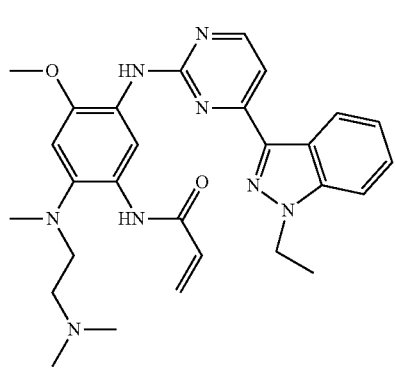
52 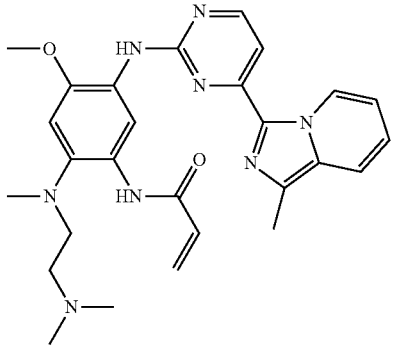
53 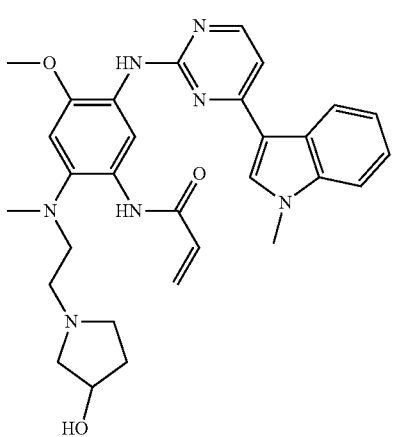
54 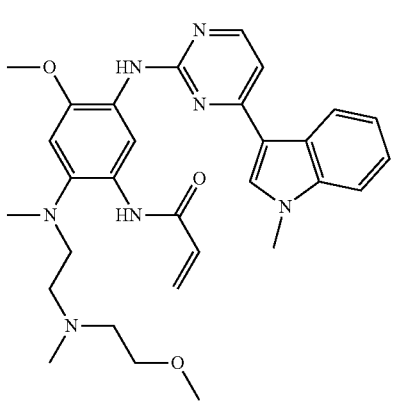
55 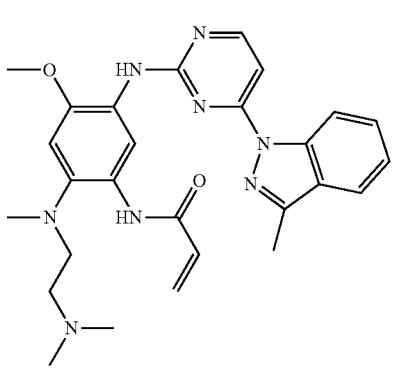

-continued
56
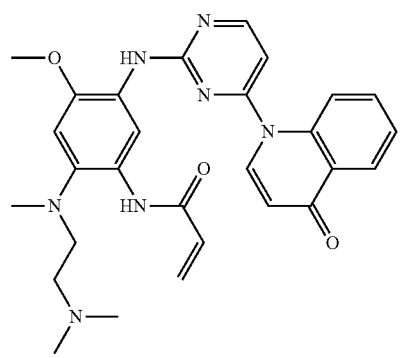
57

58
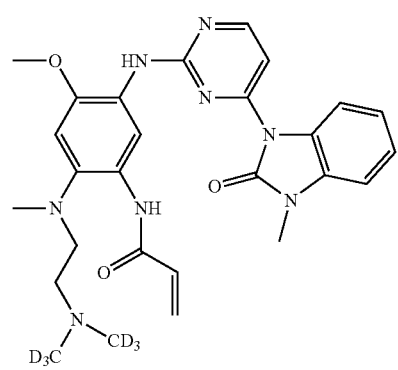
59
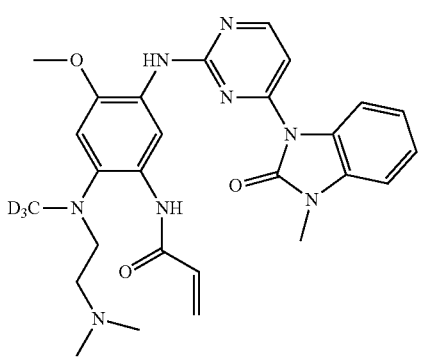
-continued
60
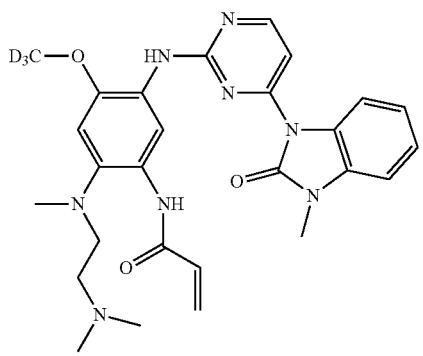
61
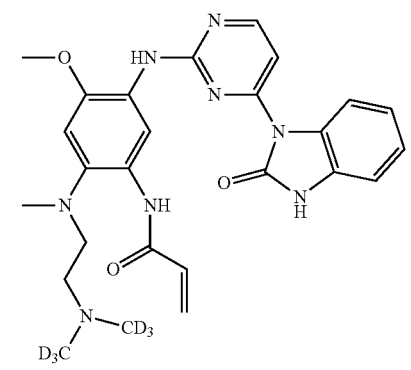
62
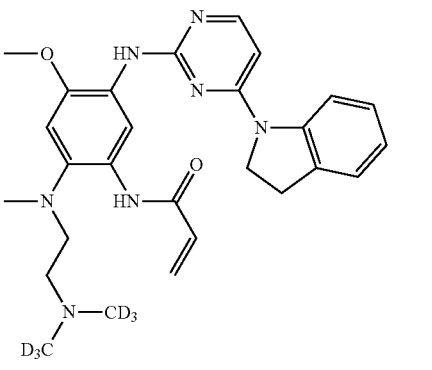
63
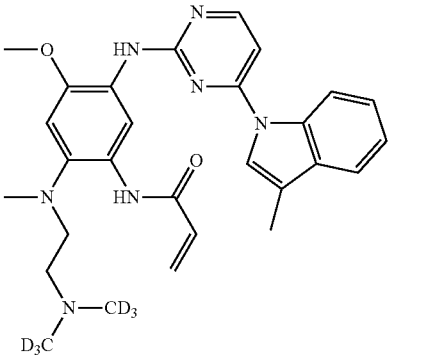

64
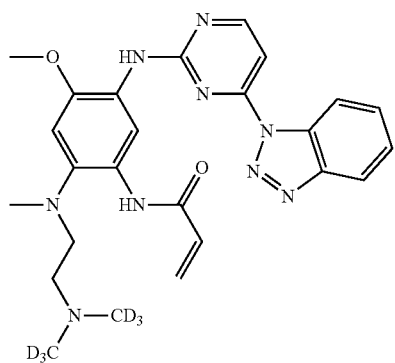
65
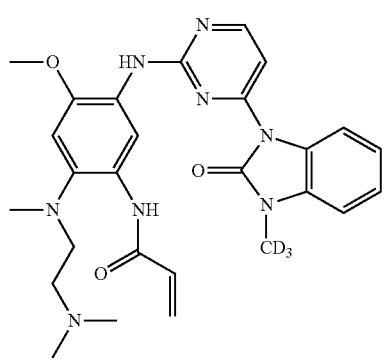
66
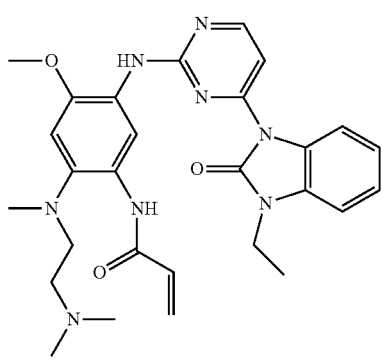
67
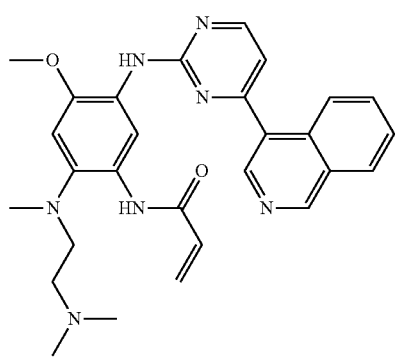
68
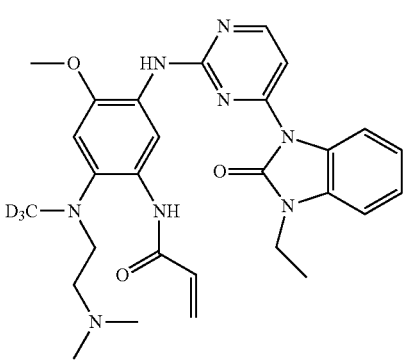
69
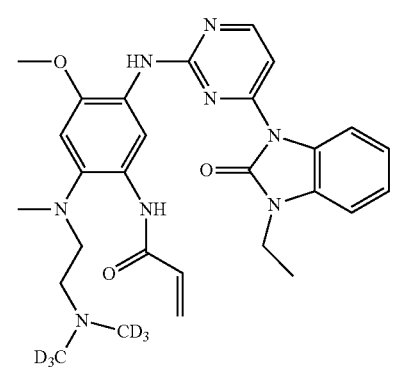
70
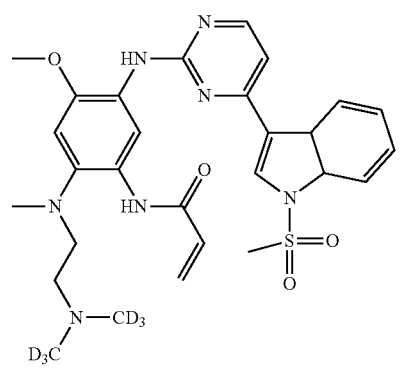
71
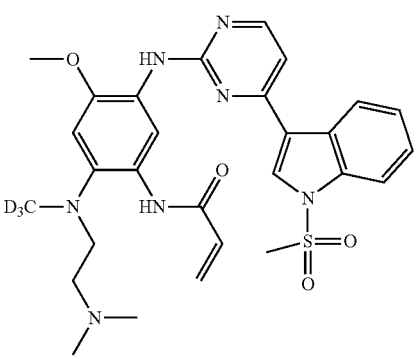

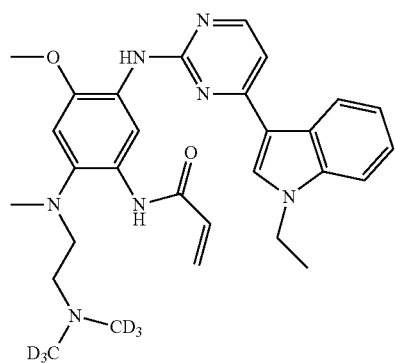
72
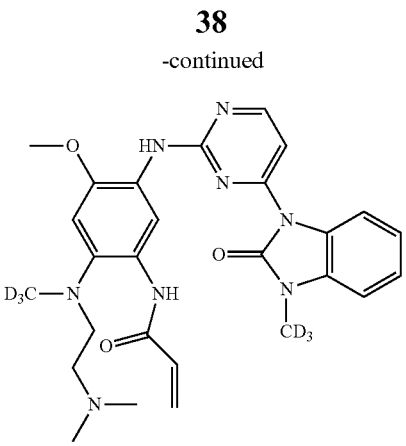
76
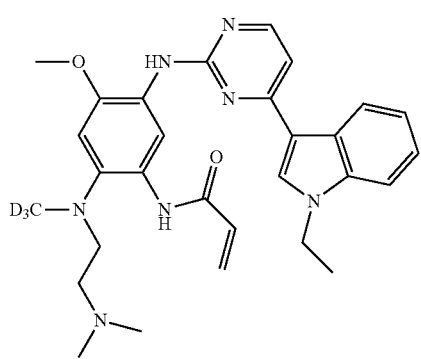
73
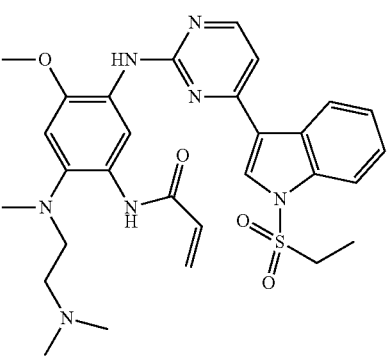
101
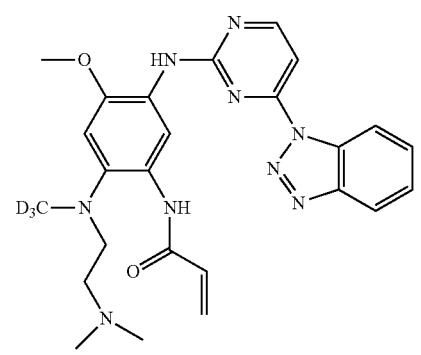
74
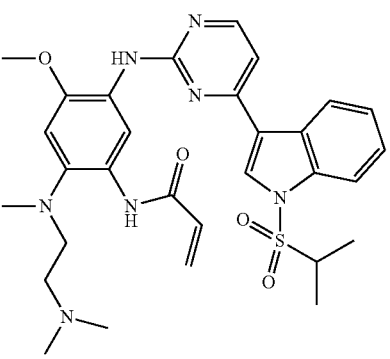
102
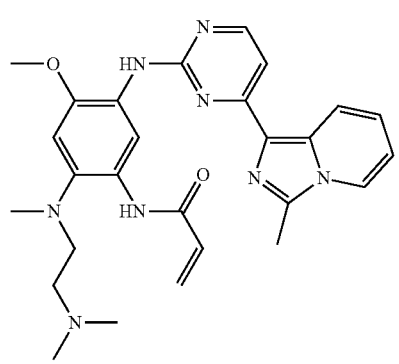
75
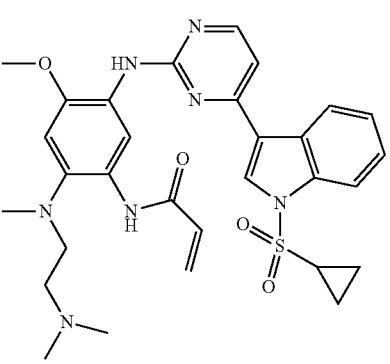
103

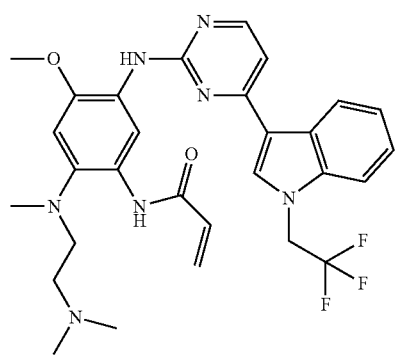
104
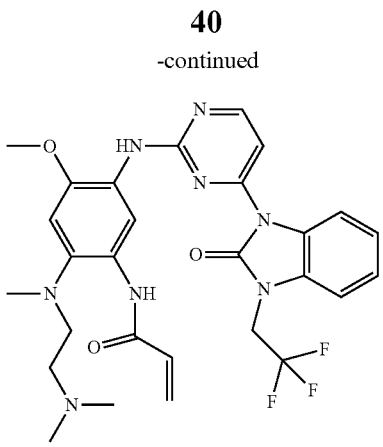
108
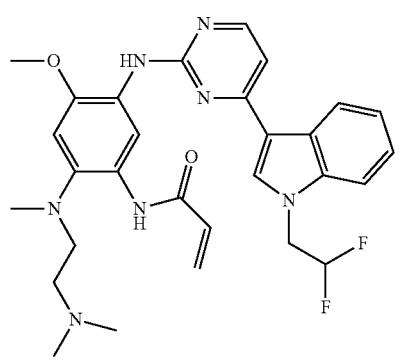
105
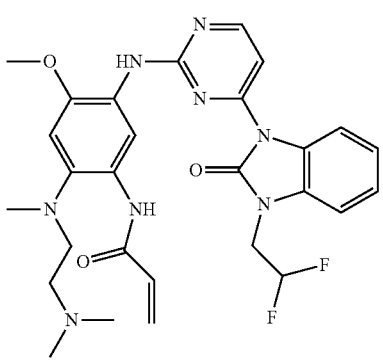
109
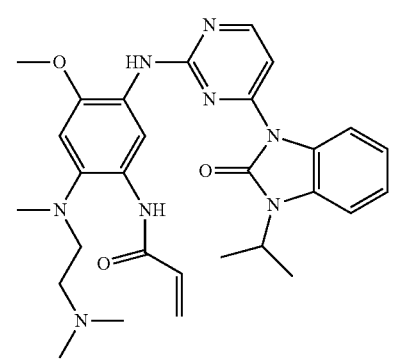
106
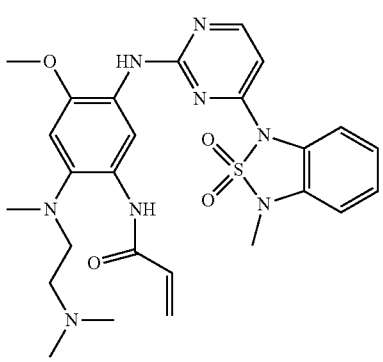
110
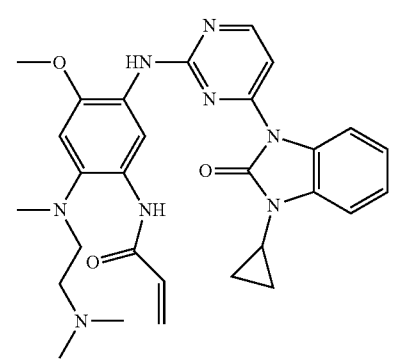
107
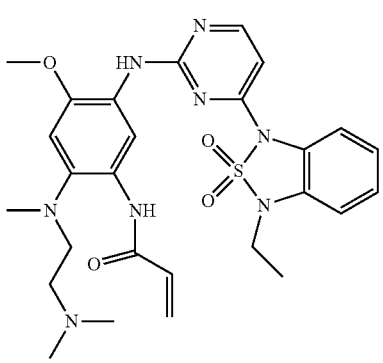
111

112 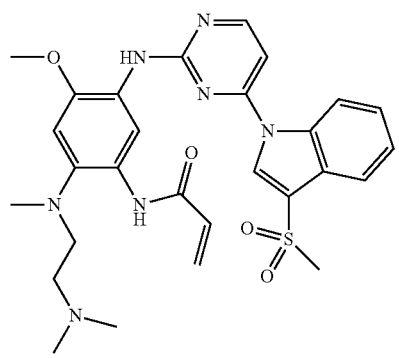
113 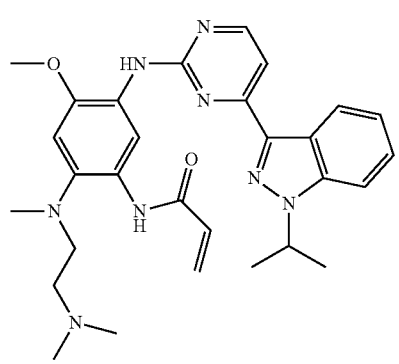
114 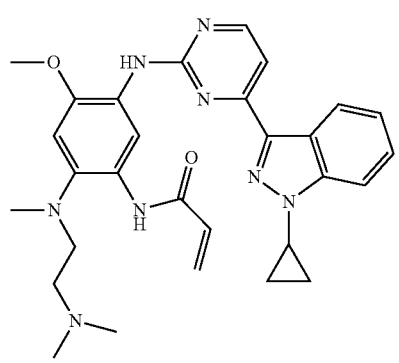
115 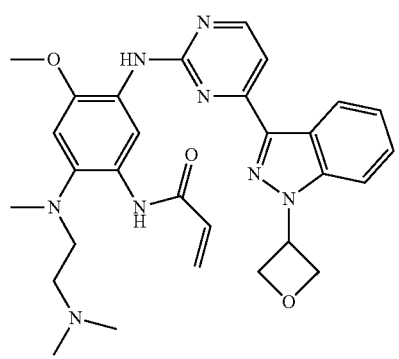
116 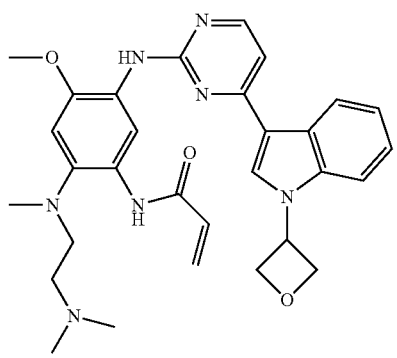
117 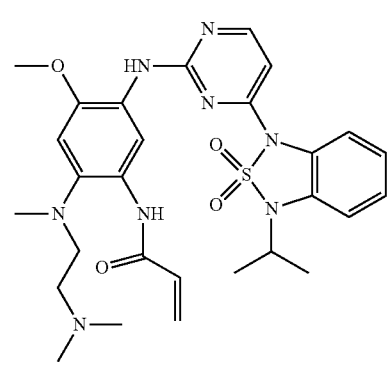
118 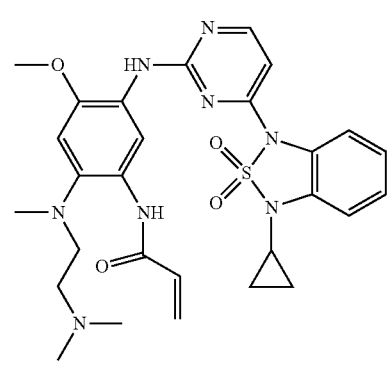
119 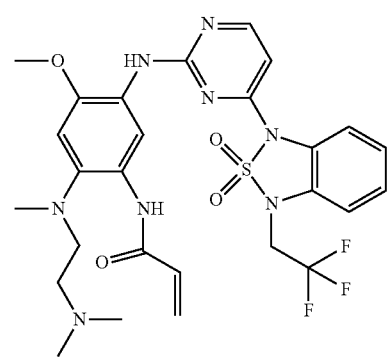

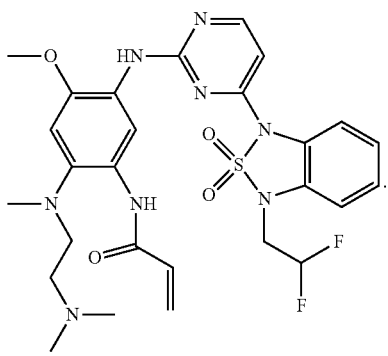

The second aspect of the present application provides a method for preparing compounds represented by the above formula (I) or a pharmaceutically acceptable salt thereof, for example, using a method represented by the following general reaction processes, in which the reaction sequences of certain two-step or multi-step reactions can be exchanged and do not necessarily have to be exactly the same as the sequences shown in the following reaction processes. Compounds A1, A2, A4, D1, R³R⁴NH, R⁴OH, R⁵H and R⁵Z in the following general reaction processes may be commercially available or may be prepared from other commercially available compounds according to methods known in the art. The preparation method is described in detail in the examples.

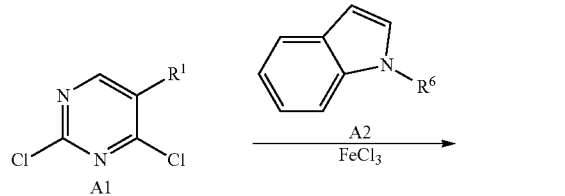

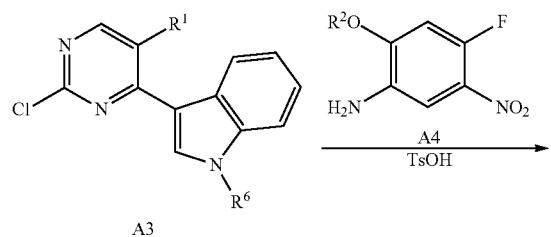

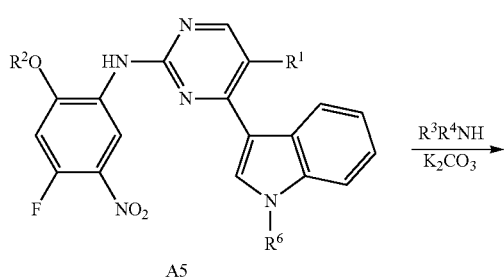

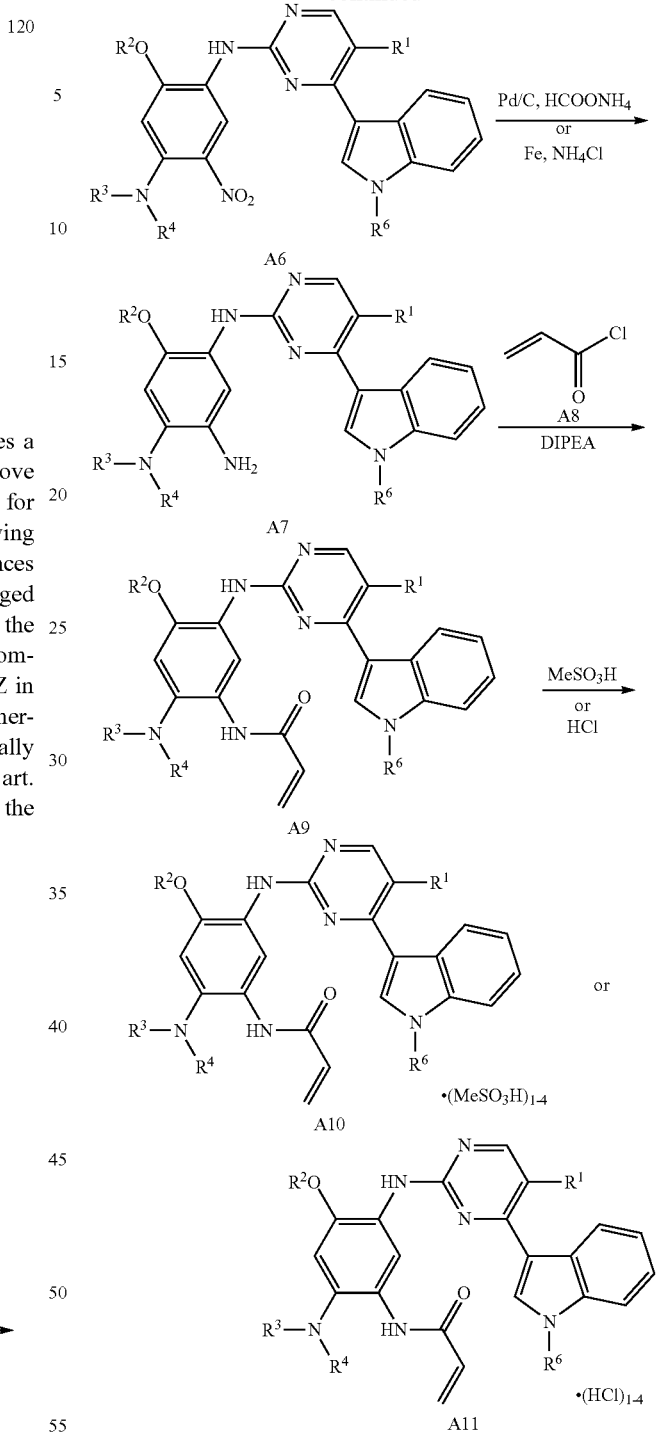

wherein R¹, R², R³, R⁴ and R⁶ are defined and preferred as described above,

In the above general reaction process, 2,4-dichloropyrimidine compound A1 reacts with indole compound A2 in the presence of ferric chloride to produce compound A3. In the presence of p-toluenesulfonic acid, compound A3 and compound A4 react to form compound A5. The fluorine atom in compound A5 is substituted with a secondary amine R³R⁴NH in the presence of potassium carbonate to give product A6. Nitrobenzene is converted into aniline compound A7 through a catalytic hydrogenation or a reduction reaction by iron powder. After reacting with acryloyl chloride A8, aniline is converted into the final product A9. Upon addition of an acid, product A9 can be converted into different salts, for example, methanesulfonate salt A10 can be obtained by treating with methanesulfonic acid, and hydrochloric acid salt A11 can be obtained by treating with hydrochloric acid. In these salts, the ratio of acid to compound A9 varies in different molecules. A compound A9 can react with 1-4 mole equivalent of acid molecules to form a salt, mostly, diacid or triacid salt

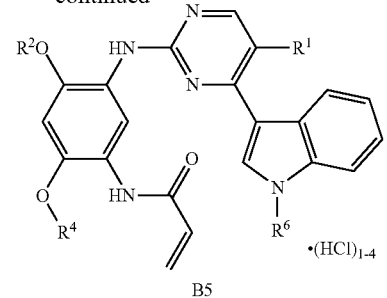

wherein, $R^1$, $R^2$, $R^4$ and $R^6$ are defined and preferred as described above, In the above general reaction sequence, the fluorine atom in compound A5 is substituted with alcohol $R^4OH$ in the presence of sodium hydride to give the product B1. Nitrobenzene is converted into aniline compound B2 through a catalytic hydrogenation or reduction reaction by iron powder. After reacting with acryloyl chloride A8, aniline is converted into the final product B3. Upon addition of an acid, the product B3 can be converted into different salts, for example, methanesulfonate salt B4 can be obtained by treating with methanesulfonic acid, and hydrochloric acid salt B5 can be obtained by treating with hydrochloric acid. In these salts, the ratio of acid to compound B3 varies in different molecules. A compound B3 can react with 1-4 mole equivalent of acid molecules to form a salt, mostly, diacid or triacid salt.

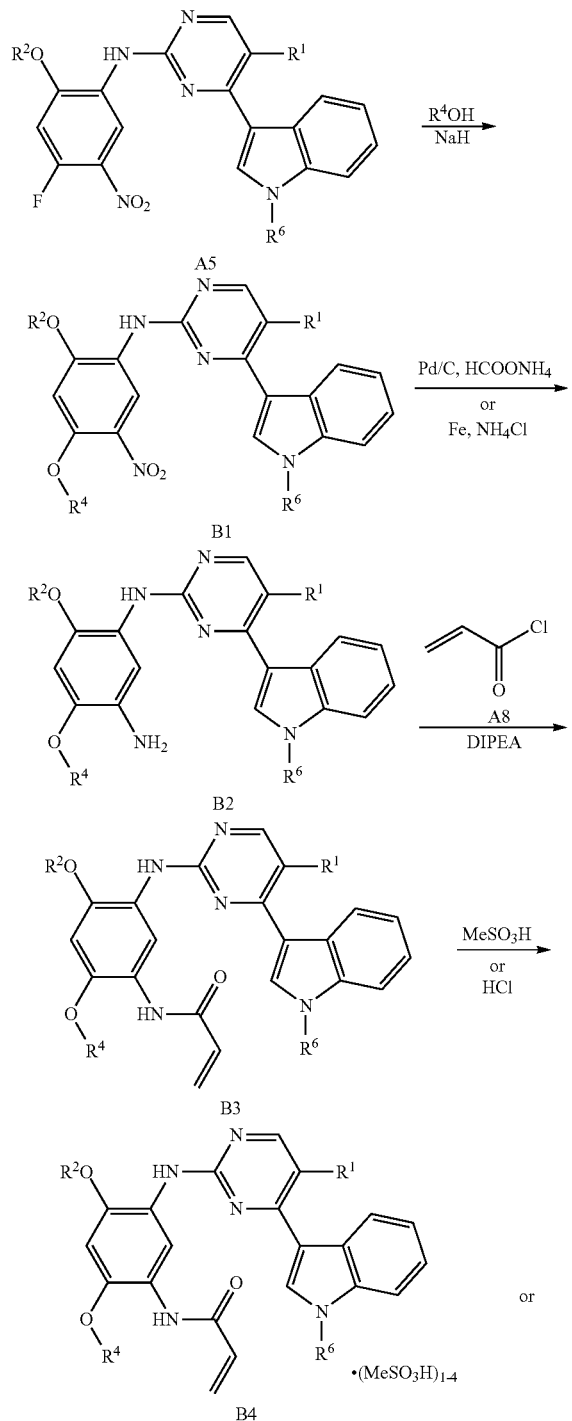

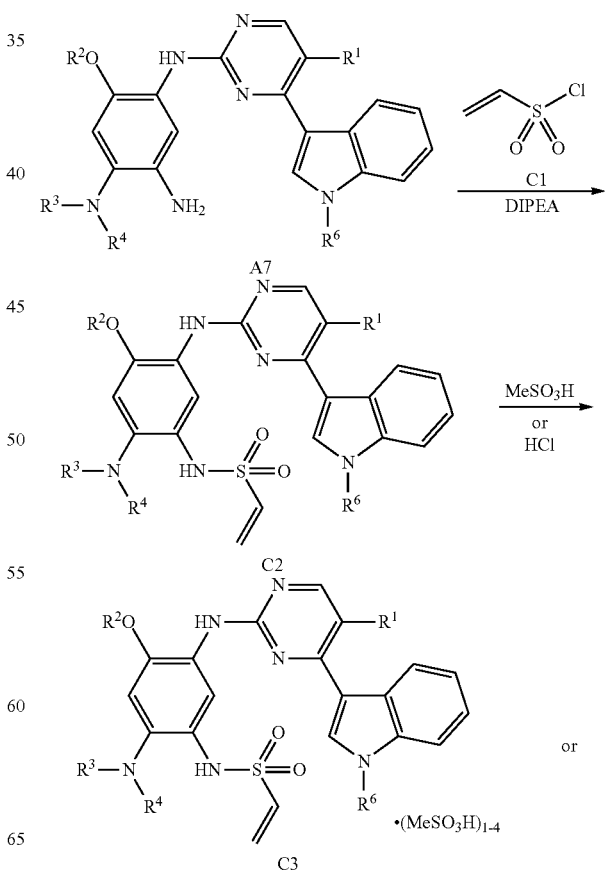

-continued

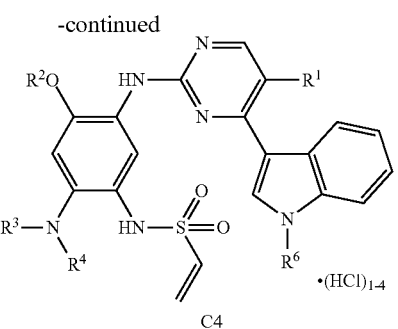

C4 wherein, $R^1$, $R^2$, $R^3$, $R^4$ and $R^6$ are defined and preferred as described above, In the above general reaction sequence, after reacting with vinyl sulfonyl chloride C1, aniline A7 is converted into the final product C2. Upon addition of acid, the product C2 can be converted into different salts, for example, methanesulfonate salt C3 can be obtained by treating with methanesulfonic acid, and hydrochloric acid salt C4 can be obtained by treating with hydrochloric acid. In these salts, the ratio of acid to compound C2 varies in different molecules. A compound C2 can react with 1-4 mole equivalent of acid molecules to form a salt, mostly, diacid or triacid salt.

wherein, $R^1$, $R^2$, $R^3$, $R^4$ and $R^6$ are defined and preferred as described above, wherein Z is a borate, a tin or zinc substituent, In the above general reaction sequence, the 2,4-dichloropyrimidine compound A1 is subjected to a substitution reaction with the two-membered fused ring compound $R^5H$ under suitable known conditions or is subjected to a catalytic coupling reaction with the compound $R^5Z$ to produce the compound D2. Alternatively, the amine group of compound D1 may be reacted with a suitable reagent and then under suitable conditions to form a two-member fused ring substituent $R^5$ in D2. In the presence of p-toluenesulfonic acid, compound D2 and compound A4 react to form compound D3. The fluorine atom in D3 is substituted with the secondary amine $R^3R^4NH$ in the presence of potassium carbonate to give product D4. Nitrobenzene is converted into aniline D5 through a catalytic hydrogenation or reduction reaction by iron powder. After reacting with acryloyl chloride A5, aniline gave the final product D6. After treating with an acid, product D6 can be converted into different salts, for example, methanesulfonate salt D7 can be obtained by treating with methanesulfonic acid, and hydrochloric acid salt D8 can be obtained by treating with hydrochloric acid. In these salts, the ratio of acid to compound D6 varies in different molecules. A compound D6 can react with 1-4 mole equivalent of acid molecules to form a salt, mostly, diacid or triacid salt.

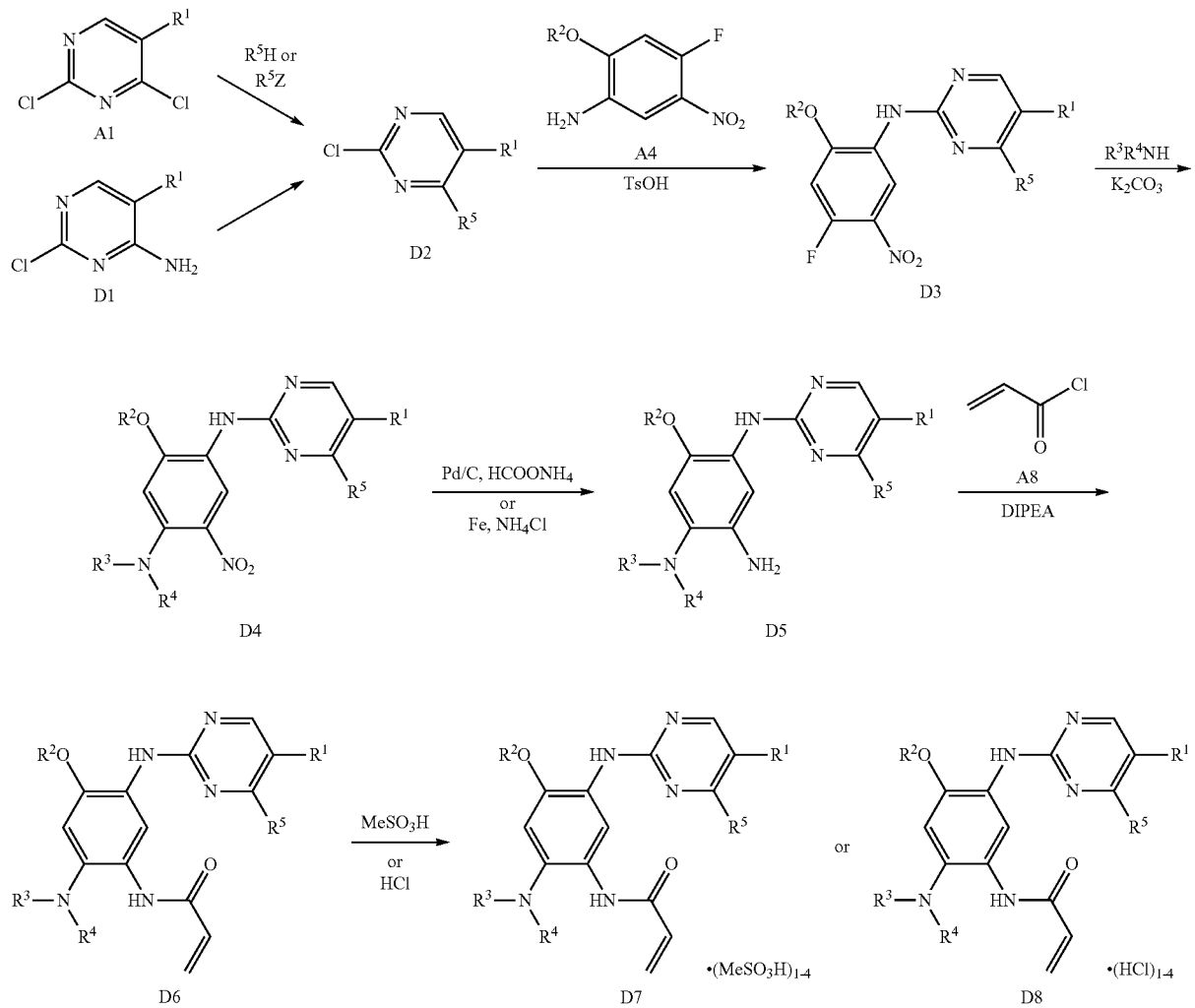

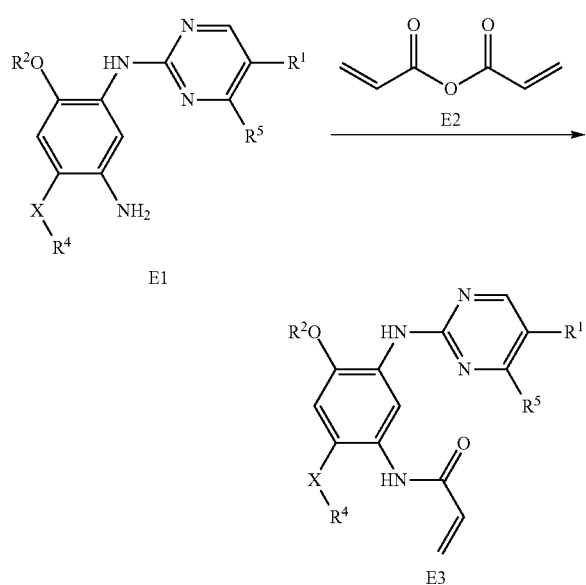

wherein, $R^1$, $R^2$, $R^4$, $R^5$ and X are defined and preferred as described above, In the above general reaction sequence, aniline intermediate compound E1 (A7, B2, D5) may be reacted with acrylic anhydride E2 to form acrylamide compound E3 (A9, B3, D6).

The third aspect of the present application provides a pharmaceutical composition comprising a therapeutically effective amount of one or more of compounds of formula (I), pharmaceutically acceptable salt thereof, stereoisomer, prodrug molecule and/or solvate thereof; and one or more pharmaceutical excipients. The above pharmaceutical composition is a medicament for the treatment or prevention of diseases, disturbances, disorders or conditions mediated by the EGFR in the form of activated mutant or resistant mutant, in particular, for the treatment or prevention of one or more cancers.

The above-mentioned medicaments, according to the objective of the treatment, may be in a variety of pharmaceutical forms, generally including: tablets, pills, capsules, granules, suspensions, solutions, creams, ointments, powders, suppositories, aerosols, injections etc.

The fourth aspect of the present application provides a use of a compound of formula (I), a pharmaceutically acceptable salt, a stereoisomer, a prodrug molecule and/or a solvate thereof in the preparation of a medicament for treating or preventing a disorder or disease mediated by EGFR in the form of activated mutant or resistant mutant. The disorder or disease includes, but is not limited to, ovarian cancer, cervical cancer, colorectal cancer (e.g., colon adenocarcinoma), breast cancer, pancreatic cancer, glioma, glioblastoma, melanoma, prostate cancer, leukemia, lymphoma, non-Hodgkin's lymphoma, gastric cancer, lung cancer (e.g., non-small cell lung cancer), hepatocellular carcinoma, gastrointestinal stromal tumors (GIST), thyroid cancer, cholangiocarcinoma, endometrial cancer, renal carcinoma, anaplastic large cell lymphoma, acute myeloid leukemia (AML), multiple myeloma or mesothelioma.

In the present invention, the EGFR in the form of activated mutant or resistant mutant may be, for example, a L858R activated mutant, an Exon19 deletion activated mutant and/or a T790M resistant mutant. Thus, the disease, disturbance, disorder or condition mediated by EGFR in the form of activated mutant or resistant mutant can be, for example, the disease, disturbance, disorder or condition mediated by L858R activated mutant, Exon19 deletion activated mutant and/or T790M resistant mutant.

The compounds of formula (I), pharmaceutically acceptable salt, stereoisomer, prodrug molecule and solvate thereof according to the invention, or pharmaceutical composition according to the invention can be particularly used for treating or preventing disease, disturbance, disorder or condition mediated by EGFR in the form of activated mutant or resistant mutant, such as a disease, disturbance, disorder or condition mediated by L858R activated mutant, Exon19 deletion activated mutant and/or T790M resistant mutant, and may be used, for example, for preventing or treating a cancer patient who has been resistant to gefitinib, erlotinib, or icotinib.

In a further aspect of the present invention, there is provided a method of combination therapy for treating cancer, comprising administering to a subject in need of treatment a therapeutically effective amount of one or more pyrimidine or pyridine compounds of formula (I), pharmaceutically acceptable salts, stereoisomers, prodrug molecules and solvates thereof; according to the invention, or a therapeutically effective amount of a pharmaceutical composition according to the invention, in combination with conventional surgical therapy, radiotherapy, chemotherapy or antitumor immunotherapy.

The compounds according to the present invention may be administrated in parallel, concurrently, sequentially, or separately with the chemotherapy or antitumor immunotherapy. The chemotherapy or immunotherapy includes, but is not limited to, one or more of the following types of antitumor agents: alkylating agent (e.g., carboplatin, oxaliplatin, cisplatin, cyclophosphamide, nitrosourea, nitrogen mustard, melphalan), antimetabolite (e.g. gemcitabine), and anti-folic acid agent (e.g., 5-fluorouracil and tegafur, raltitrexed, methotrexate, cytarabine, hydroxyurea), topoisomerase inhibitor (e.g., etoposide, topotecan, camptothecin), anti-mitotic agent (e.g., vincristine, vinblastine, vinorelbine, paclitaxel, taxotere), anti-tumor antibiotic (e.g., doxorubicin, bleomycin, doxorubicin, daunomycin, mitomycin C, actinomycin), antiestrogen drug (e.g., tamoxifen, fulvestrant, toremifene, raloxifene, droloxifene), anti-androgen drug (e.g., bicalutamide, flutamide, nilutamide), LHRH antagonist or LHRH agonist (e.g., goserelin, leuprolide, and buserelin), aromatase inhibitor (e.g., anastrozole, letrozole), CYP17 cleavage enzyme inhibitor (such as abiraterone), anti erbB2 antibody trastuzumab [Herceptin], anti-EGFR antibody cetuximab [Erbitux]; inhibitor of tyrosine kinase, serine/threonine kinases (e.g., imatinib, nilotinib, sorafenib, trametinib, crizotinib); cyclin-dependent kinase inhibitor (e.g., CDK4 inhibitor, palbociclib), anti-human vascular endothelial growth factor antibody of bevacizumab (Avastin) and VEGF receptor tyrosine kinase inhibitor (apatinib); antitumor immunotherapy, such as anti-PD-1 antibody (pembrolizumab, nivolumab), anti-PD-L1 antibody, anti-LAG-3 antibody, anti-CTLA-4 antibody, anti-4-1BB antibody, anti-GITR antibody, anti-ICOS antibody, interleukin 2.

Advantageous Effects

The pyrimidine or pyridine compounds of formula (I) of the present invention show a high inhibitory activity against one or more of EGFR-activated mutant or resistant mutant and a relatively low inhibition against a wild-type EGFR. The compounds of the present invention have a good physicochemical property and safety/toxicity parameter. Such compounds have a better clinical effect in the treatment of disease (including cancer) mediated by EGFR-activated mutant and/or drug-resistant mutant. Compared with AZD9291, such compounds have no or only a relatively low level of AZ5104 (a demethylated metabolite of AZD-9291) in animal in vivo experiments.

EXAMPLES

The following examples further illustrate the invention, but these examples are not to limit the scope of the invention.

Example 1

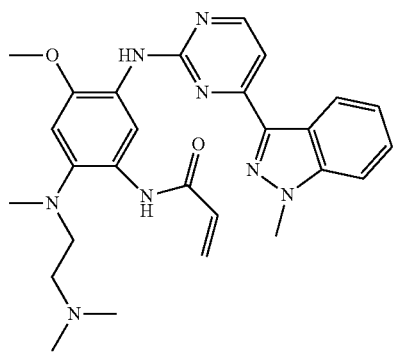

1. Synthesis of Intermediate 001-2

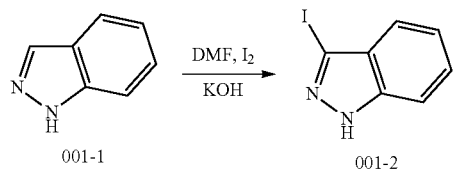

The intermediate 001-1 (10 g, 84.7 mmol) as the raw material was dissolved in N,N-dimethylformamide (DMF) (500 mL) in a 1000 mL three-necked flask under nitrogen ($N_2$) at room temperature, and then iodine ($I_2$) (21.5 g, 84.8 mmol) and potassium hydroxide (KOH) (19 g, 338.6 mmol) were added sequentially, followed by stirring the reaction overnight at room temperature. After completion of the reaction, 200 mL of 10% sodium thiosulfate ($Na_2S_2O_3$) was added to the reaction mixture, and ice water was used to quench the reaction. The mixture was extracted three times with 500 mL of ethyl acetate (EA). The organic phases were combined and washed once with 500 mL of saturated brine (NaCl), and the organic phases were dried over anhydrous sodium sulfate ($Na_2SO_4$) and concentrated to give 15.3 g of the intermediate 001-2 (74%) as an off-white solid. Liquid Chromatography Mass Spectrometry (LCMS): 245.0.

2. Synthesis of Intermediate 001-3

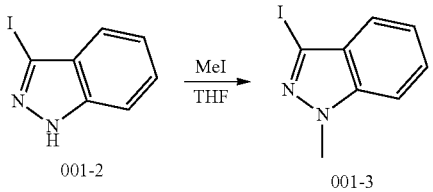

Sodium hydride (NaH) (0.6 g, 14.8 mmol) was dissolved in 100 mL of anhydrous tetrahydrofuran (THF) in a 250 mL three-necked flask under a nitrogen atmosphere at room temperature. The reaction solution was cooled to 0° C. with ice brine, and then the intermediate 001-2 (3.0 g, 12.3 mmol) was dissolved in 10 mL of anhydrous THF and added dropwisely. After the addition was completed, the temperature was raised to room temperature and the reaction mixture was stirred for 1 hour. Then, the reaction was cooled to 0° C., methyl iodide (MeI) (2 g, 14.76 mmol) was added dropwisely, and the reaction was maintained at room temperature for 3 hours. After the reaction was completed, 200 mL of ice water was added into the mixture to quench the reaction. The reaction mixture was extracted three times with 500 mL of EA. The organic phases were combined and then washed once with 100 mL of saturated brine. The organic phases were dried over anhydrous sodium sulfate and concentrated in vacuo. The residue was purified by chromatography (eluent: ethyl acetate (EA):petroleum ether (PE)=1:5) to give 2.5 g of the intermediate 001-3 (79%) as an off-white solid. LCMS: 259.0.

3. Synthesis of Intermediate 001-4

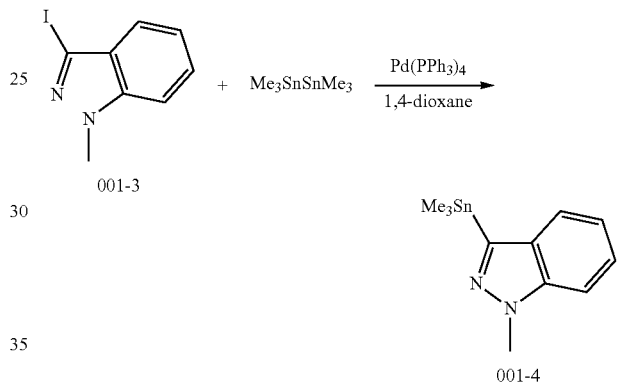

The intermediate 001-3 (2.5 g, 9.69 mmol) was dissolved in 300 mL of 1,4-dioxane at room temperature in a 500 mL four-necked flask under nitrogen protection. 1,1,1,2,2,2-hexamethyldistannane ($Me_3SnSnMe_3$) (6.0 g, 18.3 mmol) and tetrakis(triphenylphosphine)palladium ($Pd(PPh_3)_4$) (1.1 g 0.95 mmol) were added sequentially into the reaction mixture. The temperature was raised to 100° C., and the reaction mixture was stirred overnight. After the reaction was complete, the reaction system was cooled to room temperature. 15 mL of a potassium fluoride (KF) solution (1 M) and 50 mL of EA were added to quench the reaction and the reaction mixture was stirred at room temperature for 30 min. The mixture was extracted three times with 100 mL of ethyl acetate and the organic phases were collected. The organic phases were combined and washed once with 100 mL of saturated brine. The organic phase was dried over anhydrous sodium sulfate and concentrated to dryness to give 930 mg of the intermediate 001-4 as a yellow oil. LCMS: 297.0.

4. Synthesis of Intermediate 001-6

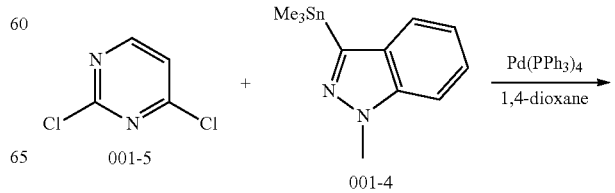

-continued

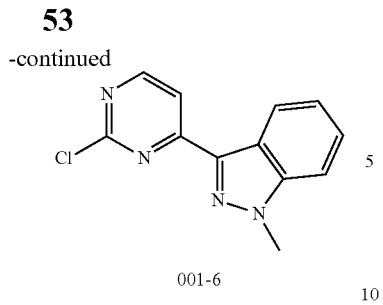
001-6

Under a nitrogen atmosphere, the intermediate 001-4 (0.93 g, 3.15 mmol) was dissolved in 30 mL of 1,4-dioxane at room temperature in a 50 mL single-necked flask, and 2,4-dichloropyrimidine (001-5) (0.47 g, 3.15 mmol) and tetrakis(triphenylphosphine)palladium (0.3 g, 0.26 mmol) were added to the reaction mixture. After the temperature was raised to 105° C., the reaction was stirred overnight. After the reaction was complete, the reaction system was cooled to room temperature with ice water and the mixture was concentrated to dryness. The mixture was purified by column chromatography (eluent: EA:PE=1:10) to give 480 mg of the intermediate 001-6 (62%) as a yellow oil. LCMS: 245.1.

5. Synthesis of Intermediate 001-8

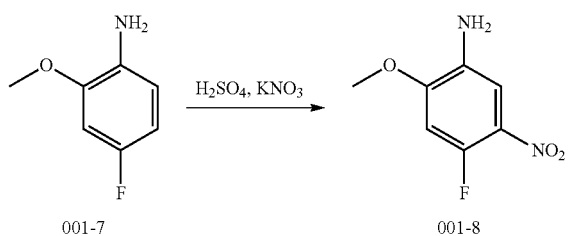
001-7                                    001-8

The intermediate 001-7 (100 g, 708.5 mmol) and 800 mL of concentrated sulfuric acid ($H_2SO_4$) were added sequentially to a 2000 mL three-necked flask under nitrogen protection and cooled to 0° C., and the reaction temperature was maintained at a temperature between 0 and 10° C. Potassium nitrate ($KNO_3$) (71.6 g, 708.19 mmol) was added in batches for 1 hour, and then the reaction was stirred overnight at room temperature. After completion of the reaction, 2 L of ice water was added to the three-necked flask to quench the reaction. The reaction mixture was adjusted to pH=10 with aqueous ammonia at low temperature and extracted three times with 1 L of dichloromethane (DCM). Then, the organic phases were combined, washed three times with 3 L of saturated brine, dried over anhydrous sodium sulfate and rotovapped. The crude product was purified by silica gel column chromatography (the used eluent, ethyl acetate (EA):petroleum ether (PE)=1:4-1:1) and eluent was rotovapped to give 79 g of the intermediate 001-8 (yield: 60%) as a yellow solid. LCMS: 187.0.

6. Synthesis of Intermediate 001-9

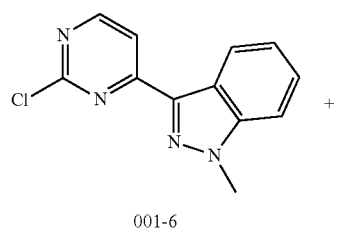
001-6

-continued

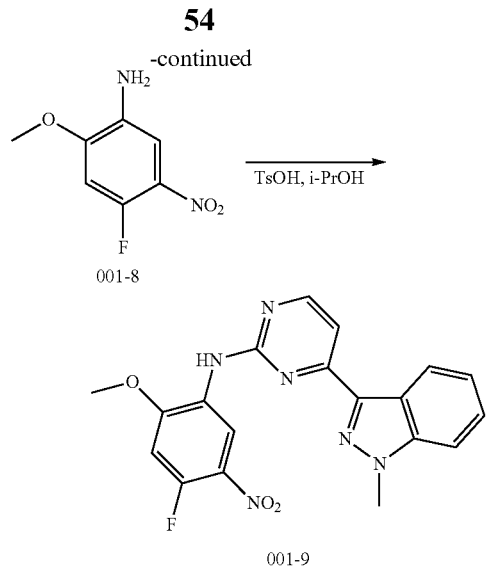
001-8

001-9

The intermediate 001-6 (480 mg, 1.96 mmol) was dissolved in 50 mL of isopropanol (i-PrOH) at room temperature in a 100 mL single-necked flask, and 001-8 (365 mg, 1.96 mmol) and p-toluenesulfonic acid (TsOH) (406 mg, 2.36 mmol) were added sequentially. The reaction was carried out at 85° C. overnight. After the reaction was completed, the reaction system was cooled to room temperature with ice water and a solid was precipitated. The mixture was filtered and the solid was collected and washed twice with 15 mL of isopropanol. The resulting solid was dried to give 450 mg of the intermediate 001-9 (58%) as yellow solid. LCMS: 395.1.

7. Synthesis of Intermediate 001-11

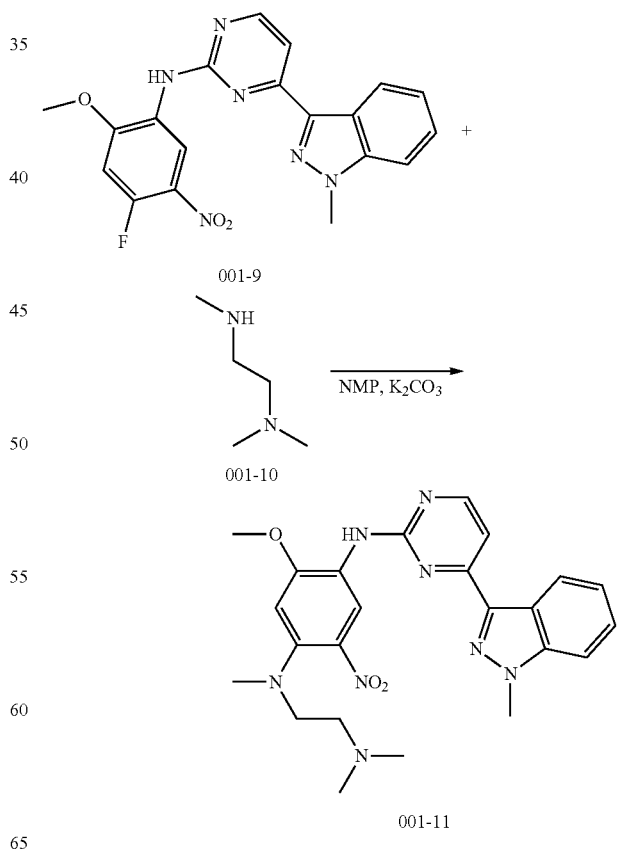
001-9

001-10

001-11

The intermediate 001-9 (100 mg, 0.25 mmol) was dissolved in N-methylpyrrolidone (NMP) (25 mL) in a 50 mL single-necked flask, and 1,1,4-N-trimethyl ethylenediamine (001-10) (33.7 mg, 0.33 mmol) and potassium carbonate (K$_2$CO$_3$) (103.5 mg, 0.75 mmol) were added sequentially. The temperature was raised to 85° C. for 2 h. After the reaction was complete, the mixture was cooled to room temperature. 70 mL of water was added to dilute the mixture and a solid was precipitated. The mixture was filtered, and the solid was collected and washed with 15 mL of water three times and dried to give 180 mg of crude product. LCMS: 477.2.

8. Synthesis of Intermediate 001-12

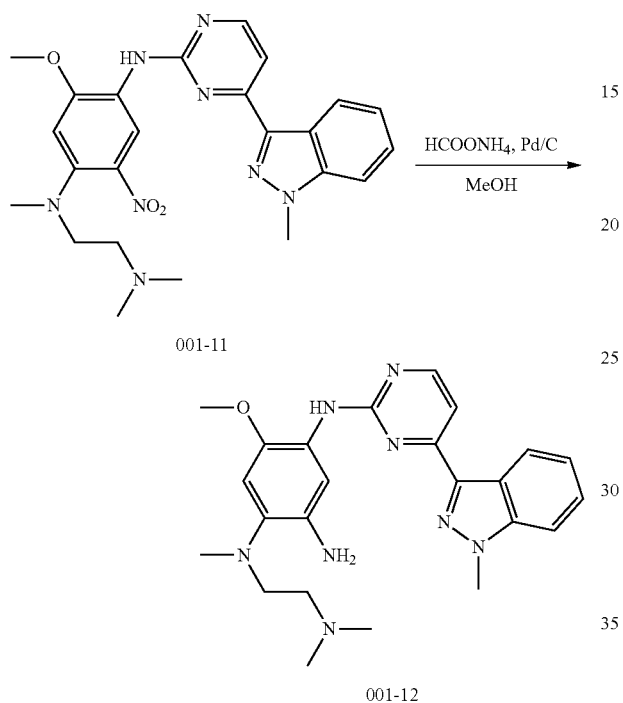

In a 100 mL single-necked flask, the intermediate 001-11 (180 mg, 0.38 mmol) was dissolved in 30 mL of anhydrous methanol (MeOH) and palladium on carbon (Pd/C) containing water (180 mg, 5% Pd), and ammonium formate (HCOONH$_4$) (180 mg) sequentially. The reaction was carried out at room temperature for 2.5 h. After the reaction was completed, the mixture was filtered, the filtrate was rotovapped and the mixture was dissolved in 40 mL of DCM. The mixture was washed three times with 40 mL of saturated brine. The organic phases were combined, dried over sodium sulfate, and rotovapped to give 157 mg of the intermediate 001-12 (93%) as a yellow solid. LCMS: 447.3.

9. Synthesis of Compound 1

Compound 001-12 (157 mg, 0.32 mmol) was dissolved in 25 mL of anhydrous THF in a 100 mL three-necked flask and diisopropylethylamine (DIPEA) (90.3 mg, 0.7 mmol) was added. The reaction system was cooled to 0° C. with ice water and acryloyl chloride (31.7 mg, 0.35 mmol) was added. The reaction mixture was stirred at room temperature for 30 minutes. After the reaction was completed, the reaction was quenched by addition of 2 drops of water to the reaction system, the mixture was concentrated to dryness, and the residue was purified by Prep-HPLC (column: Waters Sunfire C18, 19×150 mm, 5 m; flow phase: acetonitrile (CH$_3$CN)/water (H$_2$O) (0.1% trifluoroacetic acid (TFA)); 15% acetonitrile to 35% acetonitrile; 7 min; 15 mL/min; detection wavelength: 254 nm). The product fractions were collected and concentrated to remove most of the acetonitrile. An aqueous saturated sodium bicarbonate (NaHCO$_3$) solution was used to adjust the pH of the reaction system to 9 to 10 and then extracted twice with 100 mL of DCM. The organic phases were combined and dried over anhydrous sodium sulfate to give the compound 1. LCMS: 501.3.

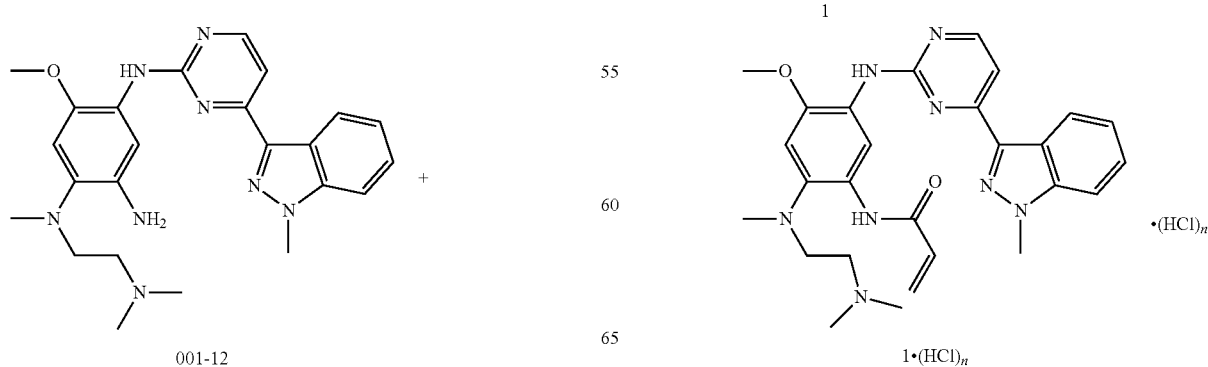

Compound 1 was dissolved in 10 mL of 0.1 N of hydrochloric acid (HCl) and freeze dried to give 4 mg of the hydrochloride of compound 1 (1. (HCl)$_n$) (2%) as a yellow solid. LCMS (parent molecule) $C_{27}H_{32}N_8O_2$: (ES, m/z): 501 [M+H]$^+$. $^1$H-NMR: (D$_2$O, 300 MHz, ppm): 87.98-7.96 (m, 1H), 7.83 (s, 1H), 7.74-7.72 (m, 1H), 7.39-7.30 (m, 2H), 7.15-7.13 (m, 1H), 6.95 (s, 2H), 6.58-6.49 (m, 1H), 6.30-6.24 (m, 1H), 5.88-5.84 (m, 1H), 3.88-3.81 (m, 6H), 3.41-3.36 (m, 2H), 3.28-3.17 (m, 2H), 2.80 (s, 6H), 2.75 (s, 3H).

Example 2

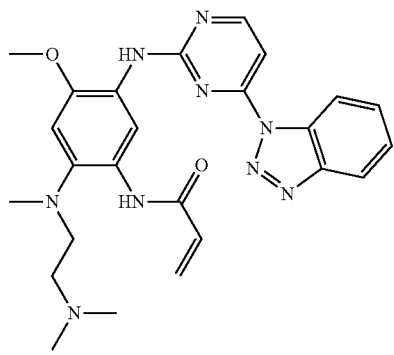

1. Synthesis of Intermediate 002-2

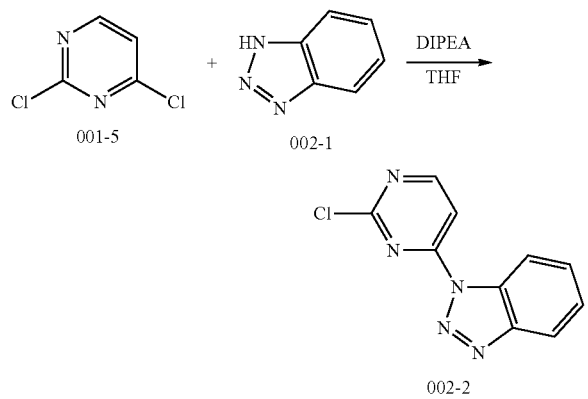

The intermediate 001-5 (5.0 g, 33.6 mmol) was dissolved in 100 mL of anhydrous tetrahydrofuran in a 250 mL three-necked flask at room temperature under a nitrogen atmosphere, and the intermediate 002-1 (3.0 g, 25.2 mmol) and N,N-diisopropylethylamine (DIPEA) (8.6 g, 66.5 mmol) were added to the reaction system sequentially. The temperature was raised to 70° C. and the reaction was stirred overnight. After the reaction was completed the next day, the reaction temperature was cooled to room temperature and the reaction solution was concentrated. The crude product was purified by silica gel column chromatography (eluent: PE/EA=50:1-5:1), the product was collected to give 2.4 g of the intermediate 002-2 (31%) as a yellow solid. LCMS: 232.0.

2. Synthesis of Intermediate 002-3

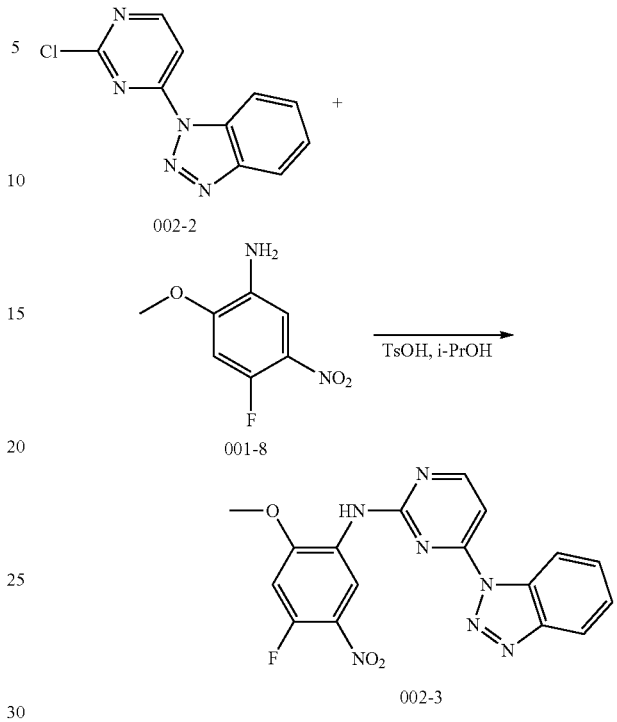

The intermediate 002-2 (2.4 g, 10.4 mmol) was dissolved in 20 mL of isopropanol a 100 mL three-necked flask at room temperature under a nitrogen atmosphere, and the intermediate 001-8 (1.92 g, 10.3 mmol) and toluenesulfonic acid (TsOH) (2.14 g, 12.4 mmol) were added to the reaction system sequentially. The temperature was raised to 105° C. and stirred for overnight.

After the reaction was completed the next day, the reaction mixture was cooled to room temperature and a solid was precipitated. The solid was filtered by suction, and the filter cake was collected and sequentially washed with 10 mL of isopropyl alcohol and 10 mL of acetonitrile once, and then dried to give 1.4 g of the intermediate 002-3 (35%) as a yellow solid. LCMS: 382.1.

3. Synthesis of Intermediate 002-4

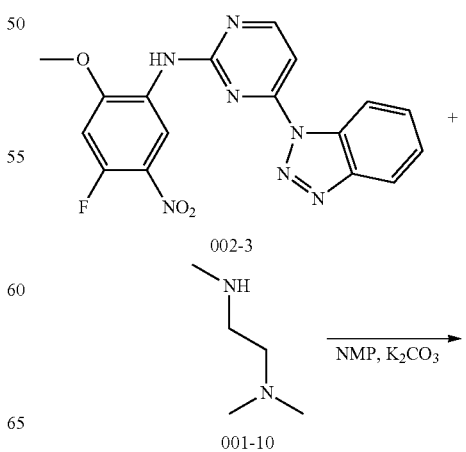

-continued

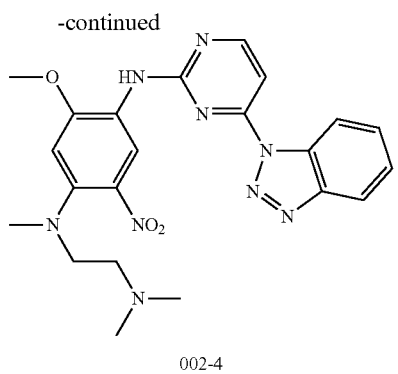

002-4

The intermediate 002-3 (1.0 g, 2.62 mmol) was dissolved in N-methylpyrrolidone (NMP) (20 mL) in a 50 mL single-necked flask at room temperature, and the intermediate 001-10 (280 mg, 2.74 mmol) and potassium carbonate ($K_2CO_3$) (720 mg, 5.17 mmol) were added sequentially. The temperature was raised to 105° C. and stirred for 2 h. After the reaction was completed, the reaction solution was poured into 50 mL of ice water to quench the reaction. The mixture was extracted three times with 100 mL of ethyl acetate. The organic phases were combined and washed once with 100 mL of saturated brine. The organic phases were dried over anhydrous sodium sulfate and concentrated to give 1.8 g of crude product 002-4 as a red oil. LCMS: 464.2.

4. Synthesis of Intermediate 002-5

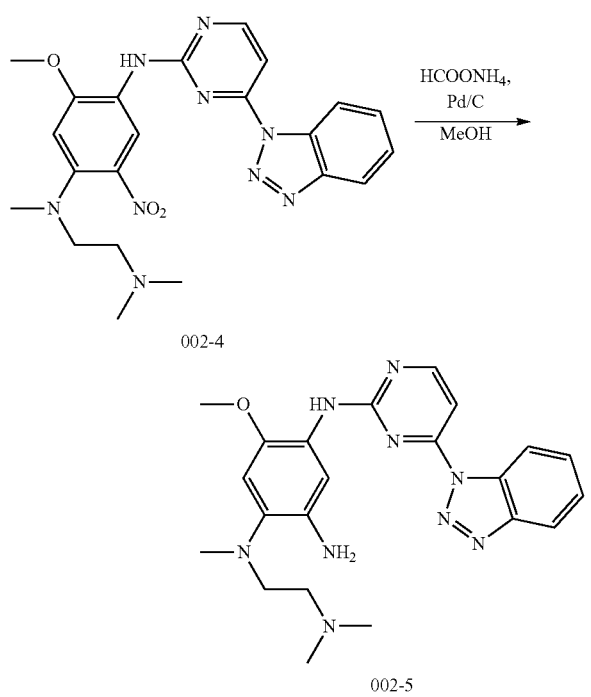

The intermediate 002-4 (1.8 g, 3.88 mmol) was dissolved in 200 mL of anhydrous methanol in a 50 mL single-necked flask at room temperature, and then palladium on carbon containing water (Pd/C) (1.0 g, 5% Pd) and ammonium formate (5.0 g, 79.3 mmol) were sequentially added to the reaction mixture. Then, the reaction was carried out at room temperature for 2 hours. After the reaction was completed, the reaction mixture was filtered to remove Pd/C, and the filtrate was collected and concentrated. The crude product was purified through silica gel column chromatography (eluent: DCM/MeOH=50:1-5:1). The product was collected and concentrated to give 810 mg of the intermediate 002-5 (48%) as a red oil. LCMS: 434.2.

5. Synthesis of Compound 2

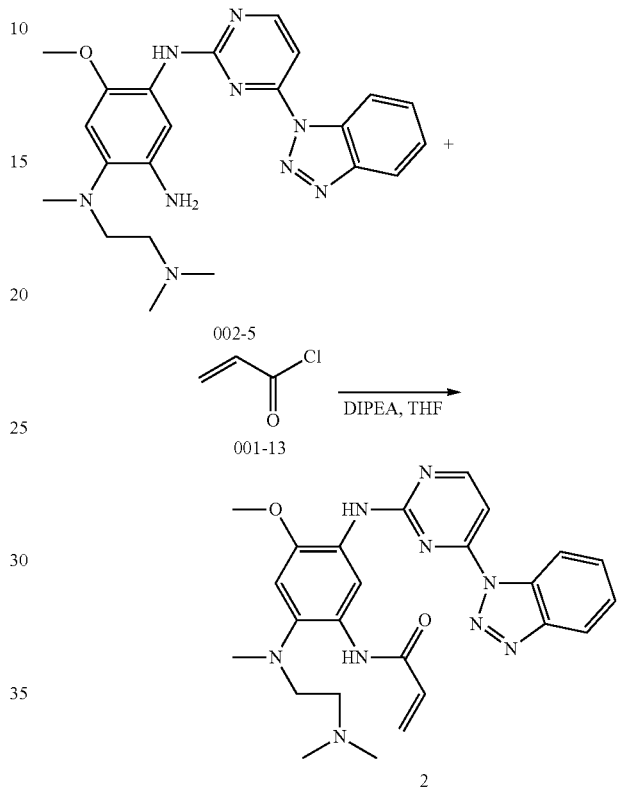

The intermediate 002-5 (150 mg, 0.35 mmol) was dissolved in 8 mL of anhydrous THF in a 50 mL three-necked flask at room temperature under a nitrogen atmosphere, and DIPEA (89.2 mg, 0.69 mmol) was added and the reaction was cooled to 0° C. 2.0 mL of a solution of acryloyl chloride (001-13) (28.2 mg, 0.31 mmol) in THF was added dropwisely to the reaction mixture at 0° C., and the reaction was carried out at 0° C. for 10 minutes. After the reaction was completed, the reaction system was concentrated directly. The crude product was purified by silica gel column chromatography (eluent: DCM/MeOH=20:1-5:1). The resulting product was collected and concentrated to give compound 2.

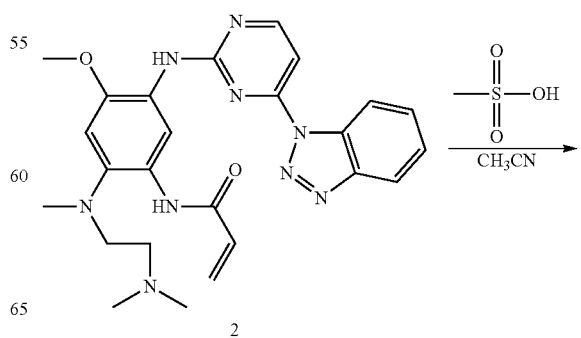

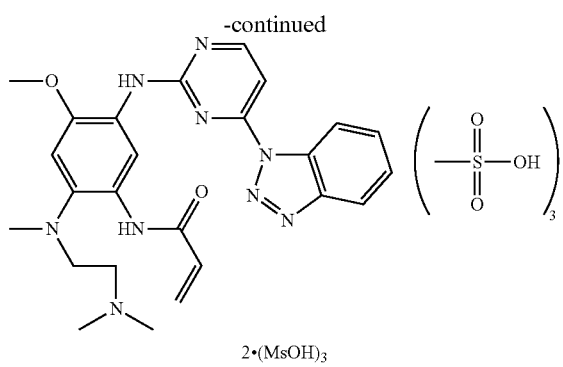

2·(MsOH)₃

The compound 2 was re-dissolved in 3 mL of acetonitrile, and methanesulfonic acid (MeSO₃H, or MsOH) (100 mg, 1.04 mmol) was added dropwisely at room temperature. After the reaction was stirred at room temperature for 2 hours, a solid was precipitated. The solid was filtered by suction, and then filter cake was collected, washed twice with 5 mL acetonitrile, frozen and dried to give 35.3 mg of methanesulfonate of compound 2 (13%) as a yellow solid. LCMS (parent molecule) $C_{25}H_{29}N_9O_2$: (ES, m/z): 488 [M+H]⁺. ¹H-NMR: (300 MHz, DMSO-$D_6$, ppm) δ 9.56 (s, 1H), 9.25-9.21 (m, 2H), 8.61-8.60 (d, J=5.4 Hz, 1H), 8.55-8.46 (m, 1H), 8.23-8.15 (m, 2H), 7.60-7.50 (m, 3H), 7.05 (s, 1H), 6.71-6.62 (m, 1H), 6.31-6.30 (m, 2H), 5.80-5.77 (m, 1H), 3.87 (s, 3H), 3.34-3.31 (m, 4H), 2.84-2.82 (d, J=4.8 Hz, 6H), 2.77 (s, 3H), 2.36 (s, 9H).

Example 3

3

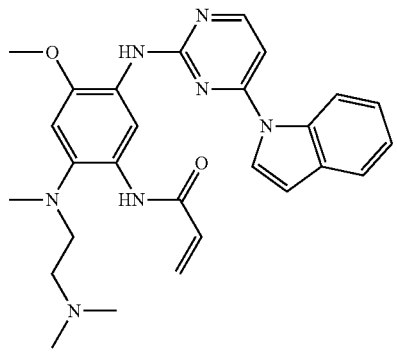

1. Synthesis of Intermediate 003-2

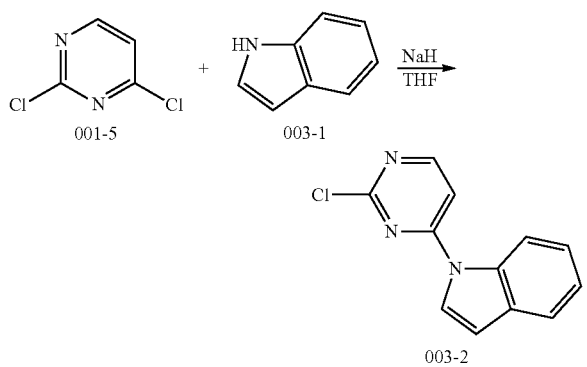

The intermediate 003-1 (3.0 g, 25.6 mmol) was dissolved in 150 mL of THF in a 500 mL of three-necked flask at room temperature under a nitrogen atmosphere, and the reaction was cooled to 0° C. Sodium hydride (NaH) (1.5 g, 40.3 mmol, 65%, stored in mineral oil) was added in batches to the reaction mixture at 0° C. After the reaction was carried out for 20 minutes, compound 001-5 was added into the reaction mixture at 0° C. and the reaction was maintained for 2 hours. After the reaction was complete, the reaction was quenched with 200 mL of ice water and the reaction system was extracted three times with 200 mL of ethyl acetate. The organic phases were combined and washed once with 200 mL of saturated brine. The organic phases were dried over anhydrous sodium sulfate and concentrated to dryness. Crude product was purified by silica gel column chromatography (eluent: EA/PE=1:50-1:5) to give 3.5 g of intermediate 003-2 (38%) of a yellow solid. LCMS: 230.0.

2. Synthesis of Intermediate 003-3

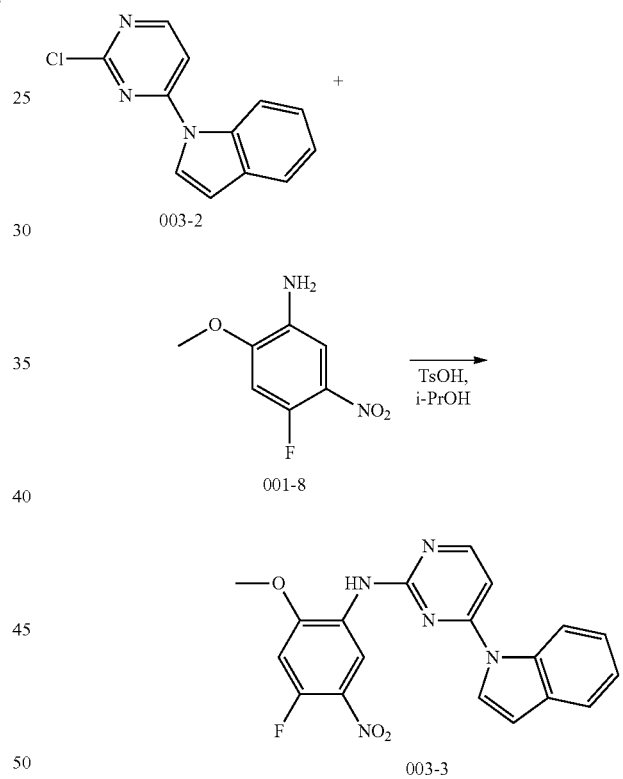

The intermediate 003-2 (3.5 g, 15.2 mmol) was dissolved in 20 mL of isopropanol in a 100 mL of single-necked flask at room temperature under a nitrogen atmosphere, and the intermediate 001-8 (2.84 g, 15.3 mmol) and TsOH (3.15 g, 18.3 mmol) were added to the reaction mixture. The reaction temperature was raised to 105° C. and the reaction was maintained overnight with stirring. After the reaction was completed the next day, the reaction system was cooled to room temperature and a solid was precipitated. The reaction mixture was filtered, and filter cake was collected and sequentially washed with 10 mL of isopropyl alcohol and 10 mL of acetonitrile once, and then dried to give 1.5 g of the intermediate 003-3 (26%) as a yellow solid. LCMS: 380.1.

3. Synthesis of Intermediate 003-4

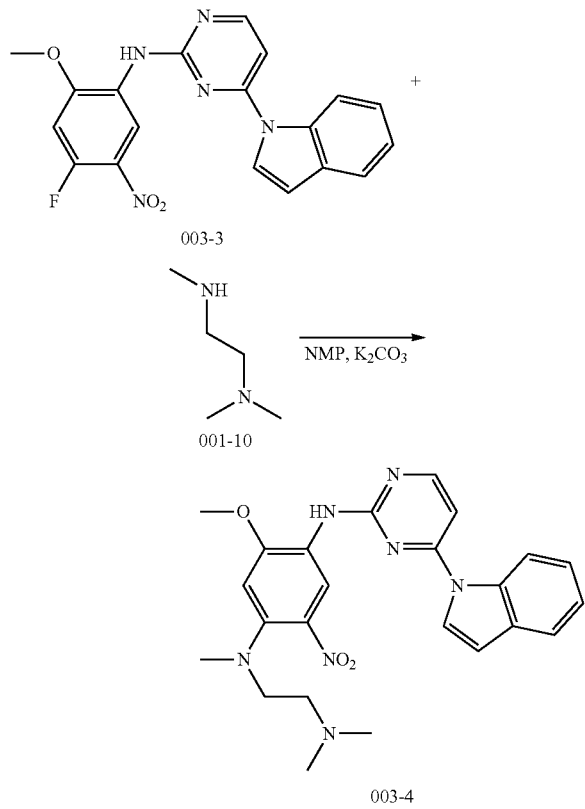

003-4

The intermediate 003-3 (1.5 g, 3.95 mmol) was dissolved in NMP (20 mL) in a 50 mL single-necked flask at room temperature, and the intermediate 001-10 (410 mg, 4.01 mmol) and K$_2$CO$_3$ (1.1 g, 7.90 mmol) were added into the reaction mixture. The temperature was raised to 105° C. and stirred for 2 h. After the reaction was completed, 50 mL of ice water was used to quench the reaction. The mixture was extracted three times with 100 mL of ethyl acetate. The organic phases were combined and washed once with 100 mL of saturated brine. The organic phases were dried over anhydrous sodium sulfate and concentrated to give 0.6 g of compound 003-4 (33%) as a red oil. LCMS: 462.2.

4. Synthesis of Intermediate 003-5

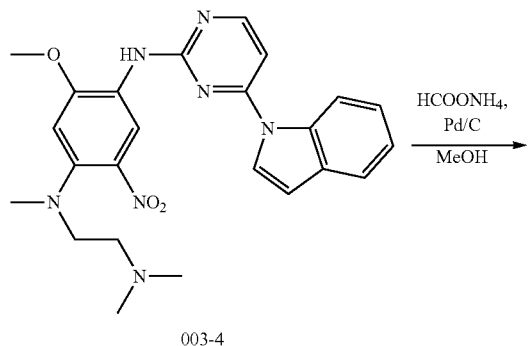

003-4

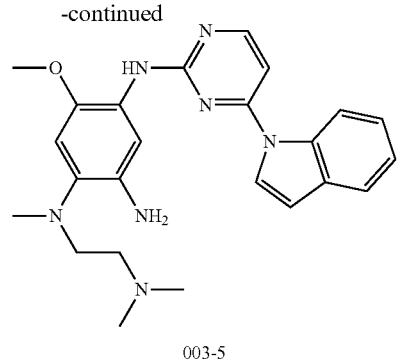

003-5

The intermediate 003-4 (600 mg, 1.30 mmol) was dissolved in 100 mL of anhydrous methanol in a 50 mL single-necked flask at room temperature, and then palladium on carbon containing water (Pd/C) (0.5 g, 5% Pd) and ammonium formate (2.0 g, 31.7 mmol) were added to the reaction mixture. Then, the reaction was carried out at room temperature for 2 hours and checked that the reaction was completed. The reaction mixture was filtered, and the filtrate was collected and concentrated to dryness. The crude product was purified through silica gel column chromatography (eluent: DCM/MeOH=50:1-5:1) to give 200 mg of the intermediate 003-5 (35%) as a yellow oil. LCMS: 432.2.

5. Synthesis of Compound 3

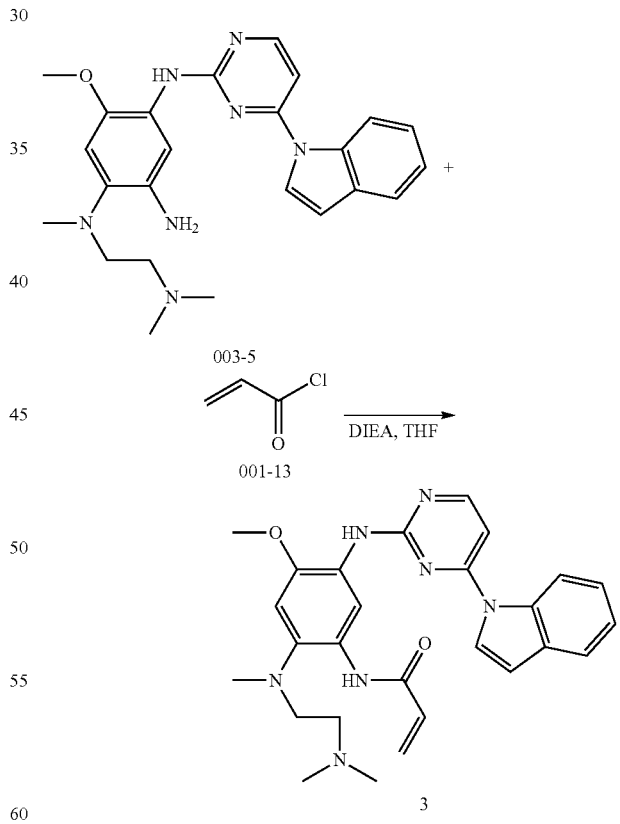

The intermediate 003-5 (110 mg, 0.25 mmol) was dissolved in THF (20 mL) in three-necked flask at room temperature under a nitrogen atmosphere, and DIPEA (65.8 mg, 0.51 mmol) was added into the reaction mixture and the reaction was cooled to 0° C. A solution of acryloyl chloride (23.1 mg, 0.26 mmol) in THF was added dropwise to the reaction mixture at 0° C., and the reaction was carried out at 0° C. for 10 minutes. The reaction mixture was concentrated, and the crude product was purified through silica gel column chromatography (eluent: DCM/MeOH=50:1-5:1) to Five compound 3.

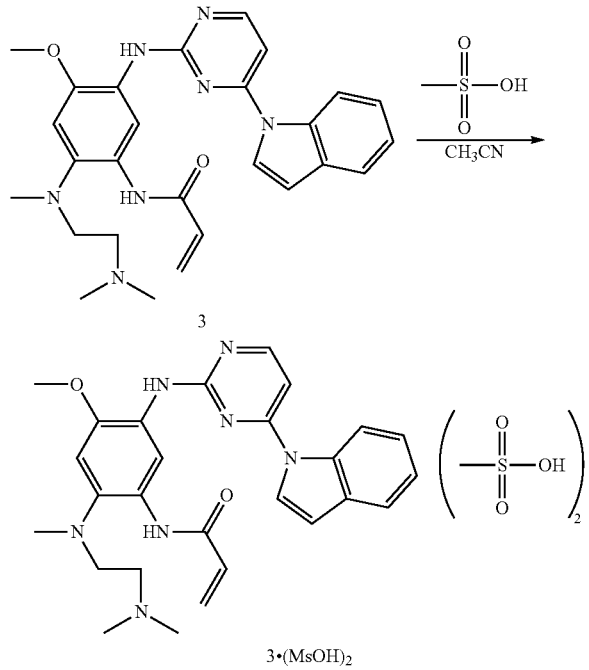

The product 3 was dissolved in 3 mL of acetonitrile, and methanesulfonic acid (73.4 mg, 0.76 mmol) was added dropwisely at room temperature and stirred at room temperature for 2 hours to precipitate a solid. After filtration, the filter cake was collected and washed twice with 5 mL of acetonitrile. After drying, 80 mg of compound 3 methanesulfonate (46%) was obtained as a yellow solid. LCMS (parent molecule) $C_{27}H_{31}N_7O_2$: (ES, m/z): [M+H]$^+$=486.

$^1$H-NMR (300 MHz, DMSO-D$_6$, ppm): δ 9.50 (s, 2H), 9.27 (s, 1H), 8.47-8.43 (d, J=12.9 Hz, 1H), 8.19-8.18 (m, 2H), 7.64-7.61 (m, 1H), 7.25-7.20 (m, 1H), 7.18-7.13 (m, 2H), 7.08 (s, 1H), 6.89 (s, 2H), 6.73-6.67 (m, 1H), 6.30-6.24 (m, 1H), 5.80-5.76 (m, 1H), 3.83 (s, 3H), 3.35 (s, 4H), 2.84 (s, 6H), 2.73 (s, 3H), 2.37 (s, 6H).

Example 4

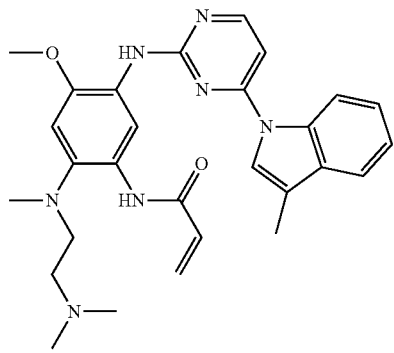

1. Synthesis of Intermediate 004-2

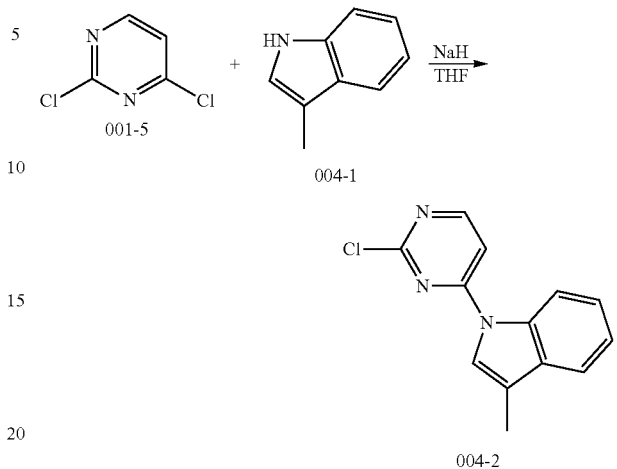

The intermediate 001-5 (3.0 g, 22.9 mmol) was dissolved in 150 mL of anhydrous THF in a 500 mL three-necked flask at room temperature under a nitrogen atmosphere, and the reaction was cooled to 0° C. NaH (65%, dispersed in mineral oil) (1.5 g, 22.9 mmol) was added in batches to the reaction mixture at 0° C. After the reaction was carried out for 20 minutes, compound 004-1 (6.0 g, 40.3 mmol) was added at 0° C. and the reaction was maintained for 2 hours. After the reaction was complete, the reaction mixture was slowly poured into a 200 mL of ice water to quench the reaction and was extracted with 200 mL of ethyl acetate three times. The organic phases were combined and washed once with 100 mL of saturated brine, dried over anhydrous sodium sulfate, and concentrated. The crude product was purified through silica gel column chromatography (eluent: PE/EA=50/1-5/1) to give 3.5 g of intermediate 004-2 (36%) as a yellow solid. LCMS: 244.1.

2. Synthesis of Compound 4

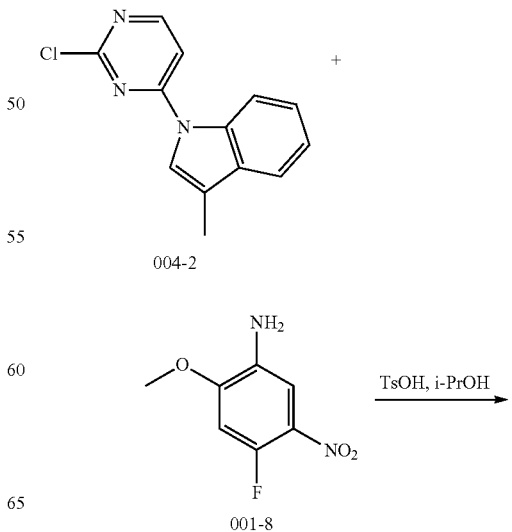

-continued

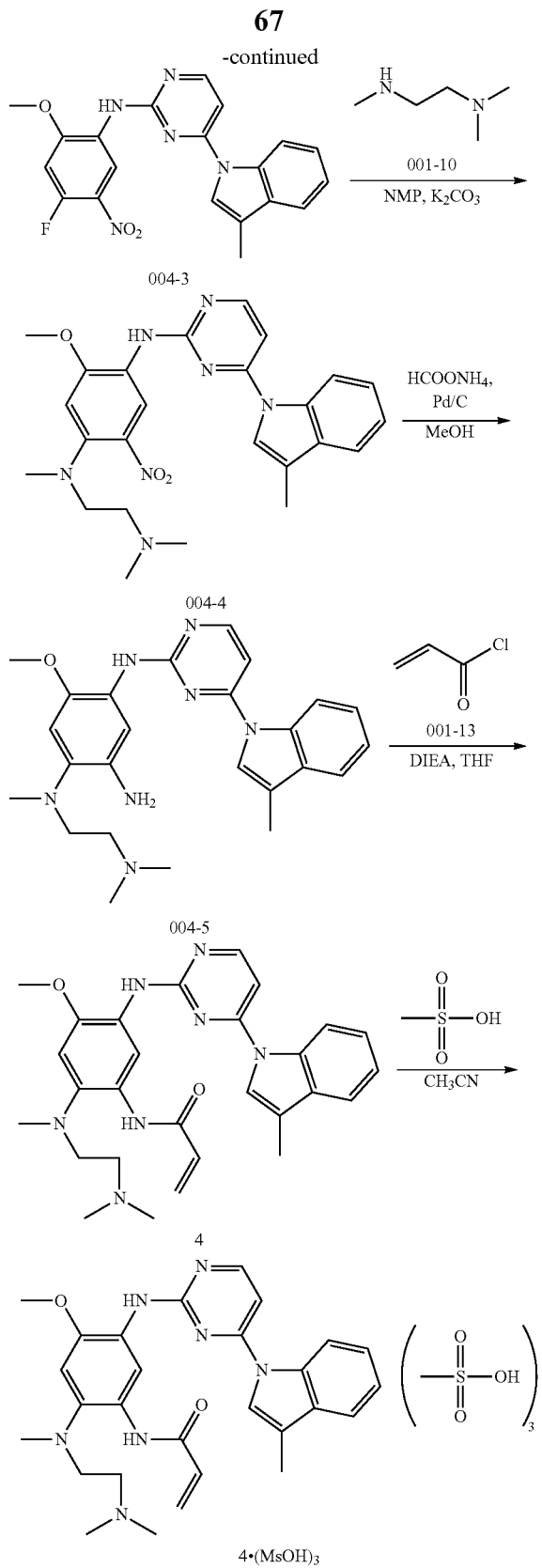

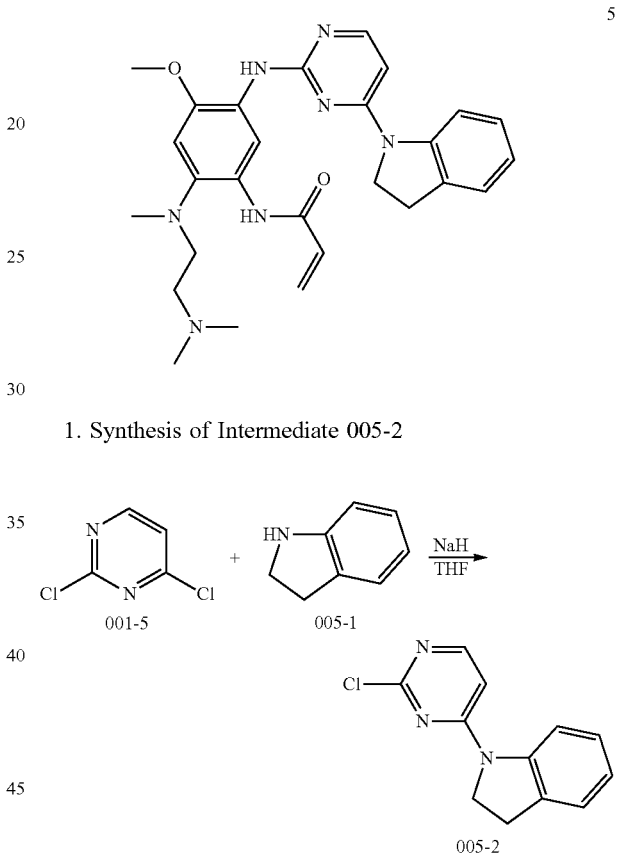

pound 4 was obtained as a yellow solid. LCMS (parent molecule): $C_{28}H_{33}N_7O_2$ (ES, m/z): $[M+H]^+=500$. $^1$H-NMR (300 MHz, DMSO-$D_6$, ppm) δ 9.65 (s, 1H), 9.25 (s, 1H), 8.40-8.32 (m, 2H), 8.19 (m, 1H), 7.64-7.61 (m, 1H), 7.25-7.20 (m, 1H), 7.18-7.13 (m, 3H), 7.08 (s, 1H), 6.73-6.64 (s, 1H), 6.30-6.24 (m, 1H), 5.81-5.77 (d, J=12 Hz, 1H), 3.88 (s, 3H), 3.34 (s, 4H), 2.84 (s, 6H), 2.83 (s, 3H), 2.35 (s, 10H), 2.23 (s, 3H).

Example 5

1. Synthesis of Intermediate 005-2

The intermediate 001-5 (3.0 g, 25.2 mmol) was dissolved in 150 mL of anhydrous THF in a 500 mL three-necked flask at room temperature under a nitrogen atmosphere, and the reaction was cooled to 0° C. NaH (65%, dispersed in mineral oil) was added in batches to the reaction mixture at 0° C. After the reaction was carried out for 20 minutes, compound 001-5 was added at 0° C. and the reaction was maintained for 2 hours. After the reaction was complete, the reaction mixture was poured into a 1.2 L of ice water to quench the reaction and was extracted with 200 mL of ethyl acetate three times. The organic phases were combined and washed once with 200 mL of saturated brine and dried over anhydrous sodium sulfate, then subjected to rotary evaporation. The crude product was purified through silica gel column chromatography (eluent: PE/EA=50/1-5/1) to give 3.8 g of intermediate 005-2 (41%) as a yellow solid. LCMS: 230.0.

The reactions from intermediate 004-2 to compound 4 and methanesulfonate(MsOH)$_3$ of compound 4 were completely the same as those from the second step to the fifth step in Example 3. Finally, 26.8 mg of methanesulfonate of com-

2. Synthesis of Compound 5

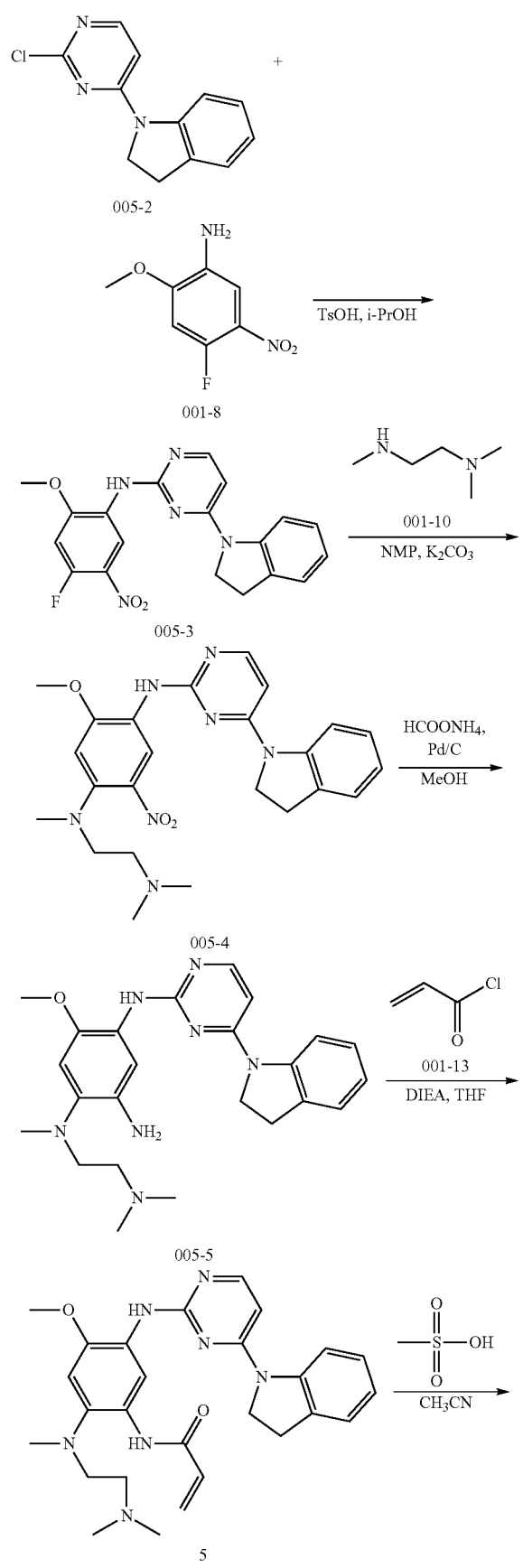

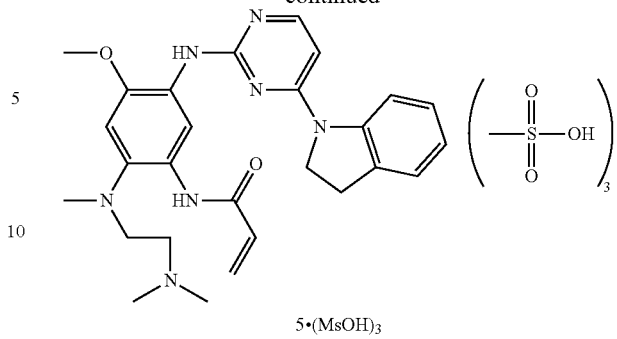

The reactions from intermediate 005-2 to compound 5 and methanesulfonate (MsOH)$_3$ of compound 5 were completely the same as those from the second step to the fifth step in Example 3. Finally, 131.6 mg of methanesulfonate of compound 5 was obtained as a yellow solid. LCMS (parent molecule) C$_{27}$H$_{33}$N$_7$O$_2$: (ES, m/z): [M+H]$^+$=488. $^1$H-NMR (300 MHz, DMSO-D$_6$, ppm): δ 9.94 (s, 1H), 9.52 (s, 2H), 8.08 (s, 3H), 7.32-7.30 (m, 1H), 7.08-7.05 (m, 2H), 6.82-6.73 (m, 1H), 6.56-6.54 (m, 1H), 6.26-6.21 (m, 1H), 5.77-5.73 (m, 1H), 4.23-4.18 (m, 1H), 3.82 (s, 3H), 3.48-3.41 (m, 4H), 3.26-3.17 (m, 2H), 2.83 (s, 6H), 2.68 (s, 3H), 2.37 (s, 9H).

Example 6

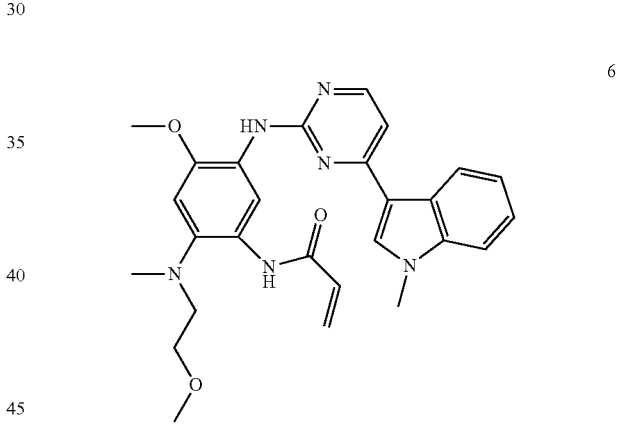

1. Synthesis of Intermediate 006-2

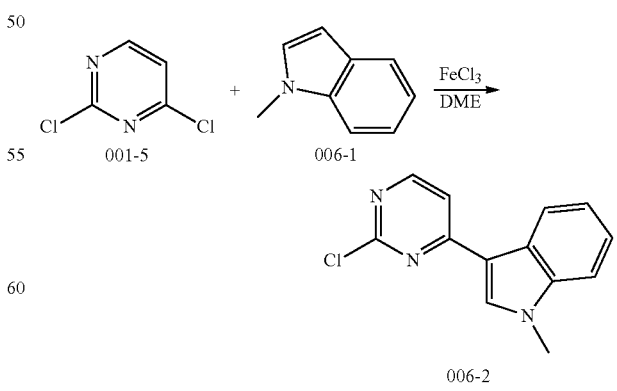

The intermediate 001-5 (1.3 g, 8.73 mmol), 13 mL of DME, FeCl$_3$ (1.414 g, 8.72 mmol) and the intermediate 006-1 (974 mg, 7.43 mmol) were added sequentially to a 100 mL three-necked flask under nitrogen atmosphere, and the reaction mixture was in an oil bath at 64° C. overnight. After the reaction was completed, the reaction mixture was cooled to room temperature and filtered. The filter cake was washed three times with 20 mL of methanol and the organic phases were combined, concentrated to dryness and 1.0 g of intermediate 006-2 (47%) was obtained as a yellow solid. LCMS: 244.1.

2. Synthesis of Intermediate 006-4

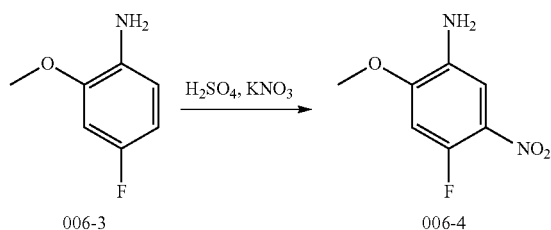

The intermediate 006-3 (100 g, 708.5 mmol) and 800 mL concentrated sulfuric acid ($H_2SO_4$) were sequentially added to a 2000 mL three-necked flask under nitrogen atmosphere, and the reaction mixture was cooled to 0° C. Potassium nitrate ($KNO_3$) (71.6 g, 708.2 mmol) was added in batches at 0-10° C. for 1 h and then the reaction was maintained at room temperature for overnight. After the reaction was complete, 2000 mL of ice water was added to quench the reaction. The reaction mixture was adjusted to pH 10 with aqueous ammonia at low temperature and extracted three times with 1 L of dichloromethane (DCM). Then, the organic phases were combined, washed three times with 3 L saturated brine, dried over anhydrous sodium sulfate and then subjected to rotary evaporation. The crude product was purified by silica gel column chromatography (eluent, ethyl acetate (EA):petroleum ether (PE)=1:4-1:1) and eluent was concentrated to give 79 g of the intermediate 006-4 (60%) as a yellow solid. LCMS: 187.0.

3. Synthesis of Intermediate 006-5

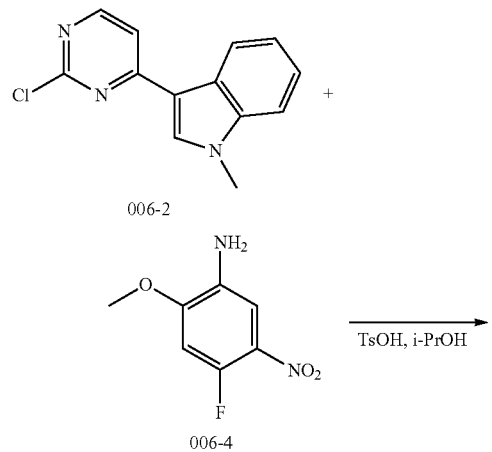

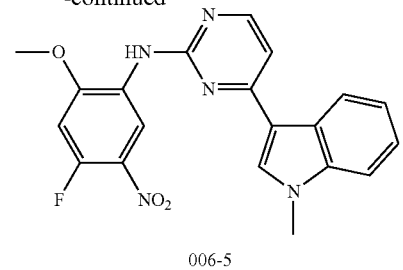

006-5

The intermediates 006-2 (75 mg, 307.8 mmol) and 006-4 (57.4 g, 308.4 mmol), 975 mL of isopropyl alcohol, and p-toluenesulfonic acid (63.7 g, 369.9 mmol) were sequentially added into a 2 L four-necked flask under nitrogen atmosphere, and the reaction was heated and maintained at 105° C. for 5 h. The reaction mixture was cooled to room temperature and filtered, and the filter cake was washed with 750 mL of isopropanol three times. The filter cake was washed three times with 750 mL of acetonitrile and dried to give 75 g of the intermediate 006-5 (62%) as a yellow solid. LC-MS: 394.1.

4. Synthesis of Intermediate 006-7

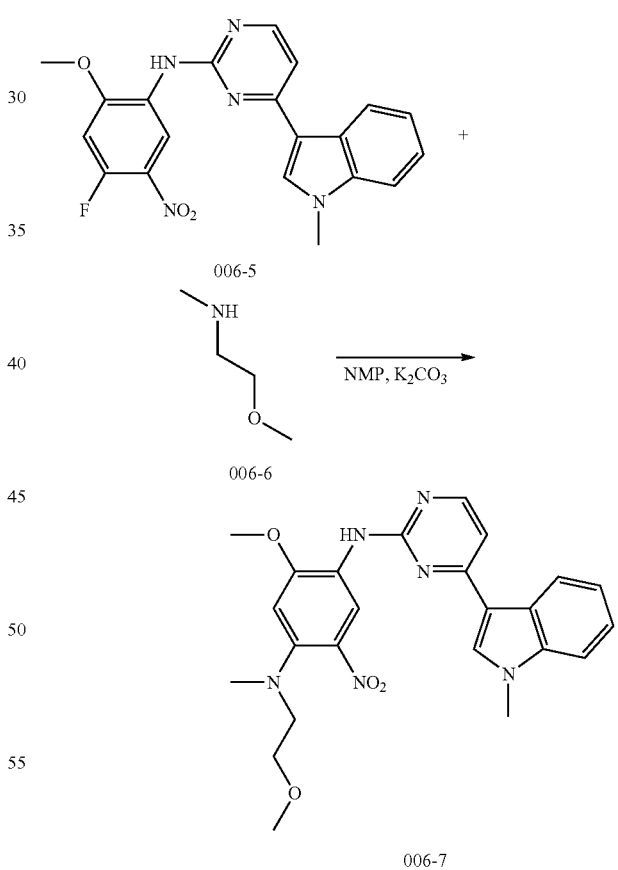

The intermediates 006-5 (500 mg, 1.27 mmol) and 006-6 (147 mg, 1.65 mmol) and $K_2CO_3$ (526 mg, 3.81 mmol) were added into a 50 mL single-necked flask, and NMP (20 mL) was added thereto at room temperature. Under nitrogen protection, the oil bath was heated to 100° C. After 2 h of reaction, the mixture was cooled to room temperature. The reaction solution was dropped into 100 mL of a mixture of ice and water, and filtered by suction. The filter cake was collected, was washed three times with 50 mL water and dried to give 430 mg of the intermediate 006-7 (68%) as a red solid. LC-MS: 463.2.

5. Synthesis of Intermediate 006-8

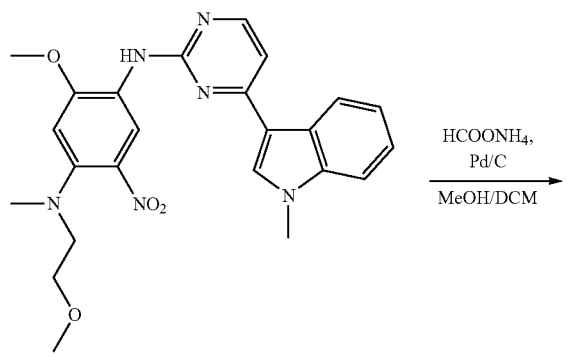

006-7

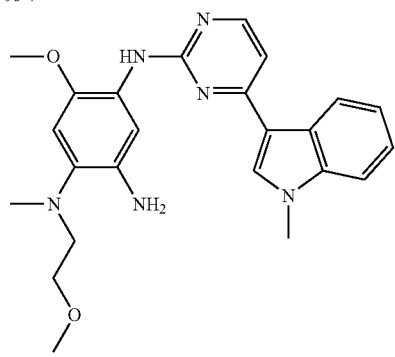

006-8

DCM:MeOH=1:1 (20 mL) was added to a 250 mL single-necked flask at room temperature, followed by addition of the intermediate 006-7 (400 mg, 0.86 mmol), ammonium formate (400 mg, 6.34 mmol) and palladium on carbon containing water (400 mg, 5% Pd). The reaction was carried out at room temperature for 3 h. The reaction mixture was filtered, and the filtrate was collected and subjected to rotary evaporation to give a crude product which was purified by silica gel column chromatography (eluent: DCM) to give 350 mg of the intermediate 006-8 (94%) as a pale red solid. LC-MS: 433.2.

6. Synthesis of Final Product 6

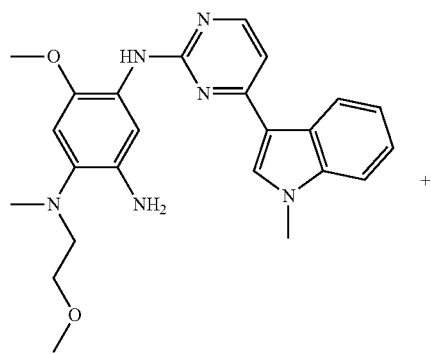

006-8

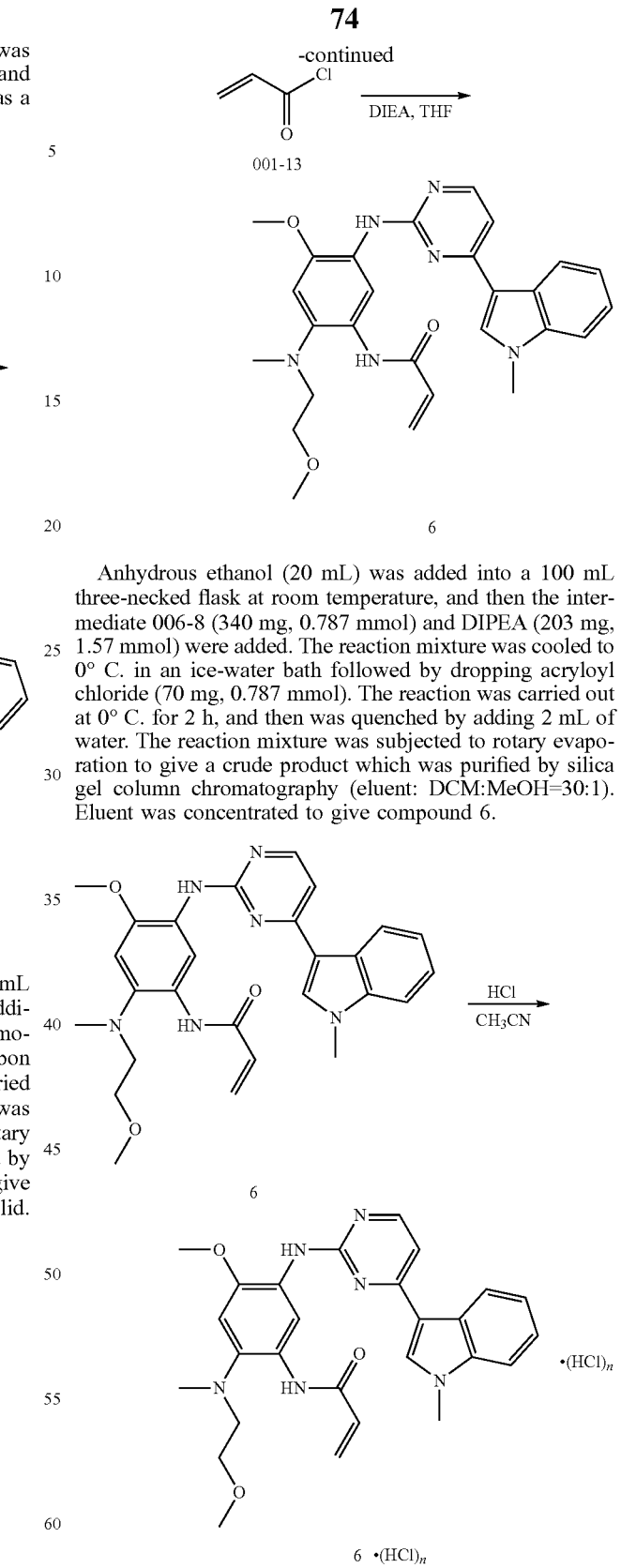

Anhydrous ethanol (20 mL) was added into a 100 mL three-necked flask at room temperature, and then the intermediate 006-8 (340 mg, 0.787 mmol) and DIPEA (203 mg, 1.57 mmol) were added. The reaction mixture was cooled to 0° C. in an ice-water bath followed by dropping acryloyl chloride (70 mg, 0.787 mmol). The reaction was carried out at 0° C. for 2 h, and then was quenched by adding 2 mL of water. The reaction mixture was subjected to rotary evaporation to give a crude product which was purified by silica gel column chromatography (eluent: DCM:MeOH=30:1). Eluent was concentrated to give compound 6.

The product 6 was dissolved in 4 mL of acetonitrile. Excess of concentrated hydrochloric acid was added dropwisely and the resulting mixture was concentrate directly. The crude was subjected to freeze drying to give 26.3 mg of hydrochloride of the product 6 (6%) as a yellow solid.

LCMS (parent molecule) $C_{27}H_{30}N_6O_3$ (ES, m/z): $[M+H]^+$= 487. $^1$H-NMR (300 MHz, $D_2O$, ppm) δ 3.13 (s, 3H), 3.21 (s, 3H), 3.32-378 (m, 7H), 3.89 (s, 3H), 5.87-5.90 (d, J=11.4 Hz, 1H), 6.32-6.41 (m, 2H), 6.74-6.77 (d, J=6.0 Hz, 1H), 6.91-6.94 (m, 1H), 7.13-7.27 (m, 3H), 7.57-7.65 (m, 2H), 7.90 (s, 1H), 7.99 (s, 1H).

Example 7

1. Synthesis of Intermediate 007-2

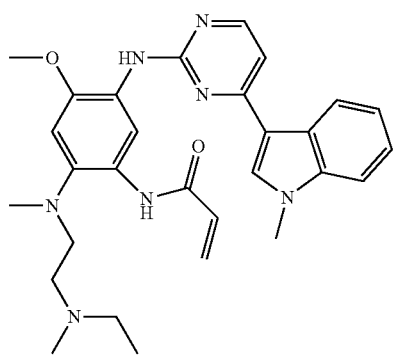

006-5

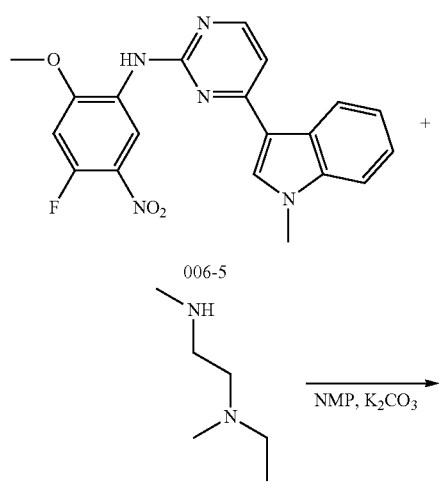

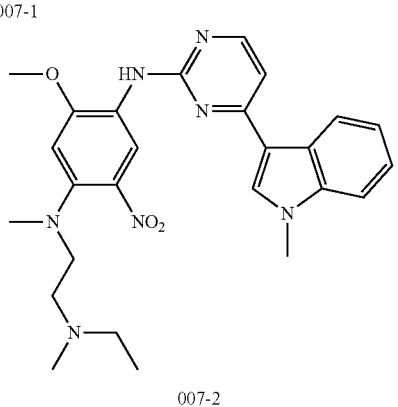

007-2

The intermediate 006-5 (100 mg, 1.78 mmol), NMP (30 mL), potassium carbonate (0.5 g, 3.56 mmol) and the intermediate 007-1 (0.268 g, 2.31 mmol) were added into a 100 mL single-necked flask and the reaction was carried out at 100° C. for 2 h. The reaction mixture was cooled to room temperature followed by addition of 70 mL of water to quench the reaction. A solid was precipitated and undergone a sucking filtration, and the filter cake was collected and washed with 20 mL of water 3 times and then dried to give 600 mg of the intermediate 007-2 (69%) as a red solid. LC-MS: 490.2.

2. Synthesis of Intermediate 007-3

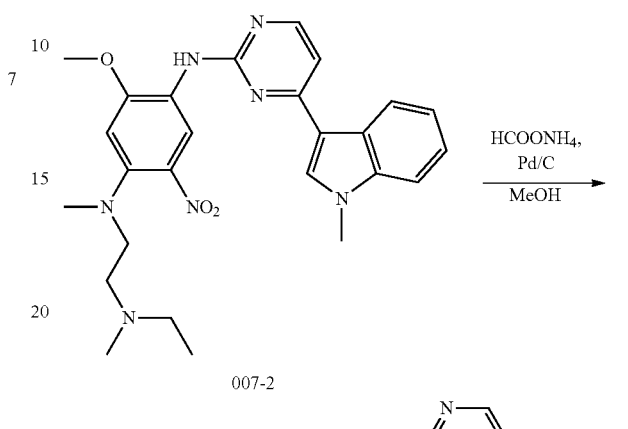

007-2

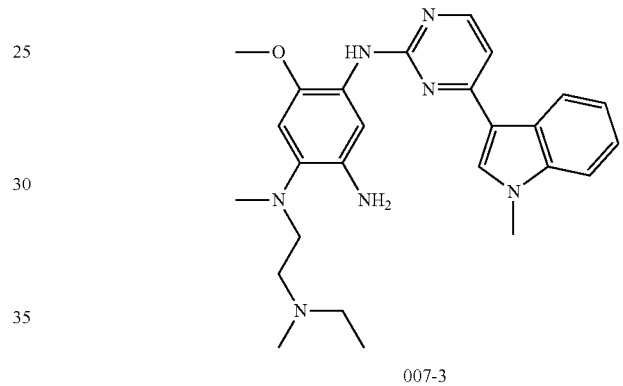

007-3

The intermediate 007-2 (600 mg 1.22 mmol), anhydrous methanol (100 mL), palladium on carbon containing water (600 mg, 5% Pd) and ammonium formate (600 mg) were added into a 250 mL single-necked flask sequentially. After the reaction was stirred for 3 h, the reaction mixture was filtered and the filtrate was collected and subjected to rotary evaporation. The crude product was dissolved with 150 mL of DCM, and then washed with 50 mL of saturated brine solution. The organic phases were dried over sodium sulfate and concentrated to give 400 mg of the intermediate 007-3 (71%) as a pale yellow solid. LC-MS: 460.3.

3. Synthesis of Compound 7

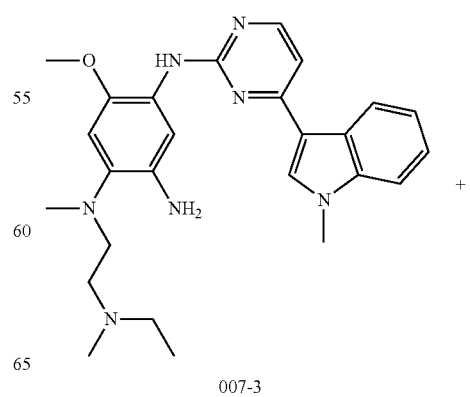

007-3

-continued

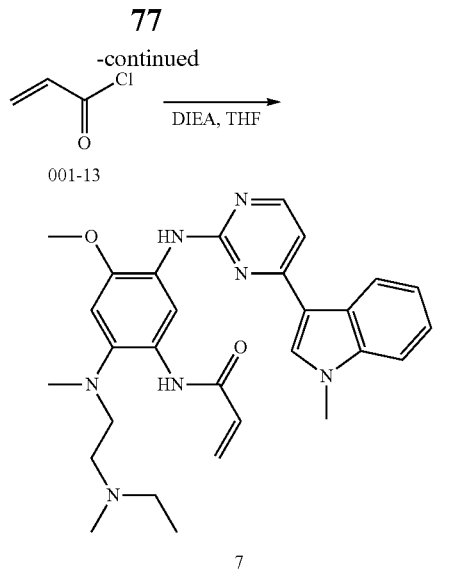

The intermediate 007-3 (400 mL, 0.871 mmol), anhydrous THF (40 mL) and DIPEA (0.224 g 1.74 mmol) were sequentially added into a 100 mL three-necked flask at room temperature, then the reaction mixture was cooled to 0° C. and the intermediate 001-13 (78 mg, 0.871 mmol) was added thereto. The reaction temperature was raised to room temperature and the reaction was stirred for 30 min. After adding 3 drops of water, the system was directly subjected to rotary evaporation and the crude product was purified by prep-HPLC (column, Waters Sunfire C18, 19×150 mm, 5 um; flow phase, acetonitrile/water (0.1% trifluoroacetic acid (TFA)), 15% to 35%, 7 min; flow rate 20 mL/min; detection wavelength, 254 nm). The product was collected and concentrated to give the compound 7.

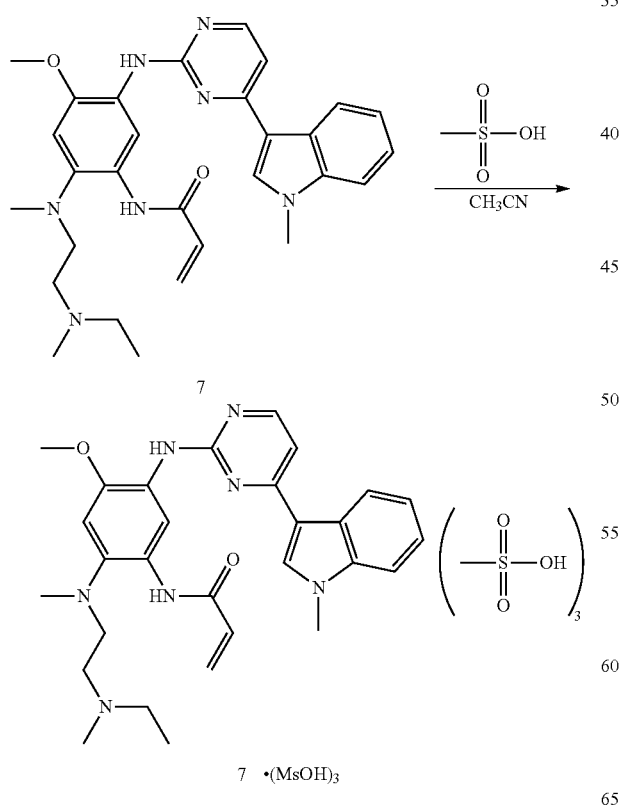

The compound 7 was dissolved in 15 mL of acetonitrile, and methanesulfonic acid (35 mg, 2.6 mmol) was added.

After stirring for 2 h at room temperature, a solid was precipitated and the mixture was filtered by suction. The solid cake was collected and dried to give 49.8 mg of sulfonate of the compound 7 (7%) as a yellow solid. LCMS (parent molecule) $C_{29}H_{35}N_7O_2$ (ES, m/z) [M+1]$^+$: 514. $^1$H-NMR (D$_2$O, 300 MHz, ppm) δ 1.15-1.20 (m, 3H), 2.68-2.79 (m, 16H), 3.11-3.18 (m, 3H), 3.33-3.38 (m, 5H), 3.84 (s, 5H), 5.87-5.91 (d, J=10.8 Hz, 1H), 6.25-6.31 (d, J=16.8 Hz, 1H), 6.54-6.60 (m, 2H), 6.97 (s, 2H), 7.13 (m, 2H), 7.32 (m, 1H), 7.78 (m, 2H).

Example 8

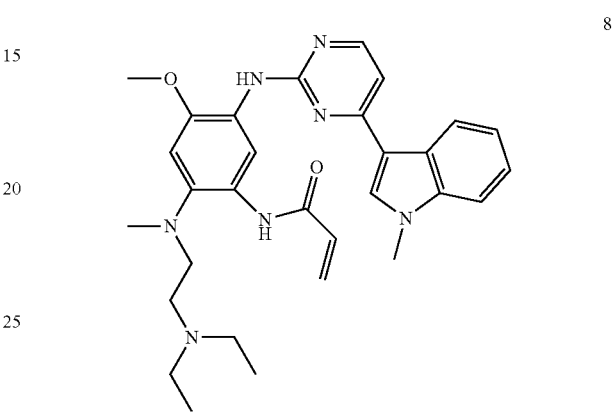

1. Synthesis of Intermediate 008-2

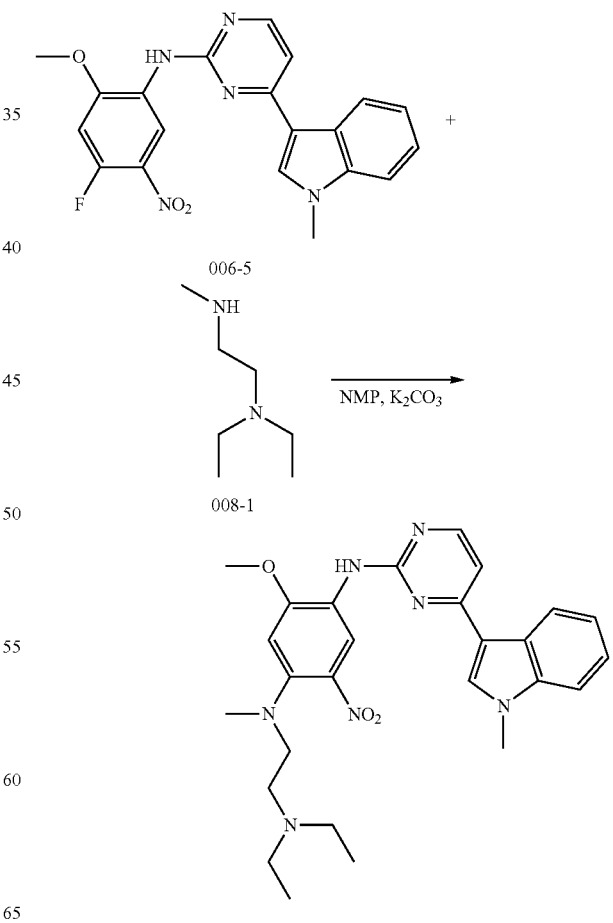

The intermediates 006-5 (1.0 g, 2.54 mmol) and 008-1 (0.430 mg, 3.31 mmol) and K$_2$CO$_3$ (1.05 g, 7.63 mmol) were sequentially added into a 50 mL single-necked flask, and NMP (20 mL) was added thereto at room temperature. Under nitrogen protection, it was heated to 100° C. in oil bath. After 2 h of reaction, the mixture was cooled to room temperature. The reaction solution was dropped into 100 mL of a mixture of ice and water, and filtered by suction. The filter cake was collected, washed three times with 50 mL water and dried to give 0.8 g of the crude product 008-2 as a red solid.

2. Synthesis of Intermediate 008-3

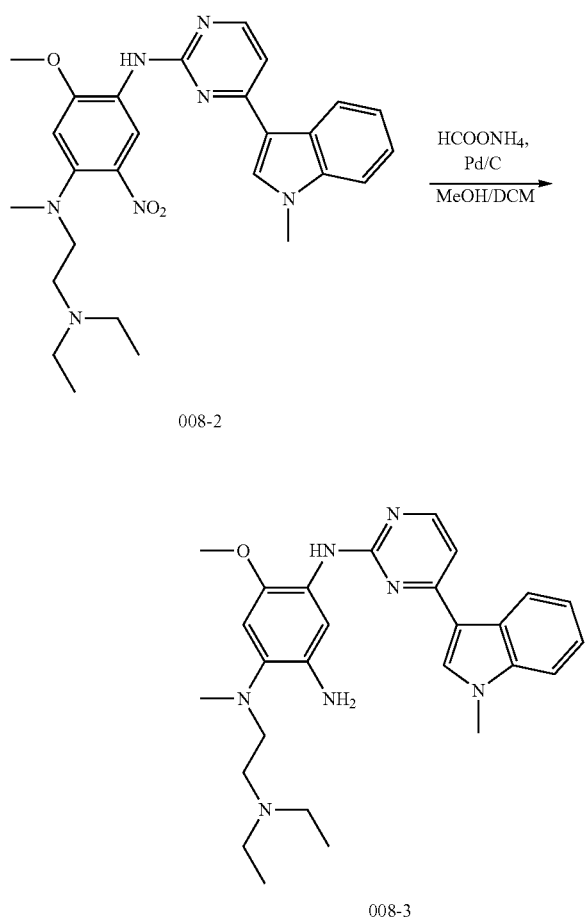

DCM/MeOH (1:1, 20 mL) was added to a 250 mL single-necked flask at room temperature, followed by the addition of the intermediate 008-2 (800 mg, 2.38 mmol), ammonium formate (800 mg, 12.7 mmol) and palladium on carbon containing water (0.800 g, 5% Pd). The reaction mixture was stirred at room temperature for 3 h. The reaction mixture was filtered, and the filtrate was collected and subjected to rotary evaporation to give a crude product which was purified by silica gel column chromatography (eluent: DCM/MeOH=30:1). Eluents were combined and concentrated to give 0.650 g of the intermediate 008-3 (86%) as a pale red solid.

3. Synthesis of Compound 8

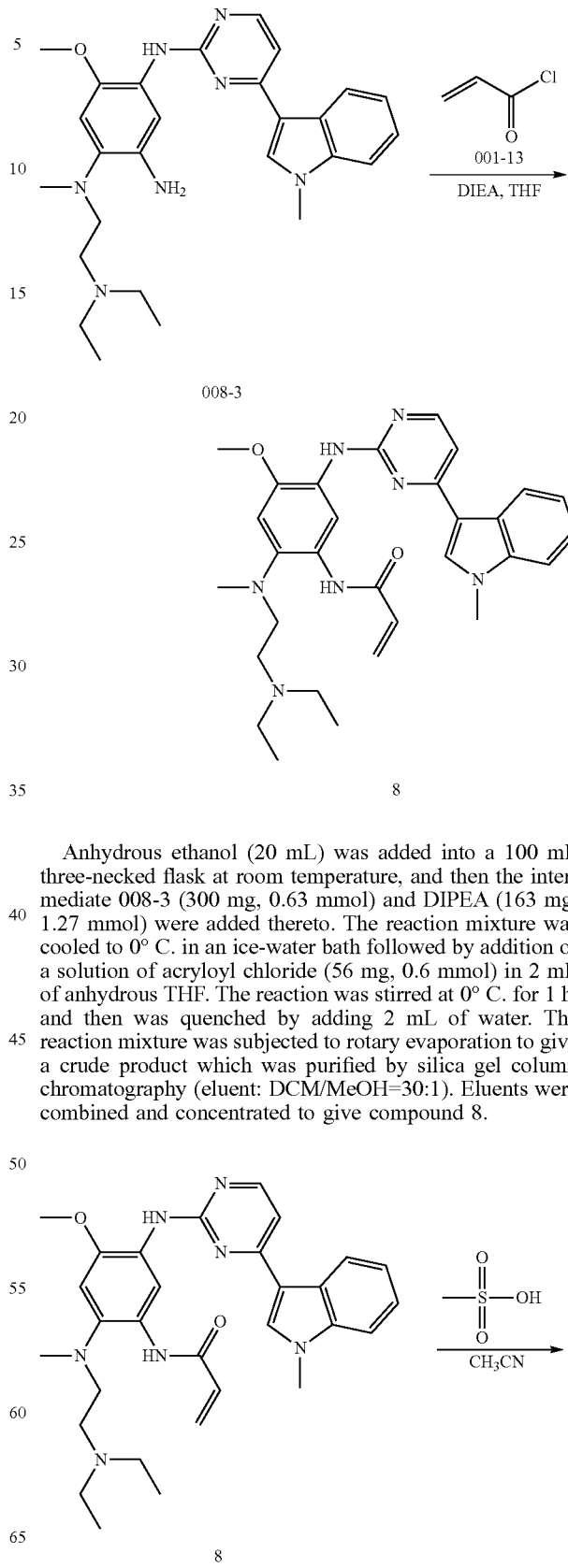

Anhydrous ethanol (20 mL) was added into a 100 mL three-necked flask at room temperature, and then the intermediate 008-3 (300 mg, 0.63 mmol) and DIPEA (163 mg, 1.27 mmol) were added thereto. The reaction mixture was cooled to 0° C. in an ice-water bath followed by addition of a solution of acryloyl chloride (56 mg, 0.6 mmol) in 2 mL of anhydrous THF. The reaction was stirred at 0° C. for 1 h, and then was quenched by adding 2 mL of water. The reaction mixture was subjected to rotary evaporation to give a crude product which was purified by silica gel column chromatography (eluent: DCM/MeOH=30:1). Eluents were combined and concentrated to give compound 8.

81

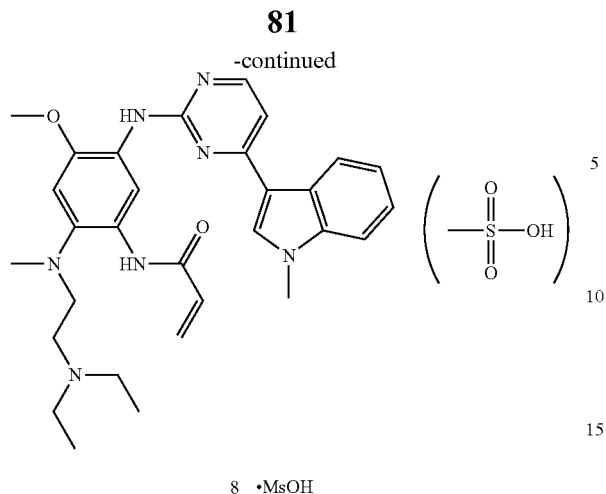

8 •MsOH

The compound 8 was dissolved in 4 mL of anhydrous acetonitrile, and a solution of methanesulfonic acid (65.6 mg, 6.8 mmol) was added dropwisely. After the reaction was carried out for 2 h at room temperature, a yellow solid was precipitated and the mixture was filtered by suction. The solid cake was collected and dried to give 53 mg of sulfonate of the compound 8 (7%) as a yellow solid. LCMS (parent molecule) $C_{30}H_{37}N_7O_2$(ES, m/z): [M+H]$^+$=528. $^1$H-NMR (300 MHz, DMSO-D$_6$, ppm) δ 9.85-9.86 (m, 1H), 9.55-9.64 (m, 1H), 8.73 (s, 1H), 8.26 (s, 3H), 7.57-7.60 (d, J=8.1 Hz, 1H), 7.37-7.39 (m, 2H), 7.29-7.28 (m, 1H), 7.05 (s, 1H), 6.82-6.95 (m, 1H), 6.29 (s, 1H), 5.75-5.79 (d, J=12.3 Hz, 1H), 3.92 (s, 3H), 3.89 (s, 3H), 3.27 (m, 4H), 3.15 (m, 4H), 2.69 (s, 3H), 2.31 (s, 3H), 1.17-1.22 (m, 6H).

Example 9

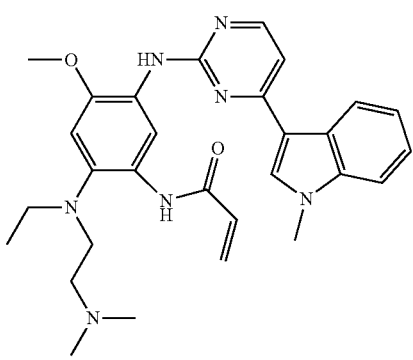

9

1. Synthesis of Intermediate 009-2

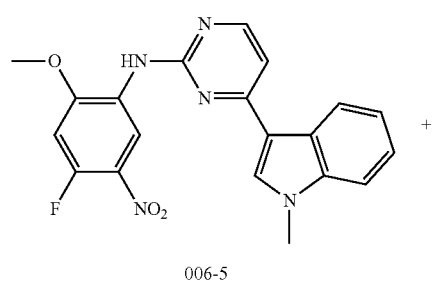

006-5

82

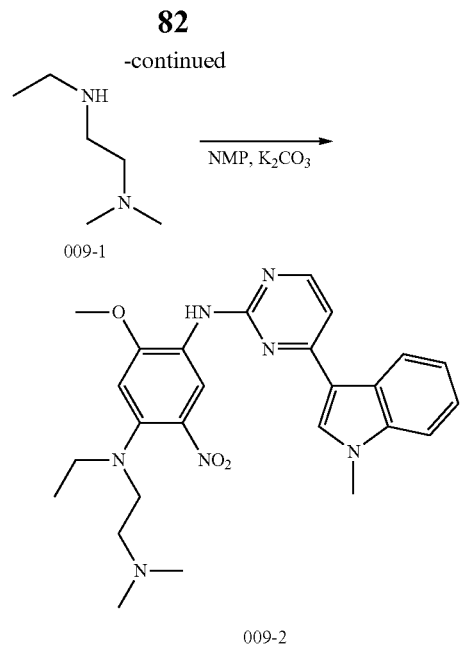

009-2

The intermediate 006-5 (1.0 g, 2.54 mmol), 009-1 (0.383 g, 3.31 mmol) and K$_2$CO$_3$ (1.05 g, 7.63 mmol) were added to a 50 mL single-necked flask at room temperature, followed by that NMP solvent (20 mL) was added. The temperature of oil bath was raised to 100° C. for 2 h. The reaction was cooled to room temperature and the reaction mixture was dropped into 100 mL of mixture contain ice and water. The reaction mixture undergone a sucking filtration and the filter cake was collected. The filter cake was washed with 50 mL of water 3 times and dried to give 650 mg of compound 009-2 (35%) as a red solid. LC-MS: 490.3.

2. Synthesis of Compound 9

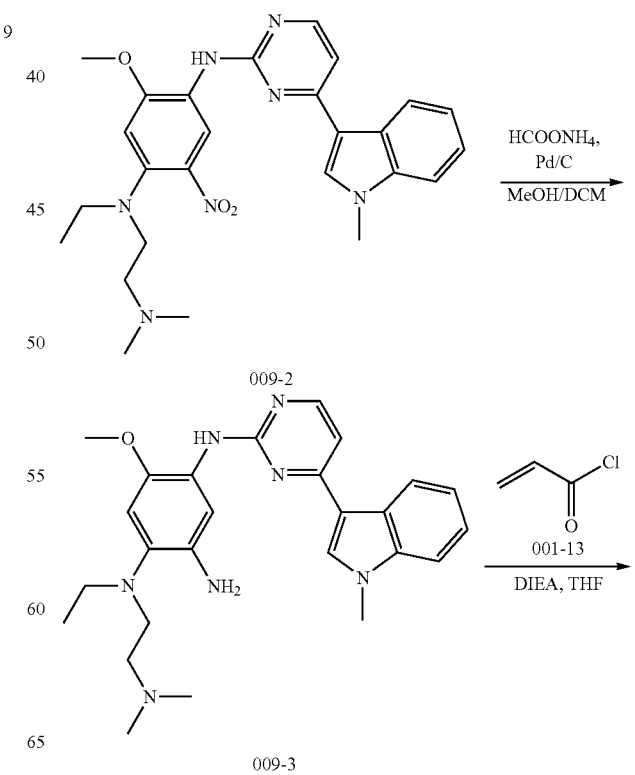

-continued

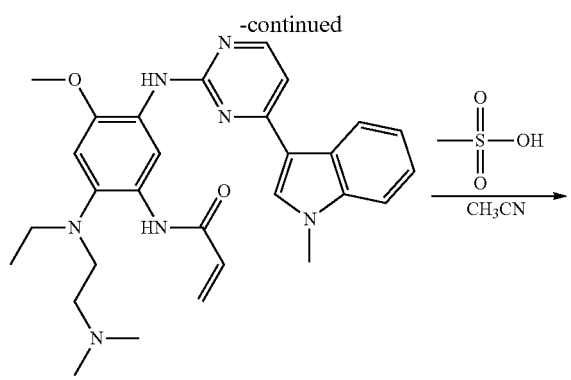

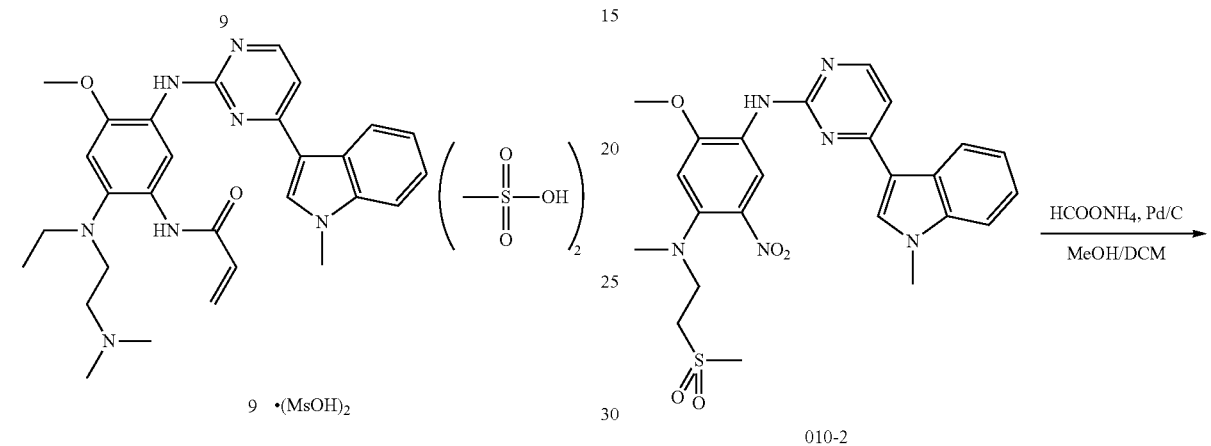

9 · (MsOH)₂

The chemical reactions from intermediate 009-2 to compound 9 and methanesulfonate (MsOH)₃ of compound 9 were completely the same as those from the second step to the third step in Example 8. Finally, 29.3 mg of methanesulfonate of compound 9 (13%) was obtained as a yellow solid. LCMS (parent molecule) $C_{29}H_{35}N_7O_2$ (ES, m/z): (ES, m/z): [M+H]⁺=514. ¹H-NMR (300 MHz, DMSO-D₆, ppm) δ 0.95-1.00 (m, 3H), 2.27-2.34 (m, 6H), 2.81-2.82 (m, 6H), 3.0-3.07 (m, 2H), 3.23-3.31 (m, 2H), 3.35-3.42 (m, 2H), 3.86 (s, 3H), 3.93 (s, 3H), 5.80 (d, J=12 Hz, 1H), 6.27-6.32 (d, J=17.1 Hz, 1H), 6.69-6.78 (m, 1H), 7.08 (s, 1H), 7.14-7.19 (m, 1H), 7.27-7.33 (m, 1H), 7.41-7.43 (d, J=6.3 Hz, 1H), 7.58-7.61 (d, J=8.4 Hz, 1H), 8.25-8.29 (m, 1H), 8.79 (s, 1H), 9.42-9.43 (d, J=2.7 Hz, 1H).

Example 10

1. Synthesis of Compound 10

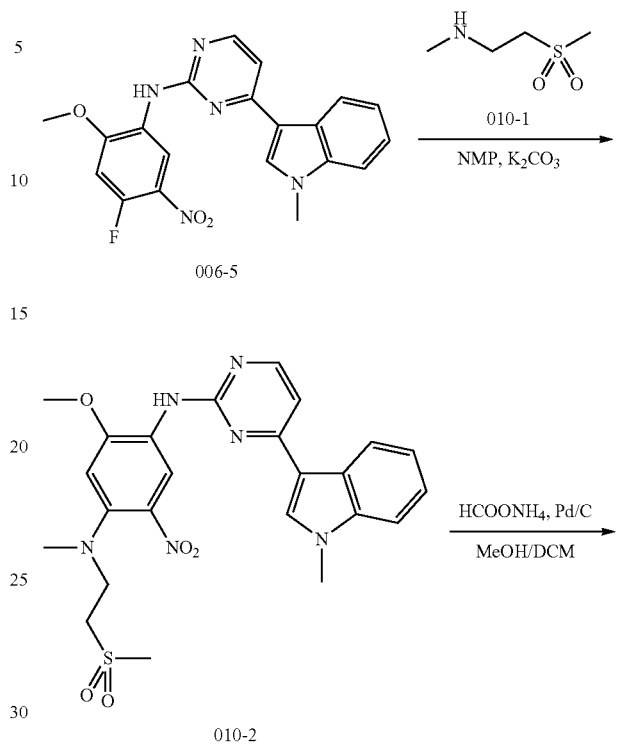

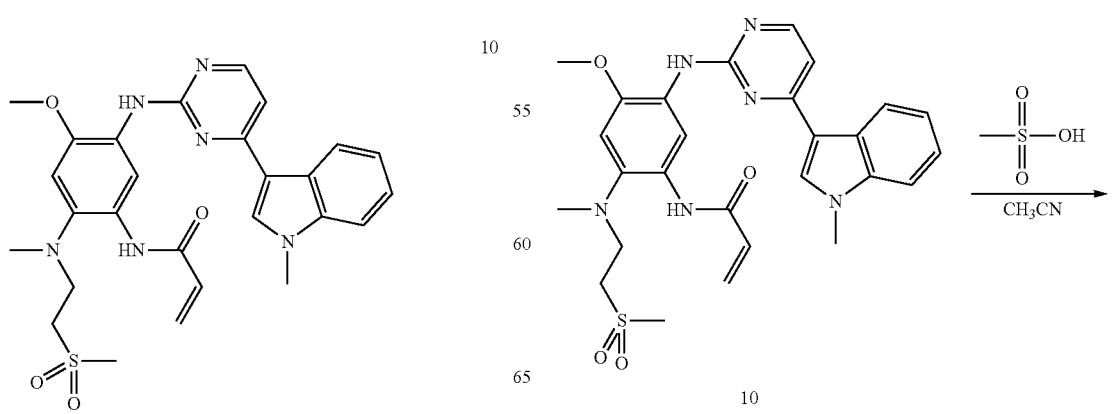

10

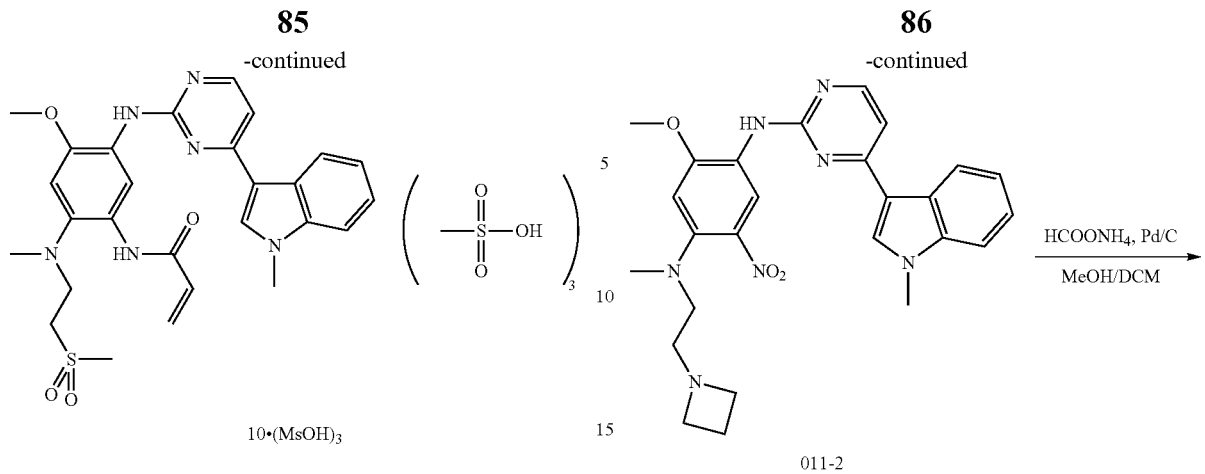

10·(MsOH)₃

The reaction steps and conditions for synthesizing compound 10 and methanesulfonate (MsOH) of compound 10 were completely the same as those from the first step to the third step in Example 8, except that the intermediate 008-1 as a raw material in the first step of the example 8 was replaced with the intermediate 010-1 in the first step. Finally, 64 mg of methanesulfonate of compound 10 was obtained as a yellow solid. LCMS (parent molecule) $C_{27}H_{30}N_6O_4S$ (ES, m/z): (ES, m/z): 535 [M+]⁺. ¹H-NMR (DMSO-D₆, ppm) δ 2.34 (s, 9H), 2.74 (s, 3H), 3.06 (s, 3H), 3.48-3.29 (m, 4H), 3.83 (s, 3H), 3.94 (s, 3H), 5.76-5.72 (m, 1H), 6.24-6.18 (m, 1H), 6.66-6.57 (m, 1H), 7.29-7.15 (m, 2H), 7.42-7.32 (m, 1H), 7.44-7.42 (m, 1H), 7.62-7.59 (m, 1H), 8.40-8.20 (m, 2H), 8.48-8.40 (m, 1H), 8.85 (s, 1H), 9.34 (s, 1H), 10.14 (s, 1H).

Example 11

11

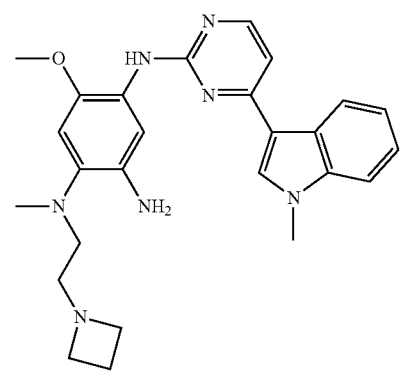

011-3

The reaction steps and conditions for synthesizing compound 011-3 were completely the same as those from the first step to the second step in Example 8, except that the intermediate 008-1 as a raw material in the first step of the example 8 was replaced with the intermediate 010-1 in the first step. Finally, compound 011-3 was obtained as a red solid.

2. Synthesis of Compound 11

1. Synthesis of Intermediate 011-3

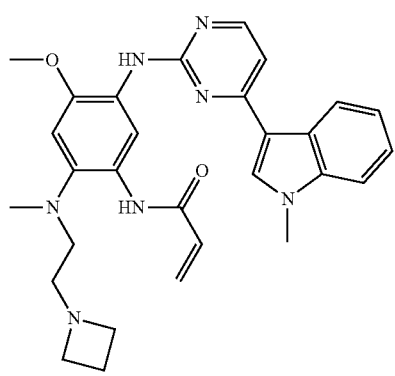

006-5

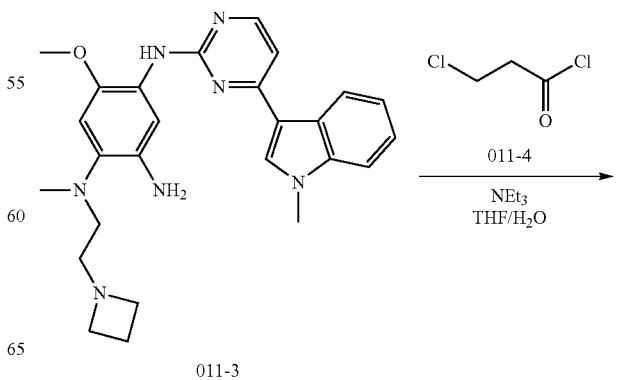

011-3

-continued

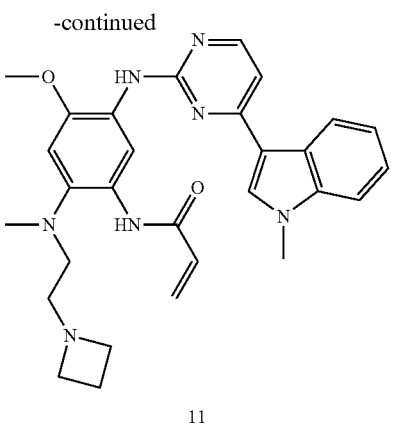

11

THF (20 mL), H₂O (2 mL), intermediate 011-3 (200 mg, 0.44 mmol) were sequentially added into a 250 mL single-necked flask at room temperature. The reaction system was cooled to 0° C., followed by the addition of 3-chloropropionyl chloride (66.7 mg, 0.53 mmol). After the reaction temperature was raised to the room temperature, the reaction was stirred for 1 h and was extracted twice with 50 mL of EA. The organic phases were collected, and then washed once with 30 mL of sodium bicarbonate (NaHCO₃) and washed twice with 40 mL of saturated salt water. After concentrated to dryness, the organic phases were dissolved in a 250 mL single-necked flask and triethylamine (Et₃N) (132 mg, 1.30 mmol) was added thereto. Then, the reaction system was heated to reflux for 2 h. The reaction mixture was cooled and concentrated to remove acetonitrile, and finally the crude product was purified by prep-HPLC: (column, Waters X-Bridge RP18, 19×150 mm, 5 um; eluent: phase A: water (0.05% TFA), phase B: acetonitrile; elution gradient: 15% B-45% B, 7 min; flow rate 20 mL/min; detection wavelength, 254 nm). The product was collected and concentrated to remove the most of acetonitrile, and then freeze-dried to give 20 mg of compound 11.

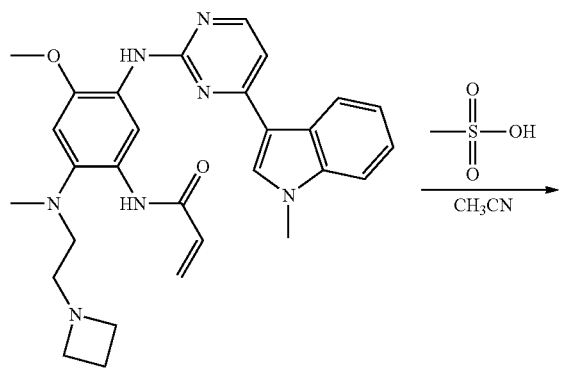

11·(MsOH)₂

The product 11 (20 mg) was dissolved in acetonitrile (2 mL), and a solution (2 mL) of methanesulfonic acid (75.0 mg) in acetonitrile was added dropwisely thereto. After the reaction mixture was stirred at room temperature for 2 h, a yellow solid was precipitated. The reaction mixture underwent a sucking filtration, and the filter cake was collected and re-dissolved with distilled water and freeze dried to give 23.1 mg of methanesulfonate of compound 11 as a yellow solid. LCMSLCMS (parent molecule) C₂₉H₃₃N₇O₂ (ES, m/z): (ES, m/z): 512 [M+H]⁺. ¹H-NMR: (300 MHz, DMSO-D₆, ppm) δ 2.32 (s, 6H), 2.63 (s, 3H), 3.18-3.20 (m, 2H), 3.37-3.39 (m, 2H), 3.87-3.92 (s, 3H), 3.95-3.98 (s, 3H), 4.05-4.14 (m, 4H), 5.81-5.84 (d, J=9 Hz, 1H), 6.30-6.35 (d, J=17.1 Hz, 1H), 6.72-6.31 (m, 1H), 7.01 (s, 1H), 7.15-7.17 (m, 1H), 7.20-7.35 (m, 2H), 7.56-7.59 (d, J=8.4 Hz, 1H), 8.28 (br s, 2H), 8.51 (br s, 1H), 8.68 (br s, 1H), 9.50 (br s, 1H), 9.70-9.73 (m, 1H).

Example 12

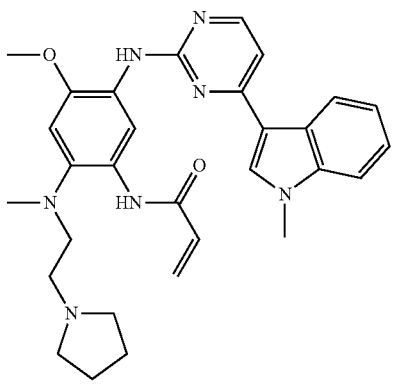

12

1. Synthesis of Compound 12

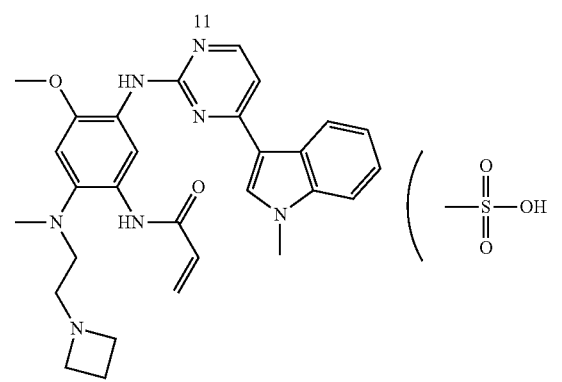

006-5

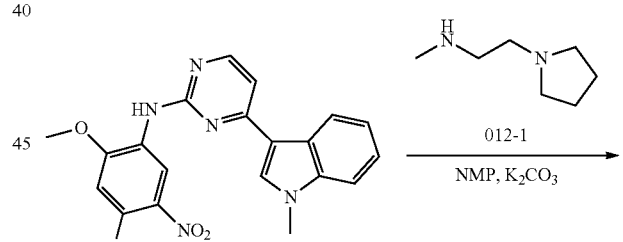

012-2

89

-continued

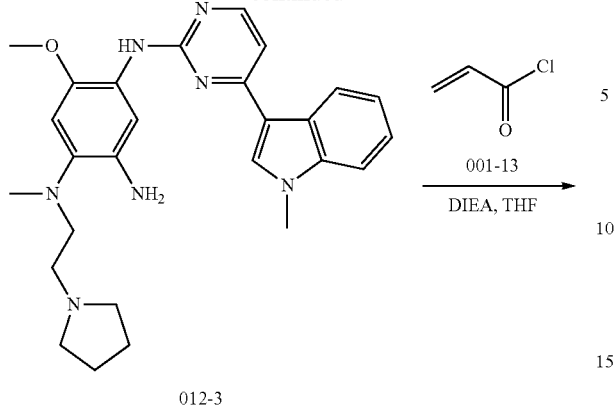

012-3

12

12·(MsOH)₂

The reaction steps and conditions for synthesizing compound 12 and the methanesulfonate (MsOH)₂ of compound 12 were completely the same as those from the first step to the third step in Example 7, except that the intermediate 007-1 as a raw material in the first step of the example 7 was replaced with the intermediate 012-1 in the first step. Finally, 180 mg of methanesulfonate of compound 12 was obtained as a yellow solid. LCMSLCMS (parent molecule) $C_{30}H_{35}N_7O_2$ (ES, m/z): 526 [M+1]⁺. ¹H-NMR: (300 MHz, DMSO-D₆, ppm) δ 1.91-2.01 (m, 4H), 2.33 (s, 7H), 2.73-2.71 (m, 3H), 3.01-3.08 (m, 2H), 3.57-3.35 (m, 5H), 3.86 (s, 3H), 3.93 (s, 3H), 5.83-5.79 (m, 1H), 6.30-6.24 (m, 1H), 6.73-6.65 (m, 1H), 7.01 (s, 1H), 7.19-7.17 (m, 1H), 7.30-7.27 (m, 1H), 7.61-7.58 (m, 1H), 8.30-8.23 (m, 3H), 8.76 (s, 1H), 9.41 (s, 1H), 9.63 (s, 1H).

90

Example 13

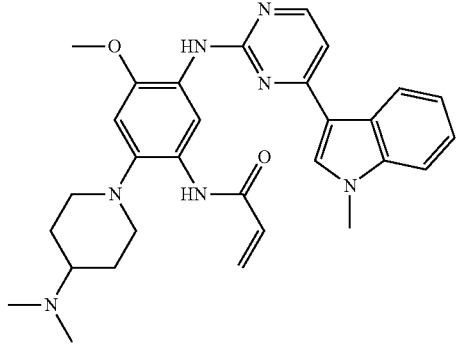

13

1. Synthesis of Compound 13

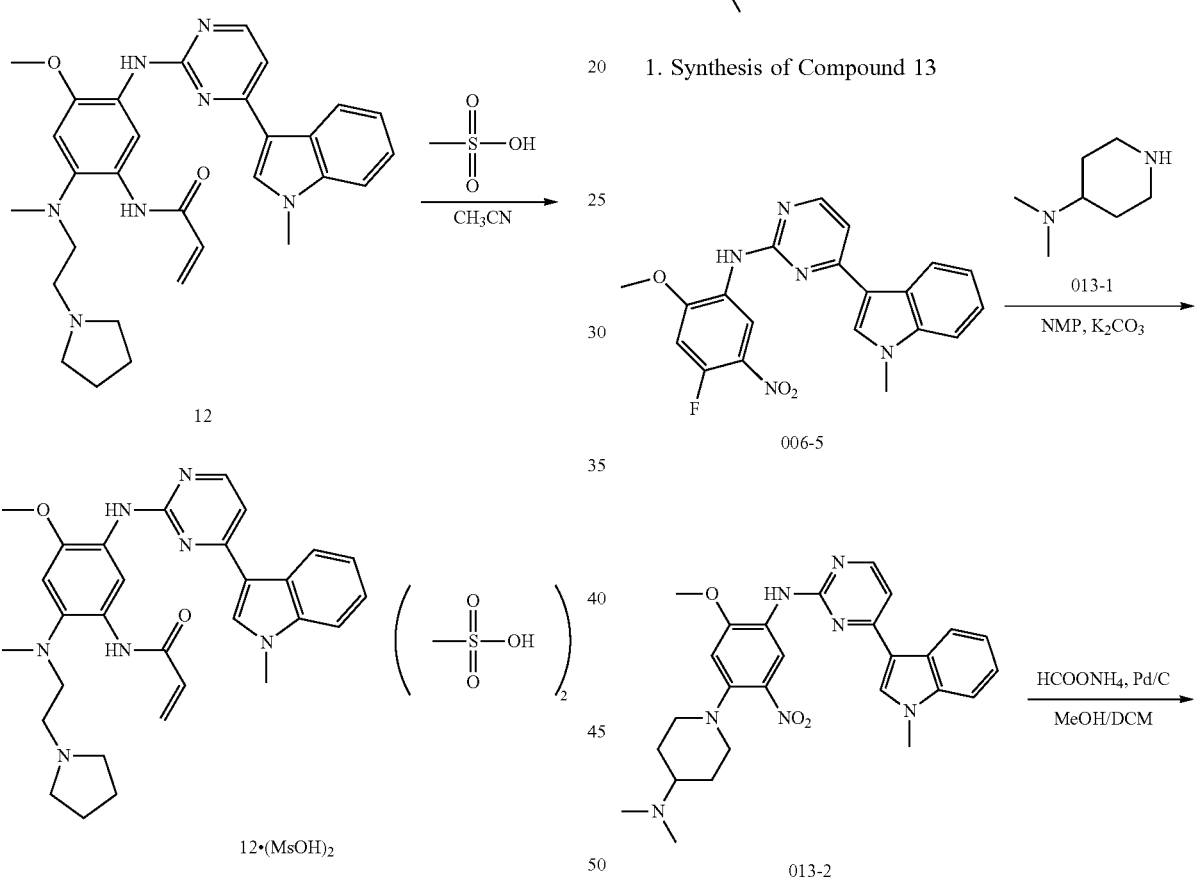

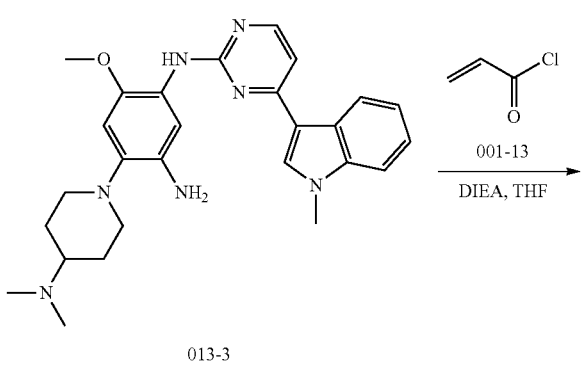

013-3

1. Synthesis of Compound 14

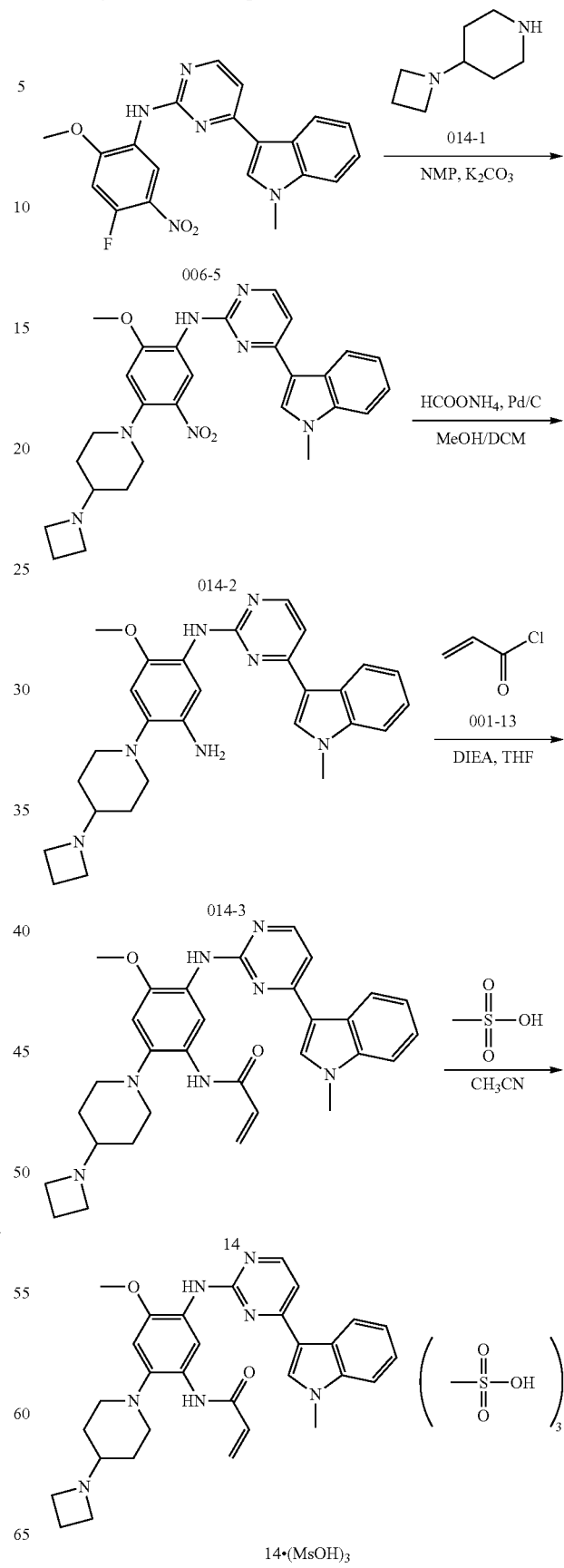

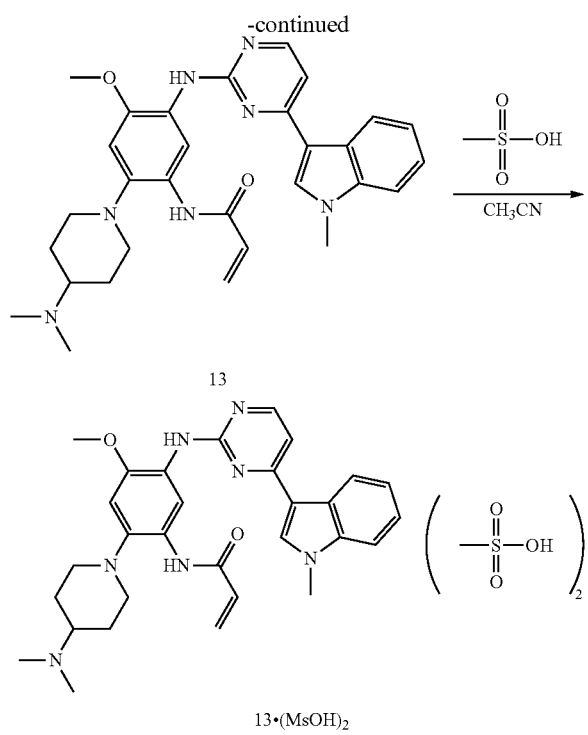

The reaction steps and conditions for synthesizing compound 13 and methanesulfonate (MsOH)₂ of compound 13 were completely the same as those from the first step to the third step in Example 8, except that the intermediate 008-1 as a raw material in the first step of the example 8 was replaced with the intermediate 013-1 in the first step. Finally, 97.5 mg of methanesulfonate (MsOH)₂ of compound 13 was obtained as a yellow solid. LCMSLCMS (parent molecule) $C_{30}H_{35}N_7O_2$(ES, m/z): [M+H]⁺=526. ¹H-NMR (300 MHz, DMSO-D₆, ppm) δ 2.00-2.15 (m, 4H), 2.498 (m, 6H), 2.74-2.81 (m, 6H), 2.87 (s, 1H), 3.12-3.43 (m, 4H), 3.82 (s, 3H), 3.94 (s, 3H), 5.73-5.77 (d, J=11.4 Hz, 1H), 6.20-6.26 (m, 1H), 6.70-6.79 (m, 1H), 6.97 (s, 1H), 7.19-7.21 (m, 1H), 7.29-7.34 (m, 1H), 7.42-7.44 (d, J=6.9 Hz, 1H), 7.59-7.62 (d, J=8.1 Hz, 1H), 8.23 (s, 3H), 8.84 (s, 1H), 9.21 (s, 1H), 10.40 (s, 1H), 10.43 (s, 1H).

Example 14

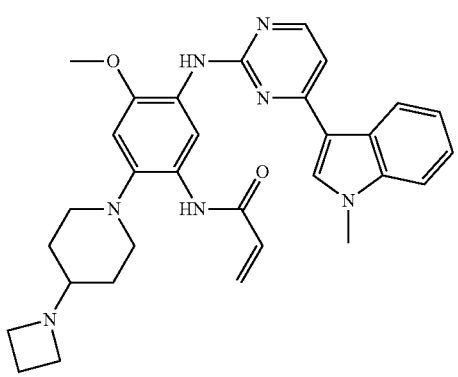

The reaction steps and conditions for synthesizing compound 14 and methanesulfonate (MsOH)₃ of compound 14 were completely the same as those from the first step to the third step in Example 8, except that the intermediate 008-1 as a raw material in the first step of the example 8 was replaced with the intermediate 014-1 in the first step. Finally, 0.125 g of methanesulfonate (MsOH)₂ of compound 14 was obtained as a yellow solid. LCMSLCMS (parent molecule) C₃₁H₃₅N₇O₂ (ES, m/z): [M+H]⁺=538. ¹H-NMR (300 MHz, DMSO-D₆, ppm) δ 10.01 (m, 2H), 9.19 (s, 1H), 8.82 (s, 1H), 8.22 (s, 3H), 7.62-7.59 (d, J=8.1 Hz, 1H), 7.43-7.41 (d, J=6.9 Hz, 1H), 7.34-7.29 (m, 1H), 7.22-7.19 (m, 1H), 6.96 (s, 1H), 6.69-6.59 (m, 1H), 6.25-6.19 (m, 1H), 5.77-5.73 (d, J=10.2 Hz, 1H), 4.21-4.04 (m, 4H), 3.94 (s, 3H), 3.83 (s, 3H), 3.55-3.43 (m, 2H), 3.28-3.17 (m, 2H), 2.80-2.72 (m, 2H), 2.51 (s, 9H), 2.35-2.27 (m, 1H), 2.07-2.03 (m, 2H), 1.73-1.66 (m, 2H), 1.23 (s, 1H).

Example 15

1. Synthesis of Compound 15

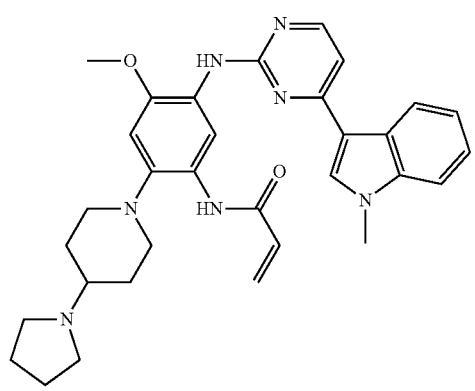

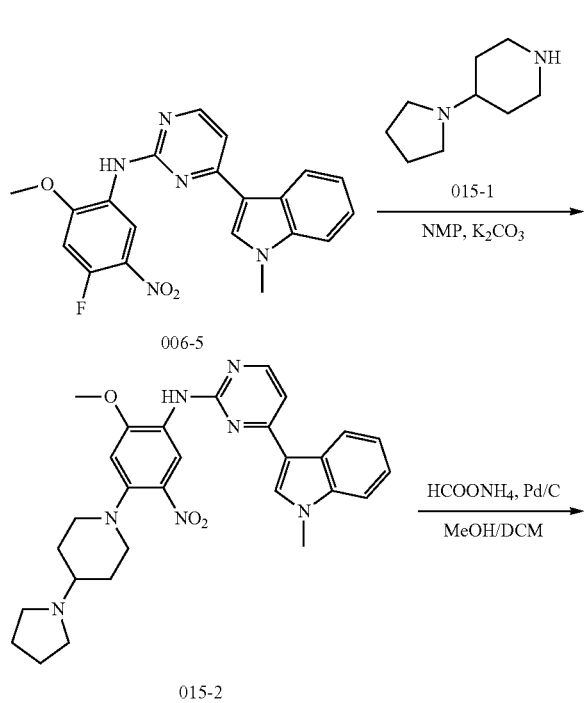

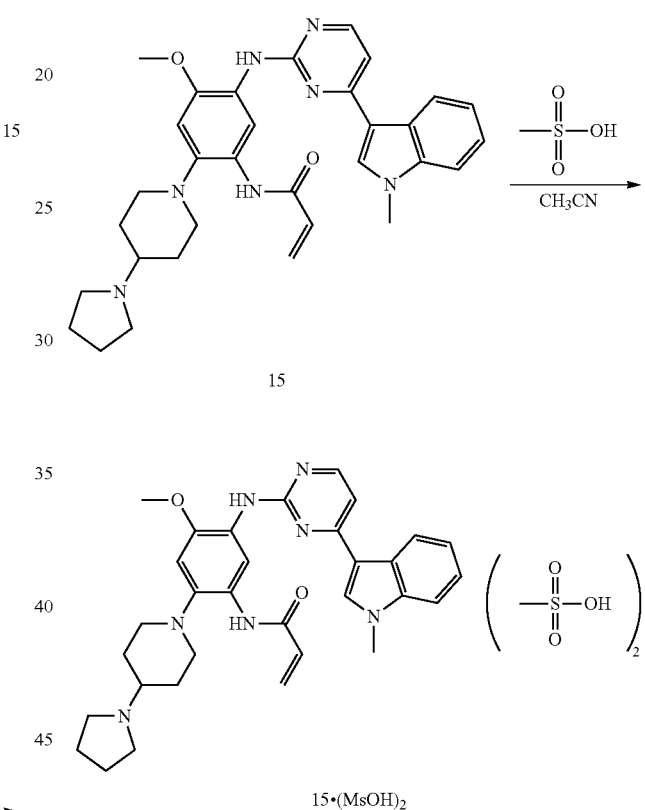

The reaction steps and conditions for synthesizing compound 15 and methanesulfonate (MsOH)₃ of compound 15 were completely the same as those from the first step to the third step in Example 8, except that the intermediate 008-1 as a raw material in the first step of the example 8 was replaced with the intermediate 015-1 in the first step. Finally, 139.7 mg of methanesulfonate (MsOH)₂ of compound 15 was obtained as a brown solid. LCMSLCMS (parent molecule) C₃₂H₃N₇O₂ (ES, m/z):(ES, m/z): [M+H]⁺=552. ¹H-NMR (300 MHz, DMSO-D₆, ppm) δ 1.90-1.99 (m, 4H), 2.05-2.10 (m, 2H), 2.15-2.19 (m, 2H), 2.27-2.32 (m, 7H), 2.72-2.83 (m, 2H), 3.09-3.21 (m, 4H), 3.26-3.29 (m, 2H), 3.83 (s, 3H), 3.93 (s, 1H), 5.74-5.78 (m, 1H), 6.21-6.26 (d, J=15.6 Hz, 1H), 6.60-6.69 (m, 1H), 6.95 (s, 1H), 7.16-7.21 (m, 1H), 7.28-7.31 (m, 1H), 7.33-7.40 (m, 1H), 7.58-7.61 (d, J=7.8 Hz, 1H, 8.22-8.33 (m, 3H), 8.78 (s, 1H), 9.19 (s, 1H), 9.64 (s, 1H).

95

Example 16

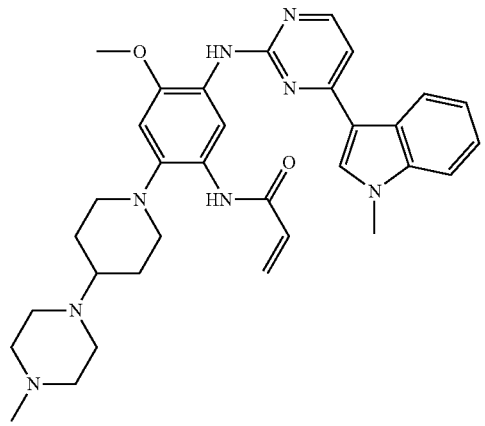

1. Synthesis of Compound 16

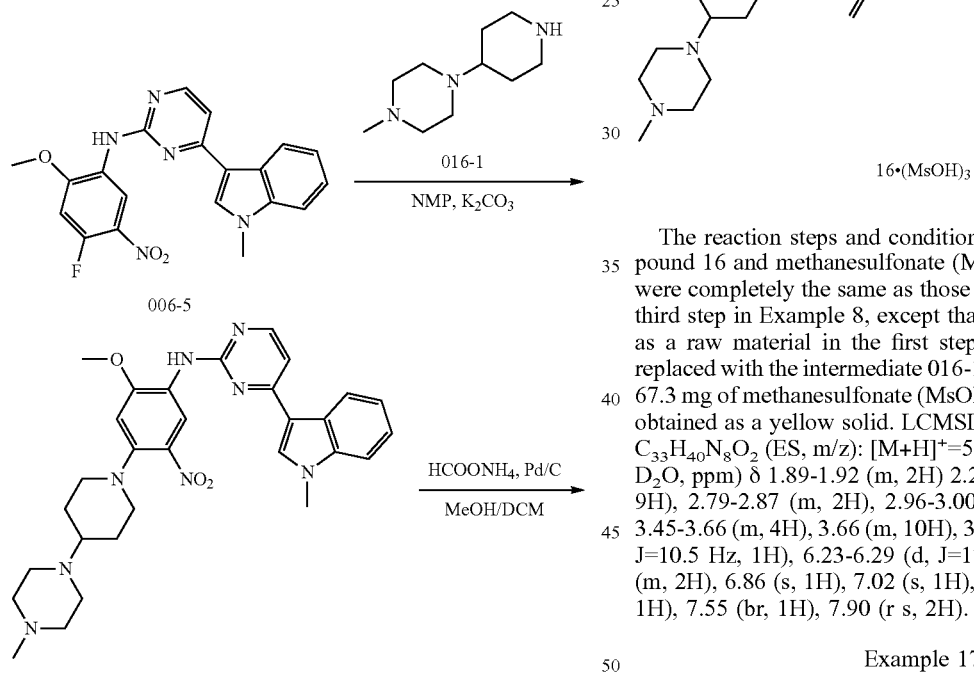

96

-continued

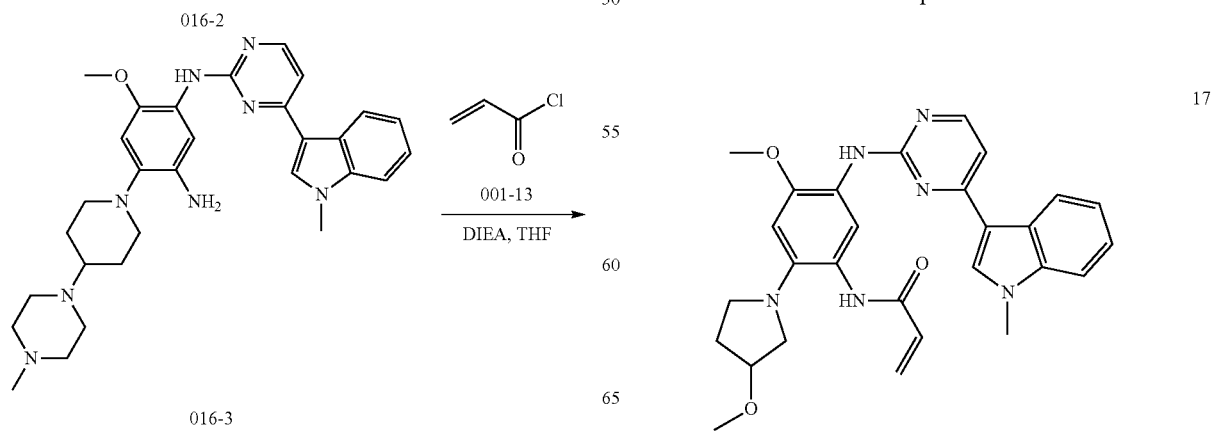

The reaction steps and conditions for synthesizing compound 16 and methanesulfonate (MsOH)$_3$ of compound 16 were completely the same as those from the first step to the third step in Example 8, except that the intermediate 008-1 as a raw material in the first step of the example 8 was replaced with the intermediate 016-1 in the first step. Finally, 67.3 mg of methanesulfonate (MsOH)$_3$ of compound 16 was obtained as a yellow solid. LCMSLCMS (parent molecule) C$_{33}$H$_{40}$N$_8$O$_2$ (ES, m/z): [M+H]$^+$=581. $^1$H-NMR (300 MHz, D$_2$O, ppm) δ 1.89-1.92 (m, 2H) 2.25-2.28 (m, 2H), 2.74 (s, 9H), 2.79-2.87 (m, 2H), 2.96-3.00 (s, 3H), 3.19 (m, 2H), 3.45-3.66 (m, 4H), 3.66 (m, 10H), 3.80 (s, 3H), 5.86-5.91 (d, J=10.5 Hz, 1H), 6.23-6.29 (d, J=17.1 Hz, 1H), 76.48-6.57 (m, 2H), 6.86 (s, 1H), 7.02 (s, 1H), 7.19 (s, 2H), 7.35 (br s, 1H), 7.55 (br, 1H), 7.90 (r s, 2H).

Example 17

1. Synthesis of Compound 17

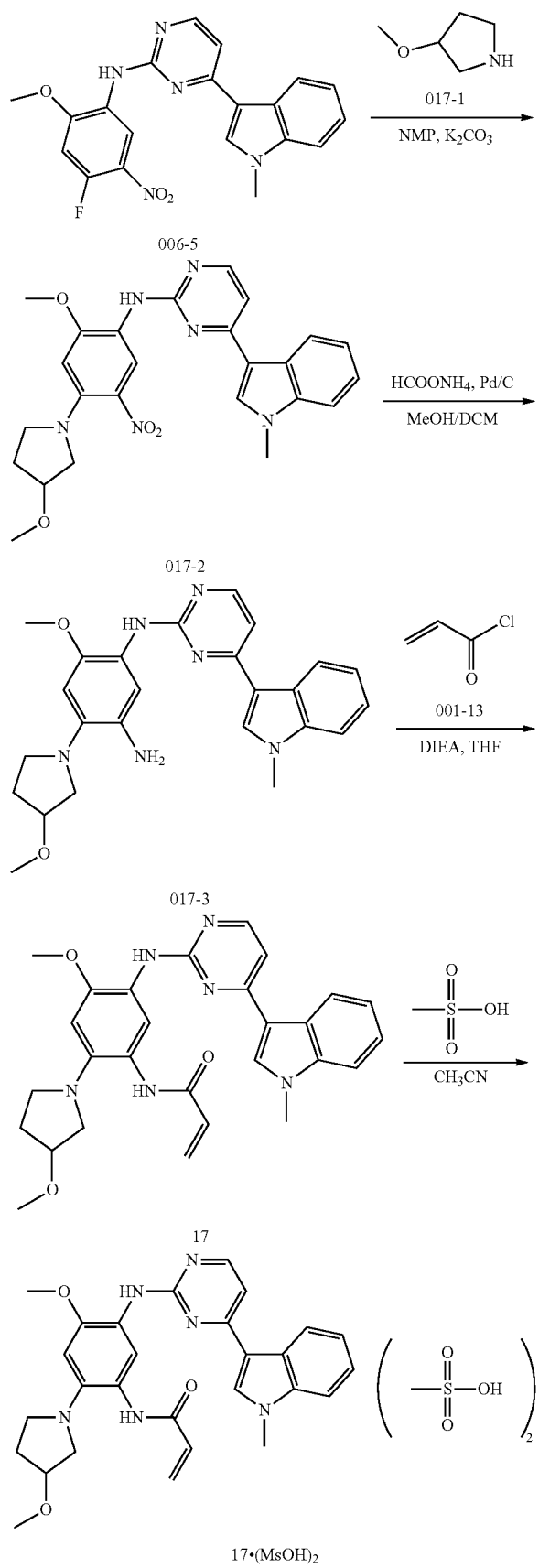

The reaction steps and conditions for synthesizing compound 17 and methanesulfonate (MsOH)$_2$ of compound 17 were completely the same as those from the first step to the third step in Example 8, except that the intermediate 008-1 as a raw material in the first step of the example 8 was replaced with the intermediate 017-1 in the first step. Finally, 130.7 mg of methanesulfonate (MsOH)$_2$ of compound 17 was obtained as a yellow solid. LCMSLCMS (parent molecule) $C_{28}H_{30}N_6O_3$(ES, m/z): [M+H]$^+$=499.

$^1$H-NMR (300 MHz, DMSO-D$_6$, ppm) δ 2.08 (m, 2H), 2.35 (s, 6H), 3.22 (m, 2H), 3.26 (s, 3H), 3.42-3.60 (m, 2H), 3.82 (s, 3H), 3.94 (s, 3H), 4.06 (s, 1H), 5.69-5.72 (d, J=10.2 Hz, 1H), 6.17-6.22 (d, J=15.6 Hz, 1H), 6.47-6.57 (m, 2H), 7.26-7.49 (m, 4H), 7.60-7.62 (d, J=8.1 Hz, 1H), 8.18 (br s, 1H), 8.18 (s, 1H), 9.51 (s, 1H).

Example 18

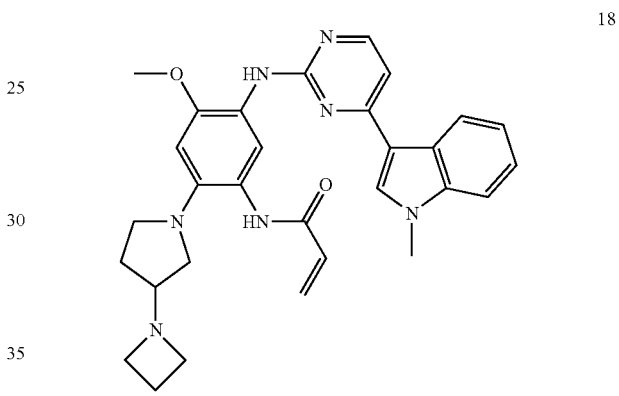

1. Synthesis of Compound 18

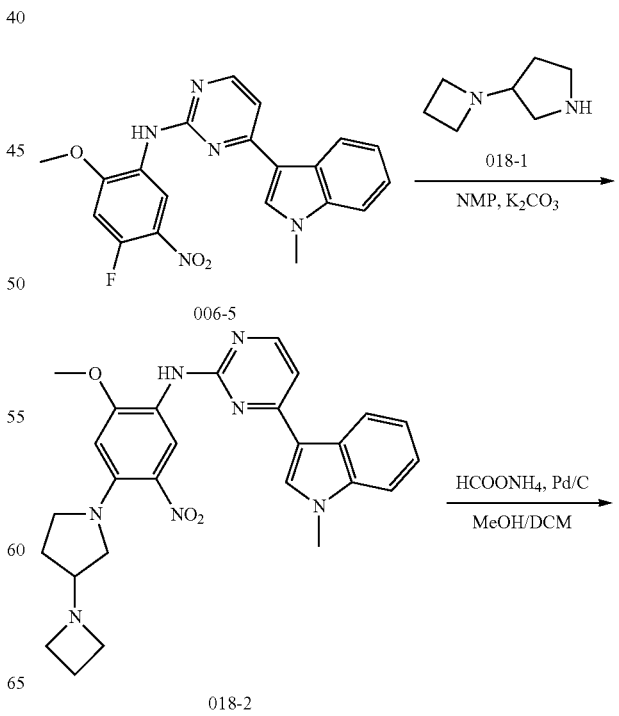

99

-continued

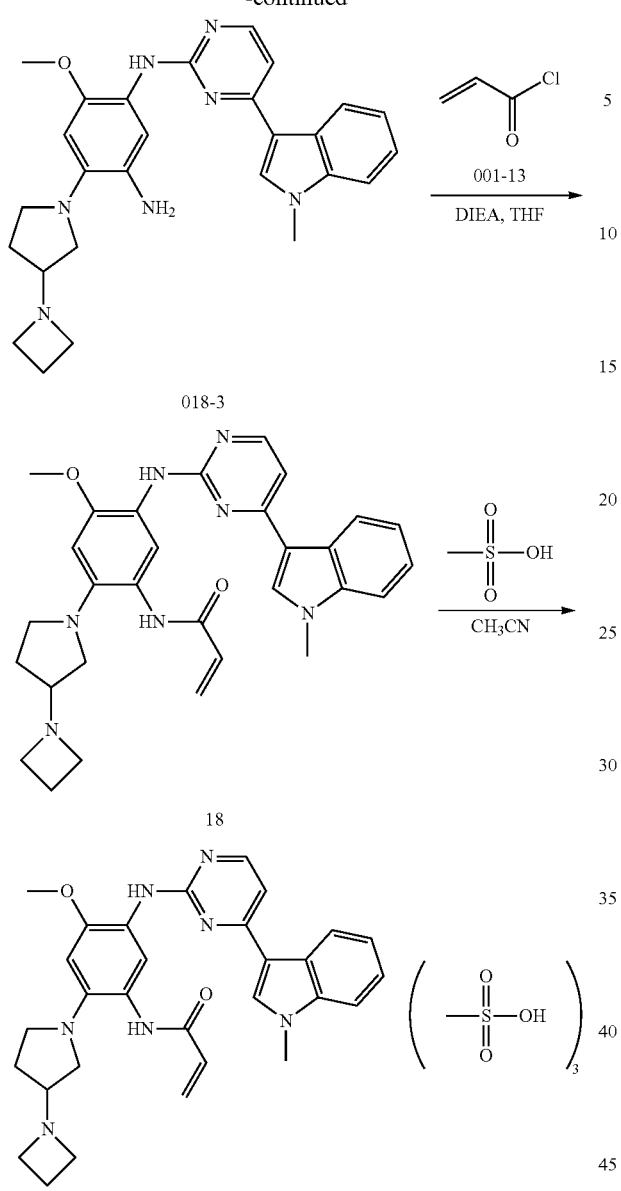

18•(MsOH)₃

The reaction steps and conditions for synthesizing compound 18 and methanesulfonate (MsOH)₃ of compound 18 were completely the same as those from the first step to the third step in Example 8, except that the intermediate 008-1 as a raw material in the first step of the example 8 was replaced with the intermediate 018-1 in the first step. LCMSLCMS (parent molecule) $C_{30}H_{33}N_7O_2$ (ES, m/z): (ES, m/z): [M+H]⁺=524.

¹H-NMR (300 MHz, DMSO-D₆, ppm) δ 11.29 (s, 1H), 9.83 (s, 1H), 8.82 (s, 1H), 8.15 (br s, 1H), 7.618-7.59 (d, J=8.1 Hz, 1H), 7.41-7.39 (d, J=6.9 Hz, 1H), 7.39-7.30 (m, 2H), 7.11-7.05 (m, 1H), 6.79 (s, 1H), 6.23-6.17 (m, 1H), 5.72-5.68 (m, 1H), 4.16-4.18 (m, 2H), 4.08-4.03 (m, 4H), 3.94 (s, 3H), 3.82 (s, 3H), 3.67 (m, 1H), 3.67-3.35 (m, 1H), 3.25-3.31 (m, 1H), 2.76-72.72 (m, 1H), 2.49-2.41 (m, 1H), 2.33 (s, 9H), 2.27-2.26 (m, 2H), 1.97-1.91 (m, 1H), 1.29-1.23 (m, 2H).

100

Example 19

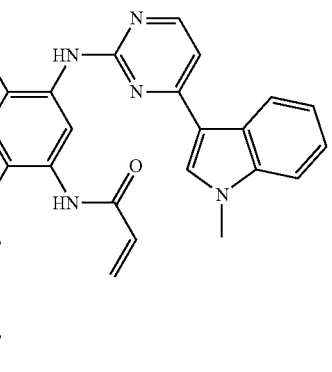

1. Synthesis of Compound 19

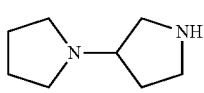

The reaction steps and conditions for synthesizing compound 19 and methanesulfonate (MsOH)₃ of compound 19 were completely the same as those from the first step to the third step in Example 8, except that the intermediate 008-1 as a raw material in the first step of the example 8 was replaced with the intermediate 019-1 in the first step. LCMSLCMS (parent molecule) $C_{31}H_{35}N_7O_2$ (ES, m/z): (ES, m/z): [M+H]⁺=538. ¹H-NMR (300 MHz, DMSO-D₆, ppm) δ 11.15 (s, 1H), 9.78 (s, 1H), 8.80 (s, 1H), 8.37-8.03 (m, 2H), 7.61-7.58 (d, J=8.1 Hz, 1H), 7.61-7.24 (m, 3H), 7.04-6.95 (m, 1H), 6.80 (s, 1H), 6.22-6.17 (d, J=13.2 Hz, 1H), 5.71-5.67 (d, J=12.3 Hz, 1H), 3.93 (s, 4H), 3.83 (s, 3H), 3.62-3.52 (m, 5H), 3.14-3.10 (m, 2H), 3.00-2.92 (m, 1H), 2.49 (s, 5H), 2.06-1.96 (m, 4H).

Example 20

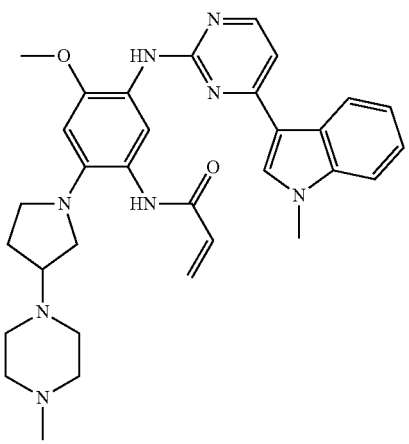

1. Synthesis of Compound 20

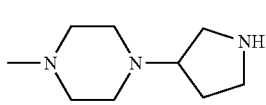

The reaction steps and conditions for synthesizing compound 20 and methanesulfonate (MsOH)₃ of compound 20 were completely the same as those from the first step to the third step in Example 8, except that the intermediate 008-1 as a raw material in the first step of the example 8 was replaced with the intermediate 020-1 in the first step. LCMS (parent molecule) C$_{32}$H$_{38}$N$_8$O$_2$ (ES, m/z): (ES, m/z): [M+H]⁺=567. ¹H-NMR (300 MHz, DMSO-D$_6$, ppm) δ 236 (s, 1H), 2.58 (s, 12H), 2.89 (s, 3H), 3.25-3.22 (m, 2H), 3.57-3.46 (m, 5H), 3.72-3.70 (m, 8H), 3.84 (s, 3H), 3.94 (s, 3H), 5.72-5.68 (m, 1H), 6.22-6.17 (m, 1H), 6.79-6.71 (m, 2H), 7.39-7.23 (m, 2H), 7.41-7.39 (m, 1H), 7.62-7.59 (m, 1H), 8.23-8.15 (m, 1H), 8.80 (s, 1H), 9.53 (s, 1H).

Example 21

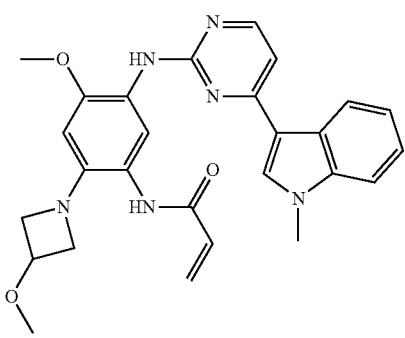

1. Synthesis of Compound 21

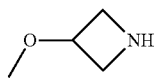

The reaction steps and conditions for synthesizing compound 21 and methanesulfonate (MsOH)₃ of compound 21 were completely the same as those from the first step to the third step in Example 8, except that the intermediate 008-1 as a raw material in the first step of the example 8 was replaced with the intermediate 021-1 in the first step. LCMSLCMS (parent molecule) C$_{27}$H$_{28}$N$_6$O$_3$(ES, m/z): (ES, m/z): [M+H]⁺=485.

¹H-NMR (300 MHz, DMSO-D$_6$, D$_2$O, ppm) δ 2.37 (m, 6H), 3.25 (s, 3H), 3.70-3.75 (m, 2H), 3.82 (s, 3H), 3.94 (s, 3H), 4.14-4.19 (m, 2H), 4.25-4.32 (m, 1H), 5.76-5.72 (m, 1H), 6.15-6.23 (m, 2H), 6.2 (s, 1H), 6.45-6.50 (m, 1H), 7.35-7.39 (m, 4H), 7.60-7.63 (d, J=8.1 Hz, 1H), 8.10 (m, 1H), 8.74 (s, 1H).

Example 22

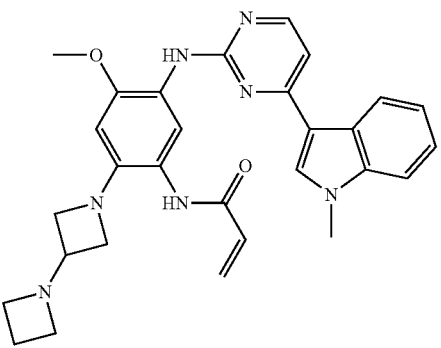

1. Synthesis of Intermediate 022-3

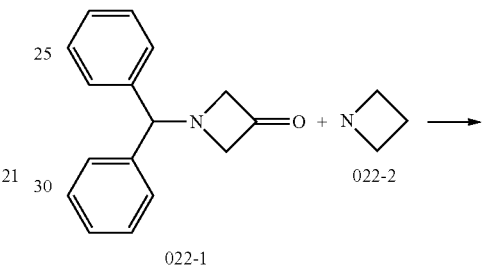

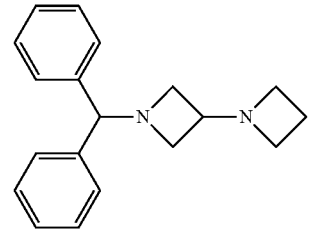

The intermediate 022-1 (10 g, 42.1 mmol) as raw material was dissolved in 100 mL of dichloromethane in a 250 mL three-necked flask at room temperature under a nitrogen atmosphere, and cyclobutylamine hydrochloride (4.7 g, 50.2 mmol) was added thereto. Then, the reaction was carried out for 1 h at room temperature, followed by that the reaction mixture was cooled to 0° C. Sodium triacetoxyborohydride (13.4 g, 63.2 mmol) was added to the reaction system in batches, and the reaction temperature was raised to room temperature and the reaction was stirred overnight. The reaction system was adjusted to pH 8-9 with anhydrous sodium carbonate aqueous solution the next day, and the mixture was extracted three times with 200 mL of methylene chloride. The organic phases were combined and washed once with 300 mL of saturated brine. The organic phases were dried over anhydrous sodium sulfate and concentrated. The crude product was purified by silica gel column chromatography (eluent: EA/PE=1:5) to give 4.7 g of intermediate 022-3 as a yellow oil. LCMS: 279.2.

2. Synthesis of Intermediate 022-4

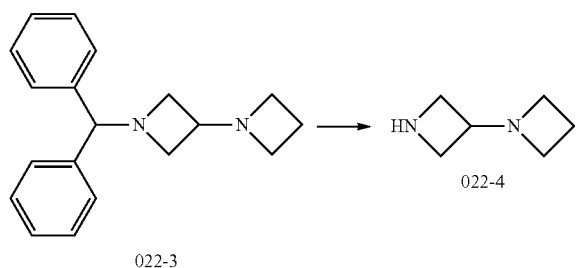 [SMILES: c1ccc(C(c2ccccc2)N2CC(N3CCC3)C2)cc1 ; C1CN(C2CNC2)C1]

The intermediate 022-3 (3 g, 10.8 mmol) as raw material was dissolved in 30 mL of anhydrous methanol in a 100 mL single-necked flask at room temperature. Palladium on carbon containing water (3 g, 5% Pd) was added and the reaction system was exchanged with hydrogen 3 times. The reaction was carried out overnight at room temperature under hydrogen. After the reaction was completed, the mixture was filtered by suction and the filtrate was collected and concentrated to give 1.2 g of crude product 022-4 as yellow oil. LCMS: 113.1.

3. Synthesis of Intermediate 022-6

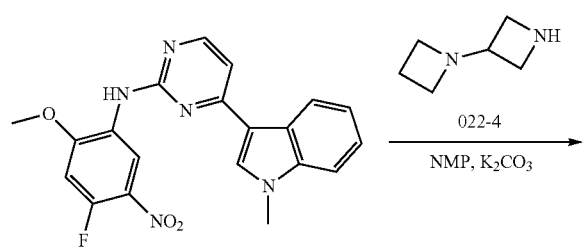

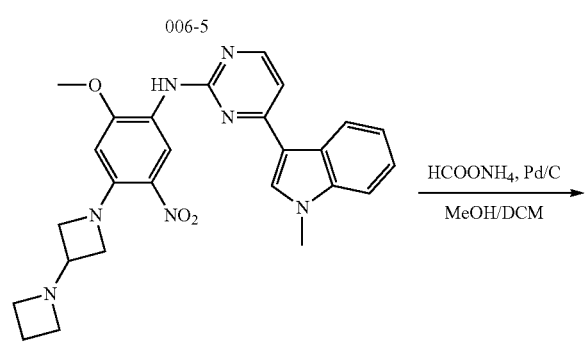

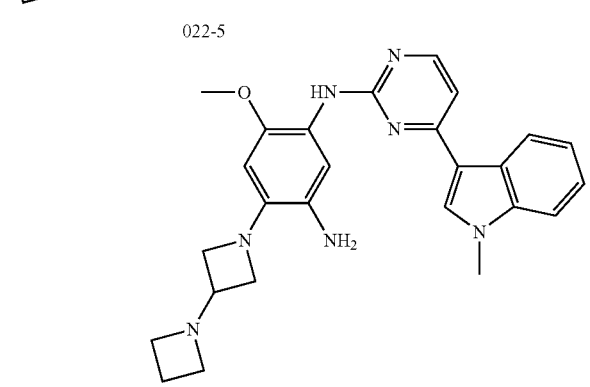

The reaction steps and conditions for synthesizing compound 022-6 were completely the same as those from the first step to the second step in Example 8, except that the intermediate 008-1 as a raw material in the first step of the example 8 was replaced with the intermediate 022-4 in the first step. LCMS: 445.3.

4. Synthesis of Compound 22

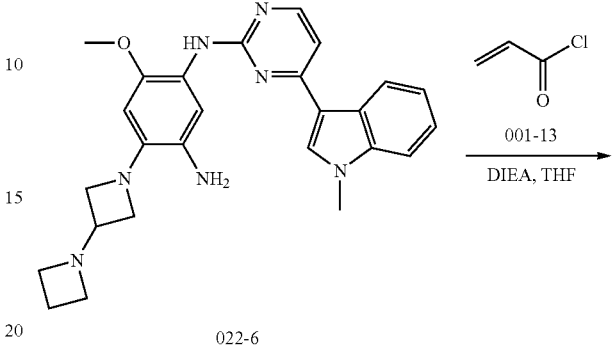

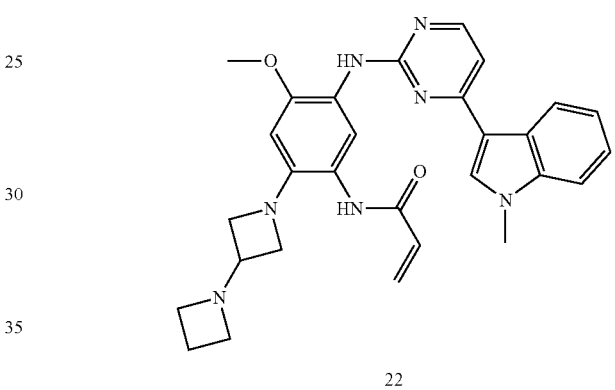

The intermediate 022-6 (250 mg, 0.55 mmol) as raw material was dissolved in 50 mL of anhydrous THF in a 100 mL single-necked flask at room temperature under a nitrogen atmosphere, and N,N-diisopropylethylamine (DIPEA) (141.8 mg, 1.10 mmol) was added thereto. After the reaction mixture was cool to 0° C., acryloyl chloride (48.9 mg, 0.540 mmol) was added dropwisely to the reaction system at 0° C. The reaction system was heated to room temperature, and stirred for 1 h. After the reaction was completed, the reaction was quenched by the addition of 2 mL of water and the mixture was concentrated to dryness. The resulting residue was purified by prep-HPLC (column: Xbridge Prep RP18, 5 um, C18, 19×150 mm; mobile phase: 0.05% ammonia+10 mmol of ammonium bicarbonate)/acetonitrile; 77% acetonitrile to 81% acetonitrile, 4 min; 5 mL/min; detection wavelength: 254 nm), concentrated and freeze dried to give 9.8 mg of product 22 (4%) as a yellow solid. LCMS (parent molecule) $C_{29}H_{31}N_7O_2$: (ES, m/z): 510 [M+H]$^+$. $^1$H-NMR: (DMSO-D$_6$, 300 MHz, ppm) δ 9.29 (s, 1H), 8.34-8.32 (m, 2H), 8.26-8.24 (d, J=5.4 Hz, 1H), 7.92 (s, 1H), 7.76 (s, 1H), 7.51-7.49 (m, 1H), 7.23-7.16 (m, 2H), 7.13-7.12 (d, J=5.1 Hz, 2H), 6.55-6.46 (m, 1H), 6.22 (s, 1H), 6.17-6.16 (d, J=2.1 Hz, 1H), 5.70-5.66 (m, 1H), 3.88 (s, 3H), 3.84 (s, 3H), 3.60-3.3.55 (m, 2H), 3.41-3.34 (m, 1H), 3.17-3.13 (t, J=6.9 Hz, 4H), 2.00-1.95 (m, 2H).

Example 23

1. Synthesis of Intermediate 023-3

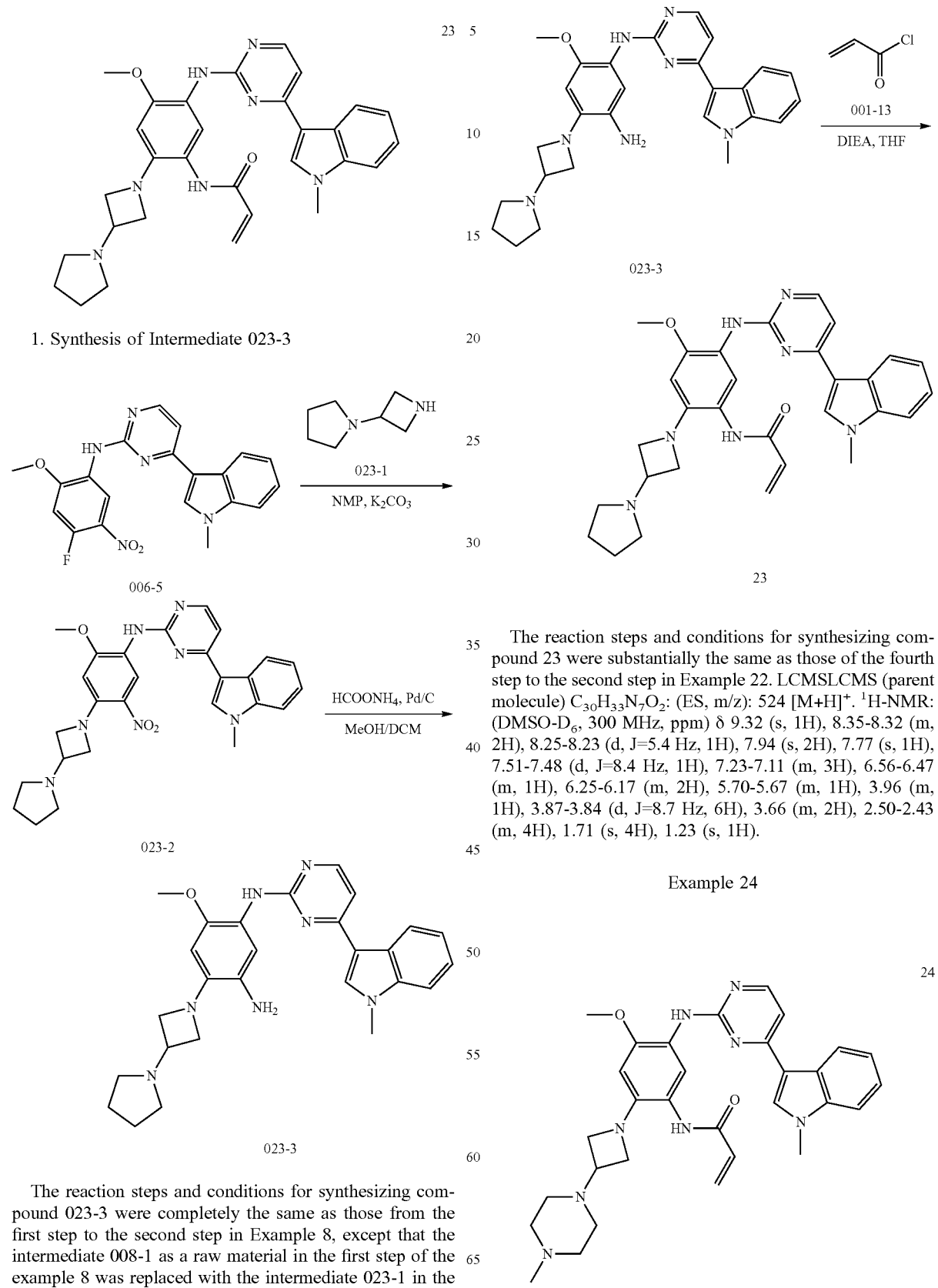

The reaction steps and conditions for synthesizing compound 023-3 were completely the same as those from the first step to the second step in Example 8, except that the intermediate 008-1 as a raw material in the first step of the example 8 was replaced with the intermediate 023-1 in the first step. LCMS: 470.3.

2. Synthesis of Compound 23

The reaction steps and conditions for synthesizing compound 23 were substantially the same as those of the fourth step to the second step in Example 22. LCMSLCMS (parent molecule) $C_{30}H_{33}N_7O_2$: (ES, m/z): 524 [M+H]$^+$. $^1$H-NMR: (DMSO-D$_6$, 300 MHz, ppm) δ 9.32 (s, 1H), 8.35-8.32 (m, 2H), 8.25-8.23 (d, J=5.4 Hz, 1H), 7.94 (s, 2H), 7.77 (s, 1H), 7.51-7.48 (d, J=8.4 Hz, 1H), 7.23-7.11 (m, 3H), 6.56-6.47 (m, 1H), 6.25-6.17 (m, 2H), 5.70-5.67 (m, 1H), 3.96 (m, 1H), 3.87-3.84 (d, J=8.7 Hz, 6H), 3.66 (m, 2H), 2.50-2.43 (m, 4H), 1.71 (s, 4H), 1.23 (s, 1H).

Example 24

1. Synthesis of Compound 24

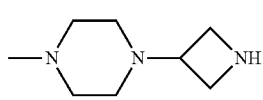

024-1

The reaction steps and conditions of compound 24 and the methanesulfonate (MsOH)$_3$ of compound 24 were completely the same as those from the first step to the third step in Example 8, except that the intermediate 008-1 as a raw material in the first step of the example 8 was replaced with the intermediate 024-1 in the first step. LCMSLCMS (parent molecule) $C_{31}H_{36}N_8O_2$ (ES, m/z): (ES, m/z): [M+H]$^+$=553. $^1$H-NMR (300 MHz, D$_2$O, ppm) δ 2.68-2.76 (m, 11H), 2.91 (s, 3H), 2.98-3.10 (m, 3H), 3.36-3.56 (m, 8H), 3.70 (s, 1H), 3.74-3.90 (m, 5H), 4.12-4.17 (m, 2H), 5.90-5.94 (d, J=10.8 Hz, 1H), 6.30-6.35 (m, 2H), 6.45-6.54 (m, 2H), 7.04 (m, 1H), 7.19-7.23 (m, 2H), 7.33-7.35 (m, 1H), 7.68-7.72 (m, 2H).

Example 25

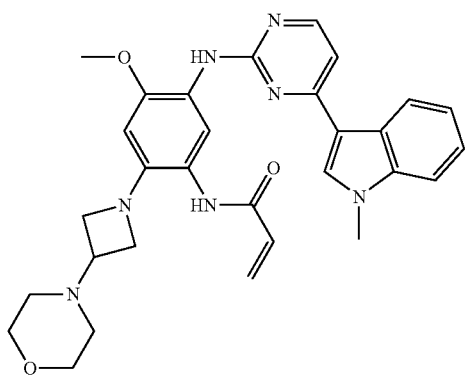

25

1. Synthesis of Compound 25

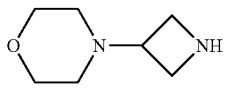

025-1

The reaction steps and conditions of compound 25 and the methanesulfonate (MsOH)$_3$ of compound 25 were completely the same as those from the first step to the third step in Example 8, except that the intermediate 008-1 as a raw material in the first step of the example 8 was replaced with the intermediate 025-1 in the first step. LCMSLCMS (parent molecule) $C_{30}H_{33}N_7O_3$ (ES, m/z): (ES, m/z): [M+H]$^+$=540. $^1$H-NMR (300 MHz)$_2$O, ppm) δ 2.72 (s, 6H), 3.20-3.28 (m, 4H), 3.63 (s, 3H), 3.81 (s, 3H), 3.93-4.02 (m, 6H), 4.09-4.11 (m, 1H), 4.21-4.27 (m, 2H), 5.87-5.91 (d, J=11.4 Hz, 1H), 6.28-6.51 (m, 3H), 6.84-6.86 (d, J=6.9 Hz, 1H), 7.12-7.15 (m, 1H), 7.23-7.34 (m, 2H), 7.37-7.60 (m, 1H), 7.88-7.95 (m, 2H).

Example 26

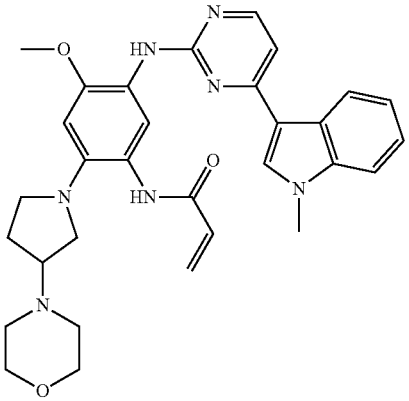

26

1. Synthesis of Compound 26

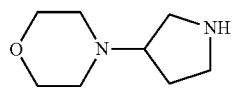

026-1

The reaction steps and conditions of compound 26 and the methanesulfonate (MsOH)$_3$ of compound 26 were completely the same as those from the first step to the third step in Example 8, except that the intermediate 008-1 as a raw material in the first step of the example 8 was replaced with the intermediate 026-1 in the first step. LCMS $C_{31}H_{38}N_7O_3$: (ES, m/z): 554 [M+H]$^+$. $^1$H-NMR: (300 MHz, 120, ppm) δ 2.12-2.17 (m, 1H), 2.38 (s, 6H), 2.50-2.56 (m, 1H), 3.25-3.27 (m, 2H), 336-3.39 (m, 2H), 3.53-3.55 (m, 1H), 3.70-3.74 (m, 2H), 3.78-3.84 (m, 2H), 3.85 (s, 3H) 3.93 (s, 3H), 4.04-4.08 (m, 4H), 5.71-5.75 (d, J=12 Hz, 1H), 6.18-6.24 (d, J=17.4 Hz, 1H), 6.53-6.63 (m, 1H), 6.74 (s, 1H), 7.23-7.39 (m, 3H), 7.59-7.61 (d, J=7.8 Hz, 1H), 8.10-8.31 (m, 2H), 8.76 (s, 1H), 9.44 (s, 1H), 10.10-10.12 (br s, 1H).

Example 27

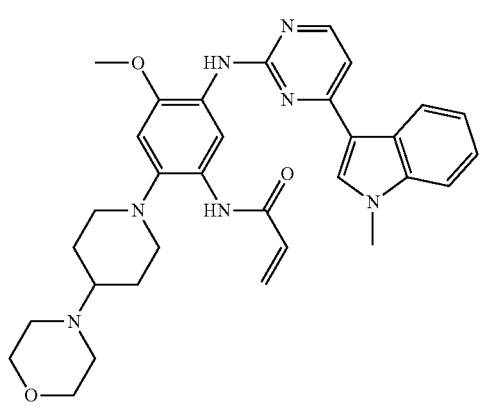

27

1. Synthesis of Compound 27

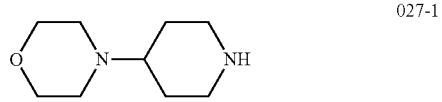 [SMILES: C1CC(N2CCOCC2)CCN1]

027-1

The reaction steps and conditions of compound 27 and the methanesulfonate (MsOH)$_3$ of compound 27 were completely the same as those from the first step to the third step in Example 8, except that the intermediate 008-1 as a raw material in the first step of the example 8 was replaced with the intermediate 027-1 in the first step. LCMS C$_{32}$H$_{37}$N$_7$O$_3$: (ES, m/z): 568 [M+H]$^+$. $^1$H-NMR: (300 MHz, D$_2$O, ppm) δ 1.84-1.98 (m, 2H), 2.26-2.22 (m, 2H), 2.76 (s, 9H), 2.80-2.84 (m, 2H), 3.17-3.28 (m, 4H), 3.38 (s, 1H), 3.48-3.58 (m, 5H), 3.78-3.86 (m, 5H), 4.12-4.16 (m, 2H), 5.86-5.89 (d, J=10.8 Hz, 1H), 6.22-6.27 (m, 1H), 6.46-6.55 (m, 1H), 6.67-6.69 (d, J=6.9 Hz, 1H), 6.85 (s, 1H), 7.02 (br s, 1H), 7.17-7.22 (m, 2H), 7.40-7.43 (d, J=6.9 Hz, 1H), 7.60 (br s, 1H), 7.879-7.99 (m, 2H).

Example 28

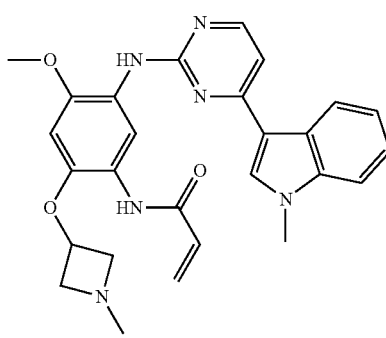

28

1. Synthesis of Intermediate 028-2

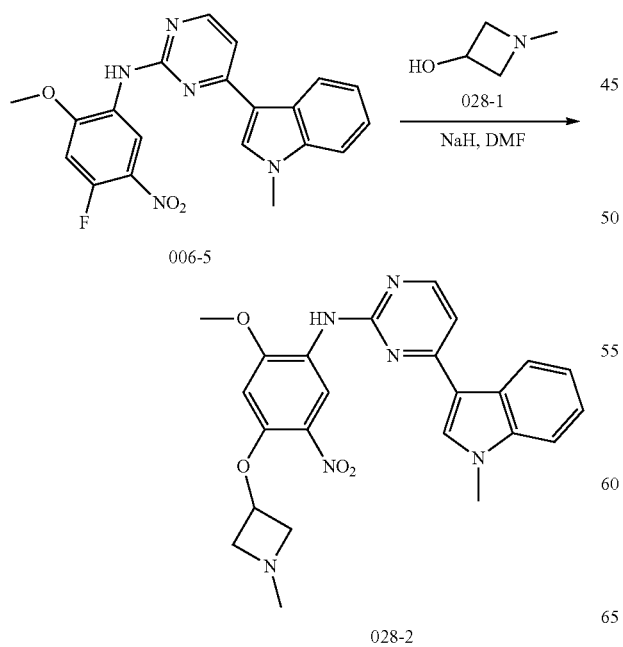

Under nitrogen protection, anhydrous N,N-dimethylformamide (DMF) (150 mL) was added to a 250 mL single-necked flask and then the intermediate 028-1 (375.5 mg, 3.05 mmol) was 1 added thereto. The reaction mixture was cooled to 0° C. under an ice-water bath. After sodium hydride (NaH) (65%, mineral oil mixture) (564 mg, 15.2 mmol) was added the reaction mixture in batches, the reaction temperature was raised to room temperature and the reaction was carried out for 0.5 h. Then, the intermediate 006-5 (1.0 g, 2.54 mmol) was added into the reaction mixture, and the reaction was carried out at room temperature overnight. After the reaction was completed, the reaction was cooled to 0° C. and quenched by the adding 2 mL of MeOH and subjected to rotary evaporation. The crude product was purified by silica gel column chromatography (eluent: DCM/MeOH=8:1-6:1) and subjected to rotary evaporation to give 0.8 g of the intermediate 028-2 (68%) as a yellow solid. LCMS: 461.2.

2. Synthesis of Compound 28

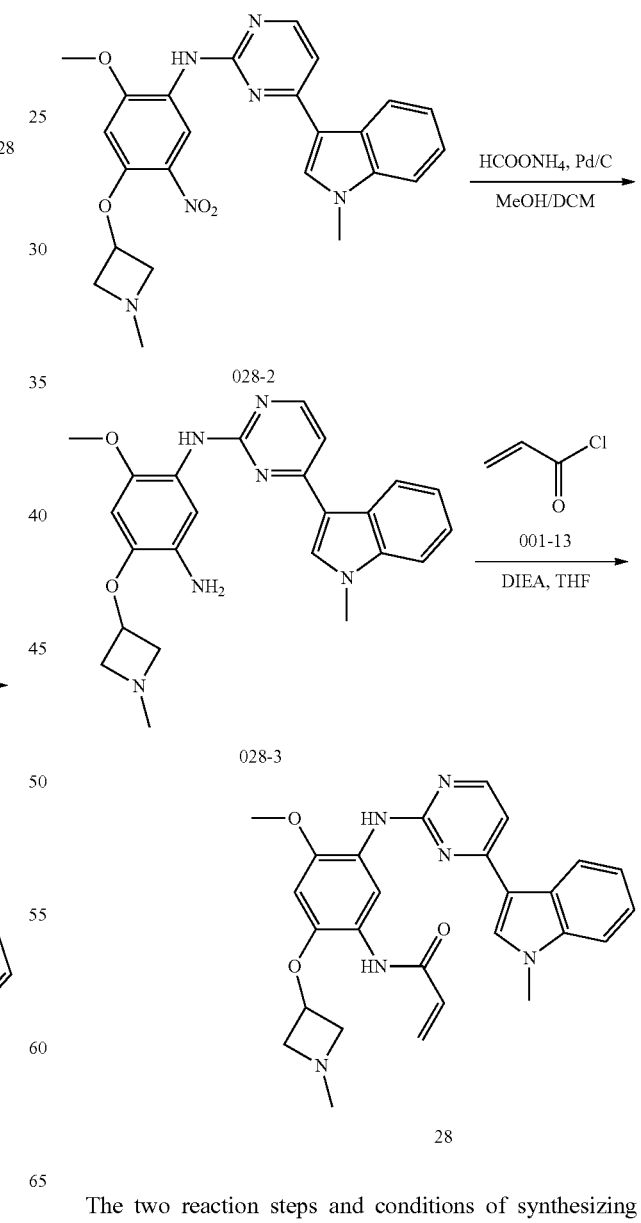

The two reaction steps and conditions of synthesizing compound 28 were completely the same as those of the second step in Example 8 and the fourth step in Example 22 respectively. LCMSLCMS (parent molecule) $C_{27}H_{28}N_6O_3$: (ES, m/z): 485 [M+H]$^+$. $^1$H-NMR (300 MHz, DMSO-D$_6$, ppm): δ 2.32 (s, 3H), 3.07-3.11 (dd, J=6.9 Hz, J=13.2 Hz, 2H), 3.76-3.80 (dd, J=8.1 Hz, J=14.4 Hz, 2H), 3.84 (s, 3H), 3.88 (s, 3H), 4.83-4.87 (m, 2H), 5.70-5.74 (d, J=12 Hz, 1H), 6.20-6.26 (d, J=16.8 Hz, 1H), 6.56 (s, 1H), 6.65-6.76 (m, 1H), 7.12-7.26 (m, 2H), 7.49-7.52 (d, J=8.4 Hz, 1H), 7.88 (s, 1H), 8.26-8.30 (m, 2H), 8.46 (s, 1H), 8.67 (s, 1H), 9.28 (s, 1H).

Example 29

1. Synthesis of Intermediate 029-2

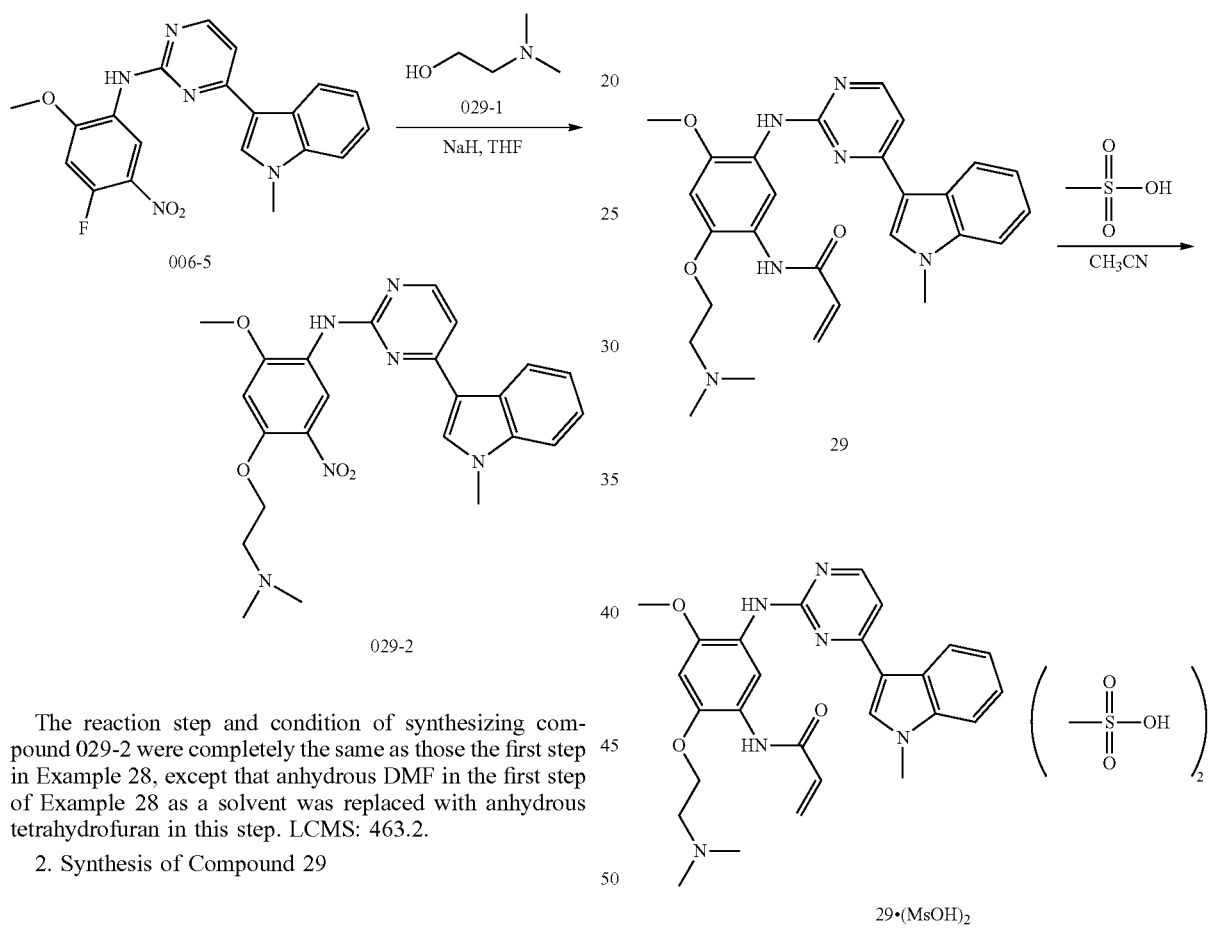

The reaction step and condition of synthesizing compound 029-2 were completely the same as those the first step in Example 28, except that anhydrous DMF in the first step of Example 28 as a solvent was replaced with anhydrous tetrahydrofuran in this step. LCMS: 463.2.

2. Synthesis of Compound 29

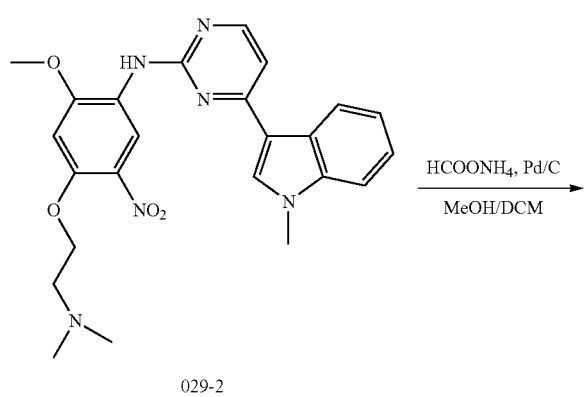

The reaction steps and conditions of synthesizing compound 29 and the methanesulfonate (MsOH)$_3$ of compound 29 were the same as those of the second step and the third step in Example 8. LCMSLCMS (parent molecule) $C_{27}H_{30}N_6O_3$: (ES, m/z): [M+H]$^+$=487. $^1$H-NMR (300 MHz, DMSO-D$_6$, ppm) δ 2.28-2.36 (m, 6H), 2.95-3.05 (m, 6H), 3.65-3.73 (m, 2H), 3.86 (s, 3H), 3.93 (s, 3H), 4.51 (s, 2H), 5.75-5.78 (d, J=10.1 Hz, 1H), 6.21-6.27 (d, J=16.8 Hz, 1H), 6.62-6.71 (m, 1H), 7.01 (s, 1H), 7.19-7.22 (m, 1H), 7.28-7.33 (t, J=7.8 Hz, 1H), 7.37-7.39 (d, J=6.3 Hz, 1H), 7.58-7.61 (d, J=8.4 Hz, 1H), 8.17-8.18 (brs, 1H), 8.33-8.76 (m, 2H), 9.41 (s, 1H), 9.61 (br s, 1H).

Example 30

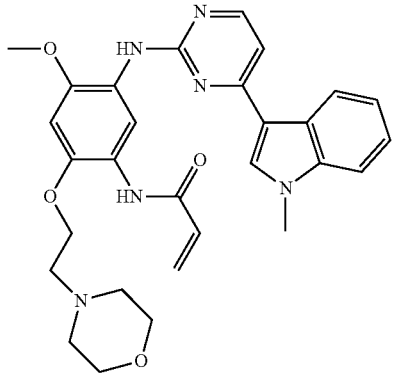

1. Synthesis of Intermediate 030-2

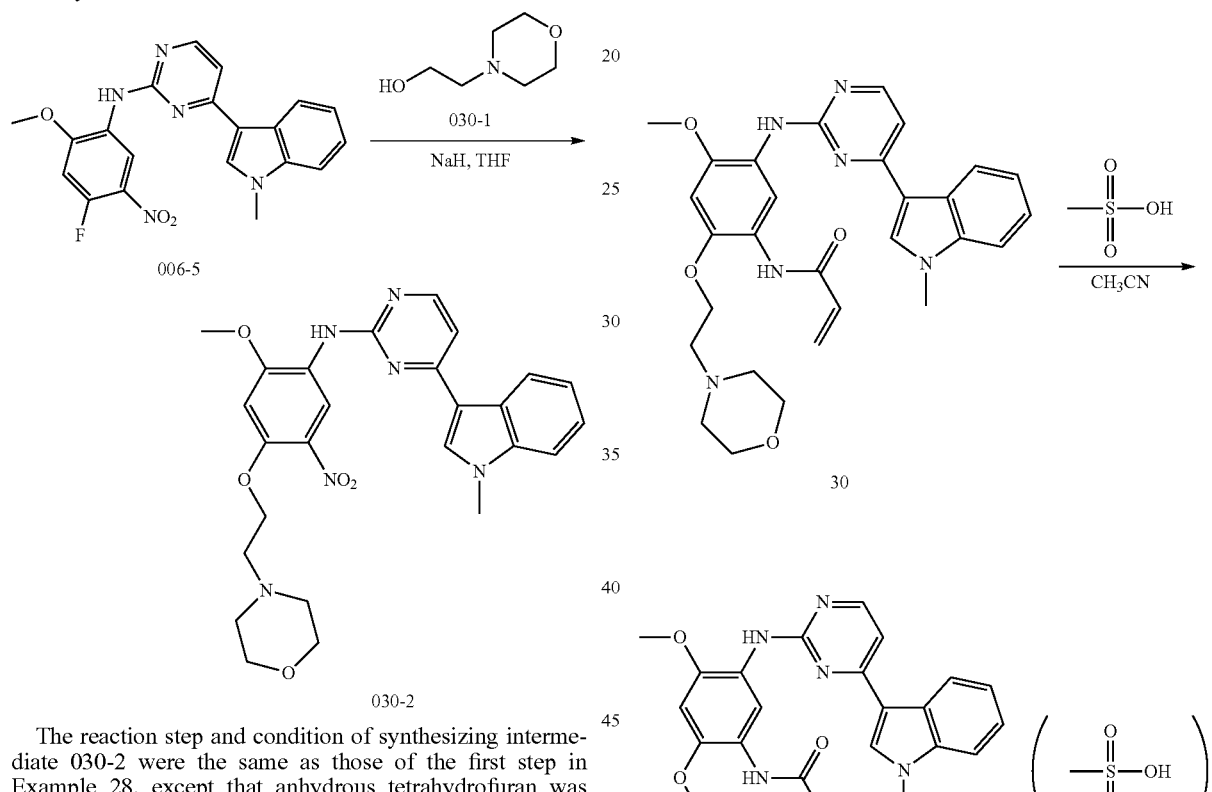

The reaction step and condition of synthesizing intermediate 030-2 were the same as those of the first step in Example 28, except that anhydrous tetrahydrofuran was used as a solvent in this step. LCMS: 505.2.

2. Synthesis of Compound 30

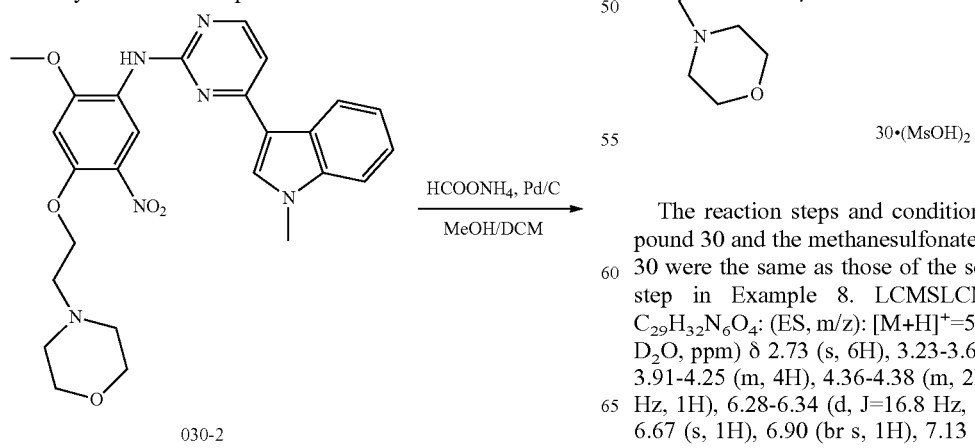

The reaction steps and conditions of synthesizing compound 30 and the methanesulfonate (MsOH)$_3$ of compound 30 were the same as those of the second step and the third step in Example 8. LCMSLCMS (parent molecule) $C_{29}H_{32}N_6O_4$: (ES, m/z): [M+H]$^+$=529. $^1$H-NMR (300 MHz, D$_2$O, ppm) δ 2.73 (s, 6H), 3.23-3.60 (m, 9H), 3.80 (s, 3H), 3.91-4.25 (m, 4H), 4.36-4.38 (m, 2H), 5.87-5.90 (d, J=10.5 Hz, 1H), 6.28-6.34 (d, J=16.8 Hz, 1H), 6.45-6.51 (m, 2H), 6.67 (s, 1H), 6.90 (br s, 1H), 7.13 (s, 2H), 7.25 (br s, 1H), 7.48 (br s, 1H), 7.70 (br s, 2H).

Example 31
2. Synthesis of Compound 31
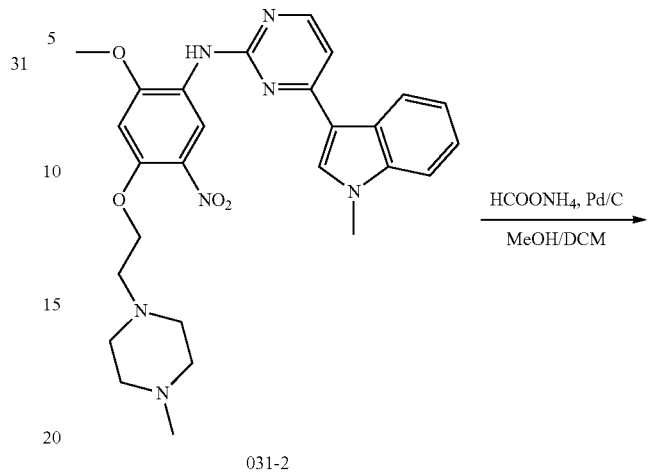
1. Synthesis of Intermediate 031-2
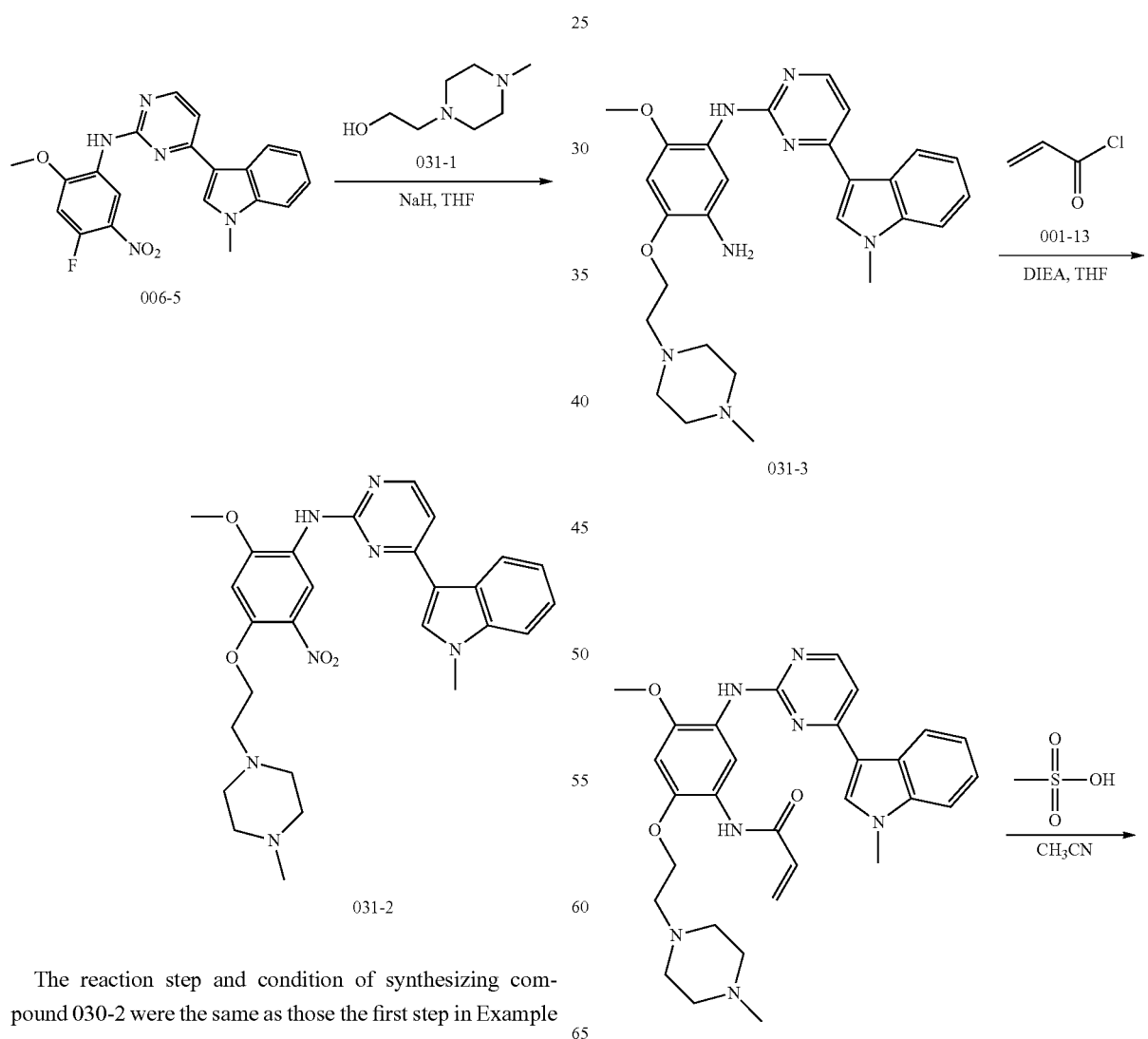
The reaction step and condition of synthesizing compound 030-2 were the same as those the first step in Example 28, except that anhydrous tetrahydrofuran was used as a solvent in this step. LCMS: 518.2.

117

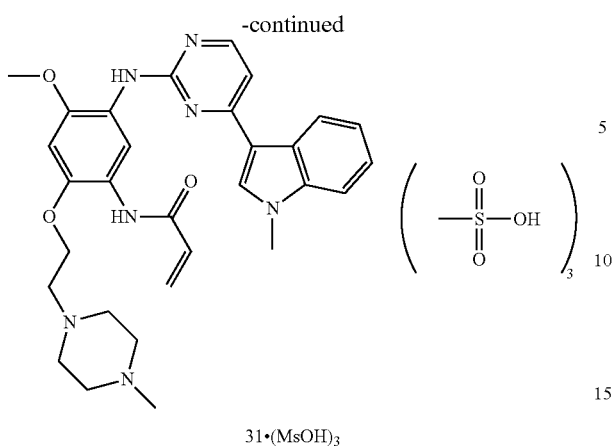

31·(MsOH)₃

The reaction steps and conditions of synthesizing compound 31 and the methanesulfonate (MsOH)₃ of compound 31 were the same as those of the second step and the third step in Example 8. LCMSLCMS (parent molecule) $C_{30}H_{35}N_7O_3$: (ES, m/z): $[M+H]^+=542$. ¹H-NMR (300 MHz, CD₃OD, ppm) δ 2.74 (9H), 3.07 (s, 3H), 3.62-3.91 (m, 1 OH), 3.97 (s, 3H), 3.97 (s, 3H), 5.83-5.86 (d, J=11.7 Hz, 1H), 6.37-6.43 (d, J=18.3 Hz, 1H), 6.68-6.73 (m, 1H), 7.05 (s, 1H), 7.26-7.39 (m, 3H), 7.53-7.56 (d, J=8.1 Hz, 1H), 7.95-7.97 (d, J=6.6 Hz, 1H), 8.14 (br s, 1H), 8.44 (br s, 1H), 8.54 (s, 1H).

Example 32

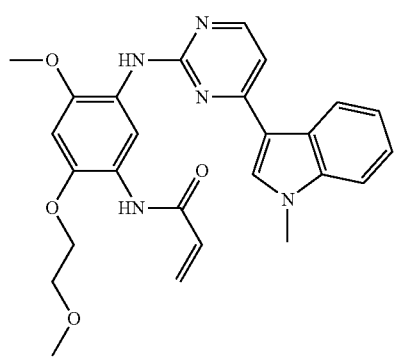

32

1. Synthesis of Intermediate 032-2

118

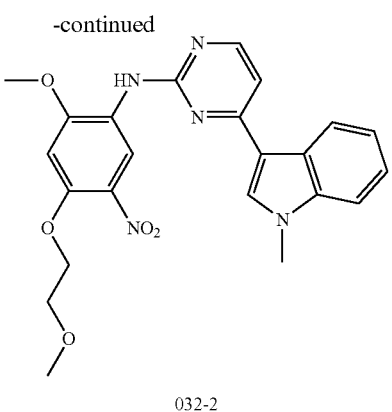

032-2

The reaction step and condition of synthesizing compound 030-2 were the same as those the first step in Example 28, except that anhydrous tetrahydrofuran was used as a solvent in this step. LCMS: 450.2.

2. Synthesis of Compound 32

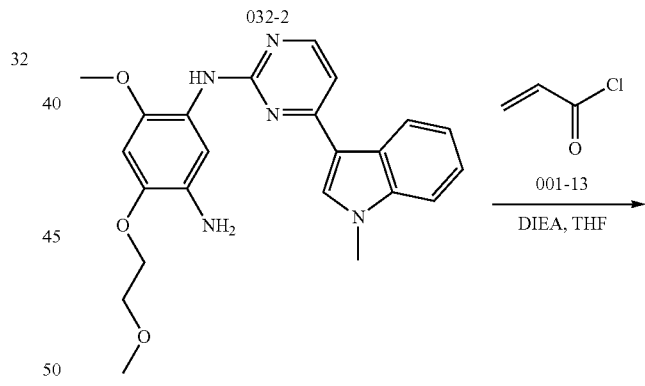

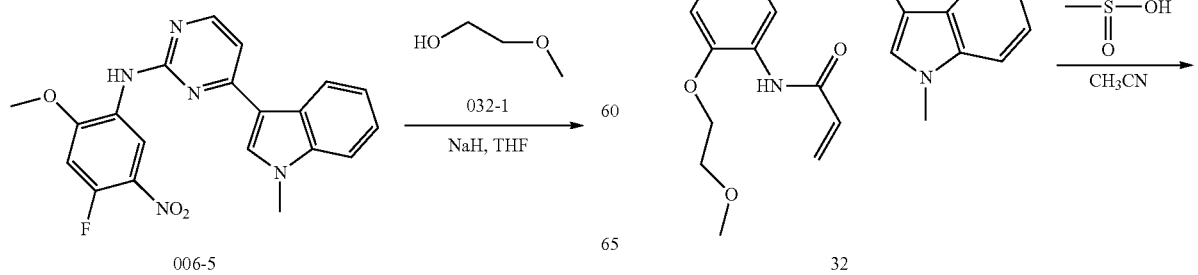

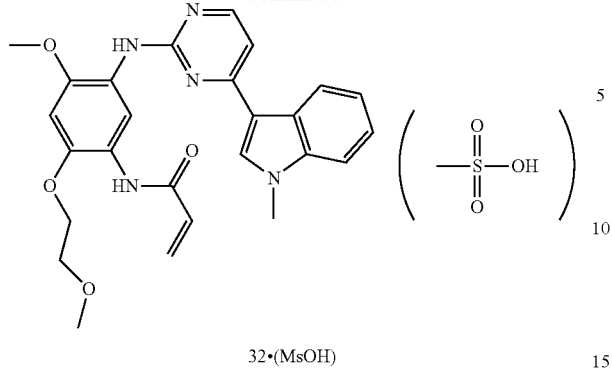

32·(MsOH)

The reaction steps and conditions of synthesizing compound 32 and the methanesulfonate (MsOH)₃ of compound 32 were the same as those of the second step and the third step in Example 8. LCMSLCMS (parent molecule) $C_{26}H_{27}N_5O_4$: (ES, m/z): [M+H]⁺=474. ¹H-NMR (300 MHz, DMSO-D₆, ppm) δ 2.27 (s, 3H), 3.37 (s, 3H), 3.75-3.78 (dd, J=4.8 Hz, J=9.3 Hz, 2H), 3.83-3.88 (s, 3H), 3.98 (s, 3H), 4.30-4.33 (dd, J=4.5 Hz, J=9.3 Hz, 2H), 5.70-5.73 (d, J=9.9 Hz, 1H), 6.17-6.22 (d, J=17.1 Hz, 1H), 6.61-6.70 (m, 1H), 7.00 (s, 1H), 7.20-7.39 (m, 3H), 7.59-7.61 (d, J=8.1 Hz, 1H), 8.16-8.27 (br s, 3H), 8.77 (s, 1H), 9.29 (s, 1H).

Example 33

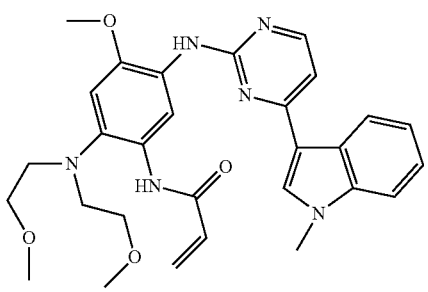

33

1. Synthesis of Intermediate 052-1

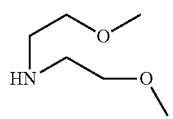

033-1

The reaction steps and conditions of synthesizing compound 33 and the methanesulfonate (MsOH)₃ of compound 33 were the same as those of the fourth step and the sixth step in Example 6, except that the intermediate 006-6 as a raw material in the fourth step of the example 6 was replaced with the intermediate 033-1 in this step. LCMS (parent molecule) $C_{29}H_{34}N_6O_4$: (ES, m/z): [M+H]⁺=531.

¹H-NMR (300 MHz, D₂O, ppm) δ 3.07-3.20 (m, 4H), 3.24 (m, 8H), 3.31-3.40 (m, 5H), 3.73-3.77 (m, 3H), 5.71-5.74 (m, 1H), 5.90-6.01 (m, 1H), 6.23-6.32 (m, 2H), 6.70-6.87 (m, 2H), 6.93-6.95 (d, J=7.2 Hz, 1H), 7.05-7.08 (m, 1H), 7.12-7.20 (d, J=22.8 Hz, 2H), 7.74-7.87 (m, 1H), 8.09-8.17 (m, 1H).

Example 34

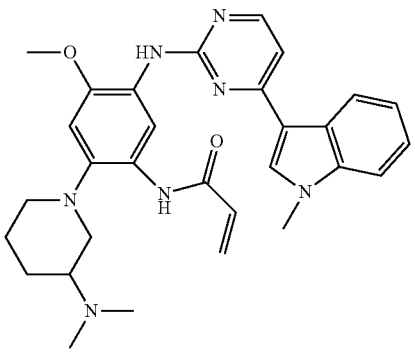

34

1. Synthesis of Compound 34

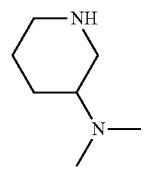

034-1

The reaction steps and conditions of synthesizing compound 34 and the methanesulfonate (MsOH)₃ of compound 34 were the same as those from the first step to the third step in Example 8, except that the intermediate 008-1 as a raw material in the first step of the example 8 was replaced with the intermediate 034-1 in the this step. LCMS (parent molecule) $C_{30}H_{38}N_7O_2$: (ES, m/z): [M+H]⁺=526. ¹H-NMR (300 MHz, DMSO-D₆, ppm) δ 1.82-1.86 (m, 3H), 2.09 (s, 1H), 2.73 (s, 9H), 2.85-2.91 (d, J=15.6 Hz, 8H), 3.08-3.14 (m, 1H), 3.29-3.33 (m, 1H), 3.52 (s, 4H), 3.82 (s, 3H), 5.88-5.91 (d, J=10.5 Hz, 1H), 6.26-6.31 (d, J=17.4 Hz, 1H), 6.54-6.63 (m, 1H), 6.71-6.74 (d, J=7.2 Hz, 1H), 6.91 (s, 1H), 7.00-7.05 (m, 1H), 7.19-7.45 (m, 2H), 7.46 (d, J=6.9 Hz, 1H), 7.65 (s, 1H), 7.89-7.93 (m, 2H).

Example 35

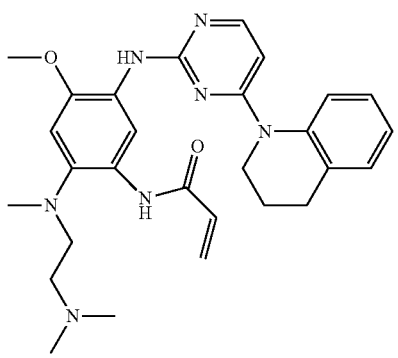

35

1. Synthesis of Intermediate 035-2

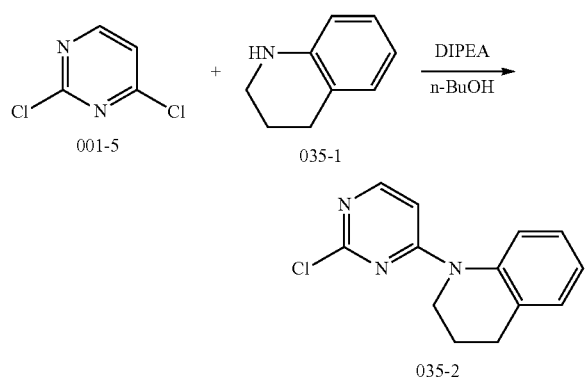

The intermediate 001-5 (3 g, 0.02 mol), 30 mL of n-butanol, the intermediate 035-1 (1.8 g, 0.013 mol) and DIPEA (3.35 g, 0.026 mol) were added into a 100 mL single-necked flask sequentially, and then the reaction was heated to 105° C. and maintained for 2.5 h. The reaction was cooled to room temperature, and the reaction mixture was subjected to rotary evaporation, and the crude product was purified through silica gel column chromatography (eluent: EA:PE=1:15) to give 1.6 g of the intermediate 035-2 (48%) as a white solid. LCMS: 246.1.

2. Synthesis of Intermediate 035-3

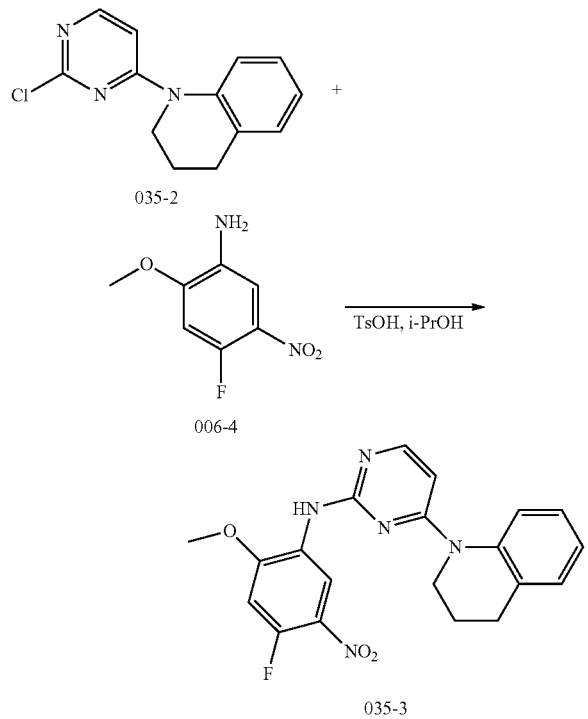

The reaction step and condition of synthesizing the intermediate 035-3 were the same as those of the third step in Example 6, except that the intermediate 006-2 in the example 6 was replaced with the intermediate 035-2 as a starting material in the this step. LCMS: 396.1.

3. Synthesis of Compound 35

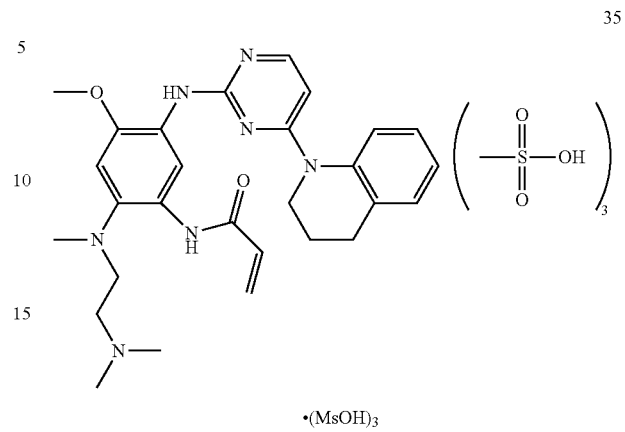

35

·(MsOH)$_3$

The reaction steps and conditions of synthesizing compound 35 and the methanesulfonate (MsOH)$_3$ of compound 35 were the same as those from the first step to the third step in Example 7, except that the intermediate 006-5 in the first step of the example 7 was replaced with the intermediate 035-3 in the this step and the intermediate 007-1 as a raw material in the first step of the example 7 was replaced with the intermediate 001-10 in the this step. The analysis data of the methanesulfonate (MsOH)$_3$ of compound 35: LCMS (parent molecule) C$_2$H$_{35}$N$_7$O$_2$: (ES, m/z): [M+H]$^+$=502.

$^1$H-NMR (300 MHz, D$_2$O, ppm) δ 1.75-1.90 (m, 2H), 2.46-2.51 (m, 2H), 2.69-2.76 (m, 18H), 3.19 (m, 2H), 3.42-3.46 (m, 2H), 3.68 (m, 2H), 3.83 (m, 2H), 5.86-5.89 (d, J=10.5 Hz, 1H), 6.23-6.29 (m, 1H), 6.51-6.54 (m, 2H), 6.97-7.11 (m, 5H), 7.5-8.2 (m, 2H).

Example 36

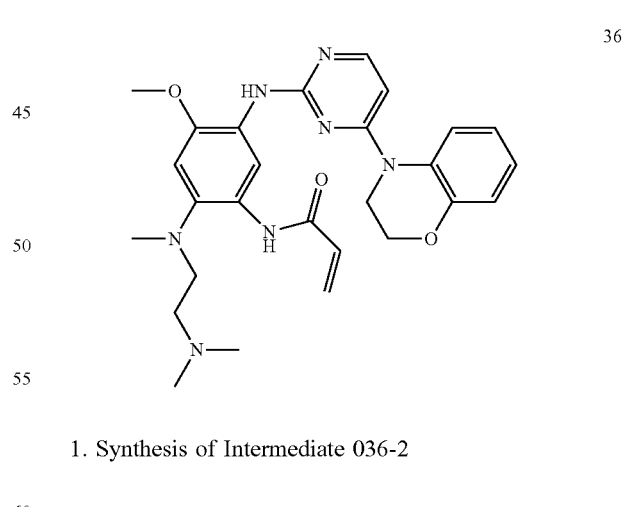

36

1. Synthesis of Intermediate 036-2

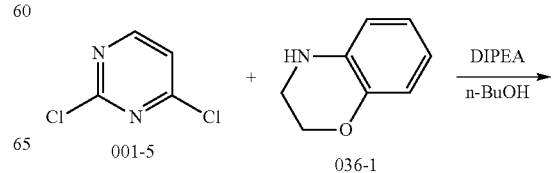

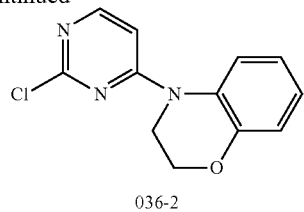

036-2

The reaction step and condition of synthesizing the intermediate 036-2 were the same as those of the first step in Example 35. LCMS: 248.1.

2. Synthesis of Intermediate 036-3

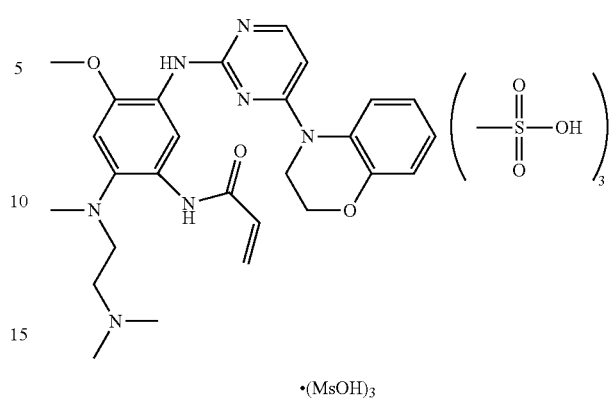

The reaction step and condition of synthesizing the intermediate 036-3 were the same as those of the third step in Example 6, except that the intermediate 006-2 in the example 6 was replaced with the intermediate 036-2 as a starting material in the this step. LCMS: 398.1.

3. Synthesis of Compound 036

The reaction steps and conditions of synthesizing compound 36 and the methanesulfonate (MsOH)₃ of compound 36 from the intermediate 036-3 were the same as those from the first step to the third step in Example 7, except that the intermediate 006-5 in the first step of the example 7 was replaced with the intermediate 036-3 in the this step and the intermediate 007-1 as a raw material in the first step of the example 7 was replaced with the intermediate 001-10 in the this step. The analysis data of the methanesulfonate (MsOH)₃ of compound 36:

36

•(MsOH)₃

LCMS (parent molecule) $C_{27}H_{33}N_7O_3$: (ES, m/z): [M+H]⁺=504 [M+1]⁺.

¹H-NMR (300 MHz, D₂O, ppm) δ 2.63 (s, 3H), 2.70 (s, 12H), 2.78 (s, 3H), 3.21 (m, 2H), 3.40-3.36 (m, 2H), 3.80 (s, 3H), 3.96 (m, 2H), 4.17 (m, 2H), 5.84-5.87 (d, J=10.8 Hz, 1H), 6.22-6.27 (m, 1H), 6.41-6.50 (m, 1H), 6.82-6.93 (m, 4H), 7.06 (br s, 1H), 7.73-7.85 (m, 2H).

Example 37

37

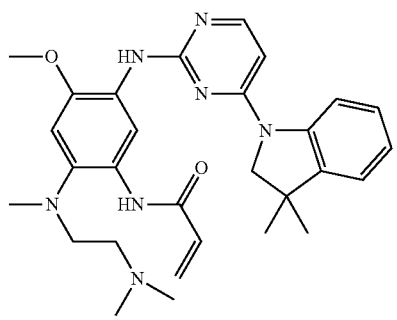

1. Synthesis of Intermediate 037-2

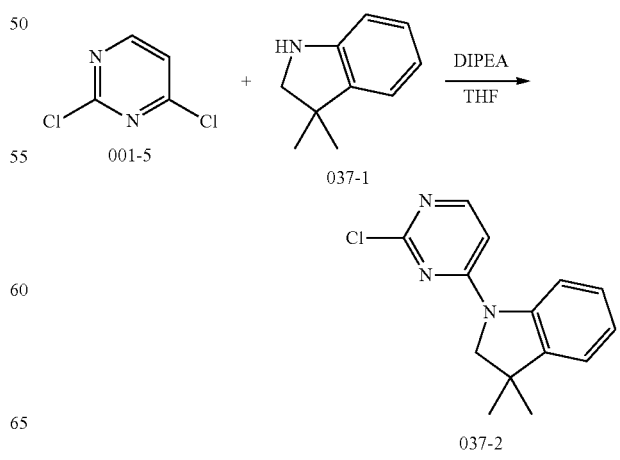

The intermediate 001-5 (2.22 g, 14.9 mmol), anhydrous THF (25 mL), 037-1 (1.5 g, 10.2 mmol) and DIPEA (2.58 g, 20.0 mmol) were added into a 100 mL single-necked flask sequentially, and then the reaction was heated to 75° C. and maintained under stirring for 2.5 h. The reaction was cooled to room temperature, and the reaction mixture was subjected to rotary evaporation, and the crude product was purified through silica gel column chromatography (eluent: EA:PE=1:15) to give 1.5 g of the intermediate 037-2 (57%) as a white solid. LCMS: 260.1.

2. Synthesis of Intermediate 037-3

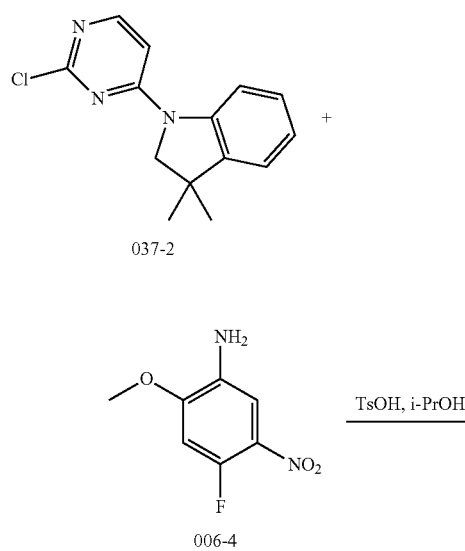

3. Synthesis of Compound 37

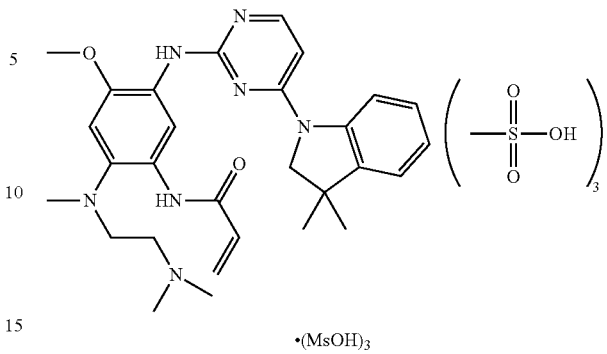

The reaction steps and conditions of synthesizing compound 37 and the methanesulfonate $(MsOH)_3$ of compound 37 from the intermediate 037-3 were the same as those from the third step to the fifth step in Example 3, except that the intermediate 003-3 in the third step of the example 3 was replaced with the intermediate 037-3 in the this step. The analysis data of the methanesulfonate $(MsOH)_3$ of compound 37:

LCMS (parent molecule) $C_{29}H_{37}N_7O_2$: (ES, m/z): $[M+H]^+=516$. $^1H$-NMR (300 MHz, $D_2O$, ppm) δ 1.03-1.12 (s, 6H), 2.70-2.79 (m, 18H), 3.24-3.26 (m, 2H), 3.43 (m, 2H), 3.65 (m, 2H), 3.79 (s, 3H), 5.78-5.82 (d, J=10.5 Hz, 1H), 6.16-6.22 (m, 2H), 6.38-6.44 (m, 1H), 6.75 (m, 1H), 6.93-7.00 (m, 2H), 7.11-7.13 (m, 1H), 7.61-7.78 (m, 3H).

Example 38

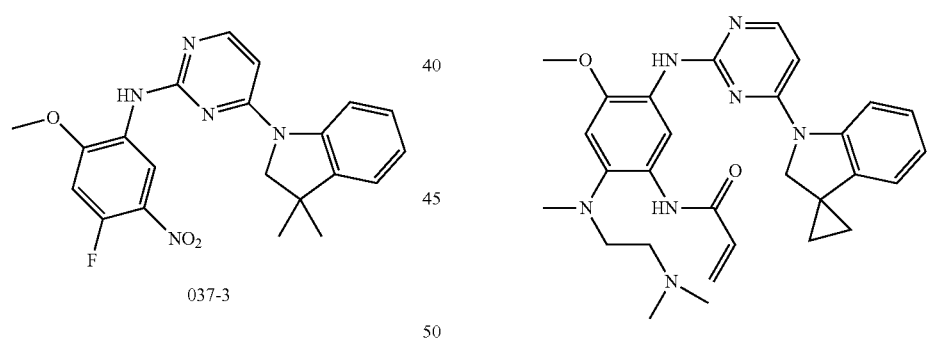

1. Synthesis of Intermediate 038-2

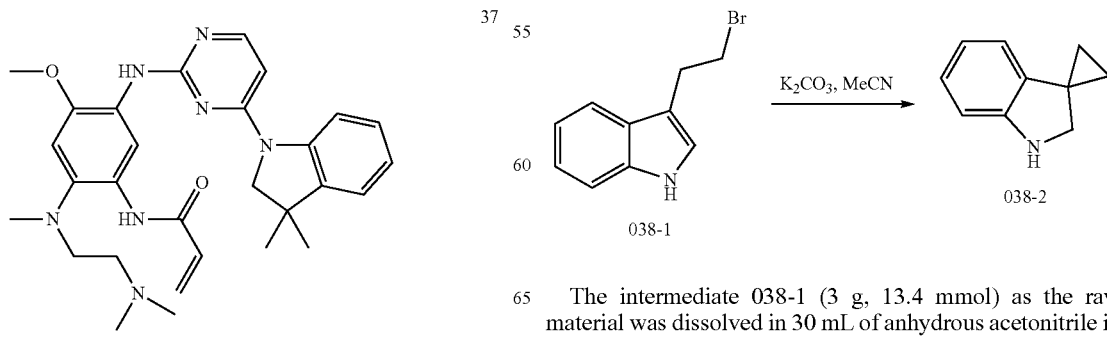

The intermediate 038-1 (3 g, 13.4 mmol) as the raw material was dissolved in 30 mL of anhydrous acetonitrile in a 100 mL three-necked flask at room temperature under a nitrogen atmosphere, followed by the addition of anhydrous potassium carbonate (5.57 g, 40.0 mmol). The temperature was raised to 60° C. overnight. The next day, the reaction system was cooled to room temperature. The mixture was filtered and the filter cake was washed once with 10 mL of anhydrous ethanol. The filtrate was collected and the filtrate temperature was reduced to 0° C. Sodium borohydride (511 mg, 13.9 mmol) was added in batches, and then heated up to room temperature and the reaction was carried out for 2 h. After the reaction was completed, the reaction was quenched by adding 1 mL of water and the reaction mixture was concentrated. The crude product was purified through silica gel column chromatography (eluent: EA/PE=1:10-1:3) to give 1.45 g of the intermediate 038-2 (75%) as a yellow oil. LCMS: 146.1.

2. Synthesis of Intermediate 038-4

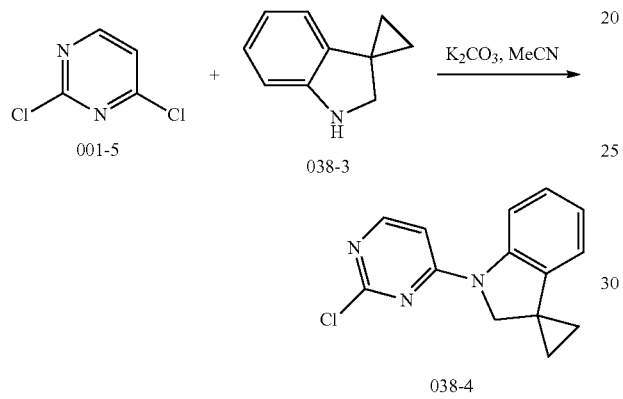

The intermediate 038-3 (1.45 g, 9.99 mmol) as raw material was dissolved in 30 mL of anhydrous acetonitrile in a 100 mL three-necked flask at room temperature under a nitrogen atmosphere, followed by adding anhydrous potassium carbonate (4.14 g, 29.7 mmol) and 2,4-dichloropyrimidine (1.48 g, 9.93 mmol). The temperature was raised to 60° C. overnight and the reaction was stirred overnight. The next day, the reaction was completed, followed by that the reaction system was cooled to room temperature, diluted with 100 mL of water and extracted with 100 mL of methylene chloride 3 times. The organic phases were combined, backwashed with 100 mL of saturated brine 3 times, dried over anhydrous sodium sulfate, and then concentrated. The crude product was purified through silica gel column chromatography (EA/PE=1:10-1:3) to give 0.9 g of the intermediate 038-4 (35%) as a white solid. LCMS: 258.1.

3. Synthesis of Intermediate 038-6

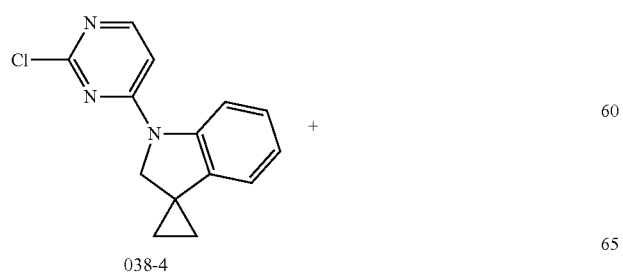

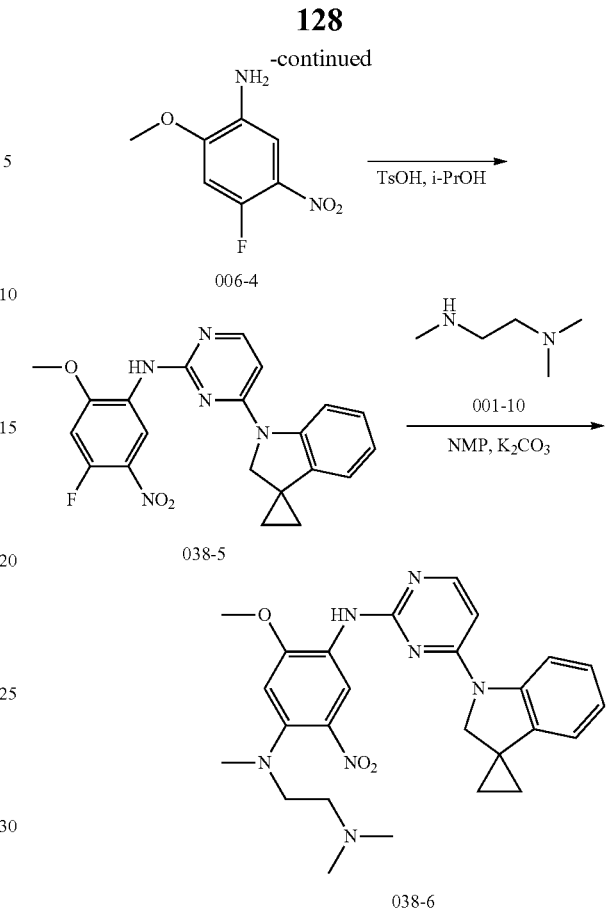

The reaction step and condition of synthesizing the intermediate 038-6 were the same as those of the sixth step and the seventh step in Example 1. LCMS: 490.2

4. Synthesis of Intermediate 038-7

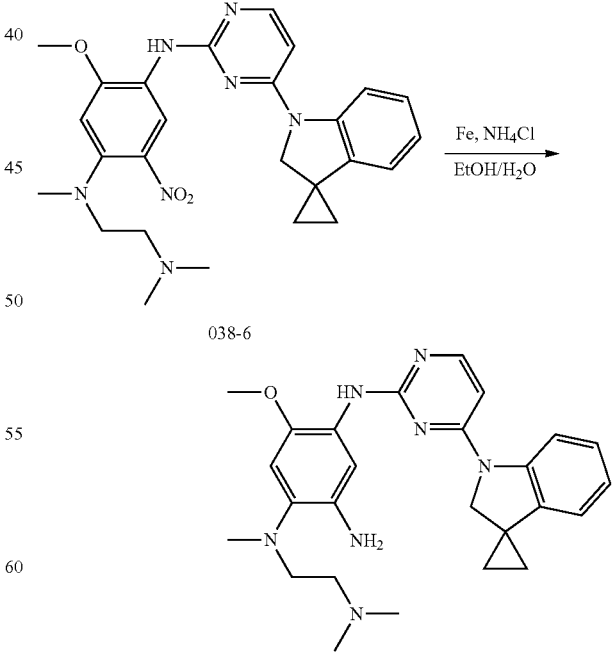

The intermediate 038-6 (700 mg, 1.43 mmol) as a raw material was dissolved in 30 mL of anhydrous ethanol and 10 mL water in a 100 mL single-necked flask at room temperature, and iron powder (481 mg, 8.61 mmol) and ammonium chloride (53 mg, 0.99 mmol) were added into the reaction system sequentially. Then, the reaction was heated to 85° C. and carried out overnight. After the reaction was completed, the reaction system was cooled to room temperature. The reaction mixture was filtered, and the filtrate was collected concentrated to dryness. The residue was purified by Prep-HPLC (column: C18 silica gel; flow phase: acetonitrile/water (0.05% trifluoroacetic acid); 30% acetonitrile to 50% acetonitrile; 5 min; detection wavelength: 254 nm) to give 600 mg of the intermediate 038-7 (73%) as a white solid. LCMS: 460.3.

5. Synthesis of Compound 38

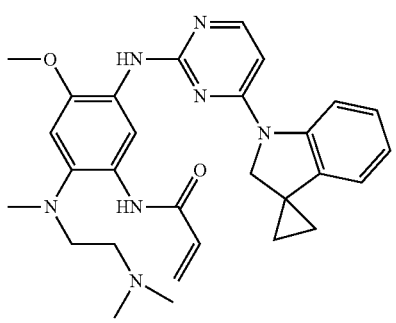

38

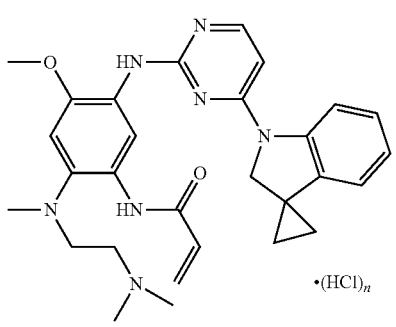

38

The reaction steps and conditions of synthesizing compound 38 and the hydrochloride (HCl)$_n$ of compound 38 from the intermediate 038-7 were the same as those of the ninth step in Example 1. The analysis data of the hydrochloride (HCl) of compound 38: LCMS (parent molecule) $C_{29}H_{35}N_7O_2$: (ES, m/z): 514 [M+H]$^+$. $^1$H-NMR: (300 MHz, DMSO-D$_6$, ppm) δ 1.09-1.21 (m, 4H), 2.66 (s, 3H), 2.74 (s, 3H), 2.76 (s, 3H), 3.27-3.35 (m, 4H), 3.83 (s, 3H), 4.23 (s, 2H), 5.67-5.71 (m, 1H), 6.16-6.22 (m, 1H), 6.87-6.88 (m, 1H), 7.02 (m, 3H), 7.14-7.22 (m, 1H), 8.03-8.17 (m, 2H), 9.94 (br s, 1H), 10.60 (br s, 1H).

Example 39

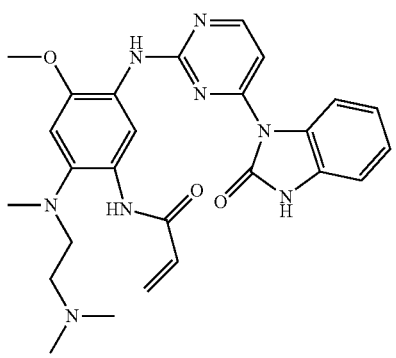

39

1. Synthesis of Intermediate 039-2

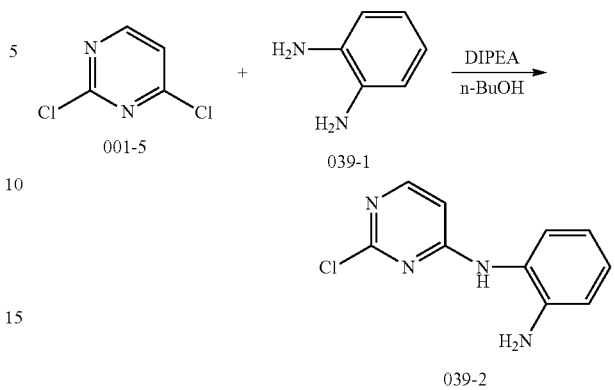

The intermediate 001-5 (8.8 g, 59.1 mmol), the intermediate 039-1 (7.06 g, 65.4 mmol), n-butanol (70 mL) and DIPEA (15.4 g, 119.2 mmol) were sequentially added in a 250 mL single-necked flask under a nitrogen atmosphere. The reaction was raised to 110° C. and stirred overnight. The reaction system was cooled to room temperature and then the reaction system was subjected to rotary evaporation. A solution of 0.1 M hydrochloric acid (HCl) (300 mL) was added and a solid was precipitated. The reaction mixture was filtered, the filter cake was collected and washed three times with anhydrous ether (100 mL). The filter cake was dried to give 5.0 g of crude product 039-2 (38%) as a white solid. LCMS: 221.1.

2. Synthesis of Intermediate 039-4

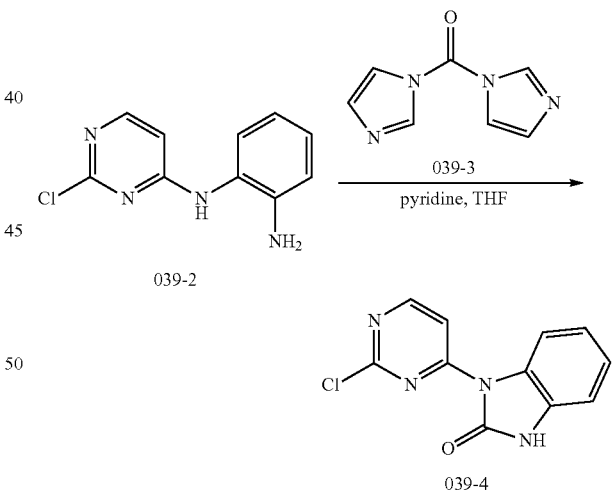

The intermediate 039-2 (5.0 g, 22.7 mmol), 100 mL of anhydrous THF, carbonyldiimidazole (CDI) (039-3) (7.37 g, 45.5 mmol) and pyridine (3.59 g, 45.4 mmol) were sequentially added in a 250 mL three-necked flask under a nitrogen atmosphere, followed by that the reaction system was heated to 64° C. and stirred for 2 h. The reaction was cooled to room temperature and quenched with 500 mL of ice water to precipitate a solid. The mixture was filtered to collect the filter cake which was dried to give 4.1 g of crude product 039-4 (73%) as a white solid product. LCMS: 247.0.

3. Synthesis of Intermediate 039-6

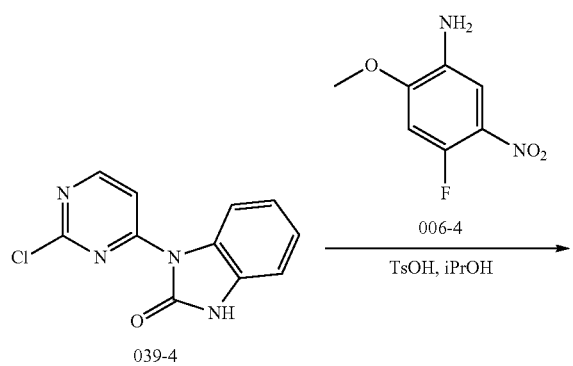
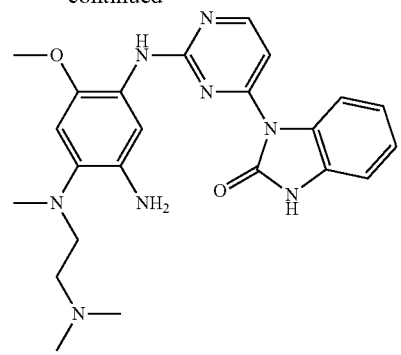

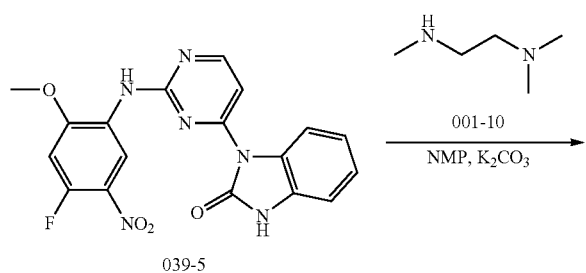

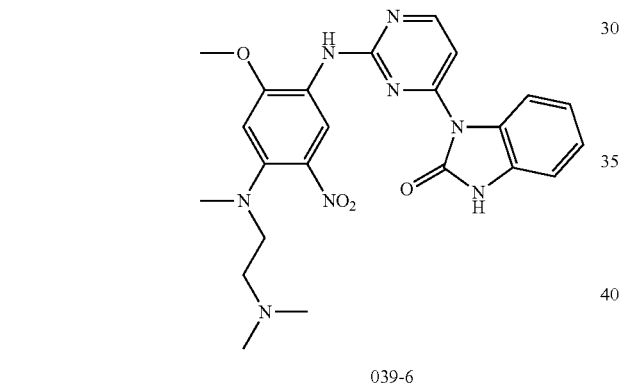

The reaction step and condition of synthesizing intermediate 039-6 were the same as those of the sixth and seventh steps in Example 1. LCMS: 479.2

4. Synthesis of Intermediate 039-7

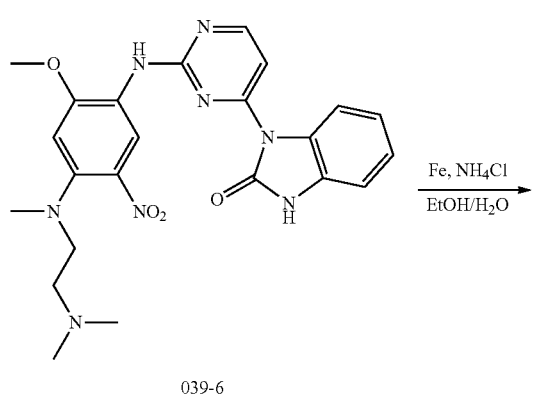

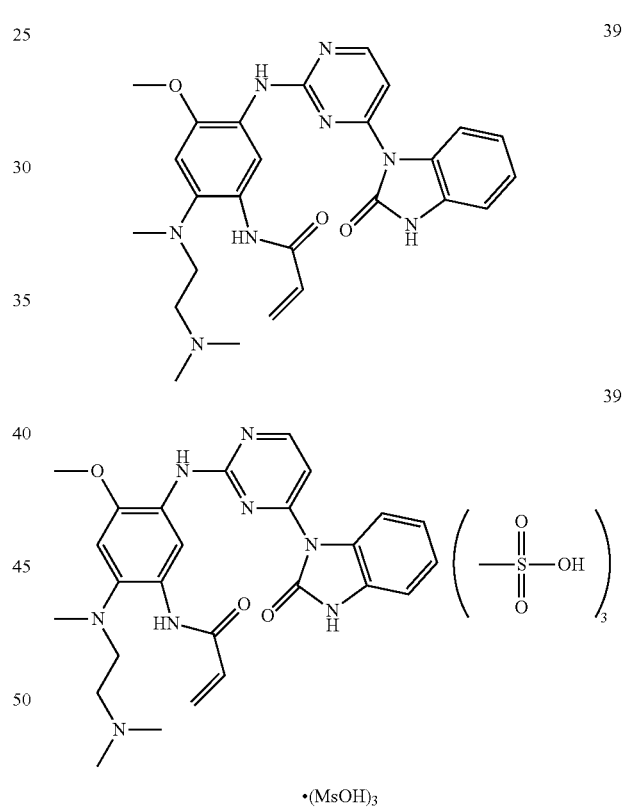

The reaction step and condition of synthesizing intermediate 039-7 were the same as those of the fourth step in Example 38. LCMS: 449.2.

5. Synthesis of Compound 39

The reaction steps and conditions of synthesizing compound 39 and the methanesulfonate (MsOH)$_3$ of compound 39 from the intermediate 038-7 were the same as those of the ninth step in Example 1. The analysis data of the methanesulfonate (MsOH)$_3$ of compound 39: LCMS (parent molecule) $C_{26}H_{30}N_8O_3$: (ES, m/z): [M+H]$^+$=503. $^1$H-NMR (300 MHz, D$_2$O, ppm) δ 2.66 (s, 3H), 2.71 (s, 9H), 2.81 (s, 6H), 3.27-3.38 (m, 4H), 3.74 (s, 3H), 5.82-5.85 (d, J=10.5 Hz, 1H), 6.22-6.28 (d, J=17.1 Hz, 1H), 6.44-6.53 (m, 1H), 6.64-6.67 (m, 1H), 6.87-7.02 (m, 3H), 7.45 (m, 1H), 7.66-7.74 (m, 2H), 8.03-8.06 (m, 1H).

Example 40

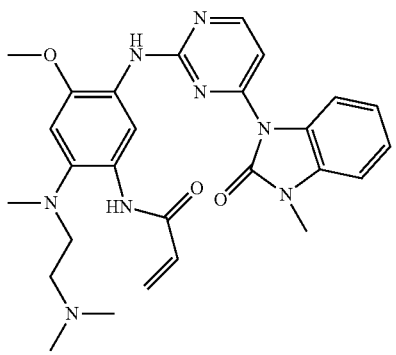

40

1. Synthesis of Intermediate 040-1

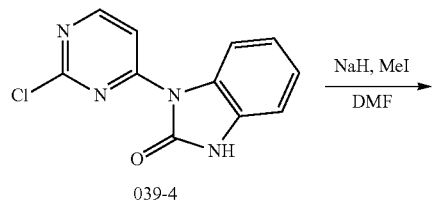

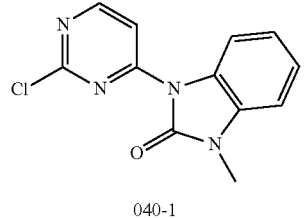

The intermediate 039-4 (1.5 g, 6.08 mmol) and anhydrous N,N-dimethylformamide (DMF) (30 mL) were sequentially added in a 100 mL three-necked flask under a nitrogen atmosphere, followed by cooling the reaction system to 0° C. Sodium hydride (NaH) (220 mg 9.17 mmol) was added in batches for 10 min. The reaction system was incubated at 0° C. for 1 h. In the condition of darkness, the reaction was carried out by adding methyl iodide (1.37 g, 9.65 mmol) for 4 h, and then quenched by adding 400 mL of ice water and a solid was precipitated. The reaction mixture was filtered, the filter cake was collected and dried to give 1.5 g of crude product 040-1 (95%) as a white solid.

2. Synthesis of Intermediate 040-2

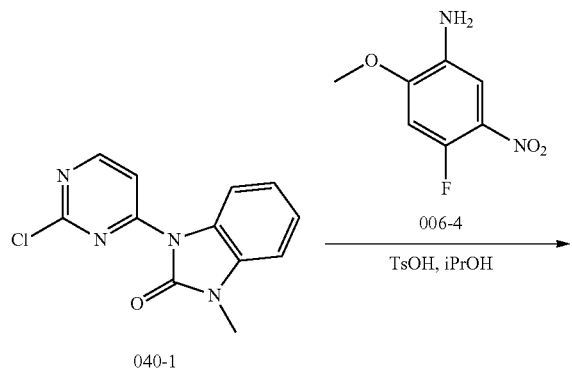

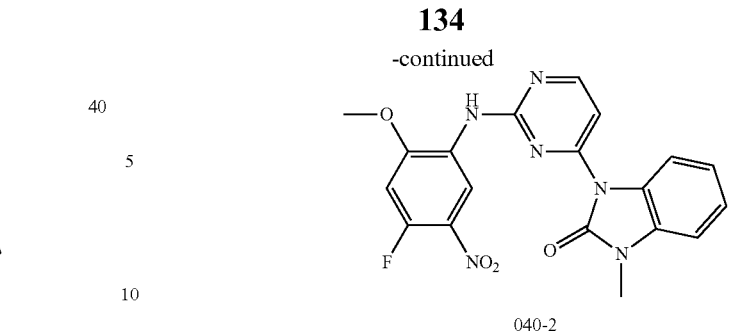

The intermediate 040-1 (1.5 g, 5.75 mmol), intermediate 006-4 (1.07 g, 5.76 mmol), isopropanol (30 mL) and p-tolunesulfonic acid (1.19 g, 6.92 mmol) were sequentially added into a 100 mL of single-necked flask under a nitrogen atmosphere, followed by heating the reaction system to 105° C. and stirred overnight. The reaction was cooled to room temperature.

The reaction mixture was filtered to collect the filter cake which was washed with 50 mL of isopropanol three times and washed with 100 mL of acetonitrile three times, and dried to give 1.3 g of crude product 040-2 (55%) as a yellow solid. LCMS: 411.1.

3. Synthesis of Intermediate 040-3

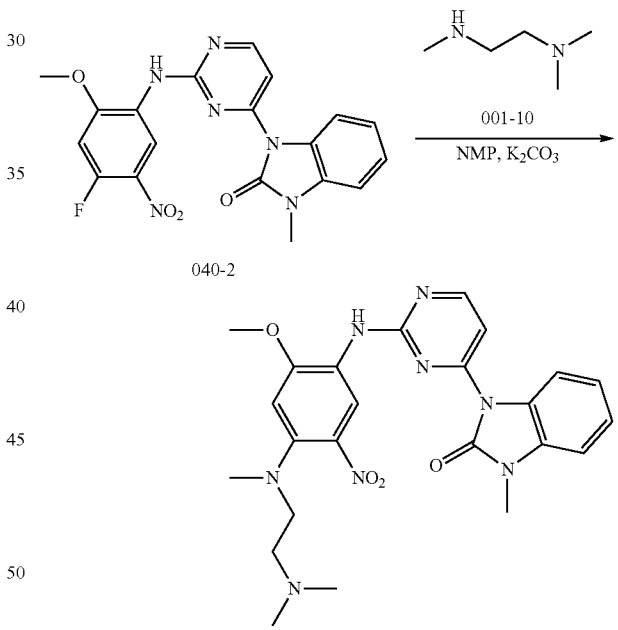

Anhydrous NMP (20 mL), the intermediate 040-2 (1.3 g, 3.17 mmol), the intermediate 001-10 (485 mg, 4.75 mmol) and anhydrous $K_2CO_3$ (1.31 g, 9.43 mmol) were sequentially added in a 100 mL single-necked flask under a nitrogen atmosphere, followed by heating the reaction system to 100° C. and stirred for 5 h. Then, the reaction system was cooled to a room temperature, and quenched by adding 500 mL of ice water. The reaction mixture was filtered, the filter cake was collected, washed with 50 mL of ether three times and dried to give 1.2 g of crude product 040-3 (77%) as a red solid.

LCMS: 493.2.

4. Synthesis of Intermediate 040-4

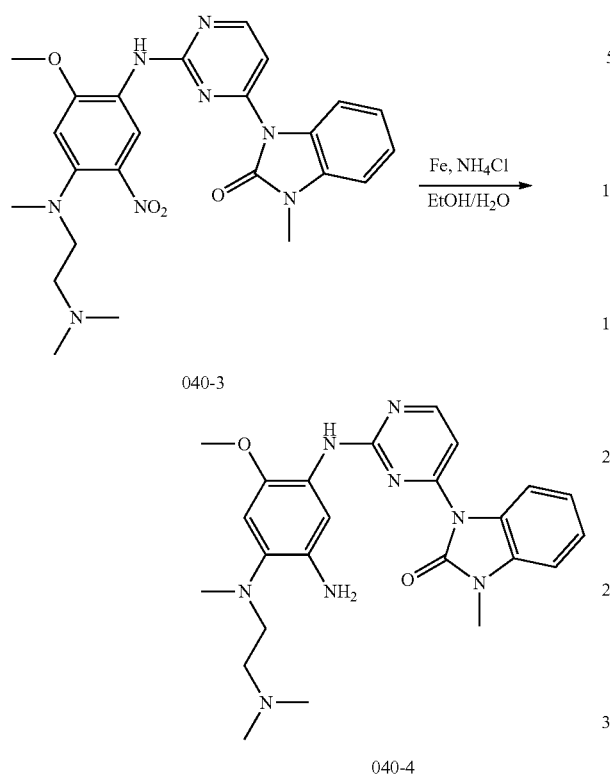

040-3

040-4

Anhydrous ethanol (180 mL), water (60 mL), the intermediate 040-3 (1.2 g 2.44 mmol), iron powder (Fe) (820 mg, 14.7 mmol) and ammonium chloride (91 mg, 1.70 mmol) were sequentially added into a 500 mL of single-necked flask under a nitrogen atmosphere, followed by heating the reaction system to 85° C. and stirred overnight. The reaction mixture was filtered, and the filtrate was concentrated to dryness. The crude product was purified by high pressure liquid chromatography (Prep-HPLC) (column type: Waters X-bridge RP18, 19×150 mm, 5 um; mobile phase: acetonitrile/water (0.05% TFA), 33% acetonitrile to 37% acetonitrile, 5 min, flow rate: 20 mL/min; detection wavelength: 254 nm). The collected product was concentrated to dryness to give 0.7 g of crude product 040-4 (62%) as a gray solid. LCMS: 463.2.

5. Synthesis of Compound 40

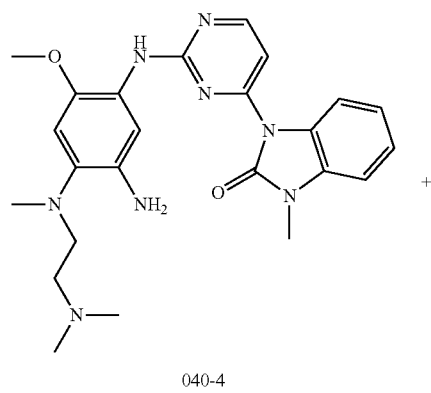

040-4

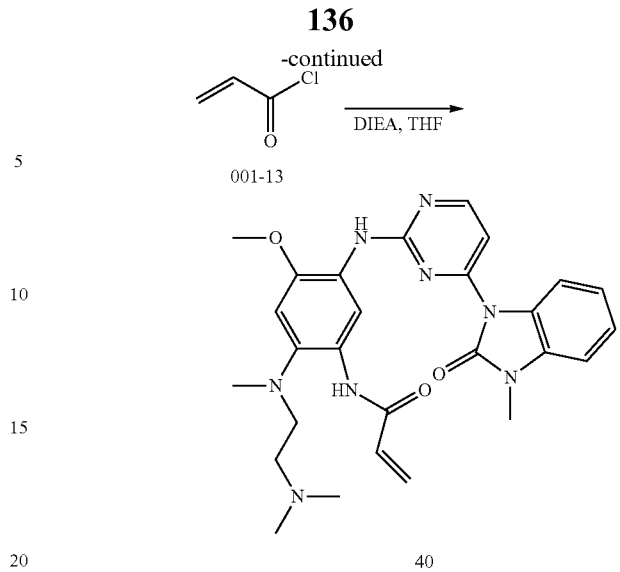

001-13

40

The intermediate 040-4 (300 mg, 0.65 mmol), anhydrous THF (20 mL) and DIPEA (167.6 mg, 1.30 mmol) were sequentially added into a 50 mL of three-necked flask under a nitrogen atmosphere, followed by cooling the reaction system to 0° C. and the intermediate 001-13 (53 mg, 0.59 mmol) was added thereto. The reaction mixture was incubated for 1 h at 0° C. and then subjected to rotary evaporation. The crude product was purified by high pressure liquid chromatography (Prep-HPLC) (column type: Waters X-bridge RP18, 19×150 mm, 5 um; mobile phase: water (0.05% aqueous ammonia)/acetonitrile, 50% acetonitrile to 55% acetonitrile, 5 min, flow rate: 20 mL/min; detection wavelength: 254 nm), collected, and concentrated to dryness to give 120 mg of product 40.

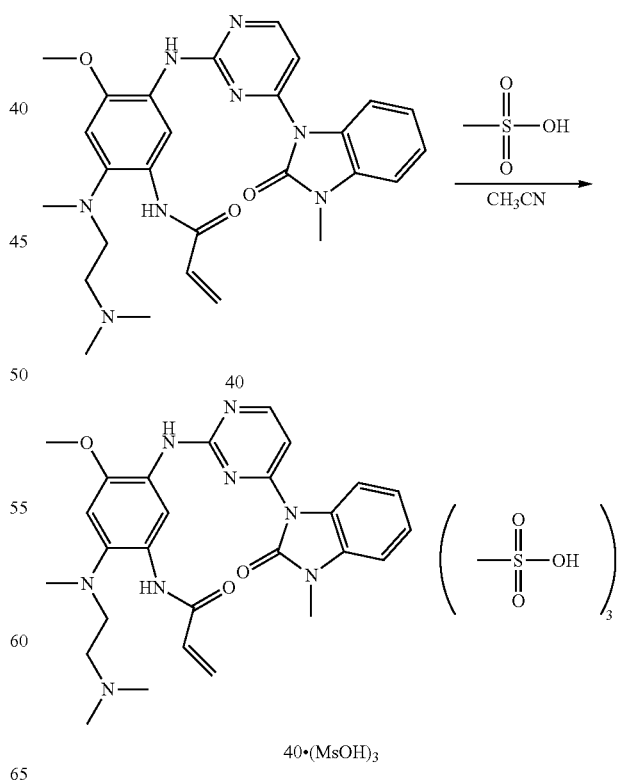

40·(MsOH)₃

120 mg of the product was dissolved in 50 mL of acetonitrile, 67 mg of methanesulfonic acid was added and stirred at room temperature for 1 h. The reaction mixture was filtered, and the filter cake was collected and dried to give 0.156 g of methanesulfonate (MsOH)₃ of compound 40 (30%) as a yellow solid. LCMS (parent molecule) C$_{27}$H$_{32}$N$_8$O$_3$: (ES, m/z): [M+H]$^+$=517. ¹H-NMR (300 MHz, D$_2$O, ppm) δ 2.66 (s, 3H), 2.71 (s, 9H), 2.82 (s, 6H), 3.04 (s, 3H), 3.29-3.38 (m, 4H), 3.78 (s, 3H), 5.83-5.86 (d, J=10.8 Hz, 1H), 6.24-6.30 (d, J=16.8 Hz, 1H), 6.46-6.61 (m, 2H), 6.80-6.82 (m, 1H), 6.96-6.99 (m, 2H), 7.45 (m, 1H), 7.63-7.70 (m, 2H), 8.03 (d, J=6.3 Hz, 1H).

Example 41

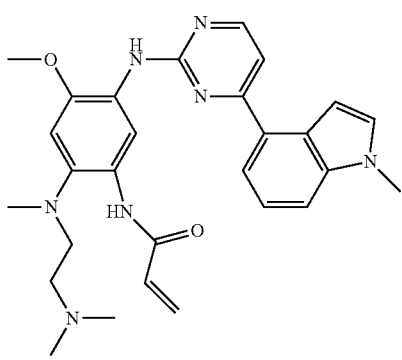

1. Synthesis of Intermediate 041-2

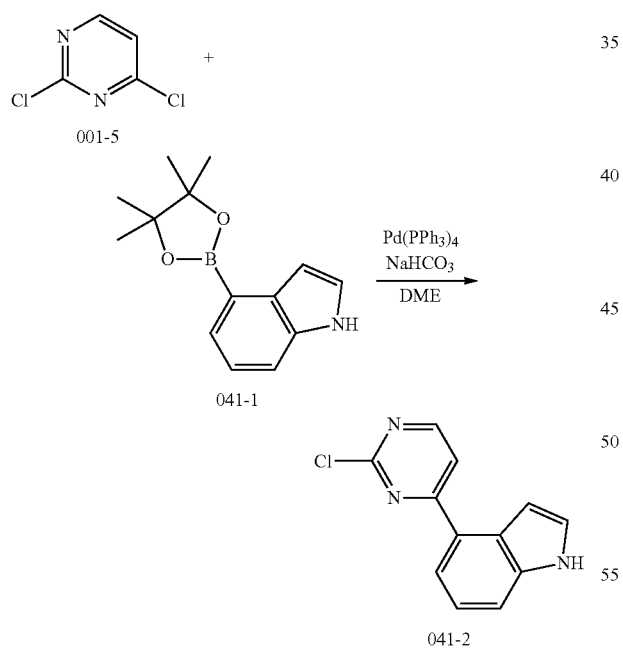

The intermediate 001-5 (2.0 g, 13.4 mmol) was dissolved in DME (100 mL) in a 250 mL of three-necked flask under a nitrogen atmosphere, followed by addition of the intermediate 041-1 (2.96 g, 12.2 mmol), tetrakis(triphenylphosphine)palladium (1.0 g, 2.68 mmol) and sodium bicarbonate (40 mL, 1.0 M of aqueous solution). The reaction system was heated to reflux for 3 hours under nitrogen. After the reaction was completed, the reaction was quenched by adding 100 mL of ice water. The reaction system was extracted with 200 mL of ethyl acetate twice. The organic phases were combined, washed twice with 100 mL of saturated brine and purified by silica gel column chromatography (100-200 mesh silica gel, eluent: PE:EA=100:1) to give 1.9 g of product 041-2 (62%) as a yellow solid. LCMS: 230.0

2. Synthesis of Intermediate 041-3

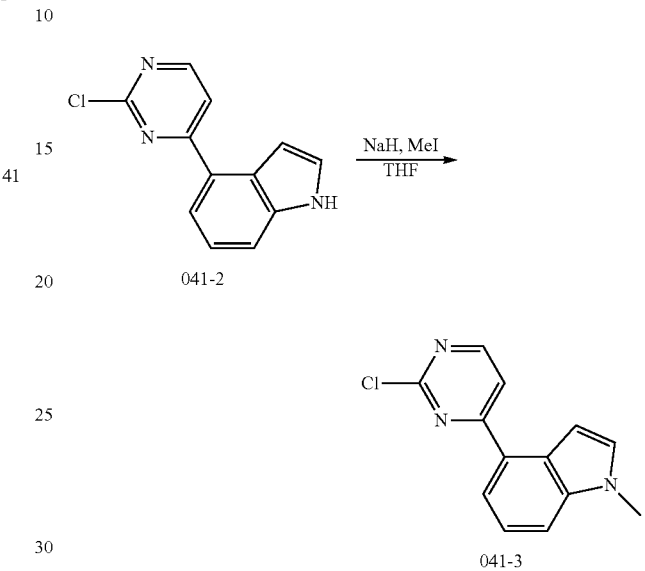

The intermediate 041-2 (1.9 g, 8.29 mmol) was dissolved in 50 mL of anhydrous tetrahydrofuran. Maintaining the reaction temperature at 0-10° C., sodium hydride (NaH) (dispersed in mineral oil at a content of 60%) (829 mg, 20.7) was added in batches, then stirring for 30 min at 0° C. Iodomethane (MeI) (1.4 g, 10.3 mmol) was added to the reaction system and then the reaction temperature was heated up to room temperature. The reaction was continued for 2 hours. After the reaction was completed, 20 mL of ice water was added to quench the reaction. The reaction mixture was extracted with 50 mL of ethyl acetate twice. The organic phases were combined, washed twice with 50 mL of saturated brine, dried over anhydrous sodium sulfate and concentrated to dryness, so as to give 1.1 g of crude product 041-3 (55%) as a yellow solid. LCMS: 244.1.

3. Synthesis of Compound 41

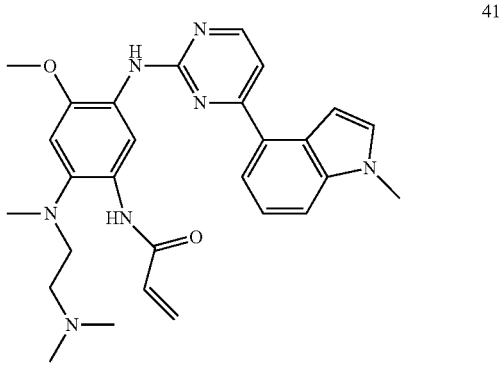

41

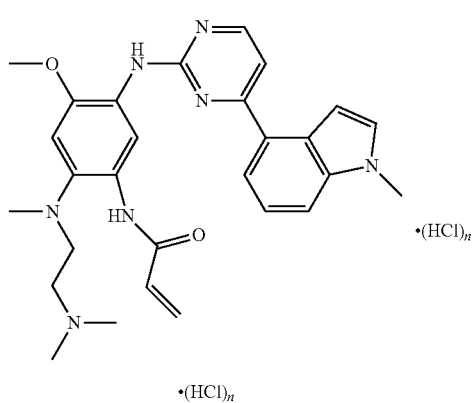

•(HCl)$_n$

The reaction steps and conditions of synthesizing the hydrochloride (HCl)$_6$ of compound 41 from the intermediate 041-3 were the same as those of the sixth to the ninth steps in Example 1. The analysis data of the hydrochloride (HCl)$_n$ of compound 41: LCMS (parent molecule) C$_{28}$H$_{33}$N$_7$O$_2$: (ES, m/z): [M+H]$^+$=500. $^1$H-NMR: (300 MHz, DMSO-D$_6$, ppm) δ 2.64 (s, 3H), 2.74-2.76 (d, J=4.8 Hz, 6H), 3.23-3.32 (m, 4H), 3.71-3.85 (m, 3H), 3.87-3.91 (d, J=14.1 Hz, 3H), 5.68-5.73 (m, 1H), 6.23-6.30 (m, 1H), 6.98 (s, 1H), 7.06-7.13 (m, 2H), 7.27-7.33 (m, 1H), 7.47-7.53 (m, 2H), 7.70 (t, J=7.8 Hz, 1H), 7.89 (t, J=7.5 Hz, 1H), 8.45-8.49 (m, 2H), 9.82 (s, 1H), 10.34-10.37 (m, 1H).

Example 42

42

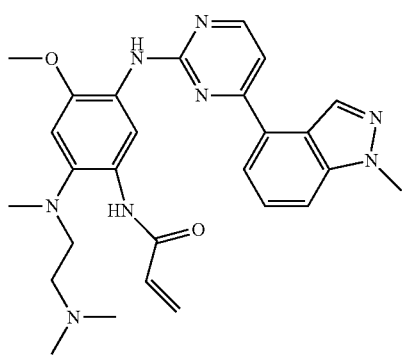

1. Synthesis of Intermediate 042-2

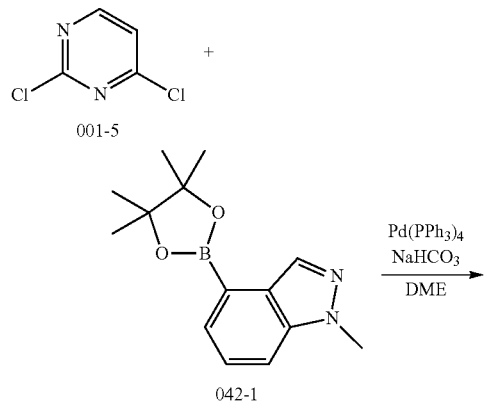

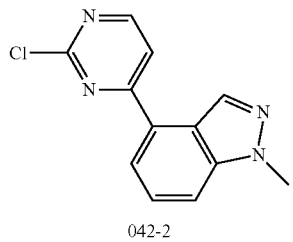

042-2

The reaction steps and conditions of synthesizing the intermediate 042-2 were the same as those of the first step in Example 41. LCMS: 245.1.

2. Synthesis of Compound 42

The reaction steps and conditions of synthesizing the compound 42 and hydrochloride (HCl)$_n$ of compound 42 from the intermediate 042-2 were the same as those of the third to the fifth steps in Example 38. The analysis data of the hydrochloride (HCl)$_n$ of compound 42: LCMS (parent molecule) C$_{27}$H$_{32}$N$_8$O$_2$: (ES, m/z): [M+H]+=501. $^1$H-NMR (300 MHz, DMSO-D$_6$, ppm) δ 2.66 (s, 3H), 2.76 (s, 3H), 2.78 (s, 3H), 3.30-3.38 (m, 4H), 3.80 (s, 3H), 4.08 (s, 3H), 5.67-5.70 (m, 1H), 6.12-6.25 (m, 1H), 7.05 (s, 1H), 7.25-7.34 (m, 1H), 7.54-7.59 (m, 1H), 7.75-7.77 (d, J=6.3 Hz, 1H), 7.95-7.96 (d, J=8.4 Hz, 1H), 8.12-8.15 (d, J=7.5 Hz, 1H), 8.29 (s, 1H), 8.39 (br s, 1H), 8.50-8.52 (m, 1H), 9.90 (s, 1H), 10.15 (br s, 1H), 10.86 (br s, 1H).

Example 43

43

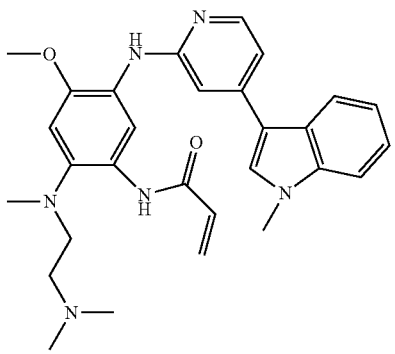

1. Synthesis of Intermediate 043-3

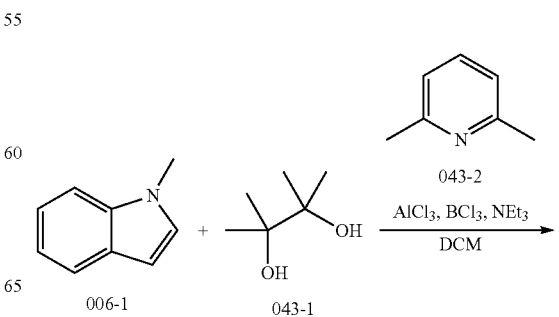

-continued

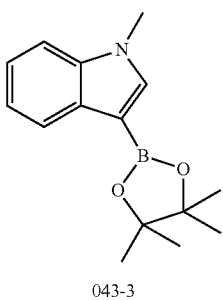

043-3

Aluminum trichloride (5.9 g, 69.5 mmol) was dissolved in methylene dichloride (DCM) (134 mL) at room temperature in a 1000 mL of three-necked flask under nitrogen atmosphere, followed by sequentially adding the intermediate 043-2 (4.9 mL) and boron trichloride ($BCl_3$) (40 mL, 1 M of dichloromethane solution). The reaction was carried out at room temperature for 0.5 h, and then the intermediate 006-1 (5 g, 38.1 mmol) added. Next, the reaction was continued at room temperature for 2 h. Then, the reaction mixture was cooled to 0° C., and dropping a solution of intermediate 043-1 (9.36 g, 83.0 mmol) dissolved in 84.2 mL of pure triethylamine ($NEt_3$, or TEA), then the reaction was continued at room temperature for 2 h. After the reaction was completed, 200 mL of ice water was added to quench the reaction. The mixture was extracted three times with 200 mL of dichloromethane. The organic phases were combined and washed three times with 100 mL of saturated brine. The organic phases were dried with anhydrous sodium sulfate, concentrated to dryness. The crude product was purified by silica gel column chromatography (EA/PE=1:50-1:20) to give 7 g of product 043-3 (71%) as brown oil. LCMS: 258.0.

2. Synthesis of Intermediate 043-5

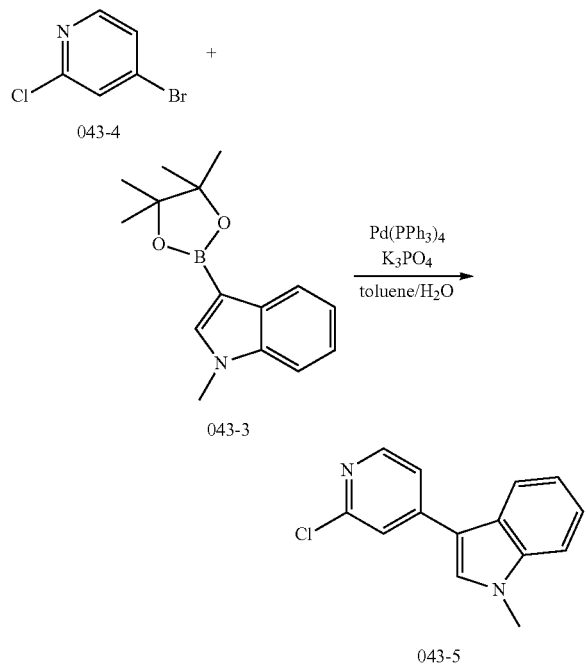

The intermediate 043-4 (0.19 g, 6.18 mmol) was dissolved in 5 mL of toluene and 2.5 mL of water at room temperature in 100 mL of a three-necked flask under nitrogen atmosphere, followed by sequentially adding the intermediate 043-3 (1.6 g, 6.22 mmol), $Pd(PhP_3)_4$ (245 mg, 0.31 mmol), potassium phosphate ($K_3PO_4$) (3.96 g, 18.7 mmol). The reaction was heated to 95° C. overnight. After the reaction was completed, the reaction mixture was cooled to room temperature. The reaction was quenched by adding 100 mL of ice water into the reaction mixture. The obtained mixture was extracted with 100 mL of dichloromethane three times. The organic phases were combined and washed with 300 mL of saturated brine three times. The organic phases were dried over anhydrous sodium sulfate and concentrated to dryness. The product was purified by silica gel column chromatography (EA/PE=1:10-1:3) to give 0.7 g of product 043-5 (47%) as a green solid. LCMS: 243.0.

3. Synthesis of Intermediate 043-6

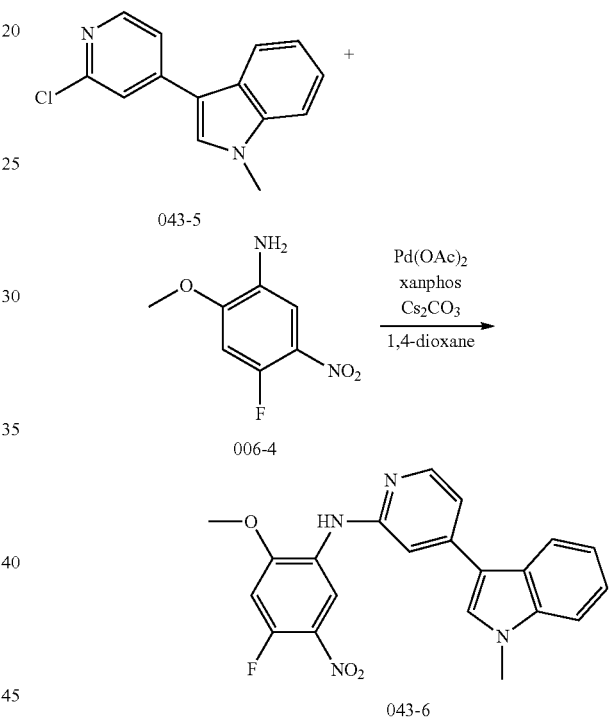

The intermediate 043-5 (0.19 g, 6.18 mmol) as a raw material was dissolved in 1,4-dioxane (10 mL) at room temperature in 100 mL of a three-necked flask under nitrogen atmosphere, followed by sequentially addition of the intermediate 006-4 (538 mg, 2.89 mmol), 4,5-bisdiphenylphosphine-9,9-dimethyloxyanthene (xantphos) (167 mg, 0.29 mmol), cesium carbonate ($Cs_2CO_3$) (1.89 g, 5.77 mmol) and palladium acetate ($Pd(OAc)_2$) (32.4 mg, 0.14 mmol) into the reaction system. After heated to 100° C., the reaction was carried out for 5 h. After the reaction was completed, the reaction mixture was cooled to room temperature. The reaction was quenched by adding 100 mL of ice water into the reaction mixture. The obtained mixture was extracted with 100 mL of dichloromethane three times. The organic phases were combined and washed with 300 mL of saturated brine three times. The organic phases were dried over anhydrous sodium sulfate and concentrated to dryness to give 0.4 g of product 043-6 (36%) as yellow oil. LCMS: 389.0.

4. Synthesis of Intermediate 043-8

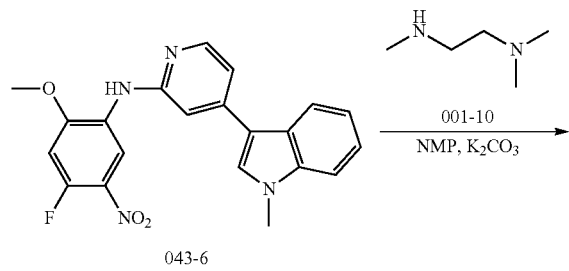

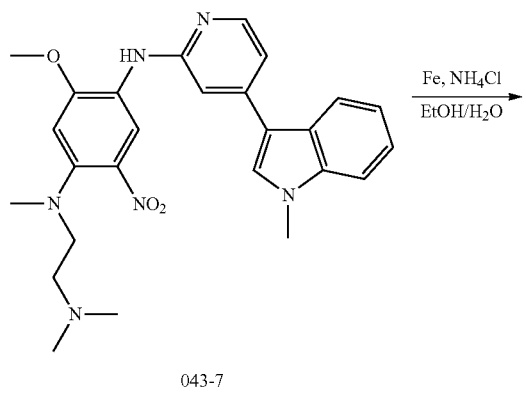

The reaction steps and conditions of synthesizing the intermediate 043-8 from the intermediate 043-6 were the same as those of the third and the fourth steps in Example 40. LCMS: 445.0.

5. Synthesis of Compound 43

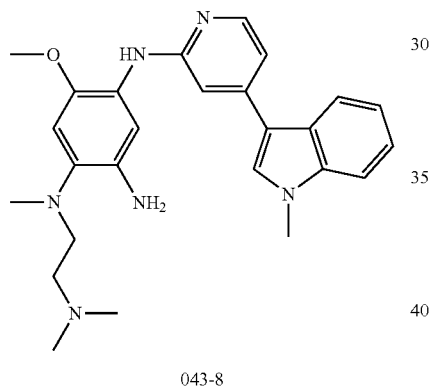

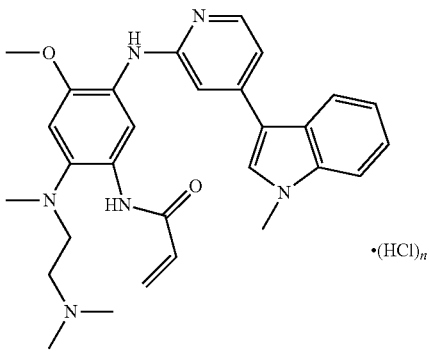

The reaction steps and conditions of synthesizing the compound 43 and hydrochloride (HCl) of compound 43 from the intermediate 043-8 were the same as those of the ninth step in Example 1. The analysis data of the hydrochloride $(HCl)_n$ of compound 43: LCMS (parent molecule) $C_{29}H_{34}N_6O_2$: (ES, m/z): $[M+H]^+=499$. $^1$H-NMR: (300 MHz, DMSO-$D_6$, ppm) δ 10.68 (br s, 1H), 10.22 (s, 1H), 9.95 (s, 1H), 8.41 (s, 1H), 8.09 (s, 1H), 8.00-8.02 (d, J=7.8 Hz, 1H), 7.84-7.86 (d, J=6.9 Hz, 1H), 7.63-7.55 (d, J=7.5 Hz, 1H), 7.55 (s, 1H), 7.22-7.38 (m, 4H), 7.04 (s, 1H), 6.22-6.28 (m, 1H), 5.70-5.74 (m, 1H), 3.91 (s, 3H), 3.86 (s, 3H), 3.36 (m, 4H), 2.75 (s, 3H), 2.73 (s, 3H), δ 2.65 (s, 3H).

Example 44

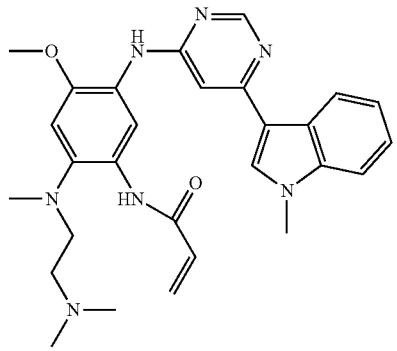

1. Synthesis of Intermediate 044-3

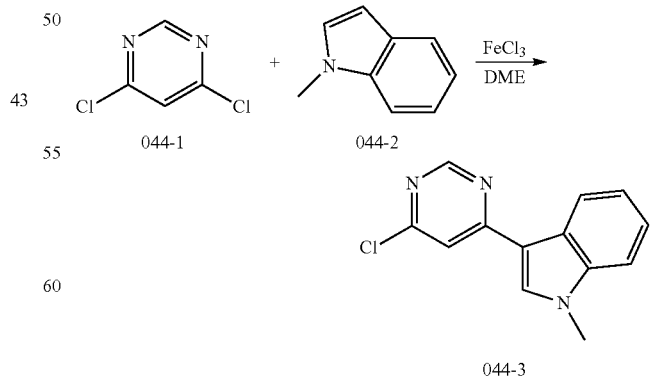

The reaction step and condition of synthesizing intermediate 044-3 were the same as those of the first step in Example 6. LCMS: 244.1.

2. Synthesis of Intermediate 044-6

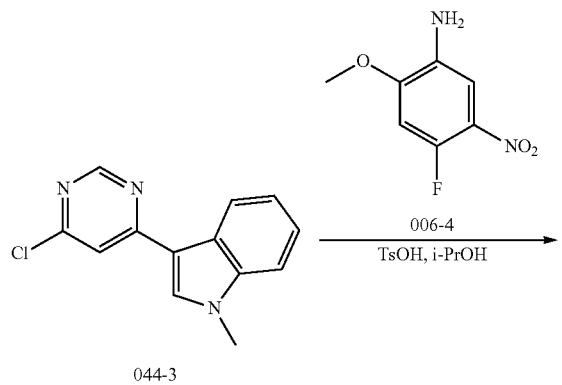

044-3

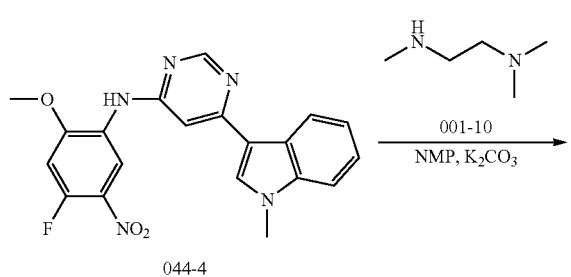

044-4

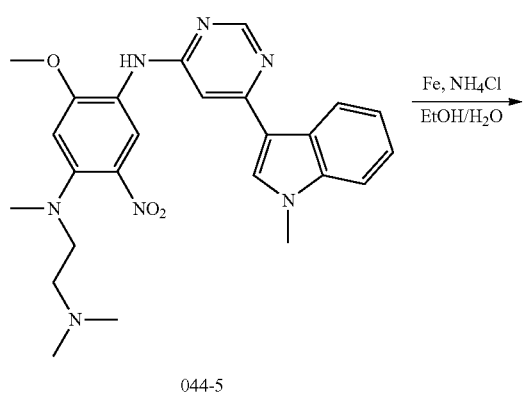

044-5

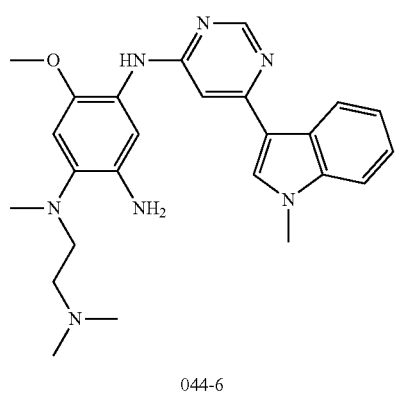

044-6

The reaction step and condition of synthesizing the intermediate 044-6 from the intermediate 044-3 were the same as those of the third and the fourth steps in Example 38. LCMS: 446.3.

3. Synthesis of Compound 44

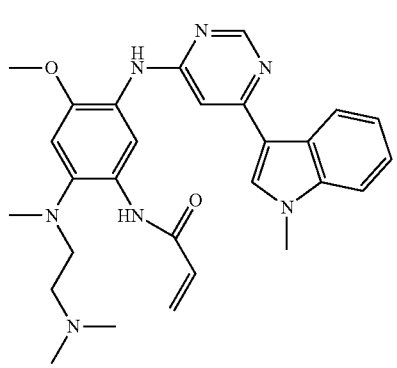

44

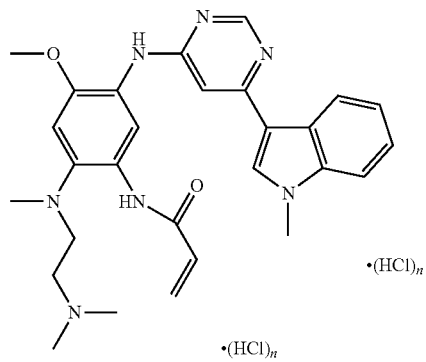

44

The reaction steps and conditions of synthesizing the compound 44 and hydrochloride $(HCl)_n$ of compound 44 from the intermediate 044-6 were the same as those of the ninth step in Example 1. The analysis data of the hydrochloride (HCl), of compound 44: LCMS (parent molecule) $C_{28}H_{33}N_7O_2$: (ES, m/z): $[M+H]^+=500$. $^1$H-NMR: (300 MHz, DMSO-D$_6$, ppm) δ 2.51 (s, 3H), 2.73 (s, 3H), 2.75 (s, 3H), 3.32-3.36 (m, 4H), 3.91 (s, 3H), 3.95 (s, 3H), 5.70-5.74 (m, 1H), 6.21-6.28 (m, 1H), 7.00 (s, 1H), 7.12-7.21 (m, 1H), 7.35-7.52 (m, 2H), 7.68-7.70 (d, 3-8.1 Hz, 1H), 8.05-8.06 (m, 1H), 8.30-8.41 (m, 1H), 8.45 (s, 1H), 8.75 (s, 1H), 9.93 (s, 1H), 10.49-10.51 (m, 2H).

Example 45

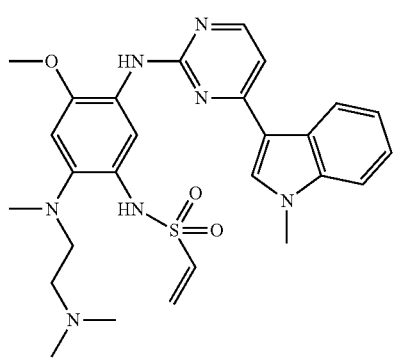

45

1. Synthesis of Intermediate 045-1

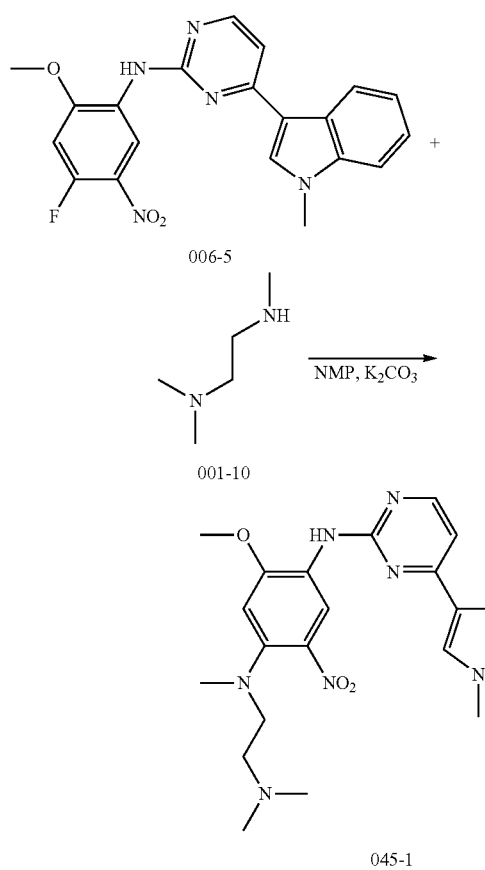

The intermediate 006-5 (1.0 g, 2.54 mmol) as a raw material was dissolved in NMP (20 mL) in 50 mL of a single-necked flask at room temperature, followed by sequentially addition of the intermediate 001-10 (250 mg, 2.45 mmol) and K₂CO₃ (1.04 g, 7.38 mmol) into the reaction system. After heated to 105° C., the reaction was carried out with a stirring for 2 h. After the reaction was completed, the reaction mixture was cooled to room temperature. The reaction was quenched by adding 50 mL of ice water into the reaction mixture. The obtained mixture was filtered by suction and the filter cake was collected and then dissolved in 200 mL of dichloromethane. The organic phases were washed with 100 mL of saturated brine once, dried over anhydrous sodium sulfate and concentrated to dryness. The crude product was purified by silica gel column chromatography (dichloromethane/methanol=100/1-50/1) to give 805 mg of the intermediate 045-1 (67%) as a red solid. LCMS: 476.2.

2. Synthesis of Intermediate 045-2

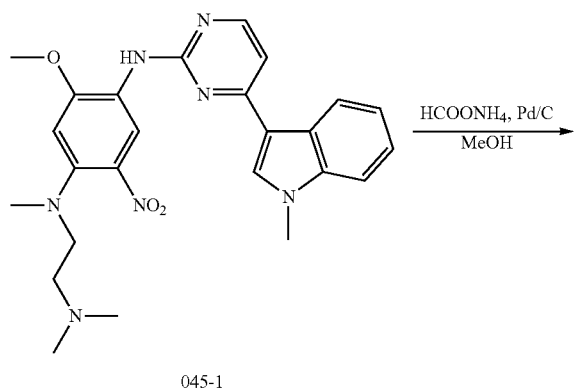

The reaction step and condition of synthesizing the intermediate 045-2 from the intermediate 045-1 were the same as those of the eighth step in Example 1. LCMS: 446.3.

3. Synthesis of Compound 45

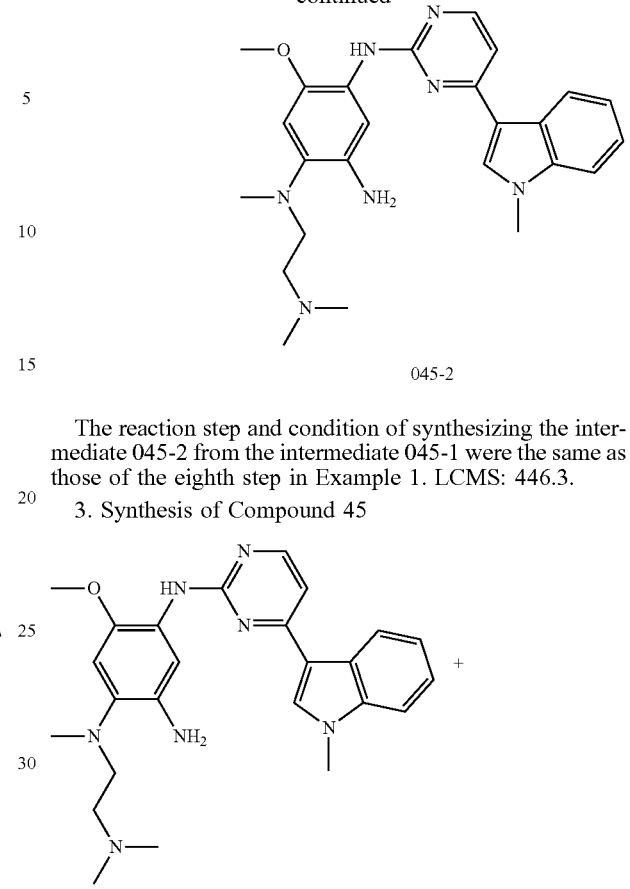

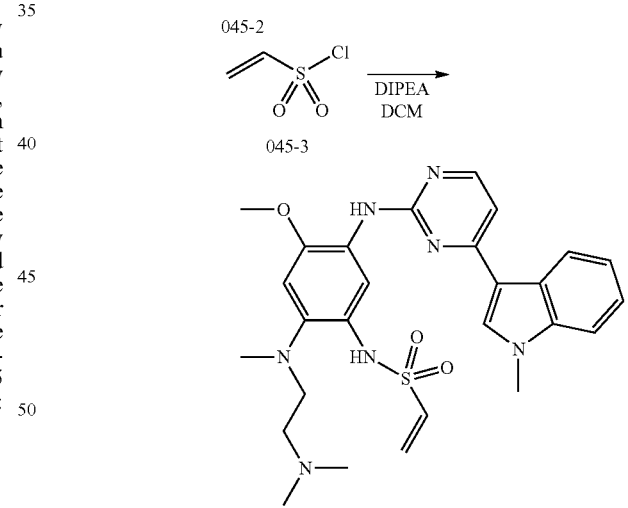

Under a nitrogen atmosphere, the intermediate 045-2 (350 mg, 0.79 mmol) as a raw material was dissolved in dichloromethane (50 mL) at room temperature in a 100 mL three-necked flask, followed by adding DIPEA (202 mg, 1.56 mmol). The reaction system was cooled to 0° C. Ethylene sulfonyl chloride (99 mg, 0.78 mmol) was added dropwisely to the reaction system at 0° C., and then the reaction was continued for 30 minutes at 0° C. After the reaction was completed, the mixture was concentrated to dryness. The crude product was purified by silica gel column chromatography (dichloromethane/methanol=100:1-50:1), collected, and concentrated to give product 45.

149

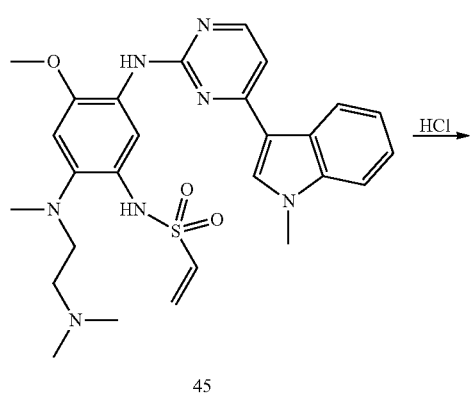

45

HCl →

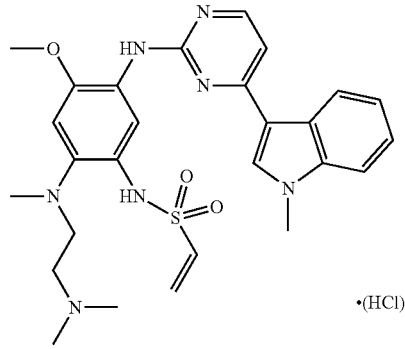

45 •(HCl)$_n$

•(HCl)$_n$

The product 45 was added and dissolved in 3 mL of aqueous hydrochloric acid (2 M), the reaction was stirred at room temperature for 30 minutes and then freeze dried to give 47.8 mg of the hydrochloride (HCl)$_n$ of compound 45 (10%) as a yellow solid. LCMS (parent molecule) C$_{27}$H$_{33}$N$_7$O$_3$S: (ES, m/z): [M+H]$^+$=536. $^1$H-NMR: (DMSO-D$_6$, 300 MHz, ppm) δ 10.30-10.23 (m, 1H), 8.77 (s, 1H), 8.21-8.16 (m, 2H), 7.62-7.59 (m, 2H), 7.42-7.40 (d, J=6 Hz, 1H), 7.35-7.30 (m, 1H), 7.23-7.17 (m, 1H), 7.05 (s, 1H), 6.93-6.84 (m, 1H), 6.12-6.09 (d, J=9 Hz, 1H), 5.96-5.93 (d, J=9 Hz, 1H), 3.92 (s, 3H), 3.80 (s, 3H), 3.38-3.35 (m, 4H), 2.79 (s, 6H), 2.63 (s, 3H).

Example 46

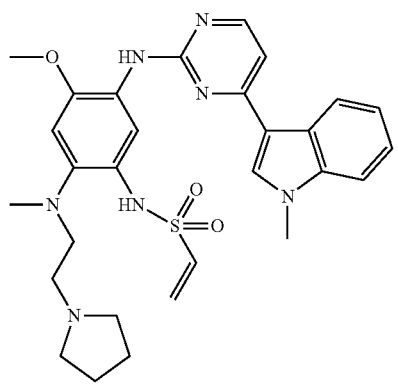

46

150

1. Synthesis of Compound 46

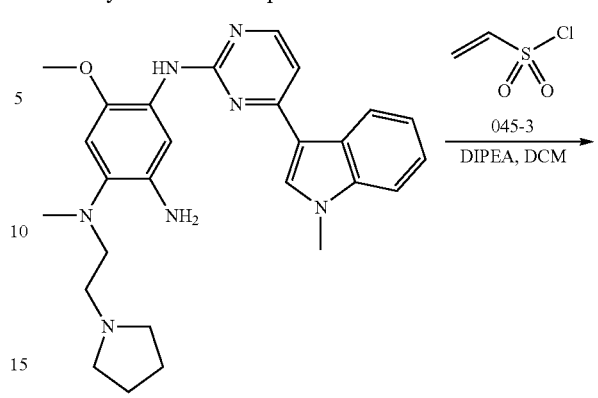

012-3

045-3
DIPEA, DCM
→

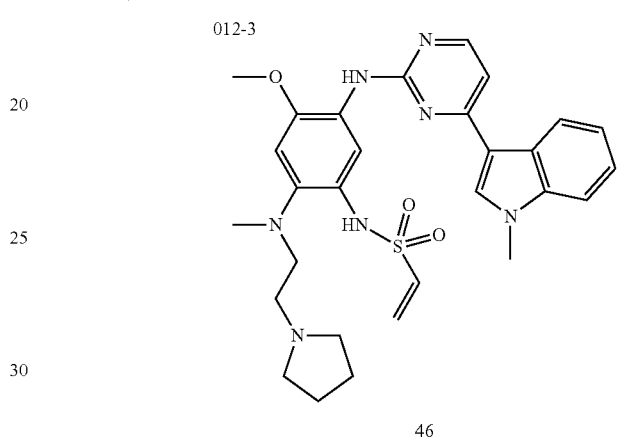

46

The reaction step and condition of synthesizing the compound 46 from the intermediate 012-3 were the same as those of the third step in Example 45.

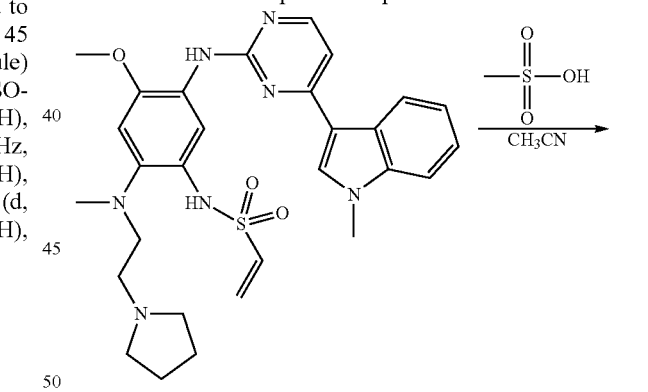

CH$_3$CN →

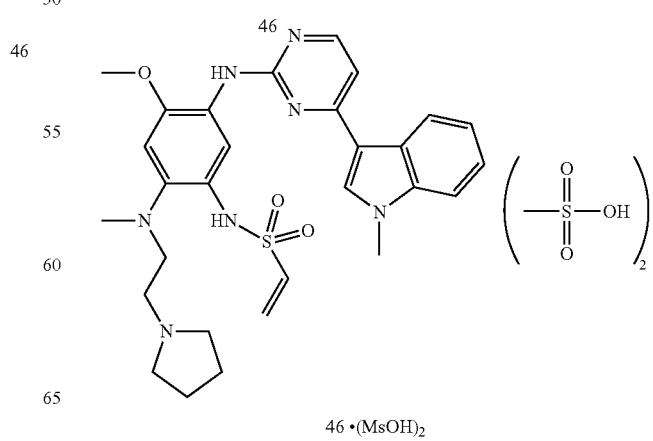

46 •(MsOH)$_2$

The obtained product 46 was dissolved in 5 mL of acetonitrile, methanesulfonic acid (115.3 mg, 1.20 mmol) was added thereto. Then, the reaction was stirred for 2 h and then freeze dried to give 108.5 mg of of methanesulfonate (MsOH)$_2$ of compound 46 (23%) as a yellow solid.

LCMS (parent molecule) $C_{29}H_{35}N_7O_3S$: (ES, m/z): [M+H]$^+$=562. $^1$H-NMR: (DMSO-D$_6$, 300 MHz, ppm) δ 8.69 (s, 1H), 8.29-8.19 (m, 1H), 7.61-7.58 (d, J=9 Hz, 1H), 7.40-7.30 (m, 2H), 7.25-7.18 (m, 1H), 7.05 (s, 1H), 6.90-6.82 (m, 1H), 6.18-6.12 (d, J=12 Hz, 1H), 6.01-5.98 (d, J=6 Hz, 1H), 3.98 (s, 3H), 3.89 (s, 3H), 3.81-3.32 (m, 6H), 3.18-3.10 (m, 2H), 2.72 (s, 3H), 2.33 (s, 6H), 2.27-1.98 (m, 4H).

Example 47

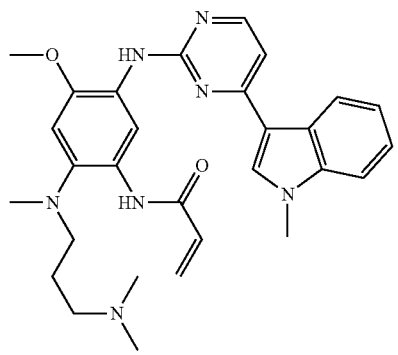

47

1. Synthesis of Intermediate 047-3

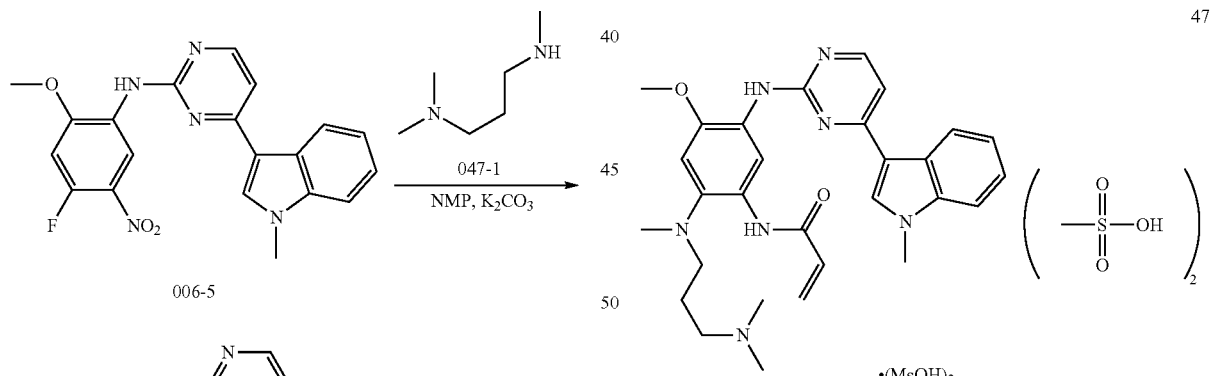

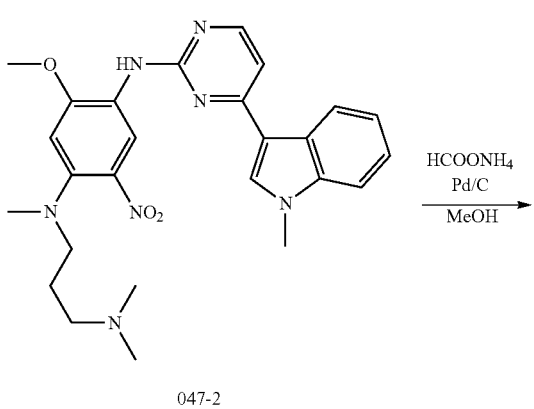

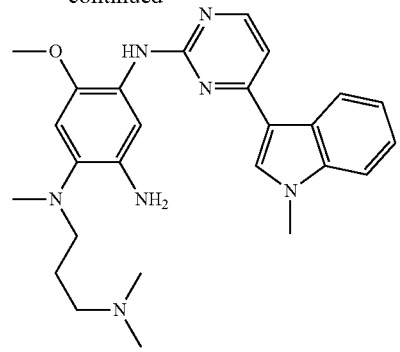

047-3

The reaction step and condition of synthesizing the intermediate 047-3 from the intermediates 006-5 and 047-1 were the same as those of the first and second steps in Example 7. LCMS: 460.3.

2. Synthesis of Compound 47

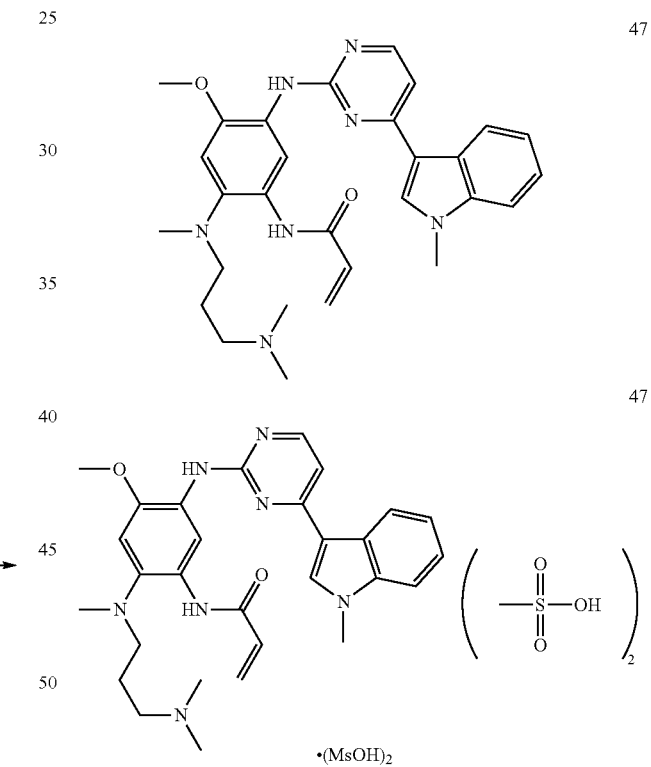

The reaction steps and conditions of synthesizing the compound 47 and methanesulfonate (MsOH)$_2$ of compound 47 from the intermediate 047-3 were the same as those of the third step in Example 7. LCMS (parent molecule) $C_{29}H_{38}N_7O_2$: (ES, m/z): [M+H]$^+$=514. $^1$H-NMR: (DMSO-D$_6$, 300 MHz, ppm) δ 9.25 (m, 2H), 8.77 (s, 1H), 8.39-8.24 (m, 2H), 7.60-7.58 (d, J=6 Hz, 1H), 7.40-7.38 (d, J=6 Hz, 1H), 7.33-7.28 (m, 1H), 7.21-7.17 (m, 1H), 7.02 (s, 1H), 6.75-6.66 (m, 1H), 6.27-6.20 (d, J=9 Hz, 1H), 5.77-5.74 (d, J=9 Hz, 1H), 3.93 (s, 3H), 3.85 (s, 3H), 3.14-3.11 (m, 2H), 3.09-3.07 (m, 2H), 2.97 (s, 9H), 2.32 (s, 6H), 1.88-1.83 (m, 2H).

Example 48

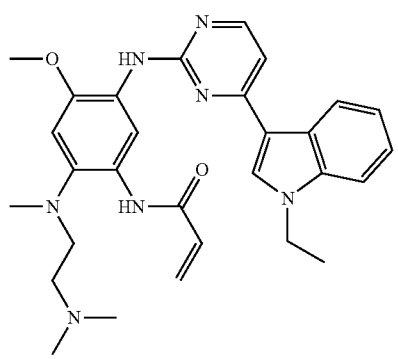

1. Synthesis of Intermediate 048-2

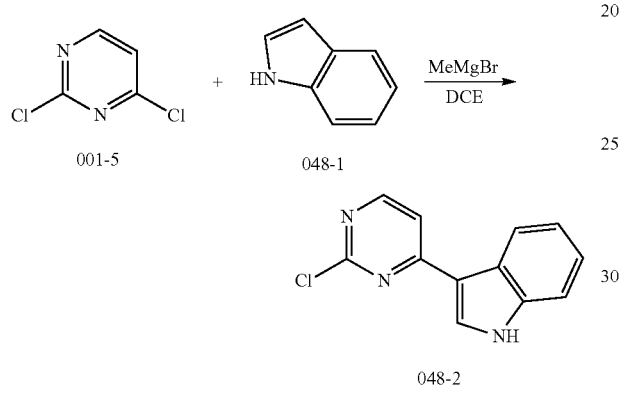

The intermediate 048-1 (3.0 g, 25.6 mmol) as a raw material was dissolved in 50 mL of 1,2-dichloroethane (DCE) in 100 mL of a three-necked flask at room temperature under a nitrogen atmosphere. The reaction mixture was cooled to 0° C. Ethylmagnesium bromide (8.5 mL, 25.6 mmol) was added dropwisely to the reaction system. After the reaction was completed, the reaction was maintained at a constant temperature for 30 min and the intermediate 001-5 (5.4 g, 36.3 mmol) was added into the reaction system at 0° C. The reaction was carried out overnight at room temperature. After the reaction was completed, the reaction mixture was quenched by adding 100 mL of ice water. The mixture was extracted with 100 mL of methylene dichloride three times. The organic phases were combined, washed with 100 mL of saturated brine three times, dried over anhydrous sodium sulfate and concentrated. The crude product was purified by silica gel column chromatography (EA/PE=1:10-1:5) to give 2.0 g of the intermediate 048-2 (34%) as a yellow solid. LCMS: 229.0.

2. Synthesis of Intermediate 048-3

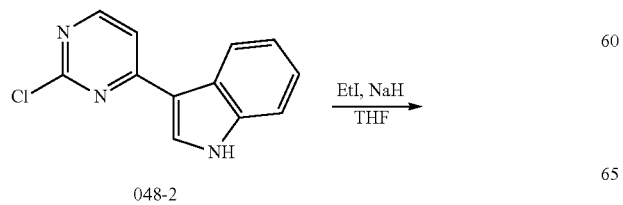

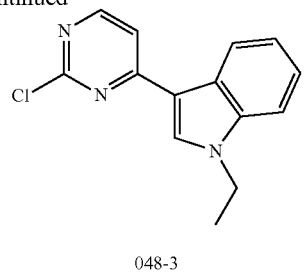

The intermediate 048-2 (80 mL) (2.0 g, 8.7 mmol) was dissolved in anhydrous tetrahydrofuran (80 mL) in a 50 mL of three-necked flask under nitrogen, and then the reaction mixture was cooled to 0-10° C. After NaH (60%, dispersed in a mineral oil) (200 mg, 8.33 mmol) was sequentially added, the reaction system was stirred for 30 min at 0° C. and then iodoethane (1.6 g, 10.3 mmol) was added thereto. The reaction mixture was heated to a room temperature and maintained for 2 h. After the reaction was completed, the reaction was quenched by adding 20 mL of ice water. The system was extracted with 50 mL of ethyl acetate 2 times, and the organic phases were combined, backwashed with 50 mL of saturated brine 2 times, dried with anhydrous sodium sulfate and concentrated to give 2.0 g of the intermediate 048-3 (89%) as a yellow solid. LCMS: 258.1.

3. Synthesis of Intermediate 048-4

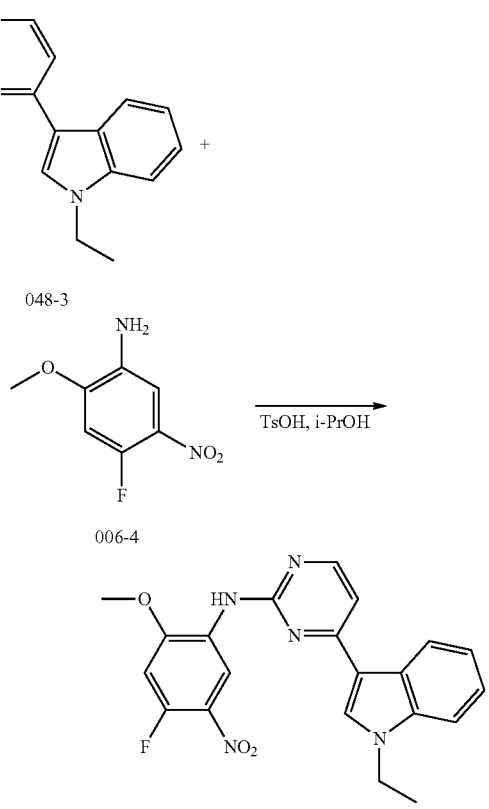

The intermediate 048-3 (80 mL) (2.0 g, 7.76 mmol) as a raw material was dissolved in isopropanol (20 mL) in a 250 mL of single-necked flask under nitrogen, followed by sequentially adding the intermediate 006-4 (1.72 mL, 9.24 mmol) and p-toluenesulfonate (1.44 g, 8.36 mmol). The reaction was then heated to 105° C., and maintained for 2.5 h. After the reaction was completed, the reaction system was cooled to room temperature. The reaction mixture was filtered, and the filter cake was collected, washed with 20 mL of isopropyl alcohol once, and washed with 20 mL of acetonitrile once. The filter cake was dried to give 1.9 g of the intermediate 048-4 (60%) as a yellow solid. LCMS: 408.1.

4. Synthesis of Intermediate 048-5

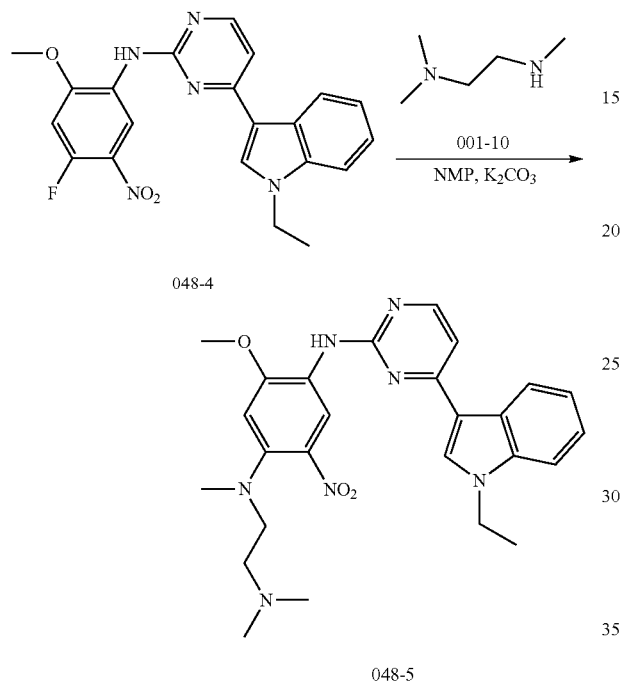

The intermediate 048-4 (1.0 g, 2.54 mmol) as a raw material was dissolved in NMP (20 mL) in a 50 mL of single-necked flask under nitrogen, followed by sequentially addition of anhydrous potassium carbonate (1.01 g, 7.36 mmol) and the intermediate 001-10 (322 mg, 3.15 mmol). The reaction was heated to 105° C. and maintained for 2 h. After the reaction was completed, the reaction mixture was cooled to room temperature. Next, the reaction was quenched with 20 mL of ice water. The filter cake was filtered by suction, collected, washed with 20 mL of water once and dried to give 0.9 g of crude product 048-5 (75%) as a red solid. LCMS: 490.2.

5. Synthesis of Intermediate 048-6

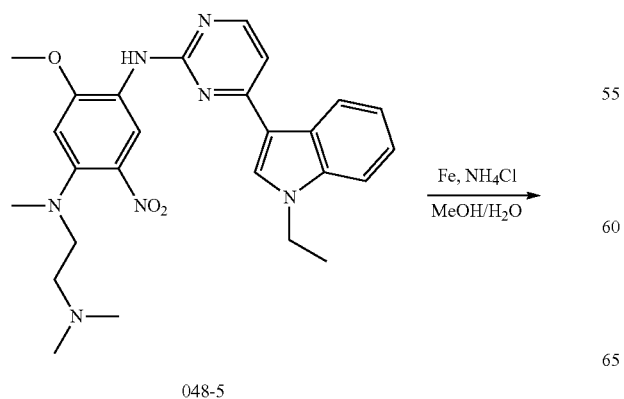

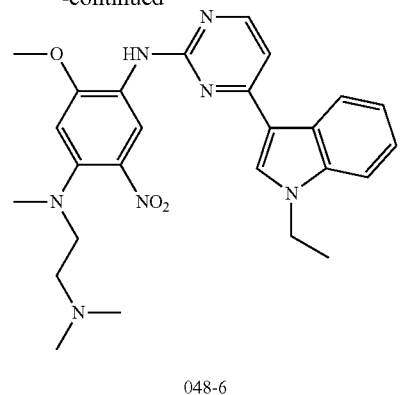

The intermediate 048-5 (900 mg, 1.84 mmol) as a raw material was dissolved in 10 mL of water and 30 mL of methanol in a 100 mL single-necked flask, followed by sequentially adding iron powder (0.618 g, 11.1 mmol) and ammonium chloride (68 mg, 1.27 mmol). The reaction was heated to 85° C. and carried out for 2 h. After the reaction was completed, the reaction was cooled to room temperature, and the iron powder was removed. Next, the filtrate was collected, spin-dried to remove most of the methanol and then extracted with 50 mL of DCM twice. The organic phases were combined and concentrated to give 0.25 g of crude product 048-6 (30%) as a yellow solid.

6. Synthesis of Compound 48

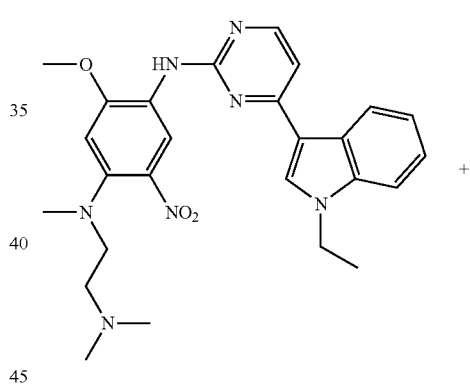

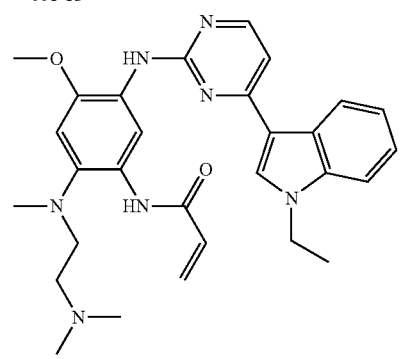

Under a nitrogen atmosphere, the intermediate 048-6 (250 mg, 0.54 mmol) as a raw material was dissolved in 50 mL of THF in a 250 mL three-necked flask, followed by addition of DIPEA (140 mg, 1.08 mmol). The reaction mixture was cooled to 0° C., and acryloyl chloride (48 mg, 0.54 mmol) was added dropwisely. After the reaction was carried out at room temperature for 1 h, 2 mL of ice water was added to quench the reaction. The reaction mixture was concentrated and the crude product was purified by high pressure liquid chromatography (column model: Waters X-bridge RP18, 19×150 mm, 5 um; mobile phase: water (0.05% ammonia)/acetonitrile, 20% acetonitrile to 25% acetonitrile, 5 min, 15 mL/min; detection wavelength: 254 nm). The obtained product was collected and dried to give compound 48.

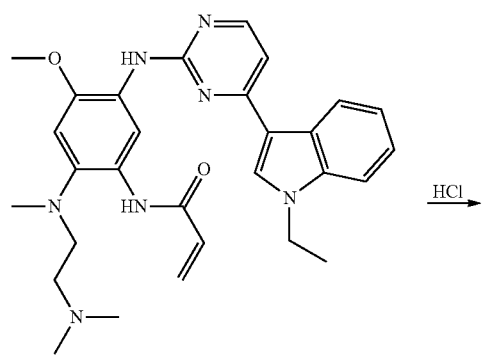

48

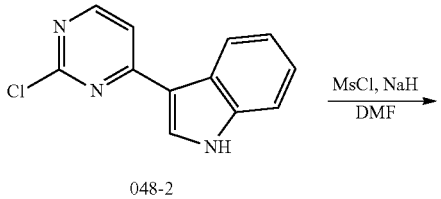

48·(HCl)$_n$

The compound 48 was dissolved in an excessive dilute HCl (10 mL, 0.1 M) and freeze dried to give 48.5 mg of hydrochloride (HCl)$_n$ of compound 48 (16%) as a yellow solid. LCMS (parent molecule) $C_{29}H_{36}ClN_7O_2$: (ES, m/z): [M+H]$^+$=550. $^1$H-NMR (300 MHz, DMSO-D$_6$, ppm) δ 1.34-1.47 (m, 3H), 2.64 (s, 3H), 2.74-2.76 (d, J=4.8 Hz, 6H), 3.33-3.40 (d, J=22.5 Hz, 4H), 3.72-3.87 (d, J=45.6 Hz, 3H), 4.30-4.37 (m, 2H), 5.68-5.73 (m, 1H), 6.20-6.26 (m, 1H), 7.00 (s, 1H), 7.16-7.29 (m, 3H), 7.35-7.37 (t, J=6.3 Hz, 1H), 7.60-7.63 (t, J=8.1 Hz, 1H), 8.27-8.29 (d, J=5.1 Hz, 2H), 8.57-8.62 (d, J=14.7 Hz, 2H), 8.75 (s, 1H), 9.90 (s, 1H), 10.59 (s, 1H).

Example 49

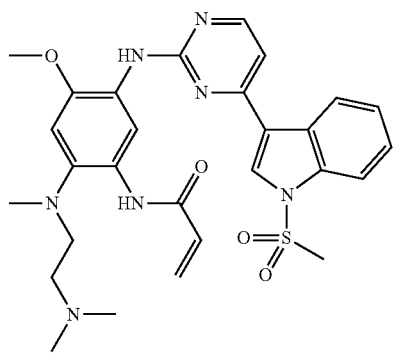

49

1. Synthesis of Intermediate 049-1

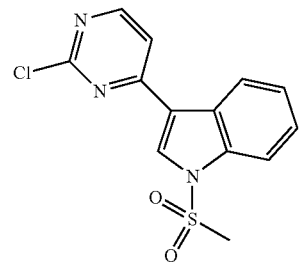

Sodium hydride (60%, dispersed in mineral oil) (400 mg, 16.7 mmol) was dissolved in anhydrous DMF (80 mL) in a 250 mL of three-necked flask at room temperature under a nitrogen atmosphere, and the reaction mixture was cooled to 0° C. in ice-water bath. The intermediate 048-2 (1.5 g, 6.53 mmol) as a raw material was added to the reaction system with stirring at 0° C. for 30 minutes. Methylsulfonyl chloride (MsCl) (1.1 g, 9.60 mmol) was added dropwisely to the reaction system and then the reaction carried out at room temperature for 2 hours. The reaction was quenched by adding 200 mL of ice water, then extracted with 100 mL of ethyl acetate 3 times. The organic phases were combined, and sequentially washed with 100 mL of water twice and 100 mL of brine once, and finally dried over anhydrous sodium sulfate and concentrated. The crude product was purified by silica gel column chromatography (eluent: EA/PE=1:50-1:5) to give 0.8 g of the intermediate 049-1 (40%) as a yellow solid.

2. Synthesis of Intermediate 049-4

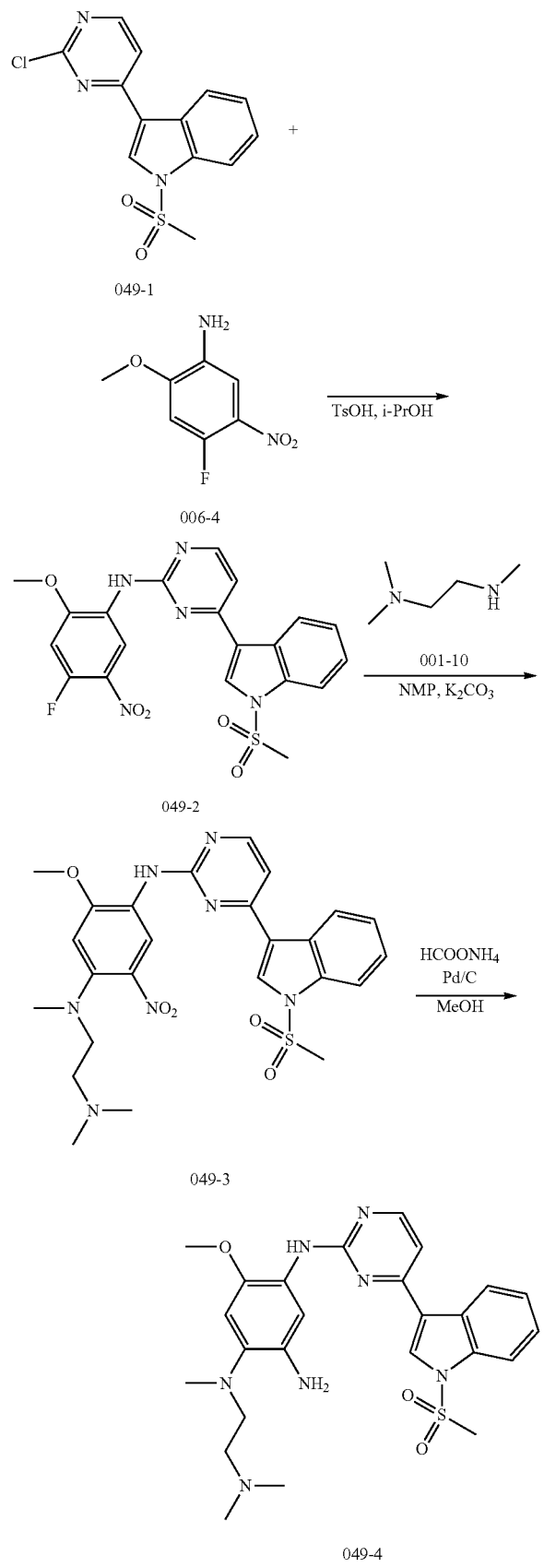

The reaction step and condition of synthesizing the compound 049-4 from the intermediate 049-1 were the same as those of the second to fourth steps in Example 3. LCMS (049-4): 510.2.

3. Synthesis of Compound 49

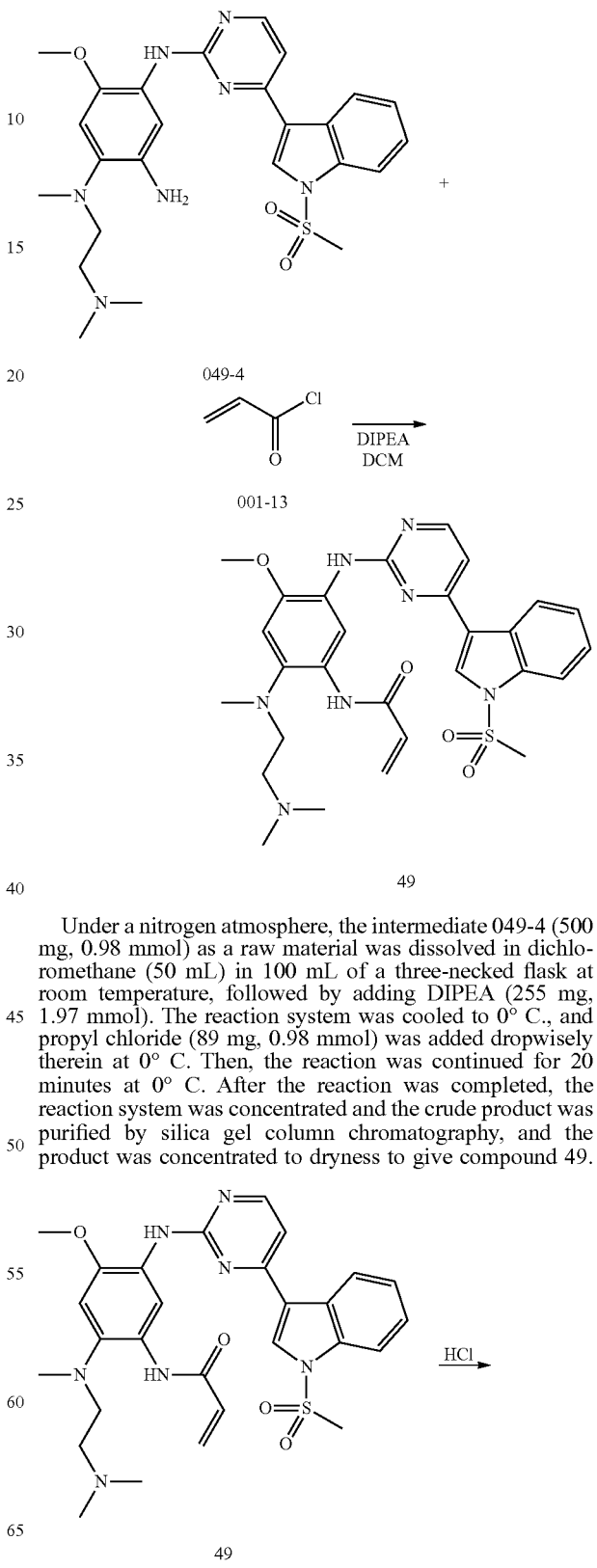

Under a nitrogen atmosphere, the intermediate 049-4 (500 mg, 0.98 mmol) as a raw material was dissolved in dichloromethane (50 mL) in 100 mL of a three-necked flask at room temperature, followed by adding DIPEA (255 mg, 1.97 mmol). The reaction system was cooled to 0° C., and propyl chloride (89 mg, 0.98 mmol) was added dropwise therein at 0° C. Then, the reaction was continued for 20 minutes at 0° C. After the reaction was completed, the reaction system was concentrated and the crude product was purified by silica gel column chromatography, and the product was concentrated to dryness to give compound 49.

161

-continued

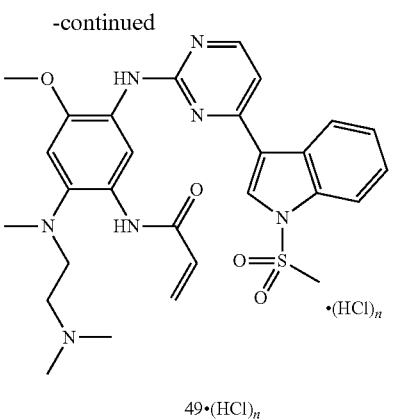

49·(HCl)$_n$

The obtained product 49 was dissolved in 3 mL (0.1 M) of aqueous solution of hydrochloric acid, followed by that the reaction mixture was stirred at room temperature for 1 hour and freeze dried to give 108 mg of the hydrochloride salt of compound 49, 49. (HCl)$_n$ (18%) as a yellow solid. LCMS (parent molecule) $C_{28}H_{33}N_7O_4S$: (ES, m/z): [M+H]$^+$=564. $^1$H-NMR: (300 MHz, DMSO-D$_6$, ppm) δ 10.38 (s, 1H), 9.84 (s, 1H), 8.75-8.74 (m, 1H), 8.59 (s, 1H), 8.56-8.39 (m, 3H), 7.91-7.88 (d, J=9 Hz, 1H), 7.51-7.33 (m, 3H), 7.14-7.05 (m, 1H), 6.98 (s, 1H), 6.23-6.17 (d, J=10 Hz, 1H), 5.71-5.67 (d, J=4.5 Hz, 1H), 3.97 (s, 1H), 6.98 (s, 3H), 3.60 (s, 3H), 3.32 (s, 4H), 2.76 (s, 6H), 2.51 (s, 1H).

Example 50

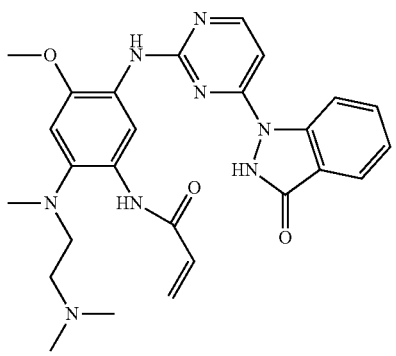

1. Synthesis of Intermediate 050-2

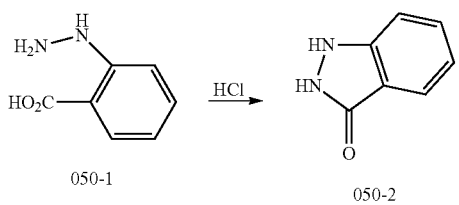 [SMILES: NNc1ccccc1C(=O)O ; Cl ; O=c1[nH][nH]c2ccccc12]

200 mL of concentrated hydrochloric acid and the intermediate 050-1 (2.0 g, 13.1 mmol) were sequentially added into a 500 mL single-necked flask under nitrogen, and then the reaction system was heated to 85° C. overnight. After the reaction was completed, the reaction system was cooled to room temperature, and directly concentrated to dryness to give 1.3 g of the intermediate 050-2 (74%) as a white solid. LCMS: 135.0

2. Synthesis of Intermediate 050-3

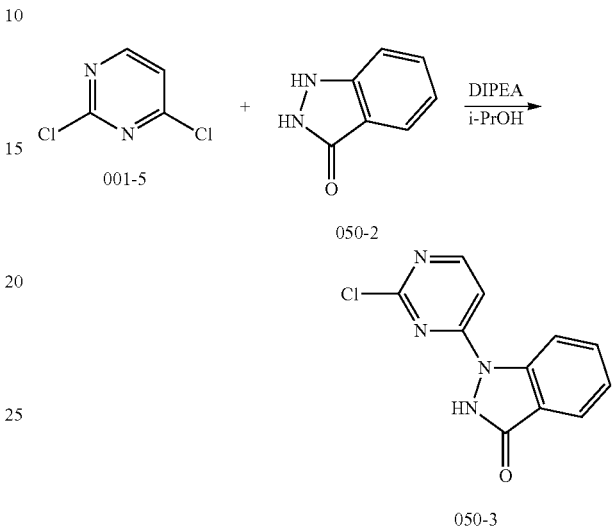

25 mL of isopropyl alcohol, the intermediates 001-5 (1.3 g, 9.69 mmol) and 050-2 (718 mg, 4.82 mmol), and DIPEA (5.0 g, 38.7 mmol) were sequentially added into a 50 mL of single-necked flask under nitrogen, and then the reaction system was heated to 45° C. overnight. After the reaction was completed, the reaction system was cooled to a room temperature, quenched by adding 100 mL of ice water, extracted with 200 mL of dichloromethane three times. The organic phases were combined and backwashed back with 500 mL of saturated brine three times, dried over sodium sulfate, concentrated to dryness, so as to give the crude product. The crude product was purified by silica gel column chromatography (eluent DCM/MeOH=3:1-1:1). The product was concentrated to dryness to give 0.650 g of the intermediate 050-3 (27%) as a yellow solid. LCMS: 247.0.

3. Synthesis of Compound 50

The reaction steps and conditions of synthesizing the compound 50 and hydrochloride (HCl)$_n$ of compound 50 from the intermediate 050-3 were the same as those of the third step to the sixth step in Example 48, except that the intermediate 048-3 in the example 48 was replaced with the intermediate 050-3 in the this step. The analysis data of the hydrochloride (HCl)$_n$ of compound 50: LCMS (parent molecule) $C_{26}H_{30}N_8O_3$: (ES, m/z): [M+H]$^+$=503. $^1$H-NMR: (300 MHz, DMSO-d$_6$, ppm) δ 2.67 (s, 3H), 2.75 (s, 3H), 2.76 (s, 3H), 3.29-3.36 (m, 4H), 3.83 (s, 3H), 4.08 (s, 3H), 5.66-5.70 (m, 1H), 6.15-6.21 (m, 1H), 7.02 (s, 1H), 7.14-7.24 (m, 2H), 7.35-7.39 (m, 1H), 7.53-7.55 (m, 1H), 7.82-7.84 (d, J=7.5 Hz, 1H), 8.21 (s, 1H), 8.28-8.30 (m, 1H), 9.97 (s, 1H), 10.63-10.65 (br s, 1H).

Example 51

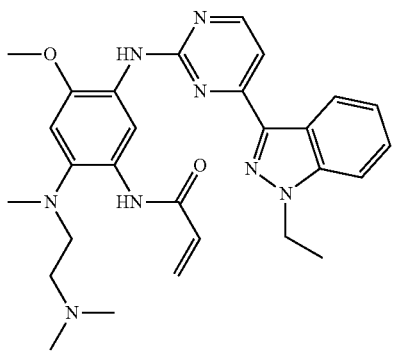

1. Synthesis of Intermediate 051-2

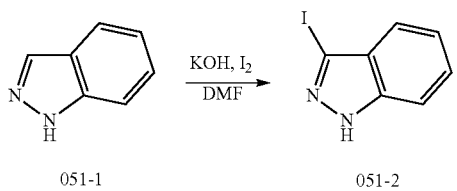

The intermediate 051-1 (10.0 g, 54.7 mmol) as a raw material was dissolved in DMF (500 mL) in a 1000 mL of four-necked flask at room temperature under a nitrogen atmosphere, then sequentially adding potassium hydroxide (19.0 g, 338.6 mmol) and iodine (21.5 g, 84.8 mmol). Then, the reaction was carried out overnight at room temperature. After the reaction was completed, 500 mL of a 10% aqueous solution of sodium thiosulfate was added to the reaction mixture to quench the reaction. The reaction mixture was extracted with 500 mL of ethyl acetate three times. The organic phases were combined and washed with 500 mL of saturated brine once, then dried over anhydrous sodium sulfate and concentrated to give 15.3 g of crude product 051-2 (74%) as an off-white solid. LCMS: 245.0.

2. Synthesis of Intermediate 051-3

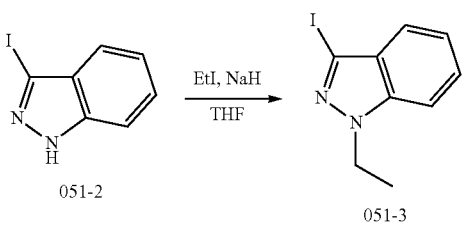

The intermediate 051-2 (4.0 g, 16.4 mmol) as a raw material was dissolved in 60 mL of anhydrous tetrahydrofuran in 250 mL of a three-necked flask at room temperature, and the reaction was cooled to 0-5° C. with ice-salt. After sodium hydride (720 M& 30.0 mmol) was added into the reaction system, the reaction system was maintained at an internal temperature of 0-5° C. and stirred for 1 h. Next, iodoethane (3.1 g, 19.9 mmol) was added to the reaction system at 0-5° C. followed by stirring for 3 h. After the reaction was completed, the reaction was quenched by adding 100 mL of water. The reaction mixture was extracted three times with 150 mL of ethyl acetate. The organic phases were combined, dried over anhydrous sodium sulfate, concentrated to dryness. The crude product was purified by silica gel column chromatography (eluent: EA:PE=1:50) to give 3.6 g of the intermediate 051-3 (81%) as a pale yellow oil. LCMS: 273.0

3. Synthesis of Intermediate 051-4

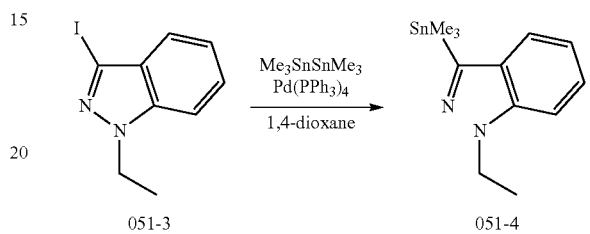

The intermediate 051-3 (3.6 g, 13.2 mmol) as a raw material was dissolved in 1,4-dioxane (50 mL) in 250 mL of a three-necked flask under nitrogen, followed by sequentially adding hexamethylditin (5.19 g, 15.84 mmol) and tetrakis(triphenylphosphine)palladium (1.5 g, 1.30 mmol) into the reaction system. Then, the reaction was heated to 105° C. and maintained overnight. After the reaction was completed, the reaction system was cooled to 25° C. with ice-water. The reaction mixture was concentrated to dryness and the resulting residue was purified by silica gel column chromatography (eluent: PE/EA=60:1) to give 1.9 g of the intermediate 051-4 (46%) as yellow oil. LCMS: 311.0.

4. Synthesis of Intermediate 051-5

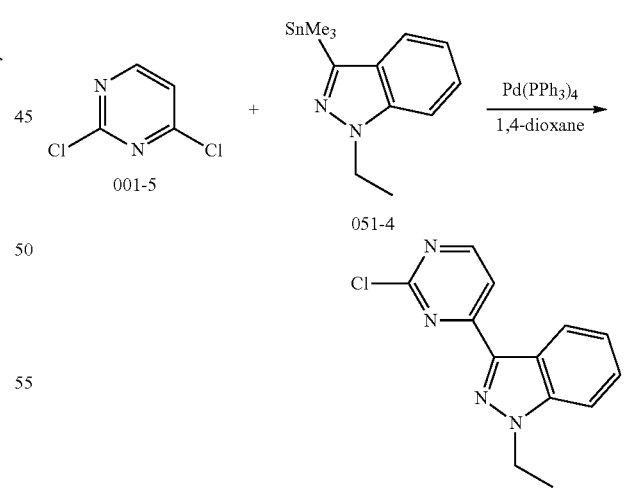

The intermediate 001-5 (1.9 g, 6.15 mmol) as a raw material was dissolved in 1,4-dioxane (50 mL) in 100 mL of a three-necked flask at room temperature under nitrogen, followed by sequentially adding the intermediate 051-4 (0.9 g, 6.04 mmol) and tetrakis(triphenylphosphine)palladium (0.71 g, 0.61 mmol) into the reaction system. Then, the reaction was heated to 105° C. and maintained overnight. After the reaction system was cooled to 25° C. with ice-water, the reaction mixture was concentrated to dryness. The resulting residue was purified by silica gel column chromatography (eluent: PE:EA=25:1) to give 680 mg of the intermediate 051-5 (43%) as a yellow solid. LCMS: 259.1.

5. Synthesis of Compound 51

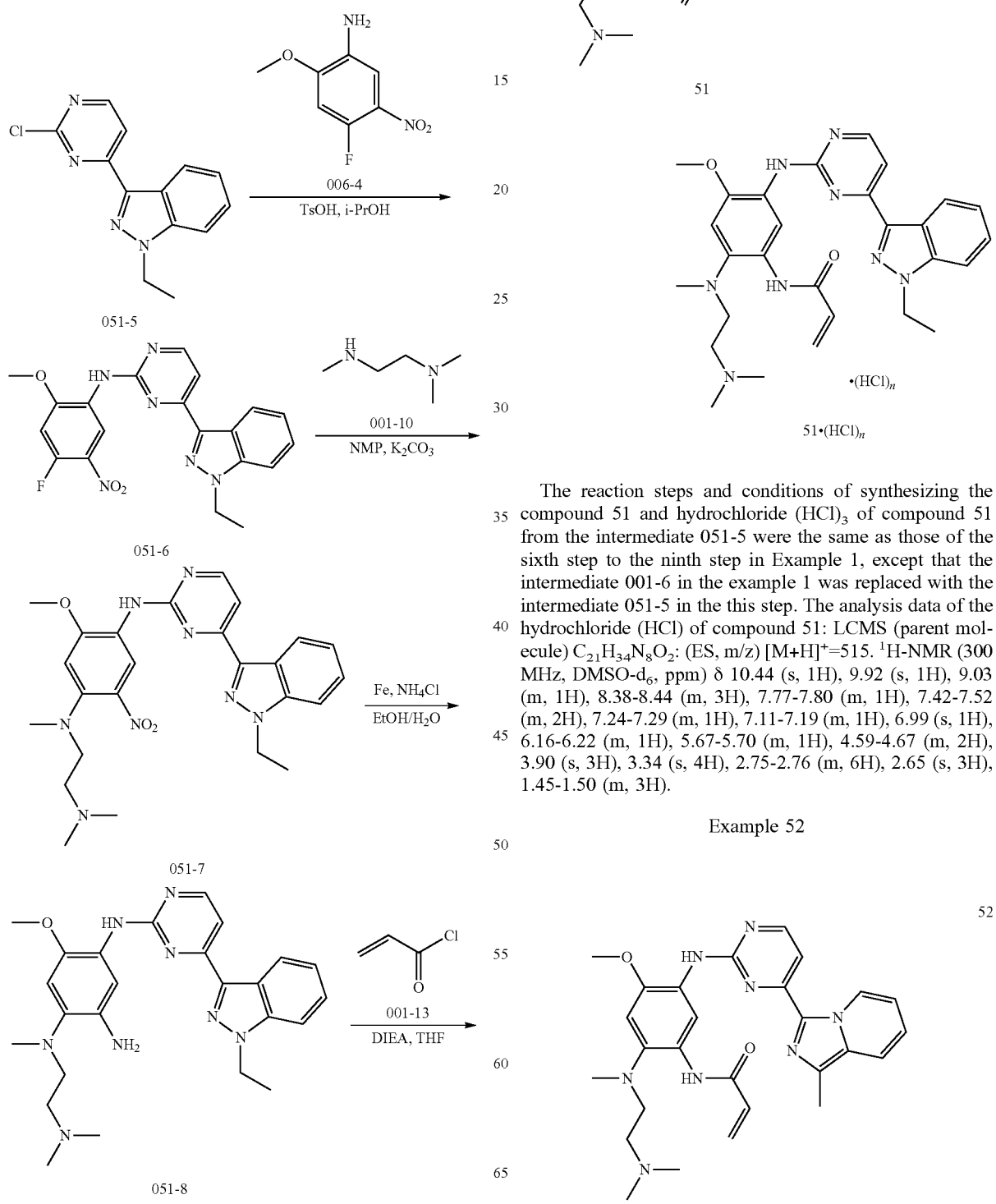

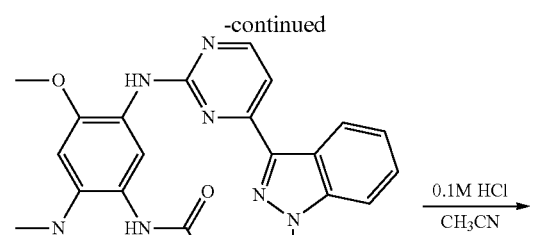

The reaction steps and conditions of synthesizing the compound 51 and hydrochloride (HCl)$_3$ of compound 51 from the intermediate 051-5 were the same as those of the sixth step to the ninth step in Example 1, except that the intermediate 001-6 in the example 1 was replaced with the intermediate 051-5 in the this step. The analysis data of the hydrochloride (HCl) of compound 51: LCMS (parent molecule) $C_{21}H_{34}N_8O_2$: (ES, m/z) [M+H]$^+$=515. $^1$H-NMR (300 MHz, DMSO-d$_6$, ppm) δ 10.44 (s, 1H), 9.92 (s, 1H), 9.03 (m, 1H), 8.38-8.44 (m, 3H), 7.77-7.80 (m, 1H), 7.42-7.52 (m, 2H), 7.24-7.29 (m, 1H), 7.11-7.19 (m, 1H), 6.99 (s, 1H), 6.16-6.22 (m, 1H), 5.67-5.70 (m, 1H), 4.59-4.67 (m, 2H), 3.90 (s, 3H), 3.34 (s, 4H), 2.75-2.76 (m, 6H), 2.65 (s, 3H), 1.45-1.50 (m, 3H).

Example 52

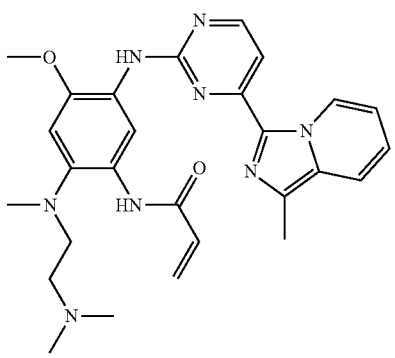

1. Synthesis of Intermediate 052-4

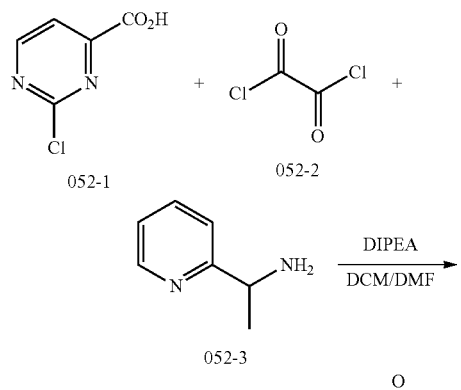

The intermediate 052-1 (3.16 g, 19.9 mmol), dichloromethane (150 mL) and DMF (0.3 mL) were added to a 250 mL of three-necked flask under nitrogen. The reaction system was cooled to 0° C., and the intermediate 052-2 (3.02 g, 23.8 mmol) was added thereto, then the reaction was carried out for 2 h. Next, DIPEA (12.9 g, 99.8 mmol) and intermediate 052-3 (2.44 g, 20.0 mmol) were added at 0° C., and the reaction was warmed up to room temperature and carried out overnight. 100 mL of ice water was added to quench the reaction, and the reaction mixture was extracted with 200 mL of DCM three times. The organic phases were combined and washed three times with 300 mL of saturated brine, and concentrated to dryness. The crude product was purified by silica gel column chromatography (eluent: EA/PE=1:5-1:1) to give 2.0 g of intermediate 052-4 (38%) as a white solid. LCMS: 263.1.

2. Synthesis of Intermediate 052-5

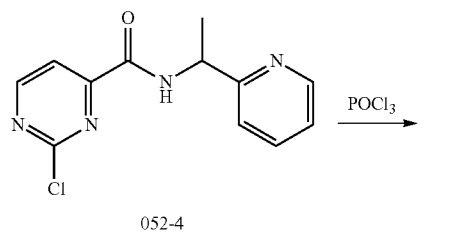

30 mL of phosphorus oxychloride and the intermediate 052-4 (2.0 g, 7.61 mmol) were sequentially added to a 100 mL of single-necked flask at room temperature under nitrogen, and then the reaction mixture was heated to 110° C. and maintained overnight. The reaction was cooled to room temperature and then 100 mL of ice water was added to quench the reaction. The reaction mixture was extracted with 100 mL of methylene chloride three times. The organic phases were combined and backwashed with 200 mL of saturated brine three times, dried over anhydrous sodium sulfate, concentrated to dryness. The crude product was purified by silica gel column chromatography (elution: DCM/MeOH=20:1-10:1) to give 1.14 g of the intermediate 052-5 (61%) as a white solid. LCMS: 245.1.

3. Synthesis of Compound 52

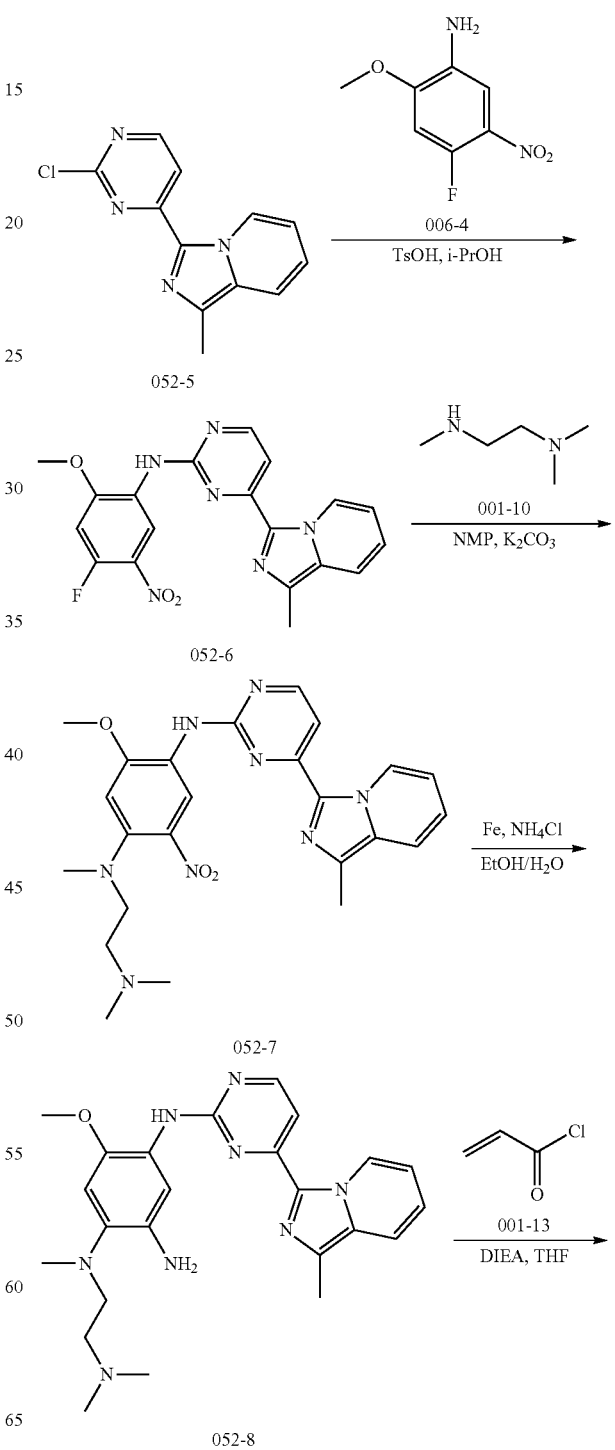

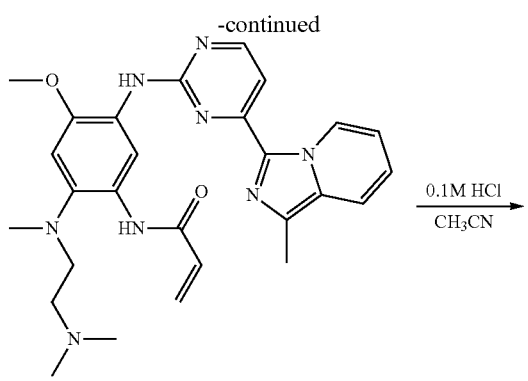

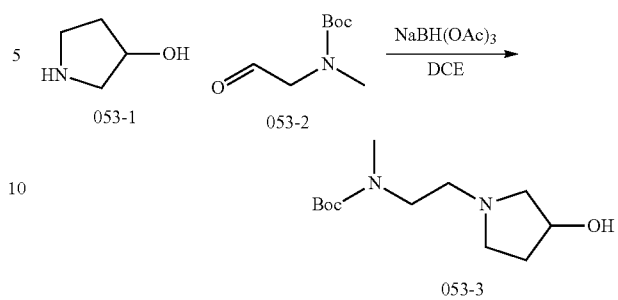

1. Synthesis of Intermediate 053-3

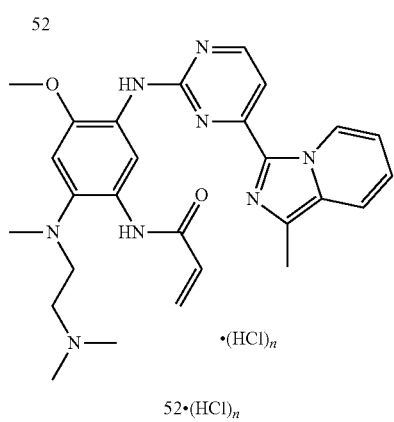

The intermediate 053-1 (2.47 g, 20.0 mmol) as a raw material was dissolved in 30 mL of 1,2-dichloroethane (DCE) in 100 mL of a three-necked flask at room temperature, followed by adding the intermediate 053-2 (2.60 g, 15.0 mmol) and at room temperature, adding sodium triacetoxyborohydride (NaBH(OAc)$_3$) in batches. After stirring 3 h at room temperature, the reaction was completed. The reaction mixture was filtered, and the filtrate was rotovapped. The obtained mixture was extracted with 30 mL of ethyl acetate three times. Next, the resulting mixture was extracted three times with 30 mL of ethyl acetate, and the organic phases were combined, dried over sodium sulfate and subjected to rotary evaporation. The resulting residue was purified with Pre-HPLC (column: C18 silica gel; mobile phase: acetonitrile/water (5% trifluoroacetic acid); 10% acetonitrile to 50% acetonitrile; 30 min; detection wavelength: 220 nm) to give 3.0 g of the intermediate 053-3 (61%) as a yellow oil. LCMS: 245.2.

2. Synthesis of Intermediate 053-4

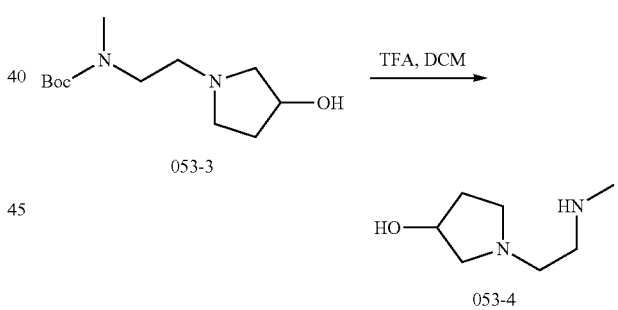

The intermediate 053-3 (3.0 g, 12.3 mmol) as a raw material was dissolved in 100 mL of dichloromethane at room temperature and then 3 mL of trifluoroacetic acid (TFA) was added to the system. Next, the reaction was carried out at room temperature for 2 h. After the reaction was completed, the reaction system was subjected to rotary evaporation to give 2.0 g of the intermediate 053-4 (67%) as a brown oil. LCMS: 145.1.

3. Synthesis of Intermediate 053-5

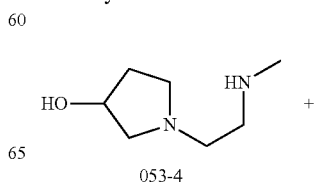

The reaction steps and conditions of synthesizing the compound 52 and hydrochloride (HCl)$_n$ of compound 52 from the intermediate 052-5 were the same as those of the six step to the ninth step in Example 1, except that the intermediate 001-6 in the example 1 was replaced with the intermediate 052-5 in the this step. The analysis data of the hydrochloride (HCl)$_n$ of compound 52: LCMS (parent molecule) $C_{27}H_{32}N_8O_2$ (ES, m/z): [M+H]$^+$=501. $^1$H-NMR: (300 MHz, DMSO-d$_6$, ppm) δ 2.58 (s, 3H), 2.67 (s, 3H), 2.74 (s, 3H), 2.76 (s, 3H), 3.26-3.48 (m, 4H), 3.84 (s, 3H), 5.15-5.69 (m, 1H), 6.15-6.21 (m, 1H), 7.02 (s, 1H), 7.14-7.33 (m, 3H), 7.55-7.58 (d, J=6.6 Hz, 1H), 7.96-7.99 (d, J=9 Hz, 1H), 8.23-8.25 (m, 2H), 9.70-9.78 (br s, 1H), 10.00 (s, 1H), 10.25-10.29 (m, 1H), 10.72 (br s, 1H).

Example 53

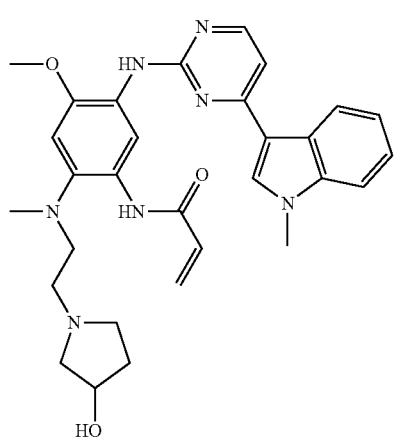

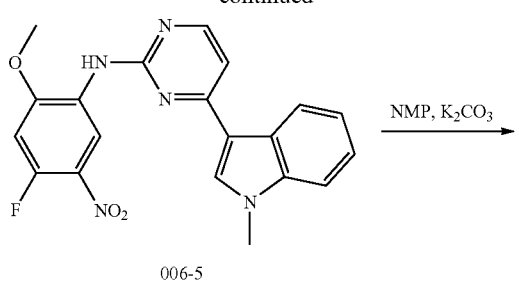

006-5

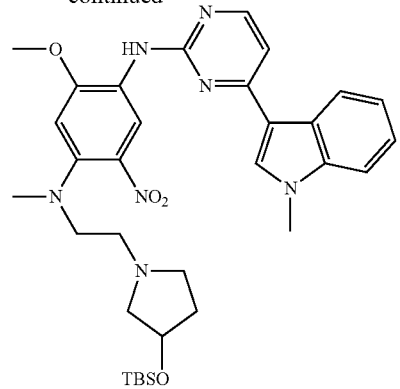

053-6

The intermediate 053-5 (0.50 g, 0.97 mmol) as a raw material was dissolved in 40 mL of dichloromethane in a 100 mL of single-necked flask at room temperature and then imidazole (528 mg, 7.76 mmol) was added to the reaction solution. The reaction system was cooled to 0° C., tert-butyldimethylsilyltrifluoromethanesulfonate (TBSOTf) (2.56 g, 9.68 mmol) was added thereto and the mixture was stirred overnight at room temperature. After the reaction was completed, the mixture was diluted with 100 mL of methyl chloride. The organic phases were washed with 40 mL of saturated sodium bicarbonate solution three times and 30 mL of saturated sodium chloride solution twice, respectively. The organic phases were dried over anhydrous sodium sulfate and concentrated to dryness. The resulting residue was purified by silica gel chromatography (eluent: EA:PE=1:1) to give 210 mg of the intermediate 053-6 (34%) as a red solid. LCMS: 632.3.

5. Synthesis of Intermediate 053-7

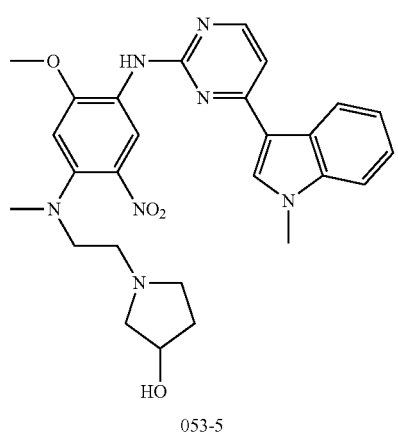

053-5

The intermediate 053-4 (1.2 g, 4.95 mmol) as a raw material was dissolved in 20 mL of NMP at room temperature in a 50 mL of single-necked flask, followed by adding the intermediate 006-5 (19.5 g, 49.6 mmol) and anhydrous potassium carbonate (2.06 g, 14.9 mmol) into the reaction system. The reaction was heated to 100° C. and then carried out for 2 h. After the reaction was completed, the reaction was quenched by adding 100 mL of ice water to the mixture. A solid was precipitated, collected, dissolved in 200 mL of methylene chloride and washed once with 100 mL of saturated sodium chloride solution. The organic phases were dried over sodium sulfate and spin-dried to give 1.2 g of the intermediate 053-5 (47%) as a brown solid. LCMS: 518.2.

4. Synthesis of Intermediate 053-6

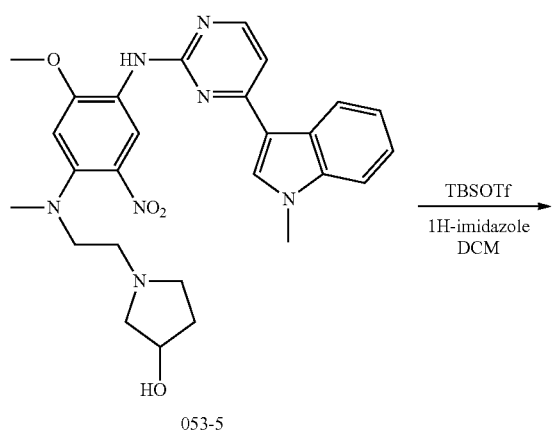

053-5

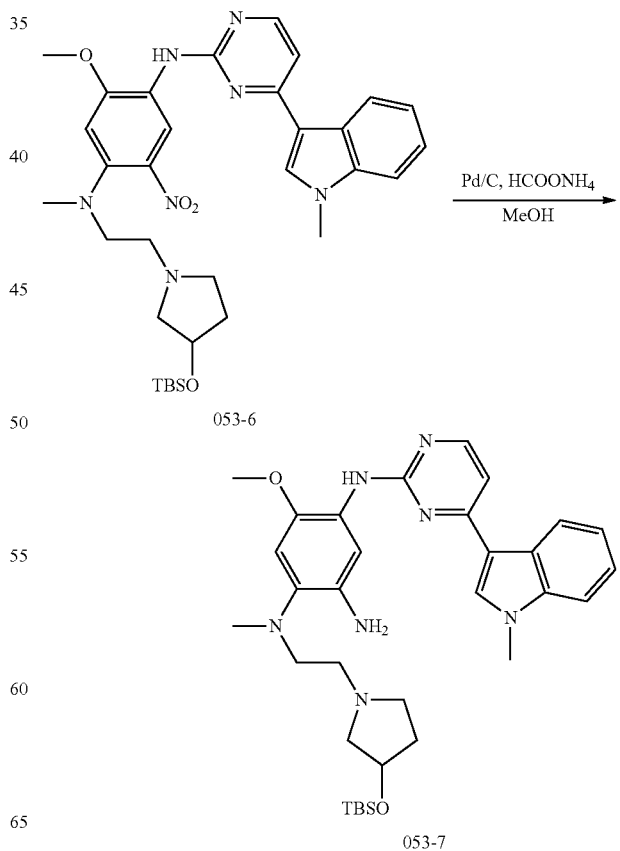

The intermediate 053-6 (210 mg, 0.33 mmol) as a raw material was dissolved in 30 mL of anhydrous methanol in a 50 mL single-necked flask, followed by adding ammonium formate (210 mg) and palladium on carbon (210 mg, 5% Pd). Next, the reaction was carried out for 3 h. The reaction mixture was filtered and the filtrate was subjected to rotary evaporation. The resulting mixture was dissolved in 50 mL of methylene chloride. The mixture was washed with 30 mL of saturated brine twice and the organic phases were dried over sodium sulfate and concentrated to dryness to give 195 mg of the intermediate 053-7 (97%) as a yellow solid. LCMS: 602.4.

6. Synthesis of Intermediate 053-8

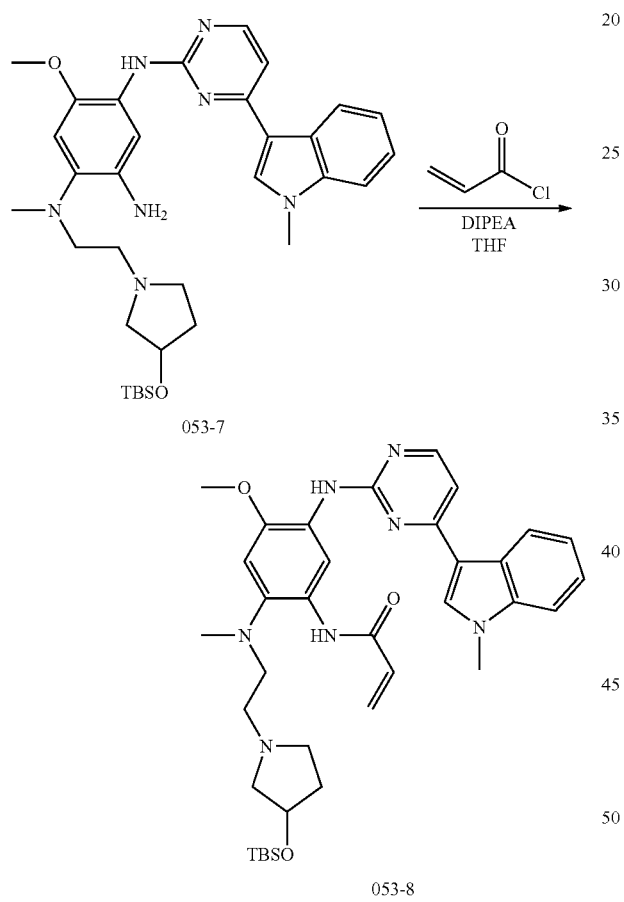

In a 50 mL of three-necked flask, the intermediate 053-7 (195 mg, 0.32 mmol) as a raw material was dissolved in 30 mL of THF, followed by adding DIPEA (83 mg, 0.64 mmol). The reaction system was cooled to 0° C. with ice water, and then acryloyl chloride (29.2 mg, 0.32 mmol) was added thereto. Next, the mixture was stirred at room temperature for 30 min. After the reaction was completed, 2 drops of water were added to the reaction system to quench the reaction and subjected to rotary evaporation to give 300 mg of crude product 053-8. LCMS: 656.4.

7. Synthesis of Compound 53

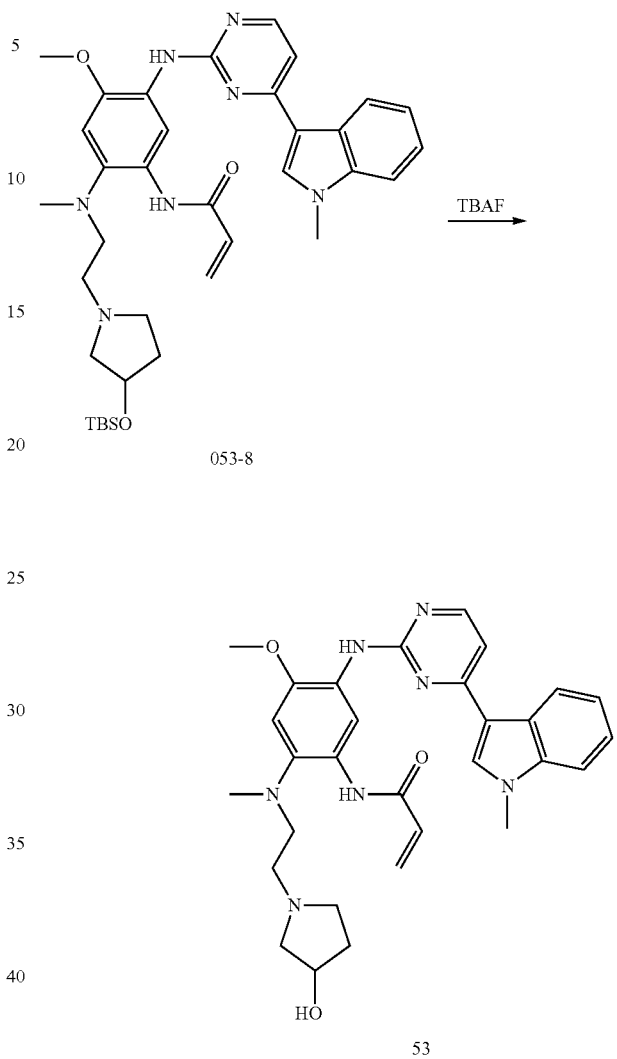

The intermediate 053-8 (0.3 g, 0.46 mmol) as a raw material was dissolved in 40 mL of THF at room temperature followed by addition of tetrabutylammonium fluoride (360 mg, 13.1 mmol), and then the reaction was stirred at room temperature for 2.5 h. After the reaction was completed, the reaction was subjected to rotary evaporation. The resulting residue was purified with high pressure Prep-HPLC (column: Waters Sunfire C18, 19×150 mm, 5 um; mobile phase: acetonitrile/water (0.05% trifluoroacetic acid); 12% acetonitrile to 40% acetonitrile; 7 min 15 mL/min; detection wavelength: 254 nm). The fractions of product were collected and most of the acetonitrile was removed. The pH value of mixture was adjusted to 9 to 10 with a saturated aqueous solution of sodium bicarbonate, and extracted twice with 100 mL of DCM. The organic phase extracted dried over anhydrous sodium sulfate, to give compound 53. LCMS: 541.64.

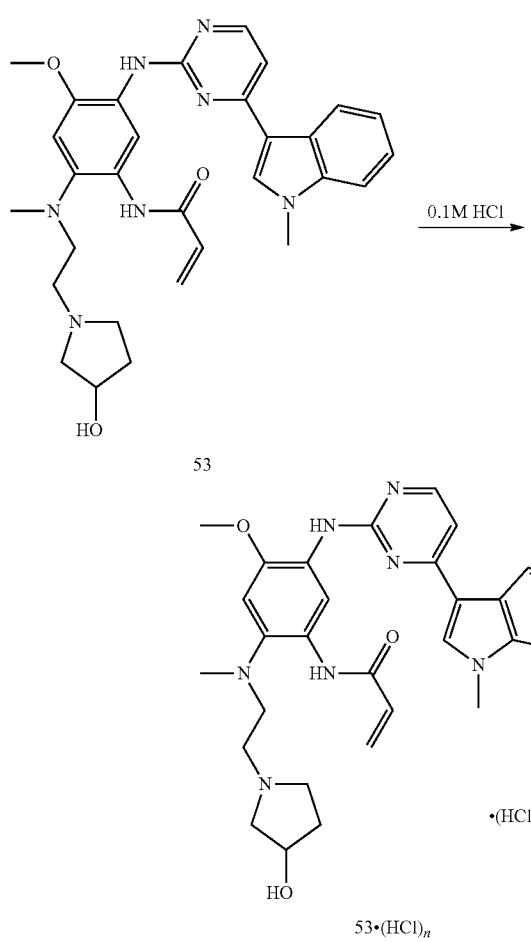

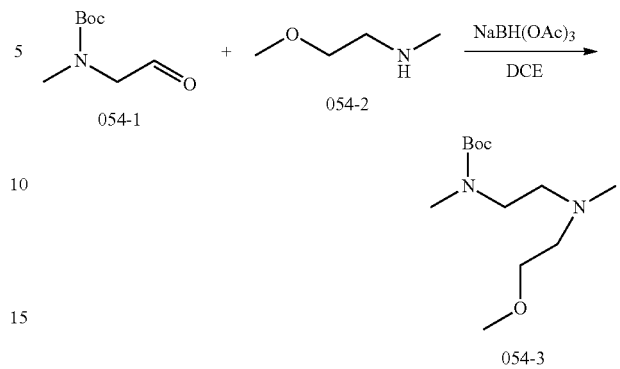

1. Synthesis of Intermediate 054-3

The raw material of N-BOC-(methylamino)acetaldehyde (the intermediate 054-1) (1.039 g, 6.00 mmol) was dissolved in 30 mL of DCE in a 50 mL single-necked flask under a nitrogen atmosphere at 0° C., followed by adding N-(2-methoxyethyl) methylamine (the intermediate 054-2) (534 mg, 5.99 mmol). After the reaction mixture was stirred at 0° C. for 30 minutes, NaBH(OAc)$_3$ (1.908 g, 6.00 mmol) was slowly added to the reaction system in batches, and then the reaction was carried out at 0° C. for 1 hour. The reaction was heated to 25° C. and maintained for 8 hours. After the reaction was completed, 50 mL of ice water was added to quench the reaction. The reaction mixture was extracted with 20 mL of ethyl acetate three times. The combined organic phases were washed with 20 mL of saturated brine once, dried over anhydrous sodium sulfate and concentrated to dryness to give 0.7 g of the intermediate 054-3 (47%) as a crude oil in yellow. LCMS: 246.3.

2. Synthesis of Intermediate 054-4

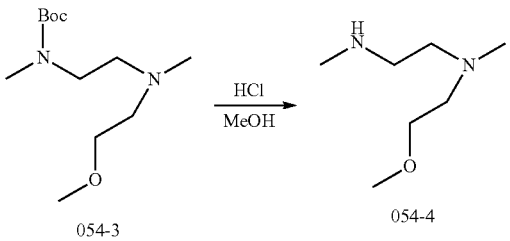

The intermediate 054-3 (700 mg, 2.84 mmol) was dissolved in 20 mL of anhydrous methanol in a 50 mL single-necked flask at room temperature. 3 mL of concentrated hydrochloric acid was slowly added to the reaction system under ice bath and the reaction was carried out for 2 h. After the reaction was completed, the system was concentrated to dryness to give 0.4 g of crude product 054-4 as a yellow solid. LCMS: 182.6.

3. Synthesis of Intermediate 054-5

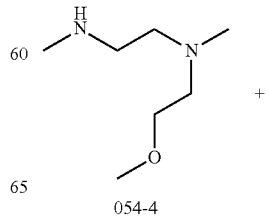

The compound 53 was dissolved in 10 mL of aqueous solution of hydrochloric acid (0.1 N), then the reaction mixture was freeze dried to give 8.3 mg of the hydrochloride (HCl), of compound 53 (3%) as a yellow solid. LCMS (parent molecule) $CH_{30}H_{35}N_7O_3$: (ES, m/z): 542.6 [M+H]$^+$.
$^1$H-NMR: (300 MHz, D$_2$O, ppm) δ 7.91 (s, 2H), 7.74 (s, 1H), 7.66-7.45 (m, 1H), 7.25-7.17 (m, 2H), 7.04-6.98 (m, 2H), 6.72-6.60 (m, 1H), 6.58-6.55 (m, 1H), 6.30 (d, J=17.1 Hz, 1H), 5.88 (d, J=10.5 Hz, 1H), 4.59 (s, 1H), 3.89 (s, 3H), 3.83-3.60 (m, 2H), 3.50 (s, 3H), 3.39 (s, 5H), 3.27-3.07 (m, 2H), 2.70 (s, 2H), 2.64-1.99 (m, 2H).

Example 54

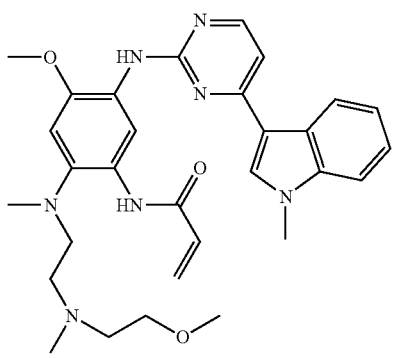

-continued

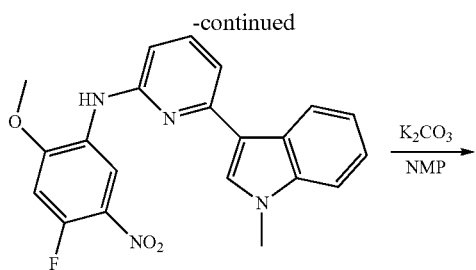

006-5

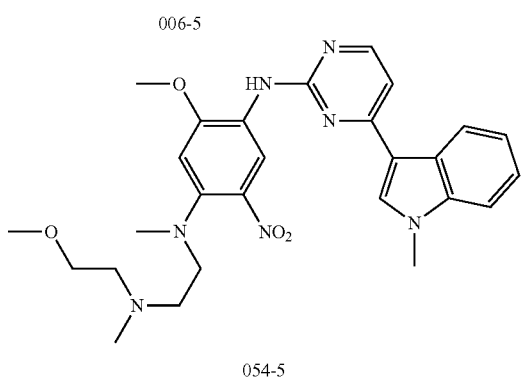

054-5

The intermediate 054-4 (400 mg, 1.02 mmol) as a raw material was dissolved in 5 mL of NMP in 100 mL three-necked flask at room temperature under a nitrogen atmosphere, followed by sequentially adding the intermediate 006-5 (400 mg, 2.37 mmol) and K$_2$CO$_3$ (907 mg, 6.56 mmol) into the reaction system. The reaction system was heated to 105° C. and carried out for 2 hours. After completion of the reaction, the reaction was cooled to room temperature, quenched by adding 30 mL of water. The reaction mixture was extracted with 30 mL of ethyl acetate three times. The organic phases were combined, washed with 30 mL of saturated brine three times, dried over anhydrous sodium sulfate and concentrated to dryness. The residue was purified by silica gel column chromatography (eluent: DCM/MeOH=15:1) to give 100 mg of the intermediate 054-5 (19%) as a white solid. LCMS: 519.6.

4. Synthesis of Intermediate 054-6

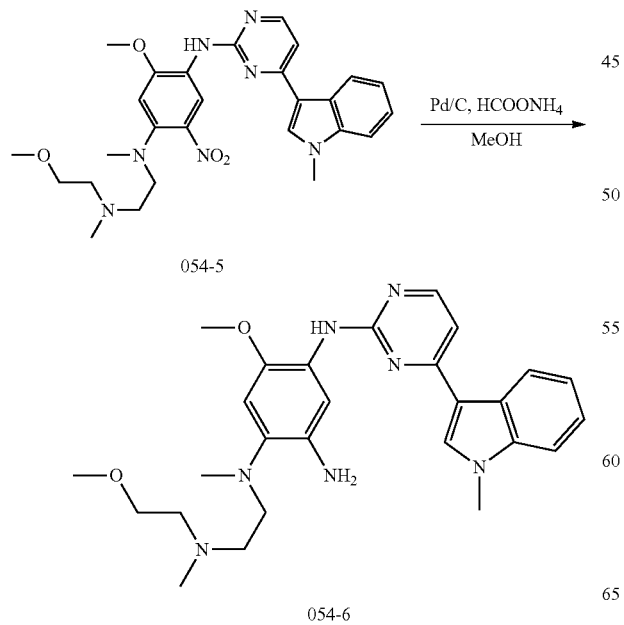

The intermediate 054-5 (100 mg, 0.19 mmol) was dissolved in 10 mL of anhydrous methanol in a 50 mL single-necked flask at room temperature, followed by adding Pd/C containing water (200 mg, 5% Pd) and ammonium formate (200 mg, 0.38 mmol) into the reaction system. The reaction was carried out at room temperature for 2 h. After the reaction was completed, the reaction mixture was undergone a sucking filtration and the filtrate was collected and concentrated to dryness to give 80 mg of the intermediate 054-6 (85%) as a white solid. LCMS: 489.6.

5. Synthesis of Compound 54

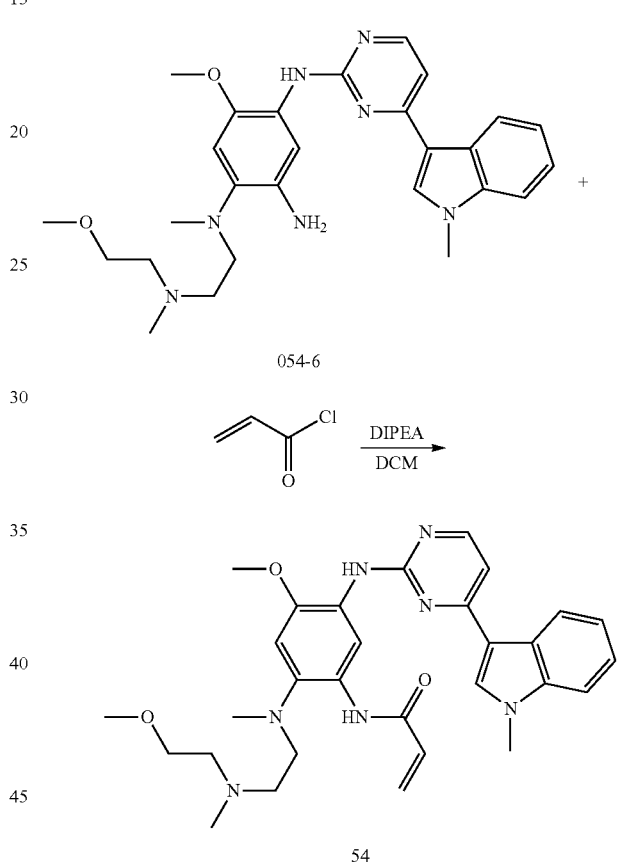

The intermediate 054-6 (62 mg, 0.48 mmol) as a raw material was dissolved in 10 mL of dichloromethane in a 50 mL single-necked flask at −5° C., then adding DIPEA (62 mg, 0.48 mmol). And then allyl chloride (13 mg, 0.14 mmol) was added dropwisely to the reaction system. Next, the reaction was carried out at 0° C. for 2 h. After completion of the reaction, the reaction system was quenched with 1 mL of water, the reaction mixture was concentrated to dryness, and the residue was purified by high pressure preparation Prep-HPLC(Column: Waters X-bridge RP18, 19×150 mm, 5 um; mobile phase: water (10 mM NH$_4$HCO$_3$+0.05% ammonia)/acetonitrile, 56% acetonitrile to 61% acetonitrile, 7 min, 20 mL/min; detection wavelength: 254 nm), and the resulting organic phases were subjected to rotary evaporation to give compound 54.

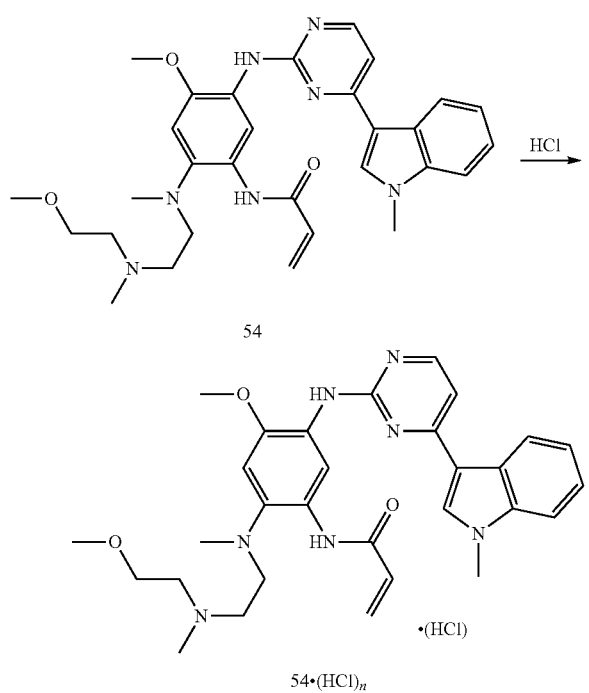

54

54·(HCl)$_n$

The compound 54 was dissolved in the aqueous solution of hydrochloric acid solution (1 M), and the reaction mixture was stirred at room temperature for 30 minutes and freeze dried to give 12.3 mg of the hydrochloride of compound 54 (13%) as a yellow solid. LCMS (parent molecule) $C_{30}H_{37}N_7O_3$: (ES, m/z): 544 [M+H]$^+$. $^1$H-NMR: (DMSO-D$_6$, 300 MHz, ppm) δ10.34-10.31 (m, 1H), 9.89 (s, 1H), 8.80 (s, 1H), 8.39-8.23 (m, 3H), 7.58-7.61 (m, 1H), 7.42-7.40 (m, 1H), 7.20-7.33 (m, 2H), 7.03-7.13 (m, 2H), 6.20-6.25 (m, 1H), 5.70-5.74 (m, 1H), 3.93 (s, 4H), 3.85 (s, 4H), 3.70 (s, 4H), 3.30 (s, 3H), 3.40 (s, 3H), 2.80 (s, 3H), 2.73 (s, 3H).

Example 55

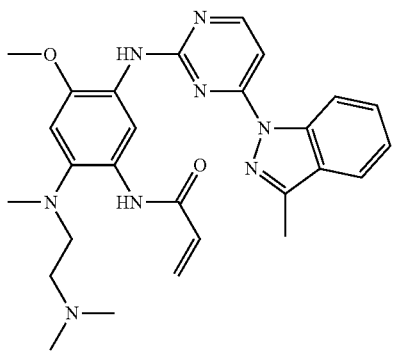

1. Synthesis of Intermediate 055-2

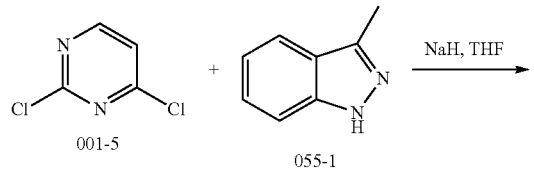

001-5     055-1

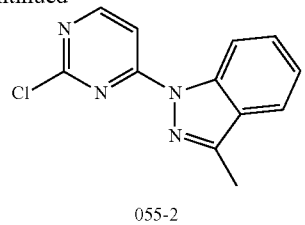

055-2

The intermediate 055-1 (2 g, 15.13 mmol) was dissolved in 100 mL of tetrahydrofuran (THF) in a 250 mL three-necked flask at room temperature under a nitrogen atmosphere, then adding NaH (65%) (620 mg, 25.83 mmol) in batches at room temperature. Next, the reaction was maintained at room temperature for 1 h. After the reaction mixture was cooled to 0° C., the intermediate 001-5 (3.36 g, 22.55 mmol) was added thereto and the reaction was carried out for 2 h. After completion of the reaction, the reaction mixture was quenched by adding 100 mL of ice water. The mixture was extracted with 100 mL of ethyl acetate three times. The organic phases were combined and washed with 50 mL of saturated brine three times, dried over anhydrous sodium sulfate and concentrated. The crude product was purified through silica gel column chromatography (EA/PE=1:10-1:3) to give 1.5 g of the intermediate 055-2 (41%) as a pale yellow solid. LCMS: 245.0.

2. Synthesis of Intermediate 055-3

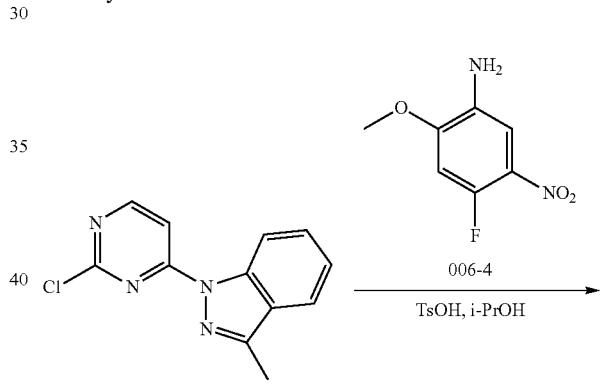

055-2

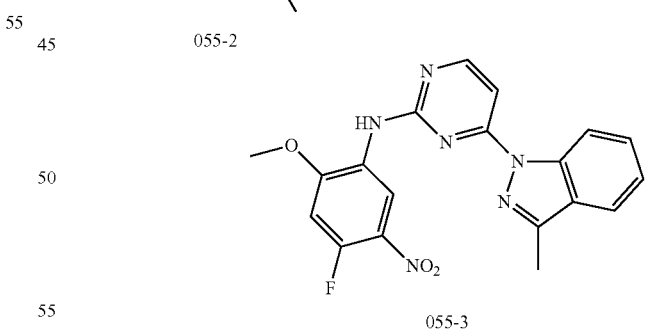

055-3

The intermediate 055-2 (1.5 g, 6.13 mmol) as a raw material was dissolved in 150 mL of isopropanol in a 250 mL three-necked flask under nitrogen atmosphere, followed by sequentially adding the intermediate 006-4 (1.13 g, 6.07 mmol) and p-toluenesulfonate acid (1.13 g, 6.07 mmol) into the reaction system. The reaction was heated to 105° C. and carried out for 2 h. After the reaction was completed, the reaction mixture was cooled to room temperature, and filtered by suction. The filter cake was collected, sequentially washed with 30 mL of water twice and 30 mL of n-hexane twice, and dried to give 2 g of the intermediate 055-3 (83%) as a yellow solid. LC MS: 381.0.

3. Synthesis of Intermediate 055-4

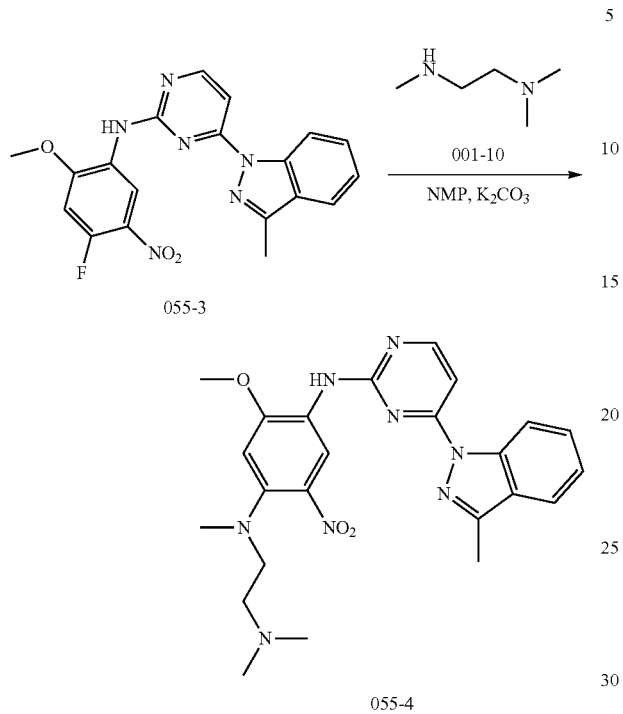

055-3

055-4

The intermediate 055-3 (2.0 g, 5.07 mmol) as a raw material was dissolved in 60 mL of NMP in a 100 mL three-necked flask at room temperature under a nitrogen atmosphere, then adding N,N,N'-trimethylethylenediamine (680 mg, 6.66 mmol) and anhydrous potassium carbonate (2.1 g, 15.2 mmol) into the reaction system. The reaction was heated to 100° C. and carried out for 2 h. After the reaction was completed, the reaction was cooled to room temperature and quenched by adding 200 mL of ice water to the reaction mixture. The mixture was filtered by suction, and the filter cake was collected, sequentially washed with 50 mL of water twice and 50 mL of n-hexane twice. The reaction mixture was dried to give 1.2 g of the intermediate 055-4 (50%) as a brown solid. LCMS: 477.0.

4. Synthesis of Intermediate 055-5

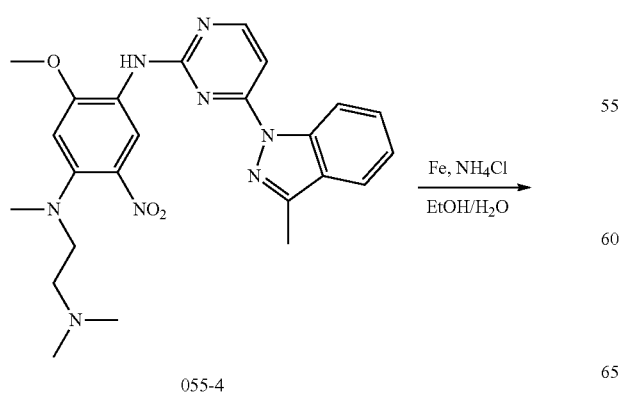

055-4

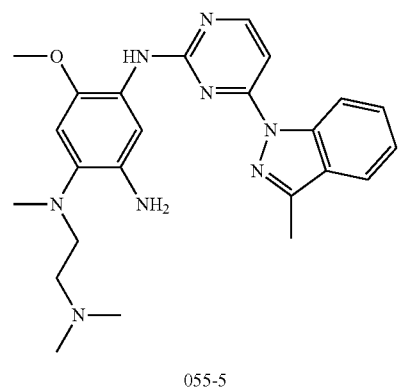

055-5

The intermediate 055-4 (1.2 g, 2.52 mmol), iron powder (853 mg, 15.3 mmol) and ammonium chloride (93 mg, 2.53 mmol) were sequentially added into 12 mL of ethanol and 4 mL of water in a 50 mL three-necked flask at room temperature under a nitrogen atmosphere. Next, the reaction was carried out at 80° C. for overnight. After the reaction was completed, the reaction system was cooled to room temperature. The mixture was filtered by suction, and the filtrate was collected, concentrated to dryness. The crude product was purified by flash chromatography (chromatography column: C18 silica gel; mobile phase: acetonitrile/water (0.05% trifluoroacetic acid); 35% acetonitrile to 50% acetonitrile; 15 min; detection wavelength: 254 nm) to give 1.02 g of the intermediate 055-5 (72%) as a yellow solid. LCMS: 447.0.

5. Synthesis of Compound 55

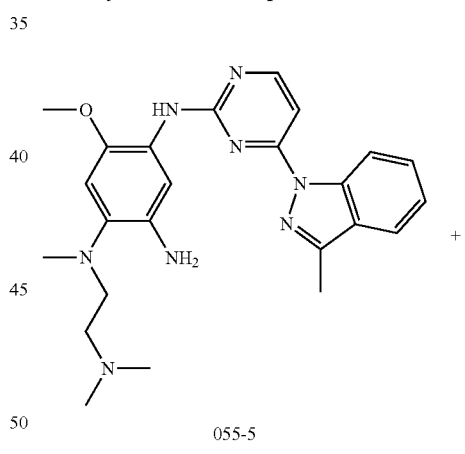

055-5

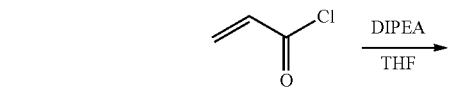

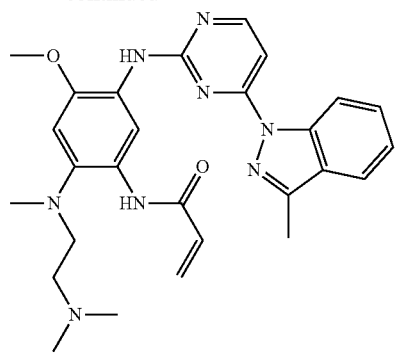

55

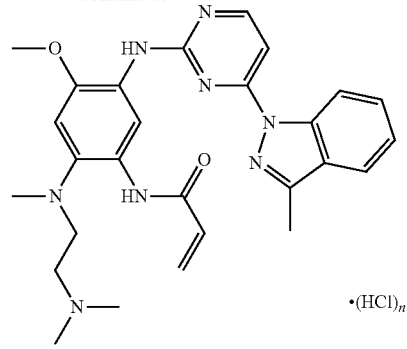

55·(HCl)$_n$

The intermediate 055-6 (280 mg, 0.50 mmol) as a raw material was dissolved in 20 mL of anhydrous THF at room temperature in a 100 mL three-necked flask at room temperature under a nitrogen atmosphere, followed by adding N,N-diisopropylethylamine (DIPEA) (193.5 mg, 1.50 mmol). After the reaction mixture was cooled to 0° C., acetyl chloride (40.5 mg, 0.45 mmol) was dissolved in 2 mL of tetrahydrofuran at 0° C. and the resulting solution was added dropwisely to the reaction system. Next, the reaction was stirred at 0° C. for 1 h. After the reaction was completed, the mixture was quenched with 1 mL of water and the residue was concentrated to dryness. The crude product was purified by high pressure preparation HPLC (column: Waters X-bridge RP 18, 19×150 mm, mobile phase: water (10 mM NH$_4$HCO$_3$+0.05% ammonia)/acetonitrile, 50% acetonitrile to 57% acetonitrile, 5 min, 20 mL/min; detection wavelength: 254 nm). The resulting organic phases were subjected to rotary evaporation to give compound 55. LCMS: 501.0.

Compound 55 was dissolved in 7.2 mL of 0.01 M aqueous solution of hydrochloric acid, and freeze dried to give 20 mg of the hydrochloride (HCl)$_n$ of compound 55 as a yellow solid. LCMS (parent molecule) C$_{27}$H$_{32}$N$_8$O$_2$: (ES, m/z): 501 [M+H]$^+$. $^1$H-NMR: (DMSO-D$_6$, 300 MHz, ppm): 11.09-11.17 (m, 1H), 10.82 (br s, 1H), 10.14 (br s, 1H), 8.27 (brs, 1H), 8.12-8.15 (d, J=7.2 Hz, 1H), 7.92-7.94 (d, J=7.8 Hz, 1H), 7.62-7.67 (m, 1H), 7.39-7.44 (m, 1H), 7.24-7.33 (m, 1H), 7.04 (s, 1H), 6.91 (br s, 1H), 6.10-6.16 (m, 1H), 5.62-5.66 (m, 1H), 3.86 (s, 3H), 3.40 (m, 4H), 2.76 (s, 3H), 2.74 (s, 3H), 2.68 (s, 3H), 2.66 (s, 3H).

Example 56

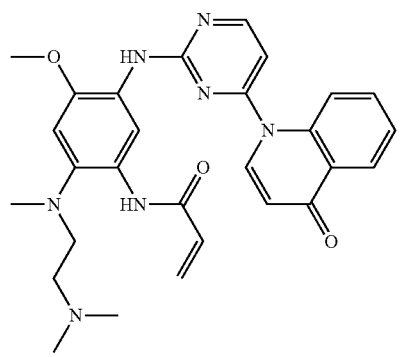

56

1. Synthesis of Intermediate 056-2

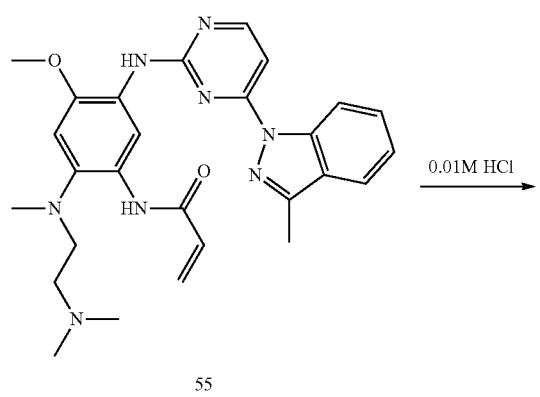

Under a nitrogen atmosphere, 2-nitroacetophenone 056-1 (8.5 g, 51.47 mmol) was added to 80 mL of DMF in a 250 mL three-necked flask at room temperature, followed by adding DMF-DMA (8.0 g, 67.2 mmol) into the reaction system. The reaction temperature was heated to 110° C. for 2 h. After detecting the reaction was completed, the reaction mixture was cooled to room temperature. The reaction was quenched with 100 mL of ice water and extracted with 100 mL of ethyl acetate three times. The organic phases were collected, washed with saturated brine three times, dried over anhydrous sodium sulfate three times and concentrated. The residue was washed with 200 mL of n-hexane once and filtered by suction. The filter cake was collected and dried to give 7.6 g of the intermediate 056-2 (67%) as a yellow solid. LCMS: 166.0.

2. Synthesis of Intermediate 056-4

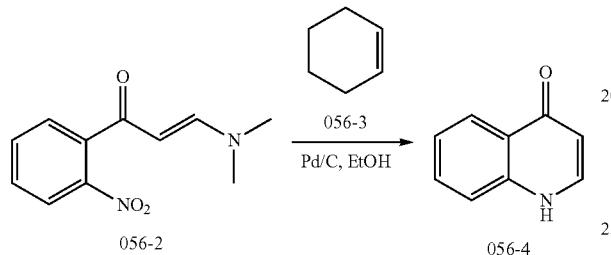

The intermediate 056-2 (75.6 g, 34.5 mmol) was dissolved in 100 mL of anhydrous ethanol in a 250 mL three-necked flask at room temperature under a nitrogen atmosphere, followed by adding cyclohexene (the intermediate 056-3) (14.2 g, 172.9 mmol) and palladium on carbon containing water (18.7 g, 10% Pd) into the reaction system at room temperature. The reaction was heated to reflux for 2 h. After the reaction was completed, the mixture was cooled to room temperature and then filtered by suction. The filtrate was collected and concentrated to dryness. The residue was washed with 100 mL of the mixed solvent (EA/PE=1:2) once. The solid was filtered by suction, and the filter cake was dried to give 4.2 g of the intermediate 056-4 (84%) as a yellow solid. LCMS: 146.1.

3. Synthesis of Intermediate 056-5

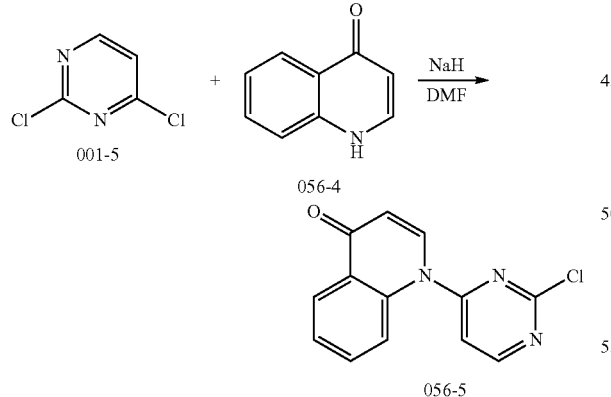

Under a nitrogen atmosphere, the intermediate 056-4 (3.0 g, 20.7 mmol) as a raw material was dissolved in 50 mL of N,N-dimethylformamide (DMF) in a 100 mL single-necked flask at room temperature, and then the reaction system was cooled to 0° C. and NaH (65%, dispersed in a mineral oil) (2.3 g, 95.8 mmol) was added thereto. The reaction was maintained at 0° C. for 30 min. Next, 2,4-dichloropyrimidine (the intermediate 001-5) (6.0 g, 40.3 mmol) was dissolved in 50 mL of DMF and the resulting solution was added dropwise to the reaction system at 0° C. The reaction was carried out at 0° C. for 2 h until the reaction was detected to confirm the reaction was completed. The reaction mixture was poured into 100 mL of aqueous solution of saturated ammonium chloride to quench the reaction, and the system was extracted with 100 mL of ethyl acetate three times. The organic phases were combined, washed with 100 mL of saturated brine three times, dried over anhydrous sodium sulfate and concentrated. The crude product was purified by flash column chromatography (column: silica gel; mobile phase:ethyl acetate/petroleum ether; 50% ethyl acetate to 85% ethyl acetate; 30 min; detection wavelength: 254 nm) to give 1 g of the intermediate 056-5 (19%) as a white solid. LCMS: 258.0.

4. Synthesis of Compound 56

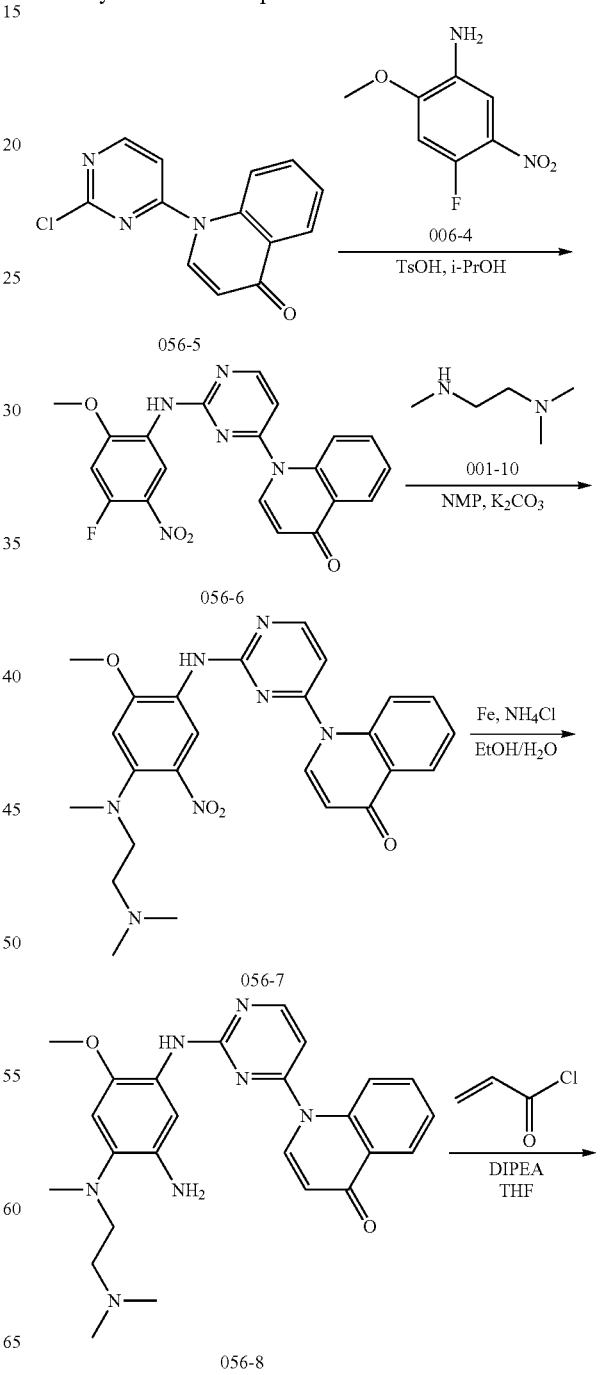

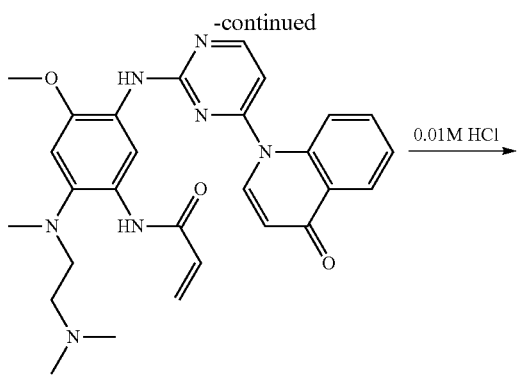

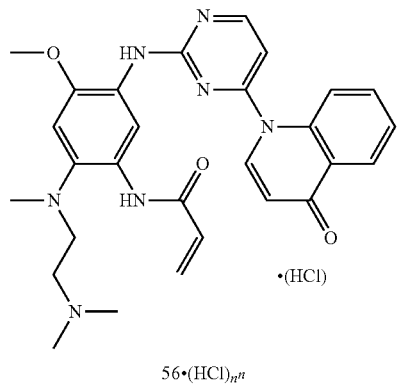

The reaction steps and conditions for the synthesis of final compound 56 and its hydrochloride 56·(HCl)$_n$ from the intermediate 056-5 were the same as those in the second and third steps of example 55, except that the intermediate 055-3 in example 55 was replaced with the intermediate 056-5. Analytical data for the hydrochloride 56·(HCl)$_n$: LCMS (parent molecule) $C_{28}H_{31}N_7O_3$: (ES, m/z): 514 [M+H]$^+$. $^1$H-NMR: (300 MHz, DMSO-D$_6$, ppm) δ 10.45 (br s, 1H), 9.73 (s, 1H), 8.92 (s, 1H), 8.67-8.65 (d, J=5.1 Hz, 1H), 8.35 (s, 1H), 8.30-8.28 (d, J=7.8 Hz, 1H), 8.21-8.19 (d, J=7.5 Hz, 1H) 7.71-7.64 (m, 2H), 7.47-7.7.42 (m, 4H), 7.17-7.02 (m, 2H), 6.92 (s, 1H), 6.28-6.22 (m, 2H), 5.73-5.60 (dd, J=10.2 Hz, 2.1 Hz, 1H), 3.88 (s, 3H), 327 (m, 4H), 2.72-2.71 (d, J=4.8 Hz, 6H), 2.65 (s, 3H).

Example 57

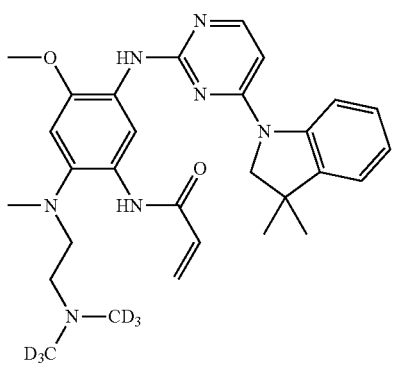

1. Synthesis of Intermediate 057-2

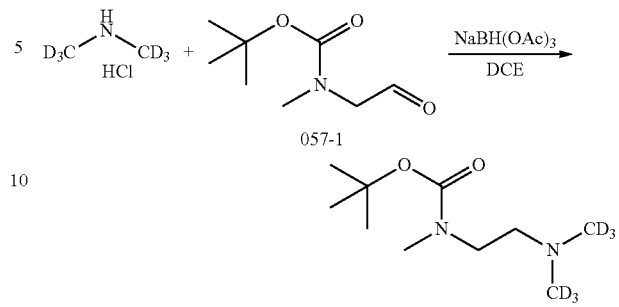

Under a nitrogen atmosphere, deuterated dimethylamine hydrochloride (1.5 g, 17.2 mmol) was added to 50 mL of 1,2-dichloroethane in a 100 mL three-necked flask at room temperature, then adding the intermediate 057-1 (3.0 g, 17.3 mmol) into the reaction system. The reaction was carried out at room temperature for 2 h. After the reaction system was cooled to 0° C., sodium triacetoxyborohydride (5.5 g, 26.0 mmol) was added in batches and the reaction was heated from 0° C. to room temperature. Then, the reaction was stirred overnight. After detecting the reaction was completed the next day, the reaction was quenched with 100 mL of saturated aqueous solution of ammonium chloride, and the reaction mixture was extracted with 100 mL of methylene chloride twice. The aqueous phases were collected, adjusted to pH 9 with saturated aqueous solution of sodium carbonate, extracted with 100 mL of methylene chloride three times, and the organic phases were combined, washed with 100 mL of saturated brine twice, dried over anhydrous sodium sulfate and concentrated to dryness to give 0.80 g of the intermediate 057-2 (22%) as yellow oil. LCMS: 209.2.

2. Synthesis of Intermediate 057-3

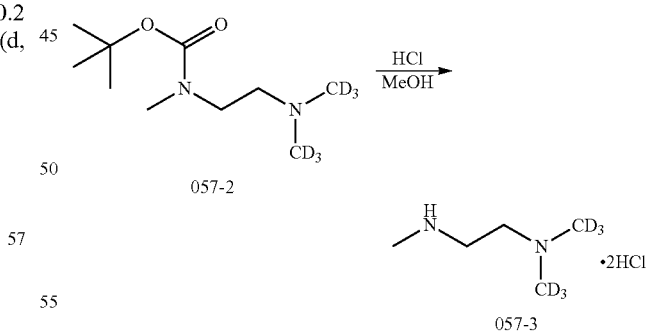

The intermediate 057-2 (800 mg, 3.85 mmol) as a raw material was dissolved in 10 mL of anhydrous methanol in a 50 mL single-necked flask at room temperature, followed by adding 10 mL of concentrated hydrochloric acid into the reaction system at room temperature. The reaction was carried out for 5 h at room temperature. After detecting the reaction was completed, the reaction mixture was concentrated directly to give 0.60 g of the intermediate 057-3 (87%) as a white solid. LCMS: 109.2.

3. Synthesis of Compound 57

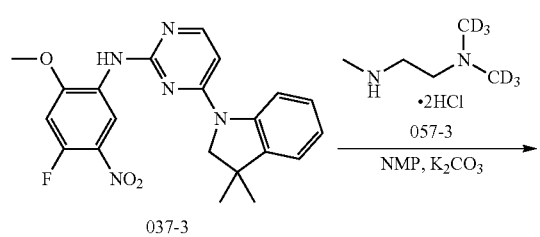

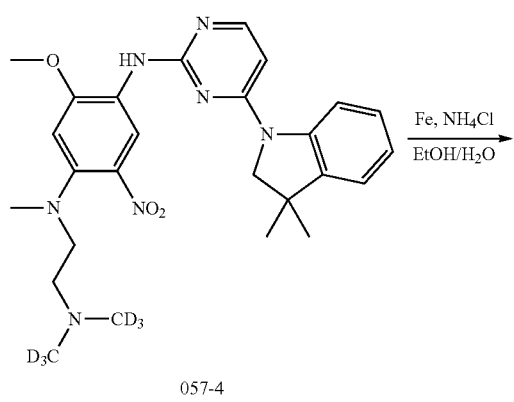

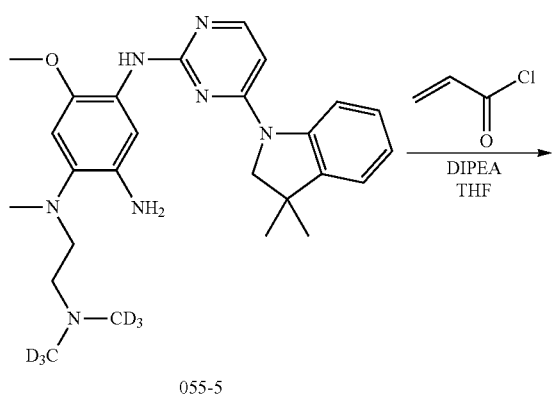

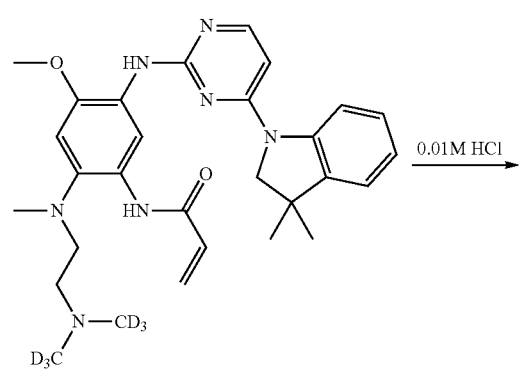

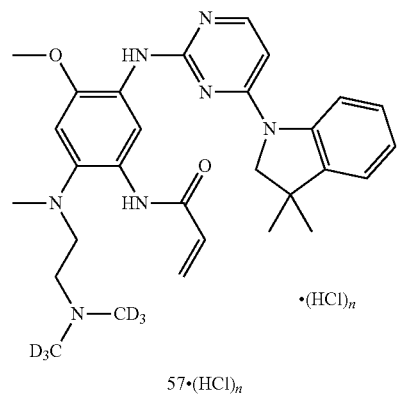 [SMILES: [2H]C([2H])([2H])N(CCN(C)c1cc(OC)c(Nc2nccc(N3CC(C)(C)c4ccccc43)n2)cc1NC(=O)C=C)C([2H])([2H])[2H]]

The reaction steps and conditions for the synthesis of final compound 57 and its hydrochloride 57·(HCl)$_n$ from the intermediates 037-3 and 057-3 were the same as those in the second to fifth steps of example 55, except that the intermediate 055-3 in example 55 was replaced with the intermediate 037-3 and the intermediate 001-10 in example 55 was replaced with the intermediate 057-3. Analytical data for the hydrochloride 57·(HCl)$_n$: LCMS (parent molecule) C$_{29}$H$_{31}$D$_6$N$_7$O$_2$: (ES, m/z): 522.3 [M+H]$^+$. $^1$H-NMR: (300 MHz, DMSO-D$_6$, ppm) δ 10.06 (br s, 1H) 9.92-9.97 (m, 2H), 8.08-8.24 (m, 3H), 7.32-7.35 (m, 1H), 7.11-7.26 (m, 3H), 7.02 (s, 1H), 6.17-6.23 (br s, 1H), 5.67-5.71 (m, 1H), 3.99 (m, 2H), 3.83 (s, 3H), 3.35 (m, 4H), 2.65 (s, 3H), 1.33 (s, 6H).

Example 58

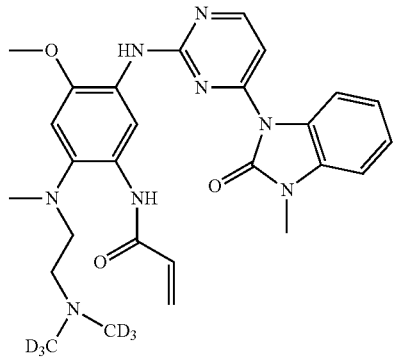

1. Synthesis of Compound 58

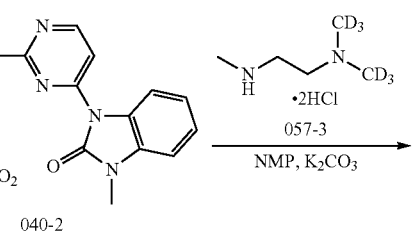

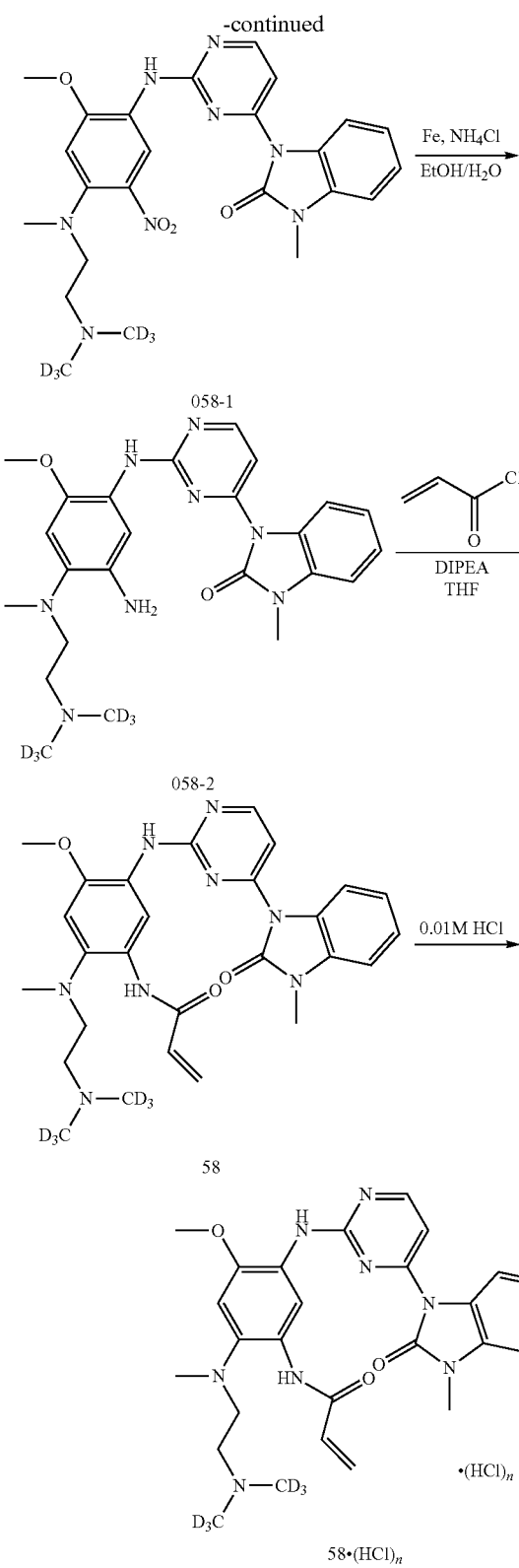

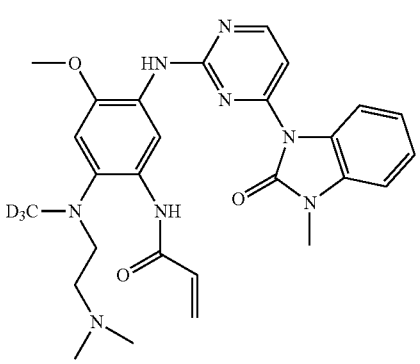

replaced with the intermediate 057-3. Analytical data for the hydrochloride 58. (HCl)$_n$: LCMS (parent molecule) $C_{27}H_{26}D_6N_8O_3$: (ES, m/z): 523.3 [M+H]$^+$. $^1$H-NMR: (300 MHz, DMSO-D$_6$, ppm) δ 10.47 (br s, 1H), 9.84 (s, 1H), 9.29-9.42 (m, 1H), 8.43-8.45 (d, J=6 Hz, 1H), 8.18 (br s, 1H), 7.83-7.51 (d, J=6.3 Hz, 1H), 7.10-7.25 (m, 3H), 6.99-7.04 (m, 2H), 6.17-6.23 (m, 1H), 5.67-5.71 (m, 1H), 3.75 (s, 3H), 3.38 (s, 3H), 3.33 (m, 4H), 2.73 (s, 3H).

Example 59

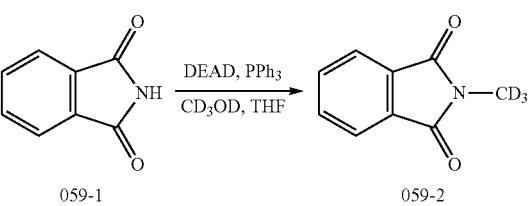 [SMILES: O=C1NC(=O)c2ccccc21 ; [2H]C([2H])([2H])N1C(=O)c2ccccc2C1=O]

1. Synthesis of Intermediate 059-2

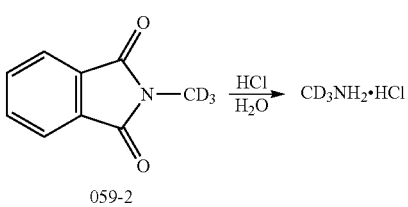

Under a nitrogen atmosphere, the intermediate 059-1 (90 g, 611.7 mmol), 1500 mL of THF, triphenylphosphine (PPh$_3$) (176.4 g, 672.6 mmol) and tetradeuteromethanol (CD$_3$OD) (22.5 g, 642.9 mmol) were sequentially added into a 3000 mL four-necked flask. After the reaction was cooled to 0° C., DEAD (117 g, 671.8 mmol) was added dropwise for 1 h. The reaction was carried out at room temperature overnight. The reaction was completed, and 5000 mL of ice was added therein to quench the reaction. The reaction mixture was extracted with 3000 mL of ethyl acetate three times and the organic phases were combined, washed with 3000 mL of saturated brine three times, dried over anhydrous sodium sulfate and subjected to rotary evaporation. The crude product was purified by silica gel column chromatography (eluent: EA:PE=1:10-1:5) to give 55 g of the intermediate 059-2 (55%) as a white solid.

2. Synthesis of Intermediate of Deuterated Methylamine

The reaction steps and conditions for the synthesis of final compound 58 and its hydrochloride 58. (HCl)$_n$ from the intermediates 040-2 and 057-3 were the same as those in the third to fifth steps of example 55, except that the intermediate 055-3 in example 55 was replaced with the intermediate 040-3 and the intermediate 001-10 in example 55 was The intermediate 059-2 (55 g, 335.0 mmol), water (440 mL) and concentrated hydrochloric acid (440 mL) were sequentially added into a 2000 mL single-necked flask. The reaction mixture was heated to 105° C. and then the reaction was carried out for 48 h. After completion of the reaction, the reaction was cool to room temperature. The solid was removed by filtration, and the filtrate was concentrated to dryness. The crude product was added to 100 mL of ethanol, the resulting mixture was heated to 75° C. and refluxed for 1 h and cooled to room temperature. The obtained solid was filtered by suction, and the filter cake was collected and dried to give 12 g of deuterated methylamine hydrochloride (51%) as a white solid.

3. Synthesis of Intermediate 059-3

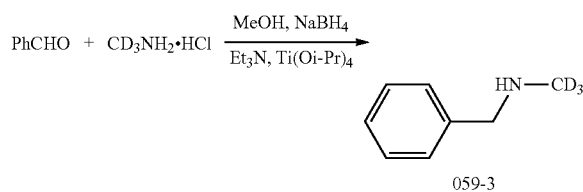

Deuterated methylamine hydrochloride (2.6 g, 36.86 mmol), 50 mL of methanol, triethylamine ($Et_3N$) (3.8 g, 37.6 mmol) and benzaldehyde (2 g, 18.9 mmol) were sequentially added to a 250 mL three-necked flask under a nitrogen atmosphere. The reaction system was cooled to 0° C., tetraisopropyltitanate ($Ti(Oi-Pr)_4$) (10.8 g, 38.0 mmol) was added dropwisely therein, and then the reaction was carried out overnight at room temperature. Next day, sodium borohydride ($NaBH_4$) (1.4 g, 37.0 mmol) was added in batches and the resulting reaction mixture was reacted for 2 h at 0° C. After the reaction was completed, 20 mL of water was added therein to quench the reaction. The solid was removed by filtration and the filtrate was collected and concentrated. The crude product was purified by Combi-FLASH (Rapid chromatography column analyzer) (Column, C18 silica gel; mobile phase: water (0.05% TFA)/$CH_3CN$=5%-15%, 12 min, detection wavelength: 200 nm). The obtained product was collected, concentrated, and dissolved in 100 mL of water. The resulting product was adjusted to pH 9 with $NaHCO_3$, and then extracted with 100 mL of chloroform three times. The organic phases were combined, washed with 100 mL of saturated solution of NaCl once, dried over anhydrous $Na_2SO_4$, and concentrated to give 600 mg of the intermediate 059-3 (26%) as colorless oil. LCMS: 125.1.

4. Synthesis of Intermediate 059-5

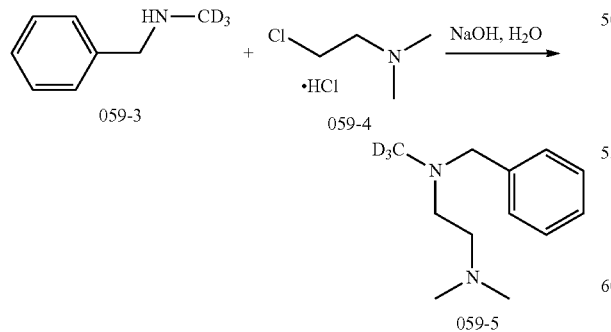

Sodium hydroxide (NaOH) (580 mg, 14.5 mmol), $H_2O$ (10 mL), dimethylamino-2-chloroethane hydrochloride 005-4 (1.4 g, 9.79 mmol) were sequentially added in a 30 mL single-necked flask, and the reaction was carried out at room temperature for 5 min. The intermediate 059-3 (600 mg, 4.83 mmol) was added at room temperature for 2 h, and the reaction was carried out for 2 h. After the reaction was completed, the reaction was extracted with 50 mL of chloroform three times. The organic phases were combined, and washed with 50 mL of saturated solution of NaCl once, dried over anhydrous $Na_2SO_4$, and concentrated to give 300 mg as yellow oil. LCMS: 196.2.

5. Synthesis of Intermediate 059-6

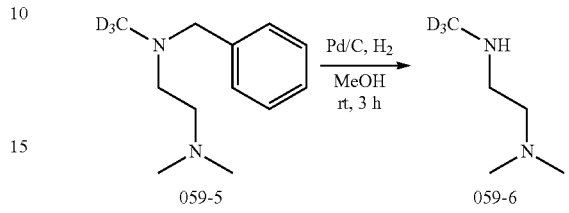

The intermediate 059-5 (300 mg, 1.54 mmol), 30 mL of methanol, and Pd/C containing water (1.0 g, 5% Pd) were sequentially added to the 100 mL single-necked flask, followed by introducing hydrogen gas. The reaction was carried out at room temperature for 3 h. After the reaction was completed, the palladium on carbon was filtered off and the filtrate was collected and concentrated to give 100 mg of the intermediate 059-6 as yellow oil. LCMS: 106.2.

6. Synthesis of Compound 59

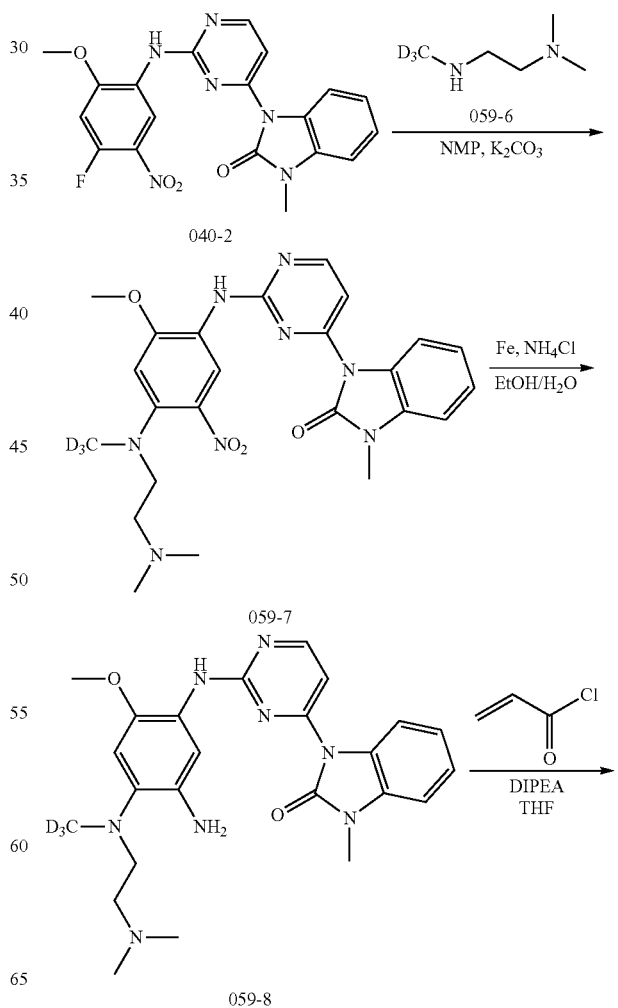

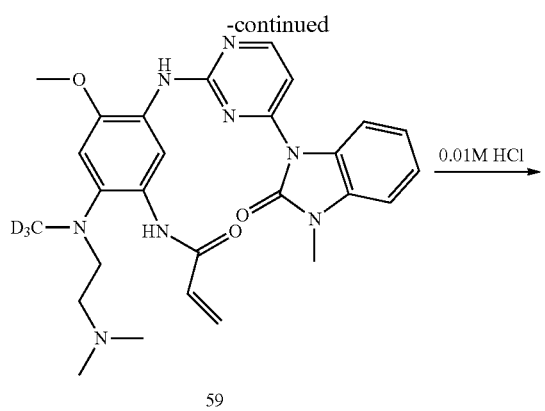

59

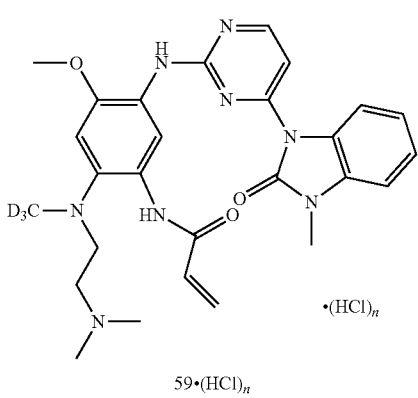 [SMILES: [2H]C([2H])([2H])N(CCN(C)C)c1cc(OC)c(Nc2nccc(-n3c(=O)n(C)c4ccccc43)n2)cc1NC(=O)C=C]

59·(HCl)$_n$

The reaction steps and conditions for the synthesis of final compound 58 and its hydrochloride 58. (HCl)$_n$ from the intermediates 040-2 and 059-6 were the same as those in the third to fifth steps of example 55, except that the intermediate 055-3 in example 55 was replaced with the intermediate 040-2 and the intermediate 001-10 in example 55 was replaced with the intermediate 059-6. Analytical data for the hydrochloride 59. (HCl)$_n$: LCMS C$_{27}$H$_{29}$D$_3$N$_8$O$_3$: (ES, m/z): 520 [M+H]$^+$. $^1$H-NMR: (DMSO-D$_6$, 300 MHz, ppm) δ 10.03-10.31 (m, 1H), 9.78-9.87 (s, 1H), 9.00-9.21 (m, 1H), 8.43-8.45 (d, J=6 Hz, 1H), 8.17 (br s, 1H), 7.78-7.80 (m, 1H), 7.17-7.24 (m, 2H), 6.99-7.09 (m, 3H), 6.19-6.25 (m, 1H), 5.69-5.72 (m, 1H), 3.81 (s, 3H), 3.37 (s, 3H), 3.32 (m, 4H), 2.75 (s, 3H), 2.76 (s, 3H).

Example 60

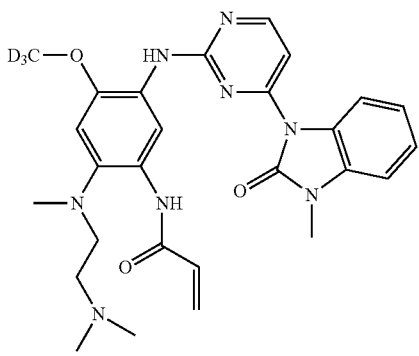

1. Synthesis of Intermediate 060-2

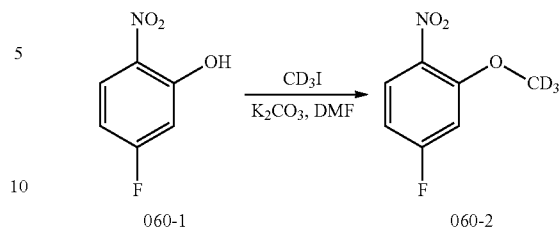

The intermediate 060-1 (10 g, 63.7 mmol), 100 mL of anhydrous DMF, K$_2$CO$_3$ (1.3 g, 9.34 mmol) and deuterated methyl iodide (11 g, 75.9 mmol) were sequentially added to a 250 mL three-necked flask under a nitrogen atmosphere. The reaction was heated to 50° C. and carried out for 2 h in an oil bath. Then, the reaction mixture was cooled to room temperature, quenched with 100 mL of ice water, extracted with 100 mL of EA three times, and filtered. The organic phases were washed with 200 mL of saturated brine three times, dried over anhydrous sodium sulfate and concentrated to dryness to give 9.7 g of the intermediate 060-2 (88%) as a yellow solid.

2. Synthesis of Intermediate 060-3

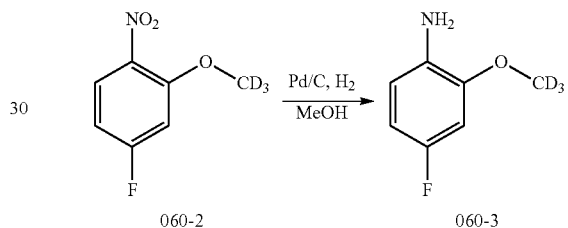

The intermediate 060-2 (9.7 g, 55.7 mmol), 240 mL of methanol and palladium on carbon (12 g, 5%) were sequentially added to a 500 mL single-necked flask, and then the reaction system was replaced by hydrogen gas. After the reaction was carried out at room temperature overnight, the palladium on carbon was filtered off and the filtrate was concentrated to dryness to give 7.2 g of the intermediate 060-3 (90%) as a light-colored liquid. LC-MS: 145.1.

3. Synthesis of Intermediate 060-4

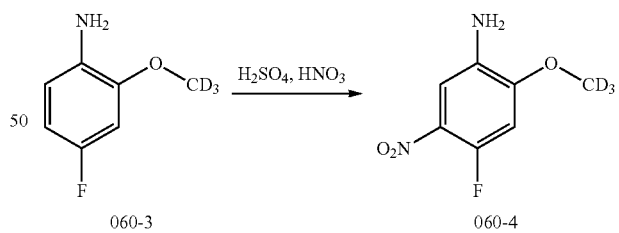

The intermediate 060-3 (7.2 g, 49.9 mmol) and 64 mL of concentrated sulfuric acid were sequentially added to a 250 mL three-necked flask under a nitrogen atmosphere. After the reaction was cooled to 0-10° C., a concentrated nitric acid (HNO$_3$) (5.05 g, 50.0 mmol) was added in batches for 15 min. The reaction was carried out at room temperature overnight. Next, the reaction mixture was added to 500 mL of ice water to quench the reaction, adjusted to pH 10 with ammonia, extracted with 100 mL of EA three times, and washed with 200 mL of saturated brine three times, dried over anhydrous sodium sulfate and concentrated to dryness to give 5.1 g of the intermediate 060-4 (54%) as a yellow solid. LC-MS: 190.1.

4. Synthesis of Compound 60

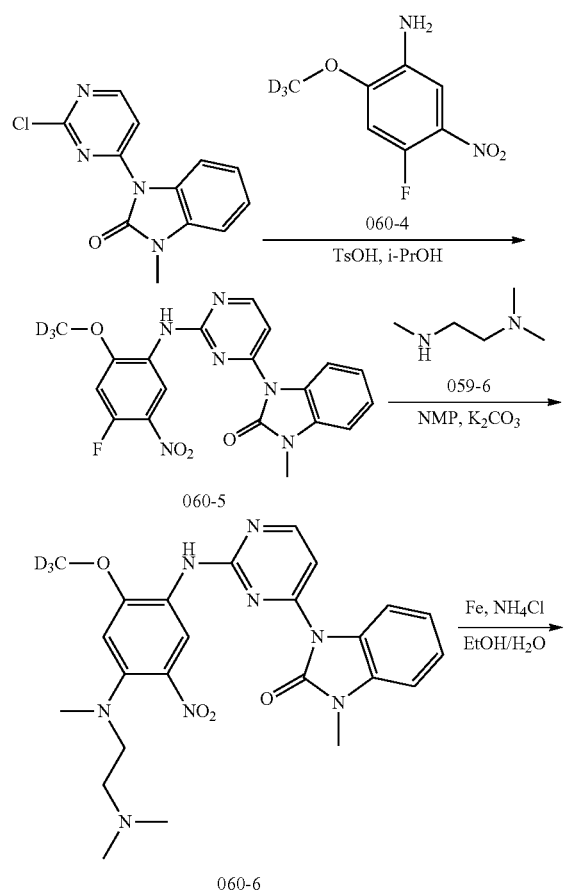

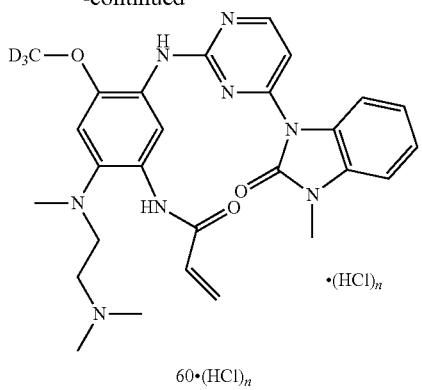

The reaction steps and conditions for the synthesis of final compound 60 and its hydrochloride 60. $(HCl)_n$ from the intermediates 040-1 and 060.4 were the same as those in the second to fifth steps of example 55, except that the intermediate 055-2 in example 55 was replaced with the intermediate 060-4. Analytical data for the hydrochloride 60. $(HCl)_n$: LCMS (parent molecule) $C_{27}H_{29}D_3N_8O_3$: (ES, m/z): 520.3 $[M+H]^+$. $^1$H-NMR: (300 MHz, DMSO-D$_6$, ppm) δ 10.21 (br s, 1H), 9.76 (s, 1H), 9.00-9.03 (m, 1H), 8.43-8.47 (d, J=14.4 Hz, 1H), 8.12-8.17 (m, 1H), 7.75-7.77 (d, J=5.7 Hz, 1H), 7.16-7.24 (m, 2H), 6.98-7.06 (m, 3H), 6.19-6.25 (m, 1H), 5.69-5.73 (m, 1H), 3.37 (s, 3H), 3.32 (m, 4H), 2.77 (s, 3H), 2.75 (s, 3H), 2.73 (s, 3H).

Example 61

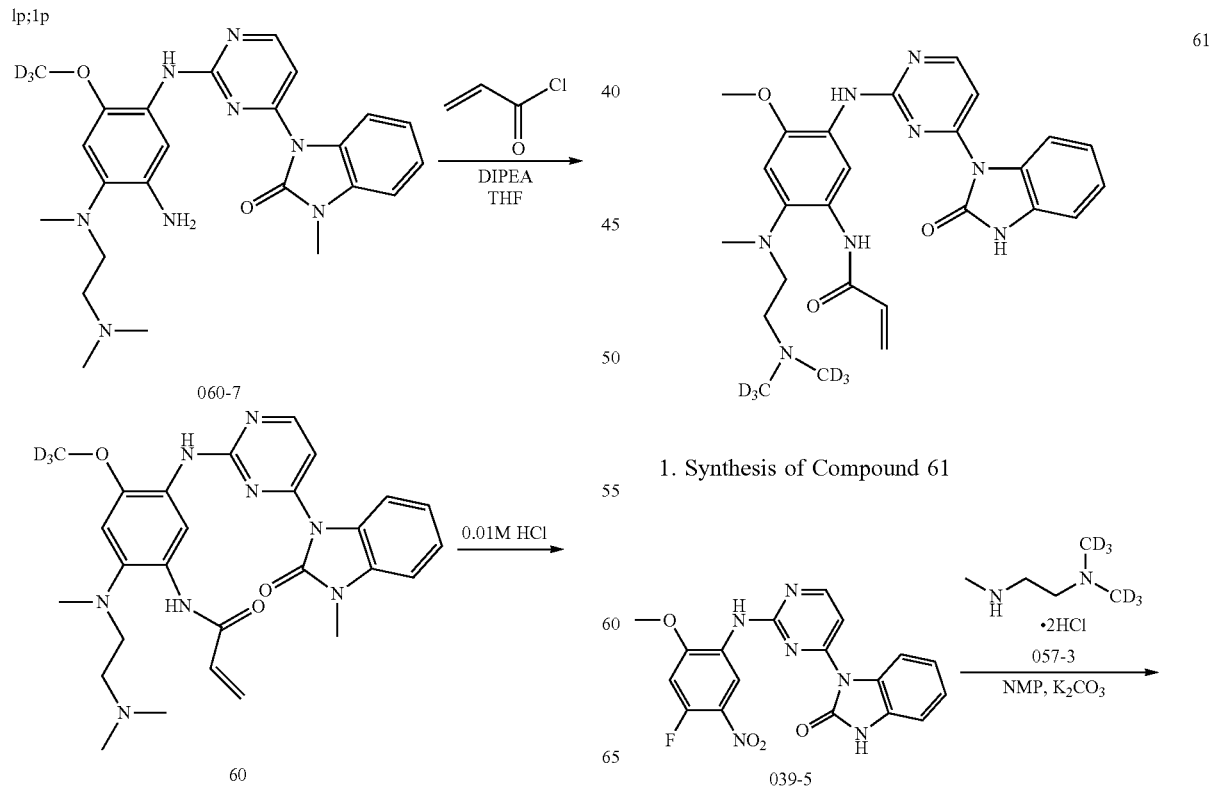

1. Synthesis of Compound 61

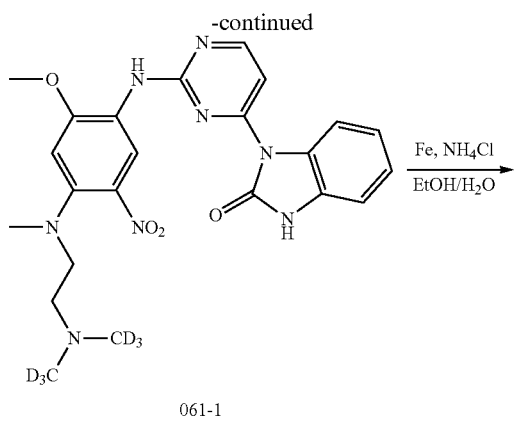

061-1

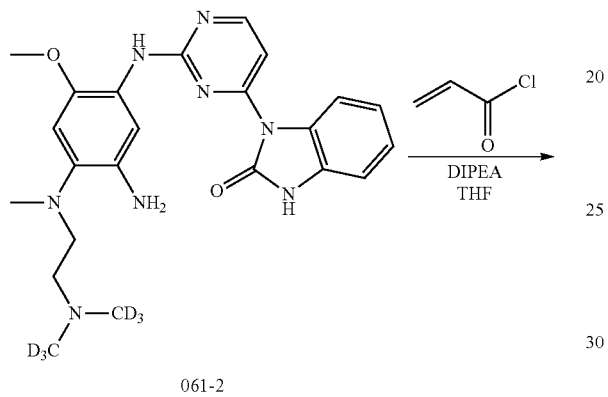

061-2

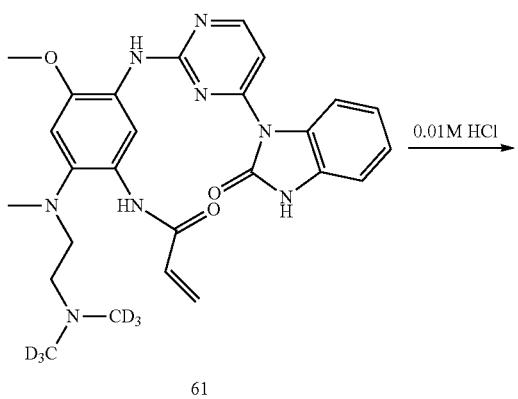

61

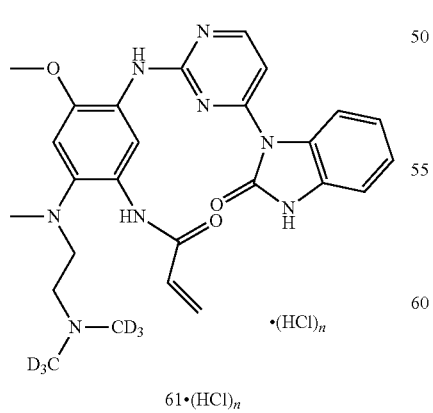

61·(HCl)$_n$

The reaction steps and conditions for the synthesis of final compound 61 and its hydrochloride 61. (HCl)$_n$ from the intermediates 039-5 and 057-3 were the same as those in the third to fifth steps of example 55, except that the intermediate 055-3 in example 55 was replaced with the intermediate 039-5 and the intermediate 001-10 in example 55 was replaced with the intermediate 057-3. Analytical data for the hydrochloride 61. (HCl)$_n$: LCMS (parent molecule) $C_{26}H_{24}D_6N_8O_3$: (ES, m/z): 509.3 [M+H]$^+$. 1H-NMR: (300 MHz, DMSO-D$_6$, ppm) δ 11.49 (s, 1H), 10.33 (br, 1H), 9.81 (s, 1H), 8.40-8.42 (d, J=6 Hz, 1H), 8.18 (s, 1H), 8.10 (m, 1H), 7.79-7.81 (d, J=6.3 Hz, 1H), 6.92-7.14 (m, 5H), 6.18-6.24 (m, 1H), 5.68-5.72 (m, 1H), 3.96 (s, 3H), 3.32 (m, 4H), 2.64 (s, 3H).

Example 62

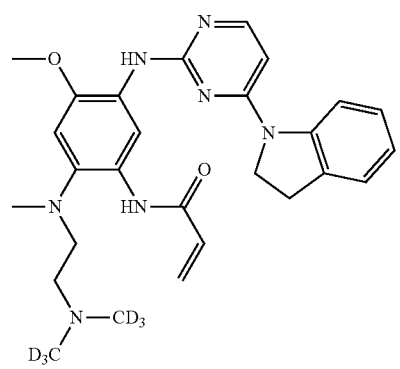

62

1. Synthesis of Compound 62

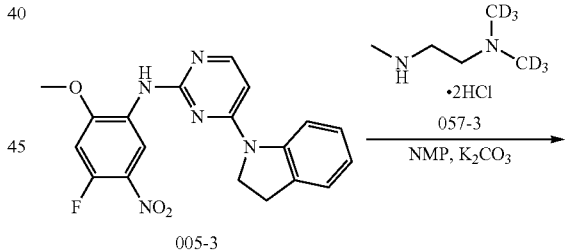

005-3

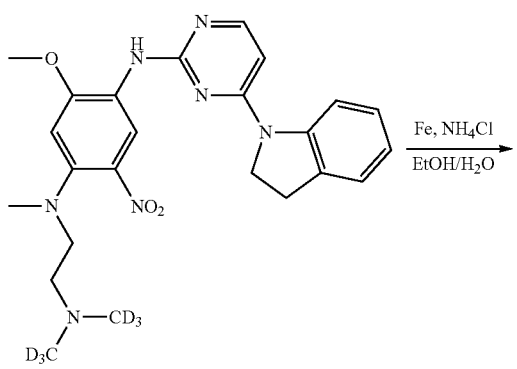

062-1

-continued

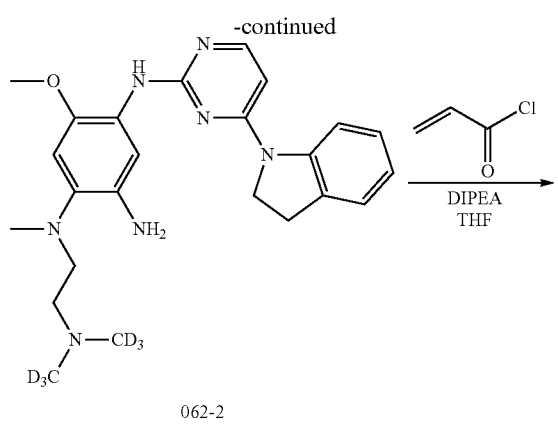
062-2

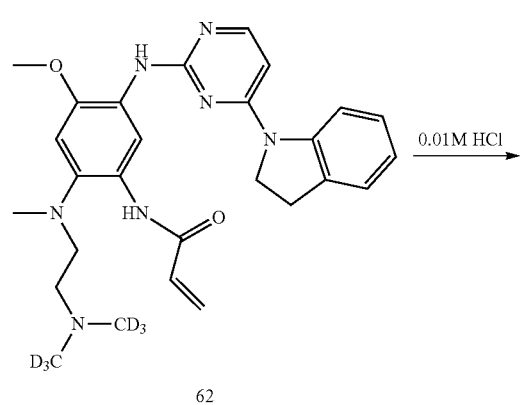
62

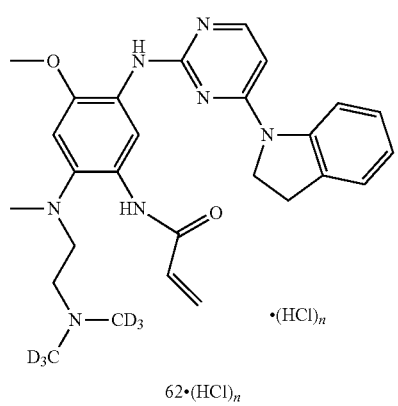 [SMILES: [2H]C([2H])([2H])N(CCN(C)c1cc(OC)c(Nc2nccc(N3CCc4ccccc43)n2)cc1NC(=O)C=C)C([2H])([2H])[2H]]
62·(HCl)$_n$

The reaction steps and conditions for the synthesis of final compound 62 and its hydrochloride 62. (HCl)$_n$ from the intermediates 005-3 and 057-3 were the same as those in the third to fifth steps of example 55, except that the intermediate 055-3 in example 55 was replaced with the intermediate 005-3 and the intermediate 001-10 in example 55 was replaced with the intermediate 057-3. Analytical data for the hydrochloride 62. (HCl)$_n$: LCMS (parent molecule) $C_2H_{27}D_6N_7O_2$: (ES, m/z): 494.3 [M+H]$^+$. $^1$H-NMR: (300 MHz, DMSO-D$_6$, ppm) δ 10.50 (br, 1H), 9.89-9.96 (m, 2H), 8.04-8.15 (m, 2H), 7.29-7.31 (m, 1H), 7.02-7.20 (m, 4H), 6.54 (br s, 1H), 6.16-6.22 (m, 1H), 5.66-5.70 (m, 1H), 4.17-4.23 (m, 2H), 3.82 (s, 3H), 3.34 (m, 4H), 3.21-3.26 (m, 2H), 2.66 (s, 3H).

Example 63

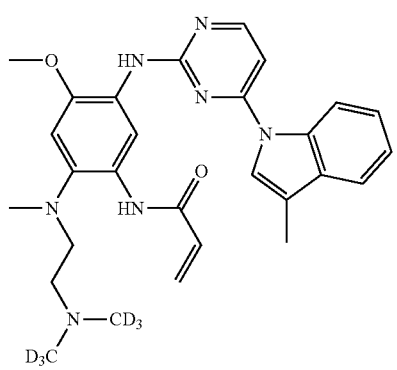
63

1. Synthesis of Compound 63

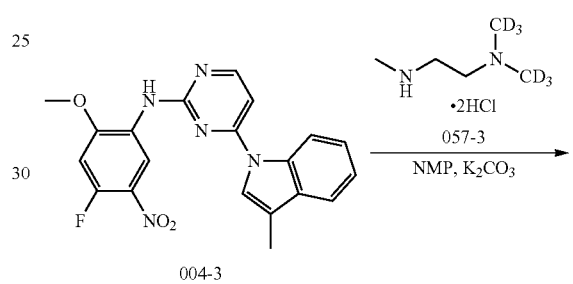
004-3

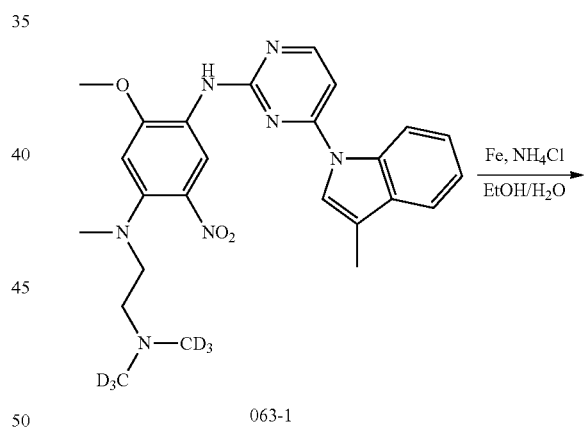
063-1

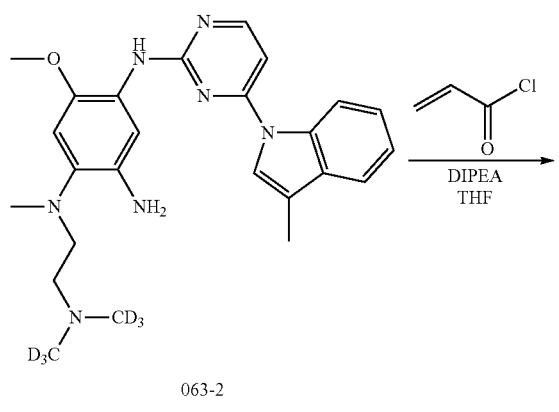
063-2

1. Synthesis of Compound 64

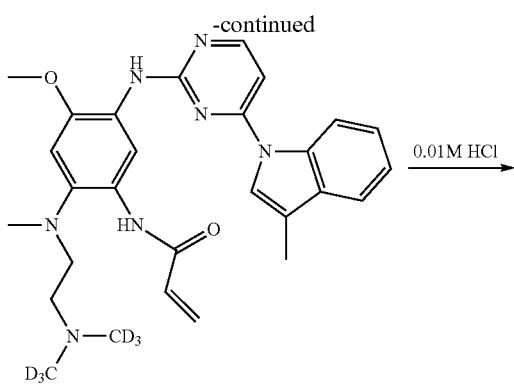

63

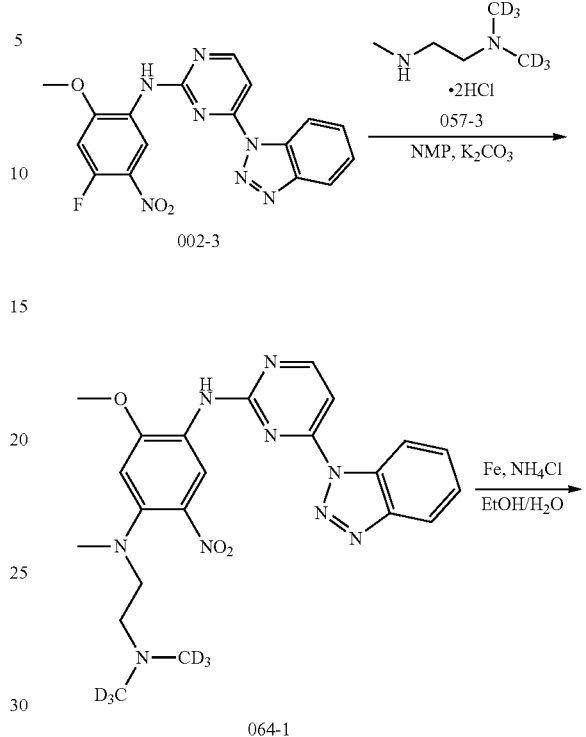

63·(HCl)$_n$

The reaction steps and conditions for the synthesis of final compound 63 and its hydrochloride 63. (HCl)$_n$ from the intermediates 004-3 and 057-3 were the same as those in the third to fifth steps of example 55, except that the intermediate 055-3 in example 55 was replaced with the intermediate 004-3 and the intermediate 001-10 in example 55 was replaced with the intermediate 057-3. Analytical data for the hydrochloride 63. (HCl)$_n$: LCMS (parent molecule) $C_{28}H_{27}D_6N_7O_2$: (ES, m/z): 506 [M+H]$^+$. $^1$H-NMR: (300 MHz, DMSO-D$_6$, ppm) δ 10.37 (br s, 1H), 9.84 (s, 1H), 8.44-8.30 (m, 3H), 8.01 (m, 1H), 7.58-7.57 (d, J=2.1 Hz 1H), 7.24-7.07 (m, 4H), 7.02 (s, 1H), 6.25-6.19 (dd, J=17.1 Hz, 2.1 Hz, 1H), 5.72-5.68 (dd, J=9.9 Hz, 2.1 Hz, 1H), 3.83 (s, 3H), 3.34-3.26 (m, 4H), 2.66 (s, 3H), 2.29 (s, 3H).

Example 64

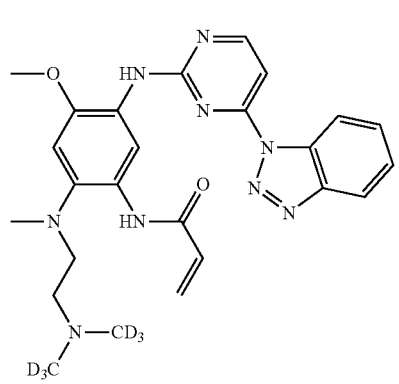

64

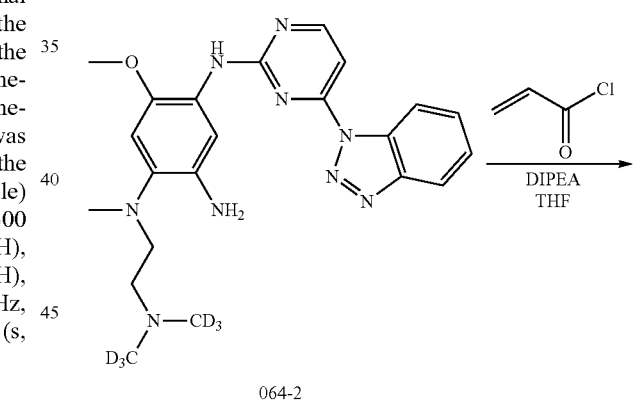

064-1

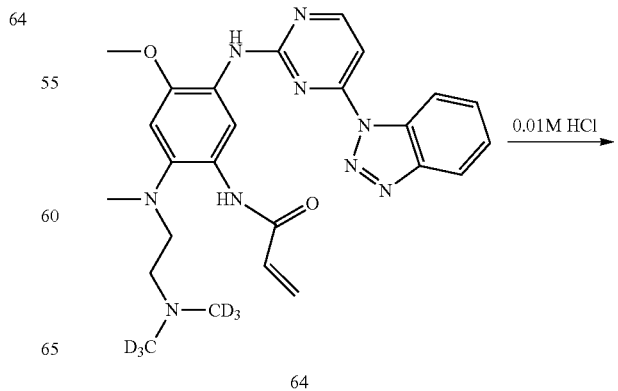

064-2

205

-continued

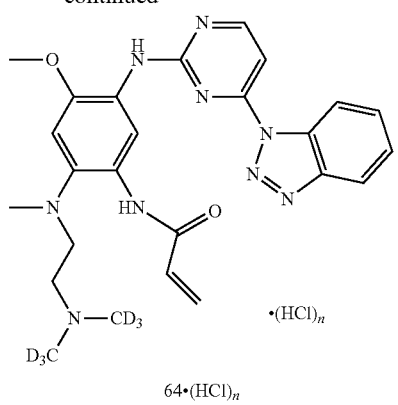

64·(HCl)$_n$

The reaction steps and conditions for the synthesis of final compound 64 and its hydrochloride 64. (HCl)$_n$ from the intermediates 002-3 and 057-3 were the same as those in the third to fifth steps of example 55, except that the intermediate 055-3 in example 55 was replaced with the intermediate 002-3 and the intermediate 001-10 in example 55 was replaced with the intermediate 057-3. Analytical data for the hydrochloride 64. (HCl)$_n$: LCMS (parent molecule) $C_{25}H_{23}D_6N_9O_2$: (ES, m/z): 494.3 [M+H]$^+$. $^1$H-NMR: (300 MHz, DMSO-D$_6$, ppm) δ 10.26 (br, 1H), 9.49 (s, 1H), 9.18-9.21 (s, 1H), 8.59-8.61 (d, J=5.7 Hz, 1H), 8.41 (br s, 1H), 8.18-8.24 (m, 2H), 7.62-7.67 (m, 1H), 7.51-7.56 (m, 2H), 7.00-7.12 (m, 2H), 6.17-6.23 (m, 1H), 5.68-5.72 (m, 1H), 3.82 (s, 3H), 3.31-3.34 (m, 4H), 2.65 (s, 3H).

Example 65

65

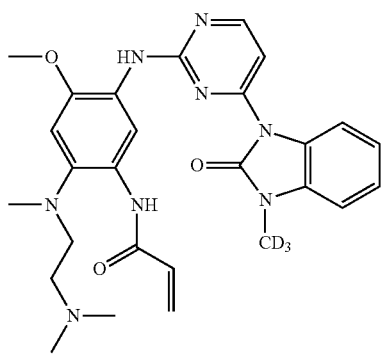

1. Synthesis of Intermediate 065-1

039-4

206

-continued

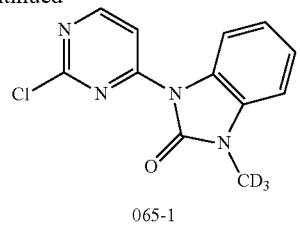

065-1

The reaction steps and conditions for the synthesis of final compound 58 and its hydrochloride 58. (HCl)$_n$ from the intermediates 039-4 and 065-1 were the same as those in the first step of example 40, except that iodomethane in example 40 was replaced with deuterated methyl iodide (CD$_3$I). LCMS: 264.1.

2. Synthesis of Compound 65

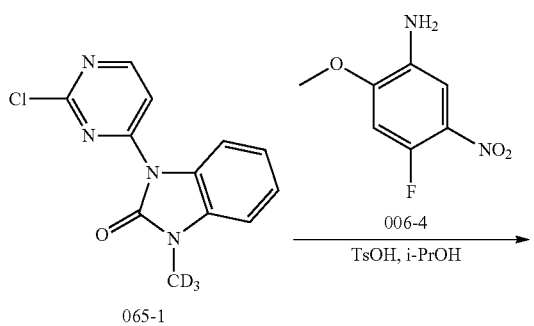

065-1

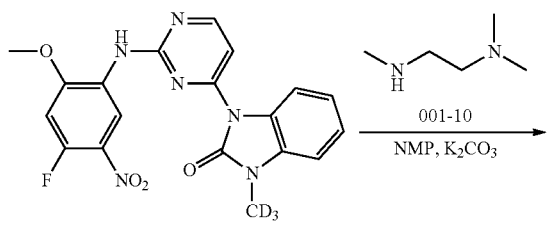

065-2

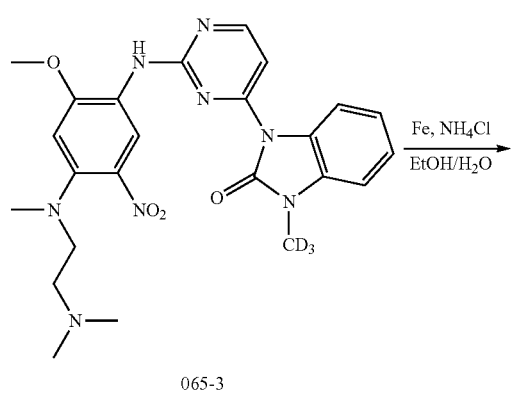

065-3

Example 66

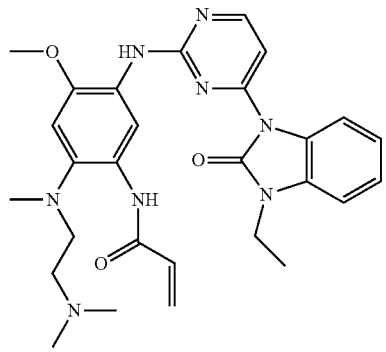

1. Synthesis of Intermediate 066-1

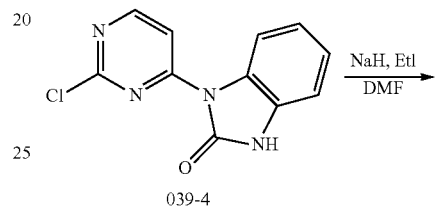

Under a nitrogen atmosphere, the intermediate 039-4 (3.7 g, 15.0 mmol) as a raw material was dissolved in 150 mL of anhydrous DMF in a 250 mL three-necked flask. Then, the reaction system was cooled to 0° C., and sodium hydride (540 mg, 22.5 mmol) was sequentially added therein. The reaction system was kept at 0° C. for 1 h, and then adding iodoethane (3.51 g, 22.5 mmol). Next, the reaction was carried out at room temperature overnight. After detecting the reaction was completed, the reaction solution was poured into 500 mL of ice water to quench the reaction. The mixture was filtered by suction, and the filter cake was collected and dried to give 2.8 g of compound 066-1 (68%) as a white solid. LCMS: 275.1.

2. Synthesis of Compound 66

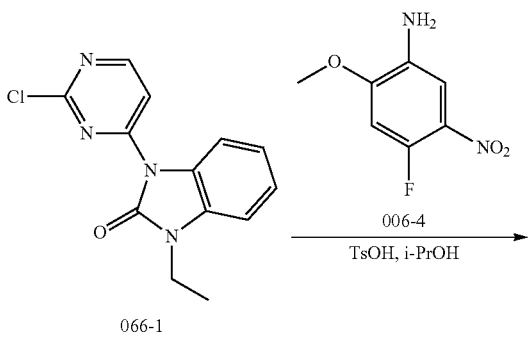

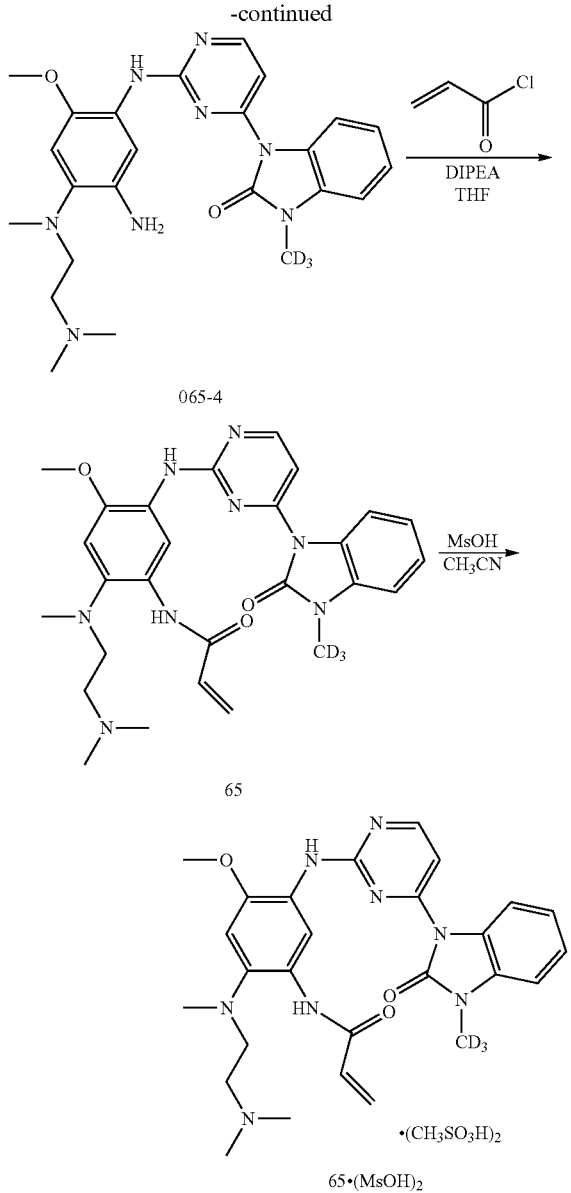

The reaction steps and conditions for the synthesis of final compound 65 and its methanesulfonate 65. (MsOH)$_2$ from the intermediates 065-1 and 006-4 were the same as those in the second to fifth steps of example 40, except that the intermediate 040-1 in example 55 was replaced with the intermediate 065-1. Analytical data for the methanesulfonate 65. (MsOH): LCMS (parent molecule) $C_{27}H_{29}D_3N_8O_3$: (ES, m/z): 520 [M+H]$^+$. $^1$H-NMR (parent molecule): (300 MHz, DMSO-D$_6$, ppm) δ 10.09 (s, 1H), 8.73 (s, 1H), 8.42-8.44 (m, 2H), 8.09-8.11 (m, 1H), 7.68-7.70 (d, J=5.7 Hz, 1H), 7.15-7.20 (m, 2H), 7.05 (s, 1H), 6.87-6.92 (in, 1H), 6.35-6.44 (m, 1H), 6.15-6.22 (m, 1H), 5.70-7.74 (m, 1H), 3.75 (s, 3H), 2.89-2.92 (m, 2H), 2.75 (s, 3H), 2.32-2.36 (m, 2H), 2.21 (s, 6H). $^1$H-NMR (methanesulfonate): (300 MHz, DMSO-D$_6$, ppm) δ 9.24 (s, 1H), 9.15 (br s, 2H), 8.45 (d, J=6.3 Hz, 1H), 8.15-8.11 (m, 2H), 7.84-7.80 (m, 1H), 7.26-7.18 (m, 2H), 7.18-6.96 (m, 2H), 6.70-6.61 (m, 1H), 6.30-6.24 (n, 1H), 5.80-5.76 (m, 1H), 3.82 (m, 3H), 3.33 (m, 4H), 2.83 (s, 3H), 2.82 (s, 3H), 2.51 (s, 3H), 2.36 (s, 3H), 2.35 (s, 3H).

209

-continued

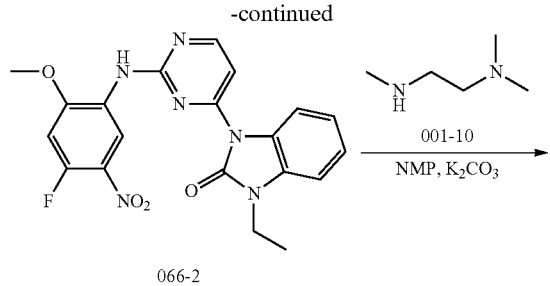

066-2

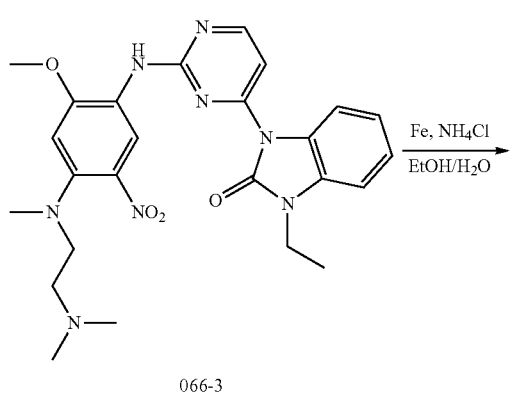

066-3

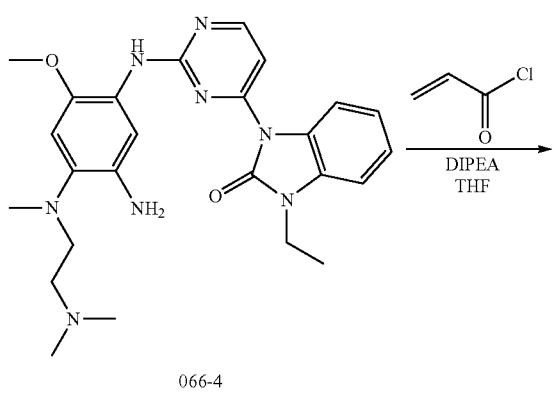

066-4

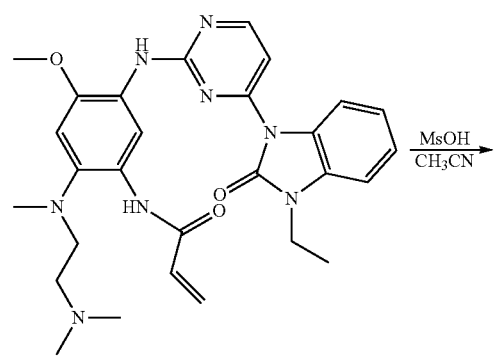

66

210

-continued

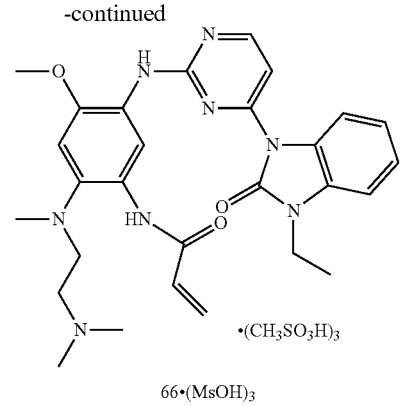

66·(MsOH)₃

The reaction steps and conditions for the synthesis of final compound 66 and its methanesulfonate 66. (MsOH)₃ from the intermediates 066-1 and 006-4 were the same as those in the second to fifth steps of example 40, except that the intermediate 040-1 in example 40 was replaced with the intermediate 066-1. Analytical data for the compound 66: LCMS (parent molecule) $C_{28}H_{34}N_8O_3$: (ES, m/z): 531 [M+H]⁺. ¹H-NMR (parent molecule): (300 MHz, DMSO-$D_6$, ppm) S 10.09 (s, 1H), 8.73 (s, 1H), 8.42-8.44 (m, 2H), 8.08-8.11 (m, 1H), 7.67-7.69 (d, J=5.7 Hz, 1H), 7.24-7.26 (m, 1H), 7.12-7.17 (m, 1H), 7.05 (s, 1H), 6.86-6.91 (m, 1H), 6.35-6.44 (m, 1H), 6.15-6.22 (m, 1H), 5.70-5.74 (m, 1H), 3.88-3.95 (m, 2H), 3.75 (s, 3H), 2.88-2.92 (m, 2H), 2.75 (s, 3H), 2.34-2.36 (m, 2H), 2.20 (s, 6H), 1.21-1.26 (m, 3H). ¹H-NMR (methanesulfonate): (300 MHz, DMSO-$D_6$, ppm): δ 6 9.49 (br s, 2H), 9.28 (br s, 1H), 8.46 (d, J=6.3 Hz, 1H), 2.89-2.82 (s, 6H), 8.14-8.10 (m, 2H), 7.90 (d, J=6.3 Hz, 1H), 7.33-7.30 (m, 1H), 7.25-7.20 (m, 1H), 7.06 (s, 1H), 7.01-6.96 (m, 1H), 6.73-6.64 (m, 1H), 6.30-6.18 (m, 1H), 5.87-5.76 (m, 1H), 3.97-3.90 (m, 2H), 3.82 (s, 3H), 3.34 (m, 4H), 2.67 (s, 3H), 2.38 (s, 9H), 1.27-1.25 (m, 3H).

Example 67

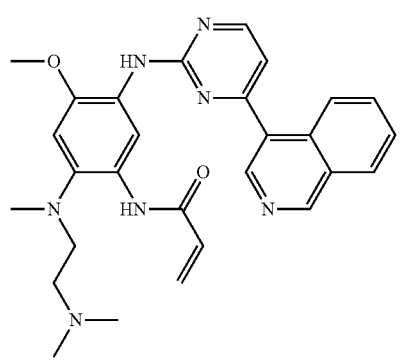

67

1. Synthesis of Intermediate 067-2

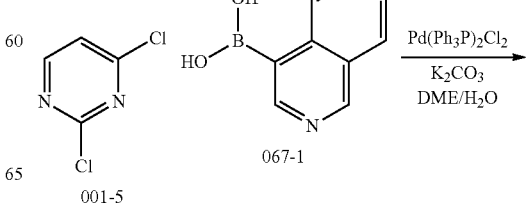

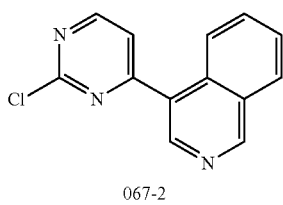

067-2

Under a nitrogen atmosphere, the intermediate 067-1 (1.1 g, 6.36 mmol) as a raw material and 2,4-dichloropyrimidine were dissolved in 80 mL of a mixed solvent of DME/H$_2$O (3:1) in a 250 mL three-necked flask at room temperature, followed by adding potassium carbonate (2.9 g, 20.8 mmol) and dichlorobis(triphenylphosphine)palladium (470 mg, 0.67 mmol). The reaction system was heated to 90° C. and carried out overnight. Next day, after detecting the reaction was completed, and then the reaction system was cooled to room temperature. The reaction mixture was filtrated by suction, and the filtrate was collected, directly concentrated to dryness. The crude product was washed with 30 mL of anhydrous ether once. The reaction mixture was filtered by suction to collect the filter cake which was dried to give 1.25 g of the intermediate 067-2 (77%) as a brown solid. LCMS: 242.0.

2. Synthesis of Compound 67

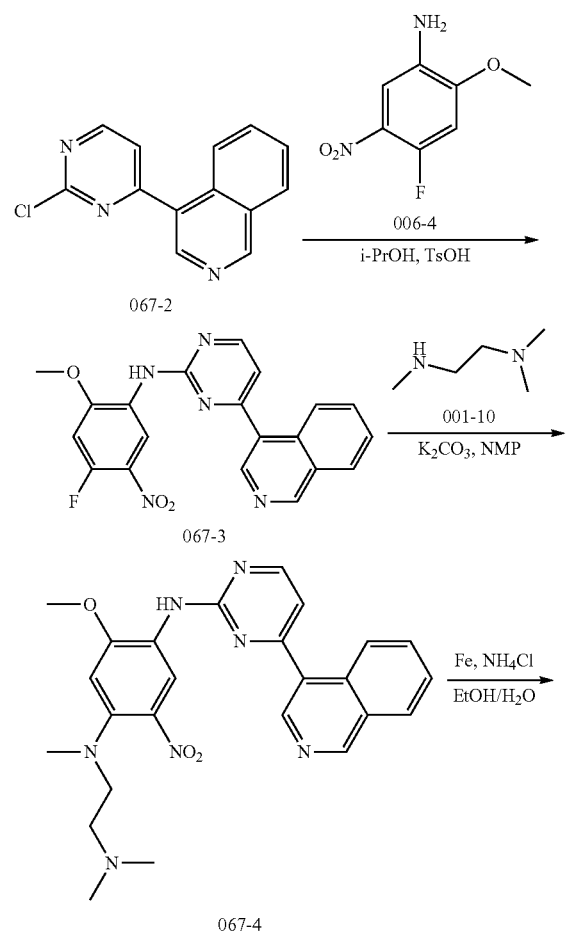

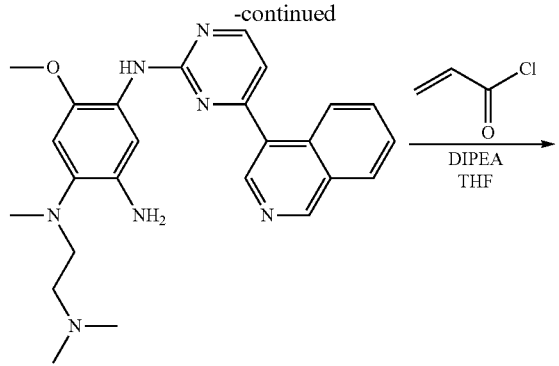

067-5

67

The reaction steps and conditions for the synthesis of final compound 67 from the intermediates 067-2 and 006-4 were the same as those in the second to fifth steps of example 40, except that the intermediate 040-1 in example 40 was replaced with the intermediate 067-2. Analytical data for the compound 67: LCMS (parent molecule): C$_{28}$H$_{31}$D$_6$N$_7$O$_2$: (ES, m/z): 498 [M+H]$^+$. $^1$H-NMR: (300 MHz, DMSO-D$_6$, ppm) δ 10.04 (s, 1H), 9.41 (s, 1H), 8.71 (s, 1H), 8.65 (s, 1H), 8.58-8.57 (d, J=4.8 Hz, 1H), 8.49 (s, 1H), 8.45-8.35 (m, 1H), 8.20 (m, 1H), 7.85-7.70 (m, 1H), 7.16 (d, J=4.8 Hz, 1H), 7.00 (s, 1H), 6.45-6.30 (m, 1H), 6.20-6.15 (m, 1H), 5.80-5.70 (m, 1H), 3.82 (s, 3H), 2.84 (m, 2H), 2.70 (s, 3H), 2.28 (m, 2H), 2.18 (s, 3H).

Example 68

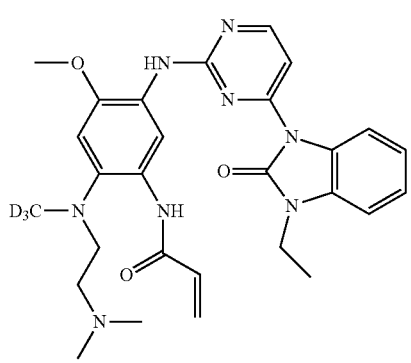

68

The reaction steps and conditions for the synthesis of final compound 68 and its methanesulfonate were the same as those in the third to fifth steps of example 40, except that the intermediate 040-2 in example 40 was replaced with the intermediate 066-2 and the intermediate 001-10 in example 40 was replaced with the intermediate 059-6.

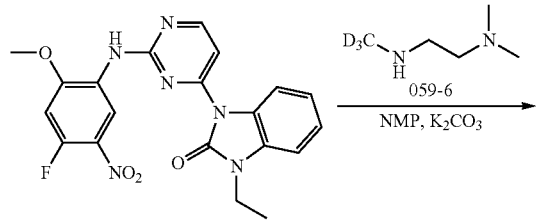

066-2

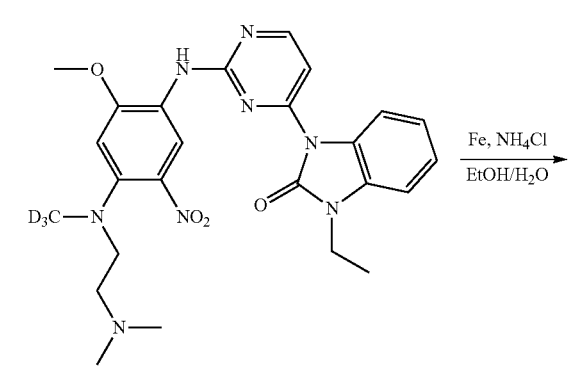

068-1

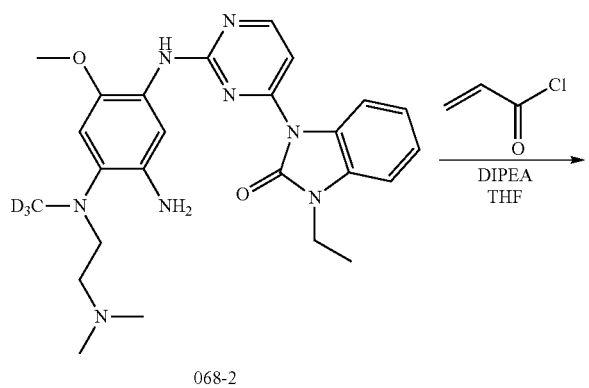

068-2

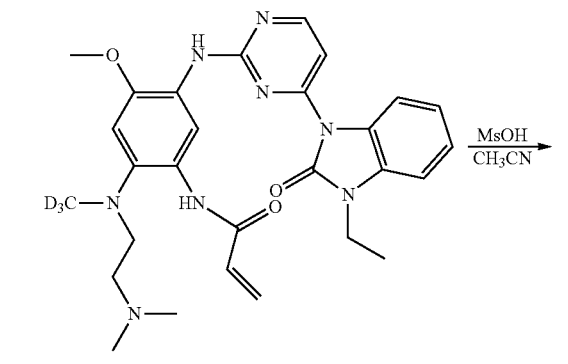

68

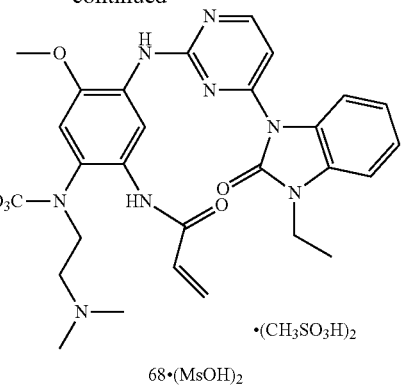

68·(MsOH)₂

Analytical data for the compound 68: LCMS (parent molecule) $C_{28}H_{31}D_3N_8O_3$: (ES, m/z): 534.3 [M+H]⁺. ¹H-NMR (methanesulfonate): (300 MHz, DMSO-D₆, ppm): δ 9.51 (s, 1H), 9.12 (br s, 2H), 8.45 (d, J=6 Hz, 1H), 8.15-8.10 (m, 2H), 7.80 (d, J=5.7 Hz, 1H), 7.31-7.23 (m, 1H), 7.20-7.18 (m, 1H), 7.04-6.95 (m, 2H), 6.70-6.61 (m, 1H), 6.30-6.25 (m, 1H), 5.80-5.76 (m, 1H), 3.97-3.90 (m, 2H), 3.82 (s, 3H), 3.32 (m, 4H), 2.83 (s, 3H), 2.82 (s, 3H), 2.35 (s, 6H), 1.27-1.22 (m, 3H).

Example 69

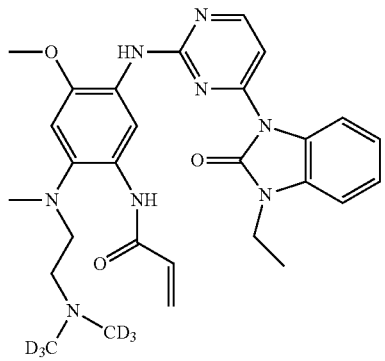

69

The reaction steps and conditions for the synthesis of final compound 69 and its methanesulfonate were the same as those in the third to fifth steps of example 40, except that the intermediate 040-2 in example 40 was replaced with the intermediate 066-2 and the intermediate 001-10 in example 40 was replaced with the intermediate 057-3.

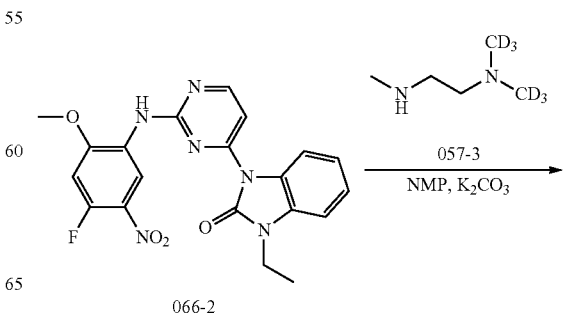

066-2

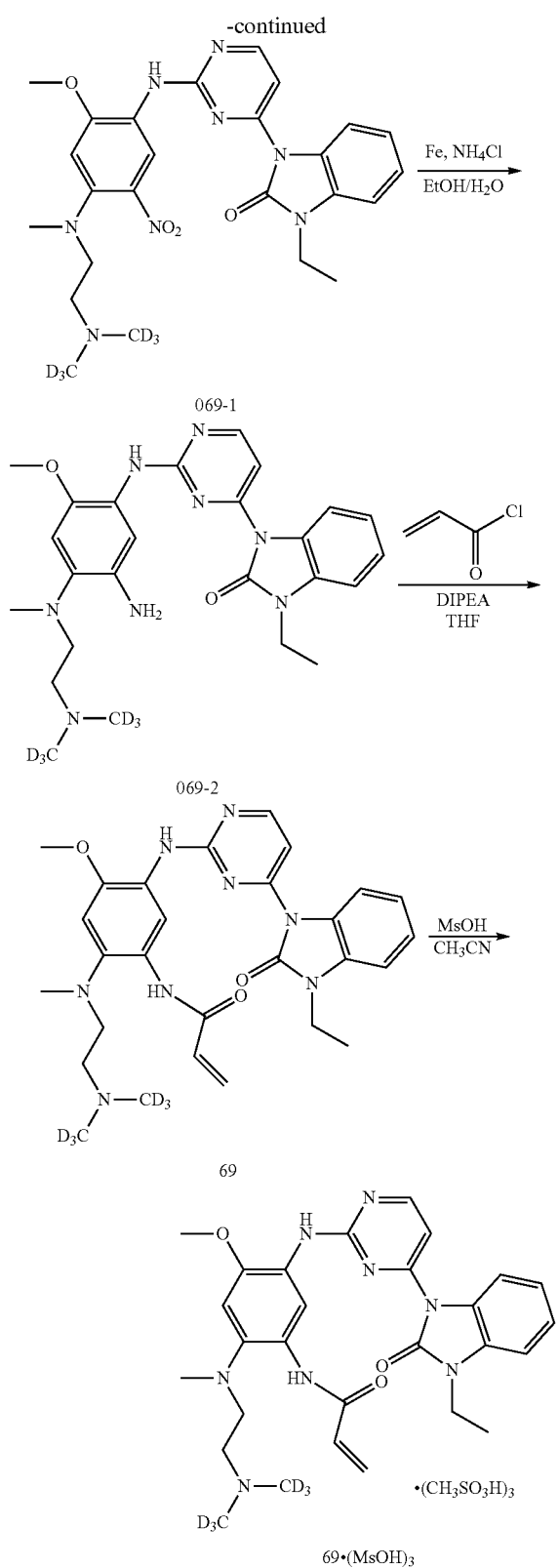

Analytical data for the compound 69: LCMS (parent molecule) $C_{28}H_{28}D_6N_8O_3$: (ES, m/z): 537.3[M+H]$^+$.
$^1$H-NMR (methanesulfonate): (300 MHz, DMSO-D$_6$, ppm): δ 9.54 (s, 1H), 9.22 (br s, 1H), 8.87 (br s, 1H), 8.46-8.44 (m, 1H), 8.18-8.11 (m, 2H), 7.75-7.73 (m, 1H), 7.30-7.28 (m, 1H), 7.21-7.16 (m, 1H), 7.02-6.95 (m, 2H), 6.69-6.60 (m, 1H), 6.31-6.25 (m, 1H), 5.80-5.76 (m, 1H), 3.95-3.82 (m, 2H), 3.32-3.29 (m, 4H), 2.51 (s, 3H), 2.30 (s, 9H), 1.27-1.22 (m, 3H).

Example 70

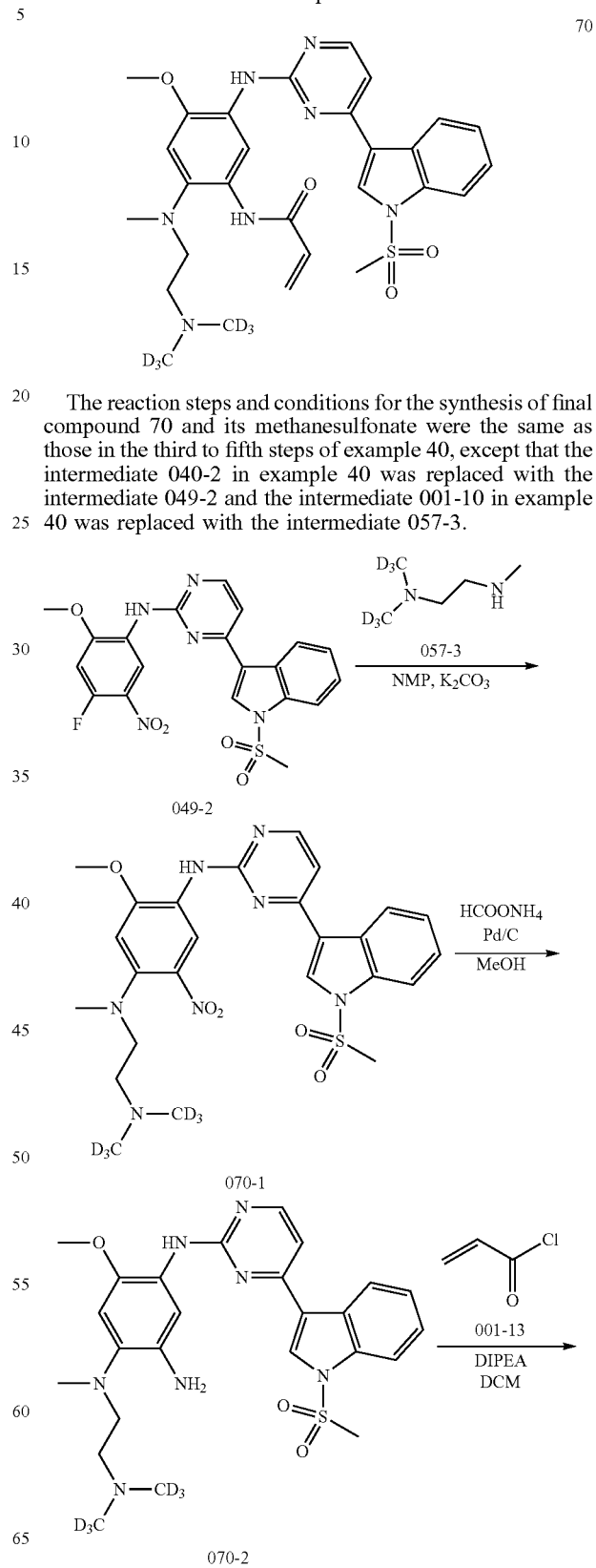

The reaction steps and conditions for the synthesis of final compound 70 and its methanesulfonate were the same as those in the third to fifth steps of example 40, except that the intermediate 040-2 in example 40 was replaced with the intermediate 049-2 and the intermediate 001-10 in example 40 was replaced with the intermediate 057-3.

-continued

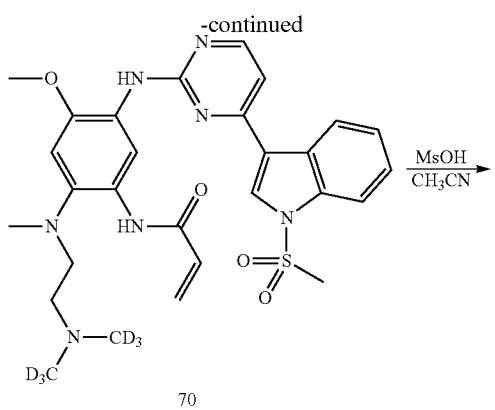
70

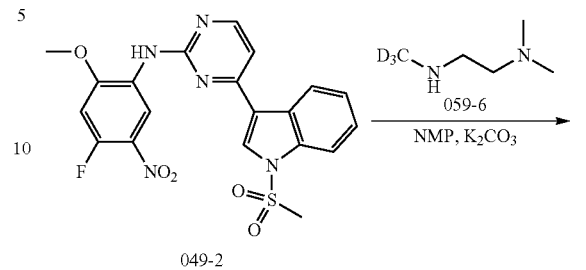

intermediate 049-2 and the intermediate 001-10 in example 40 was replaced with the intermediate 059-6.

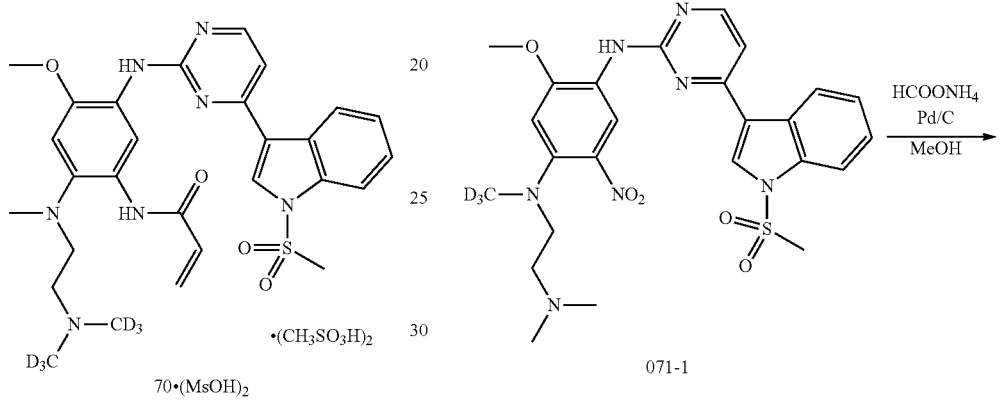

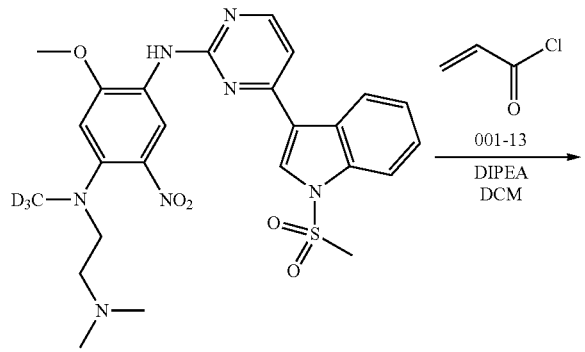

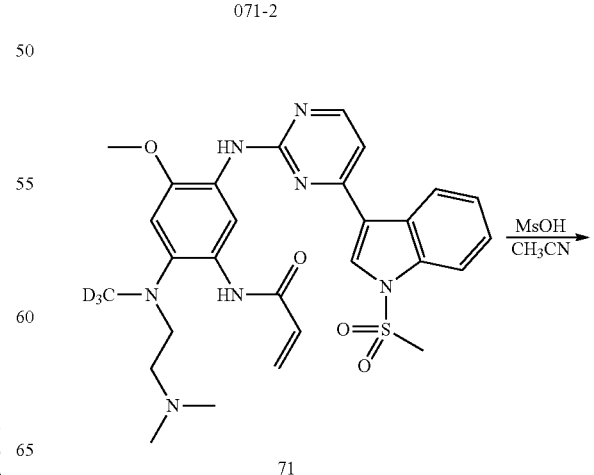

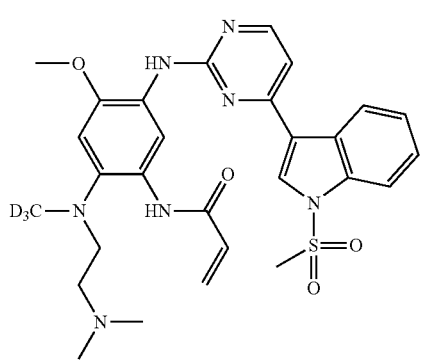
70·(MsOH)₂

Analytical data for the compound 70: LCMS (parent molecule) C₂₈H₂₇D₆N₇O₄S: (ES, m/z): 570.3 [M+H]. ¹H-NMR (methanesulfonate): (300 MHz, DMSO-D₆, ppm): δ 9.56 (s, 1H), 9.26 (br s, 1H), 8.65 (s, 1H), 8.48-8.41 (m, 2H), 8.33 (s, 1H), 7.91 (d, J=8.4 Hz, 1H), 7.57 (d, J=5.4 Hz, 1H), 7.47-7.42 (m, 2H), 7.35-7.27 (m, 1H), 7.05 (s, 1H), 6.71-6.61 (m, 1H), 6.31-6.26 (m, 1H), 5.81-5.77 (m, 1H), 3.87 (s, 3H), 3.61 (s, 3H), 3.30-3.32 (m, 4H), 2.66 (s, 3H), 2.34 (s, 6H).

Example 71

71

The reaction steps and conditions for the synthesis of final compound 71 and its methanesulfonate were the same as those in the third to fifth steps of example 40, except that the intermediate 040-2 in example 40 was replaced with the -continued

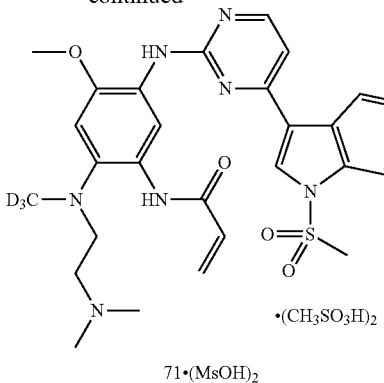

71·(MsOH)₂

Analytical data for the compound 71: LCMS (parent molecule) C₂₈H₃₀D₃N₇O₄S: (ES, m/z): 567.3[M+H]⁺. ¹H-NMR (methanesulfonate): (300 MHz, DMSO-D₆, ppm): δ 9.56 (s, 1H), 9.29 (br s, 1H), 8.69 (s, 1H), 8.47-8.41 (m, 2H), 8.30 (s, 1H), 8.15-8.11 (m, 2H), 7.91 (d, J=8.4 Hz, 1H), 7.60 (d, J=5.7 Hz, 1H), 7.47-7.42 (m, 1H), 7.34-7.29 (m, 1H), 7.05 (s, 1H), 7.18-6.96 (m, 2H), 6.72-6.63 (m, 1H), 6.31-6.25 (m, 1H), 5.80-5.77 (m, 1H), 3.86 (s, 3H), 3.61 (s, 3H), 3.32 (m, 4H), 2.83 (s, 3H), 2.82 (s, 3H), 2.35 (s, 3H).

Example 72

72

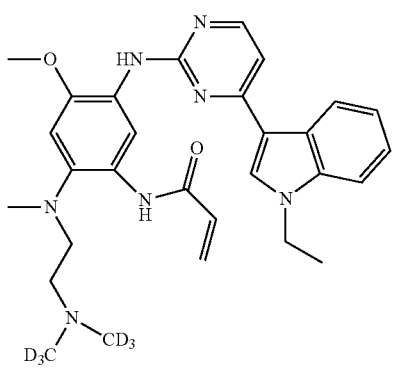

The reaction steps and conditions for the synthesis of final compound 72 and its methanesulfonate were the same as those in the third to fifth steps of example 40, except that the intermediate 040-2 in example 40 was replaced with the intermediate 048-4 and the intermediate 001-10 in example 40 was replaced with the intermediate 057-3.

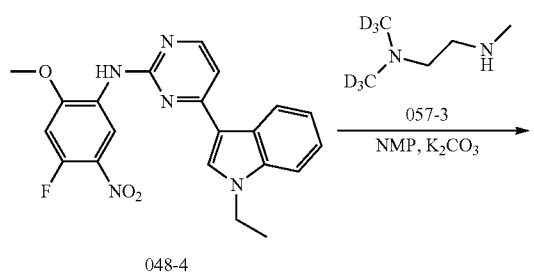

048-4

-continued

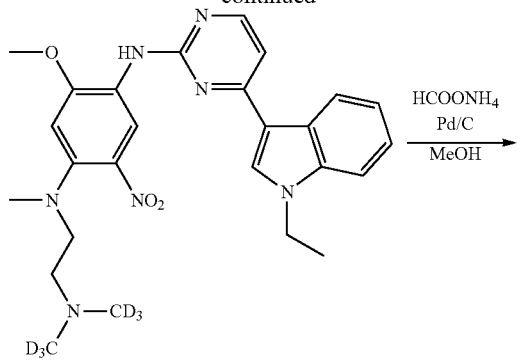

072-1

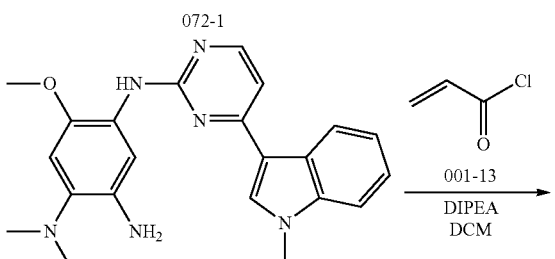

072-2

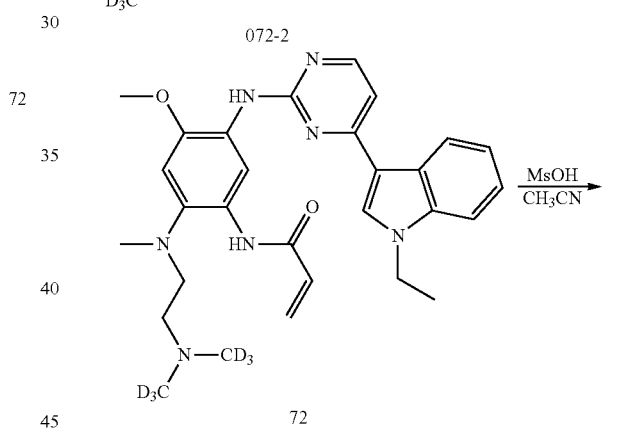

72

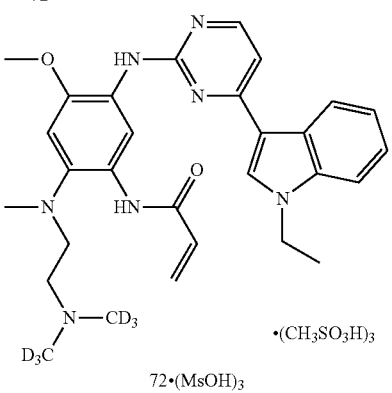

72·(MsOH)₃

Analytical data for the compound 72: LCMS (parent molecule) C₂₉H₂₉D₆N₇O₂: (ES, m/z): 520.3[M+H]⁺. ¹H-NMR (methanesulfonate): (300 MHz, DMSO-D₆, ppm): δ 9.52 (s, 1H), 9.25 (br s, 1H), 8.81 (s, 1H), 8.43-8.42 (br s, 1H), 8.27-8.25 (m, 2H), 7.65 (d, J=8.4 Hz, 1H), 7.42 (d, J=6.3 Hz, 1H), 7.31-7.26 (m, 1H), 7.19-7.14 (m, 1H), 7.08

(s, 1H), 6.77-6.68 (m, 1H), 6.32-6.25 (m, 1H), 5.81-5.77 (m, 1H), 4.38-4.24 (m, 2H), 3.87 (s, 3H), 3.33 (m, 4H), 2.67 (s, 3H), 2.32 (s, 9H), 1.48-1.43 (m, 3H).

Example 73

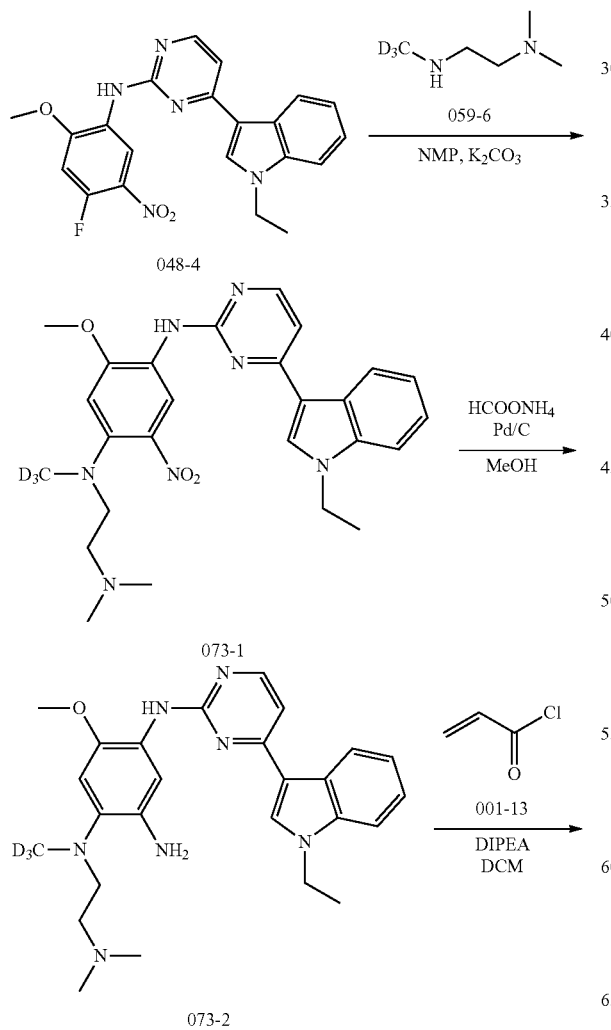

The reaction steps and conditions for the synthesis of final compound 73 and its methanesulfonate were the same as those in the third to fifth steps of example 40, except that the intermediate 040-2 in example 40 was replaced with the intermediate 048-4 and the intermediate 001-10 in example 40 was replaced with the intermediate 059-6.

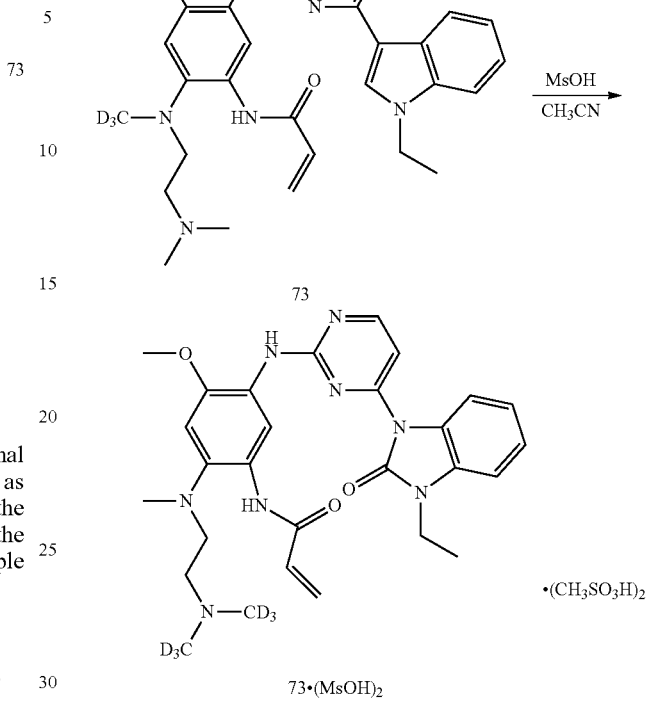

Analytical data for the compound 72: LCMS (parent molecule) $C_{29}H_{32}D_3N_7O_2$: (ES, m/z): 517.3[M+H]$^+$.
$^1$H-NMR (methanesulfonate): (300 MHz, DMSO-D$_6$, ppm): δ 9.51 (s, 1H), 9.33 (br s, 1H), 8.85 (s, 1H), 8.36-8.24 (br s, 3H), 7.67-7.64 (m, 2H), 7.47-7.44 (m, 1H), 7.26-7.18 (m, 2H), 7.18-6.96 (m, 2H), 6.70-6.61 (m, 1H), 6.31-6.25 (m, 1H), 5.81-5.77 (m, 1H), 4.38-4.25 (m, 2H), 3.86 (s, 3H), 3.37-3.33 (m, 4H), 2.85 (s, 3H), 2.84 (s, 3H), 2.36 (s, 6H), 1.49-1.44 (m, 3H).

Example 74

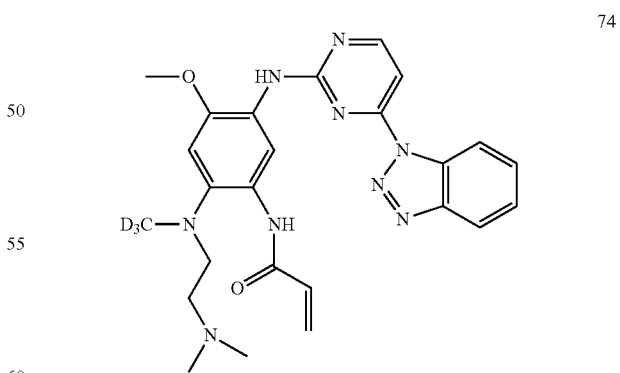

The reaction steps and conditions for the synthesis of final compound 74 and its methanesulfonate were the same as those in the third to fifth steps of example 40, except that the intermediate 040-2 in example 40 was replaced with the intermediate 040-2 and the intermediate 001-10 in example 40 was replaced with the intermediate 059-6.

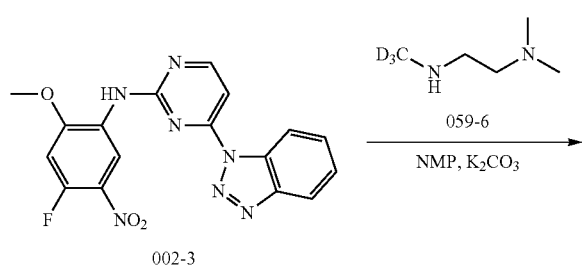

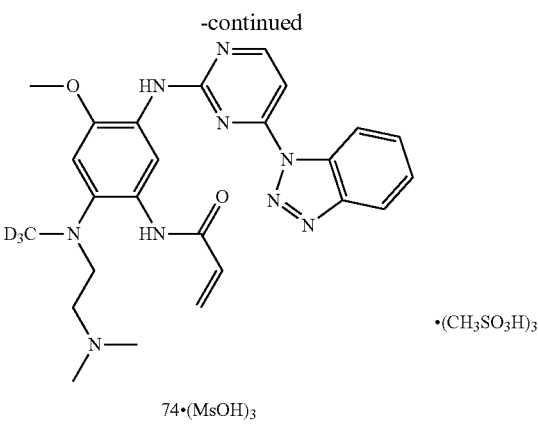

74·(MsOH)₃

Analytical data for the compound 74: LCMS (parent molecule) $C_{29}H_{32}D_3N_7O_2$: (ES, m/z): 491.3[M+H]⁺. ¹H-NMR (methanesulfonate): (300 MHz, DMSO-D₆, ppm): δ 9.55 (s, 1H), 9.25 (br s, 2H), 8.60-8.62 (m, 1H), 8.45 (br s, 1H), 8.16-8.23 (m, 2H), 7.52-7.66 (m, 3H), 7.05 (s, 1H), 6.59-6.73 (m, 1H), 6.24-6.30 (m, 1H), 5.76-5.80 (m, 1H), 3.83 (s, 3H), 3.34 (m, 4H), 2.84 (s, 3H), 2.83 (s, 3H), 2.38 (s, 9H).

Example 76

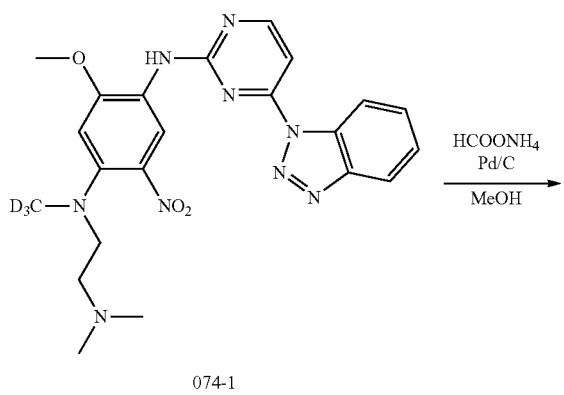

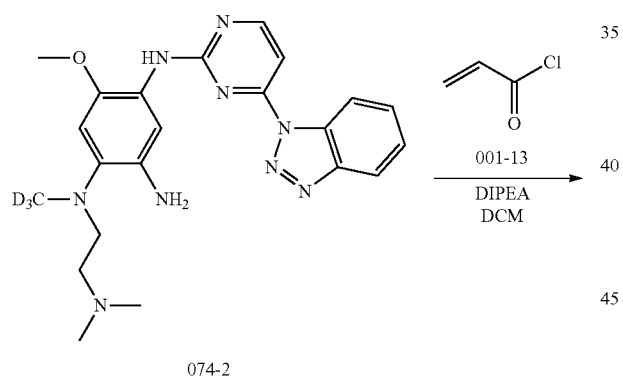

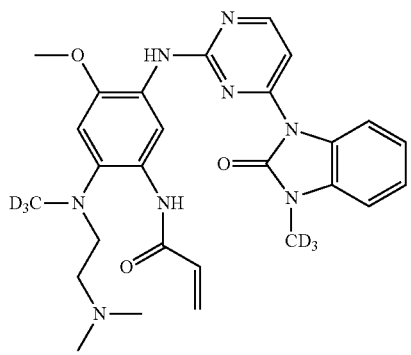

The reaction steps and conditions for the synthesis of final compound 76 and its methanesulfonate were the same as those in the third to fifth steps of example 40, except that the intermediate 040-2 in example 40 was replaced with the intermediate 065-2 and the intermediate 001-10 in example 40 was replaced with the intermediate 059-6.

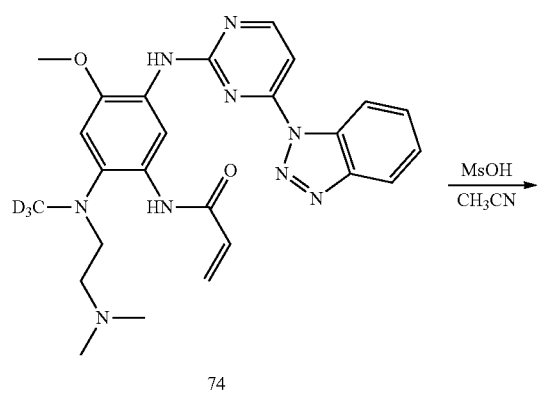

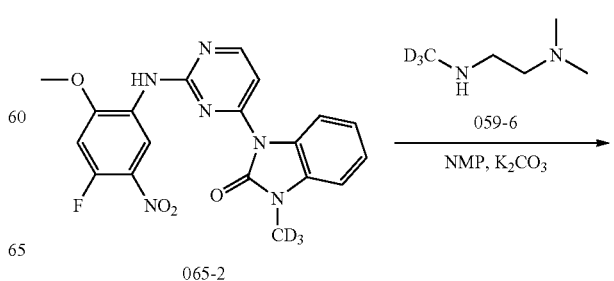

1H), 5.76-5.79 (m, 1H), 3.82 (s, 3H), 3.32 (m, 4H), 2.83 (s, 3H), 2.81 (s, 3H), 2.34 (s, 6H).

Example 101

1. Synthesis of Intermediate 101-1

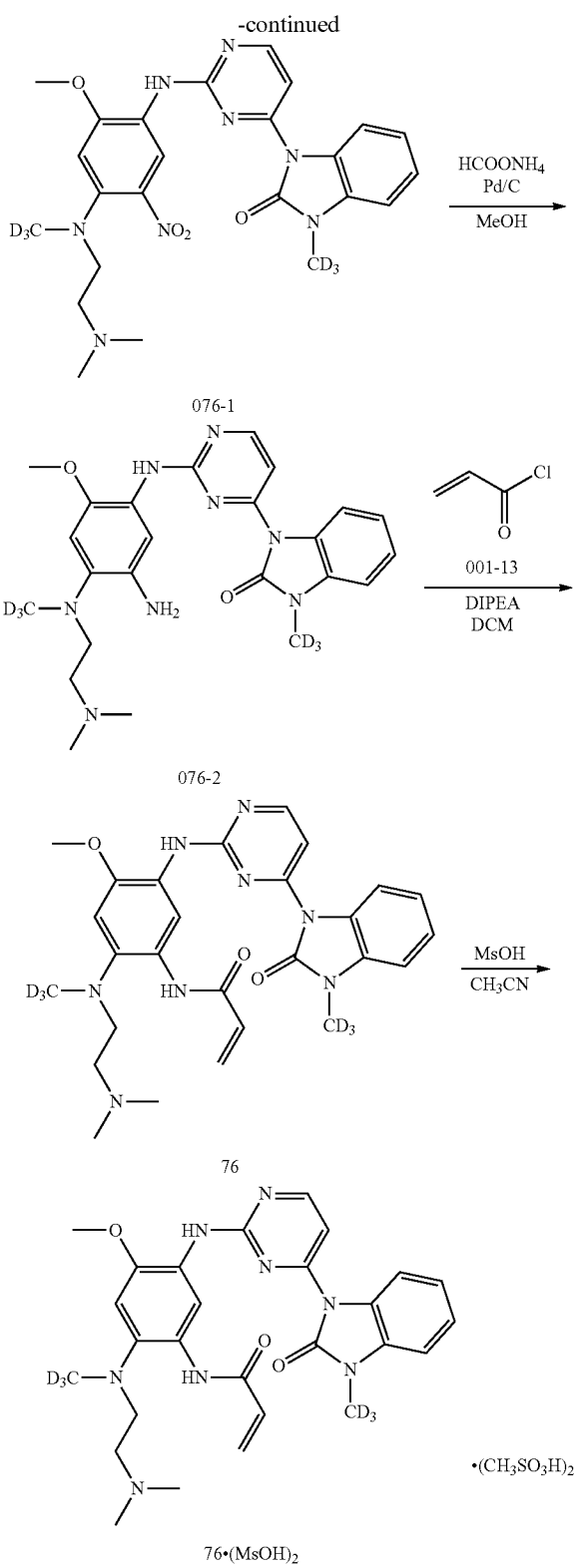

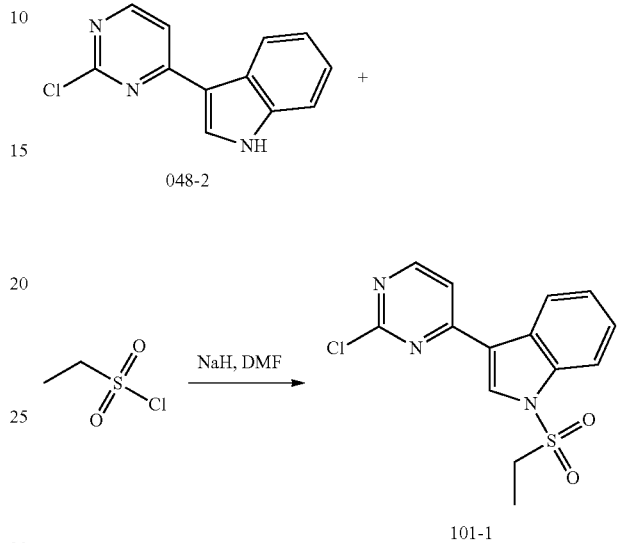

Under a nitrogen atmosphere, the intermediate 048-2 (1.5 g, 6.53 mmol) as a raw material was dissolved in 20 mL of anhydrous DMF in a 100 mL three-necked flask at room temperature. The reaction was cooled to 0° C. and sodium hydride (393 mg, 9.82 mmol) was added thereto in batches. Next, the reaction was carried out at 0° C. for 0.5 h, ethylsulfonyl chloride (1.08 g, 8.41 mmol) was added into the reaction system at 0° C., and then the reaction was carried out at room temperature for 2 h. After detecting the reaction was completed, the reaction mixture was poured into 10 ML of ice water to quench the reaction. The resulting mixture was extracted twice with 100 mL of ethyl acetate (EA). The organic phases were collected and washed twice with 100 mL of brine. The organic phases were dried over anhydrous sodium sulfate and concentrated to dryness. The resulting residue was purified with silica gel column chromatography (eluent: petroleum ether (PE):ethyl acetate (EA)=10:1). The product was collected and concentrated to give 2.0 g of the intermediate 101-1 (95%) as a red solid. LCMS: 322.

2. Synthesis of Intermediate 101-2

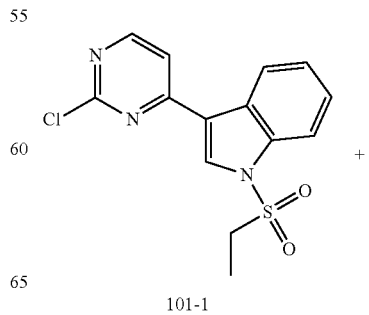

Analytical data for the compound 76: LCMS (parent molecule) $C_{27}H_{26}D_6N_5O_3$: (ES, m/z): 523.5 [M+H]+. $^1$H-NMR (methanesulfonate): (300 MHz, DMSO-D$_6$, ppm): δ 9.51 (s, 1H), 9.24-9.25 (br s, 2H), 8.44 (d, J=5.7 Hz, 1H), 8.10-8.15 (m, 2H), 7.81 (d, J=5.7 Hz, 1H), 7.18-7.25 (m, 2H), 6.98-7.04 (m, 2H), 6.61-6.70 (m, 1H), 6.24-6.30 (m,

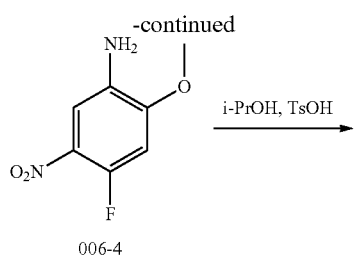

Under a nitrogen atmosphere, 20 mL of isopropyl alcohol, the intermediate 101-1 (2.0 g, 6.22 mmol), the intermediate 001-1 (1.15 g, 6.18 mmol) and p-toluenesulfonic acid (1.39 g, 8.07 mmol) were sequentially added into a 100 mL single-necked flask at room temperature. Next, the reaction was heated to 105° C. and carried out for 2 h. After detecting the reaction was completed, the reaction system was cooled to room temperature and quenched by adding 100 mL of ice water. The reaction mixture was filtered, and the solid was collected and dried to give 2.1 g of the intermediate 101-2 as a red solid. LCMS: 472.

3. Synthesis of Intermediate 101-3

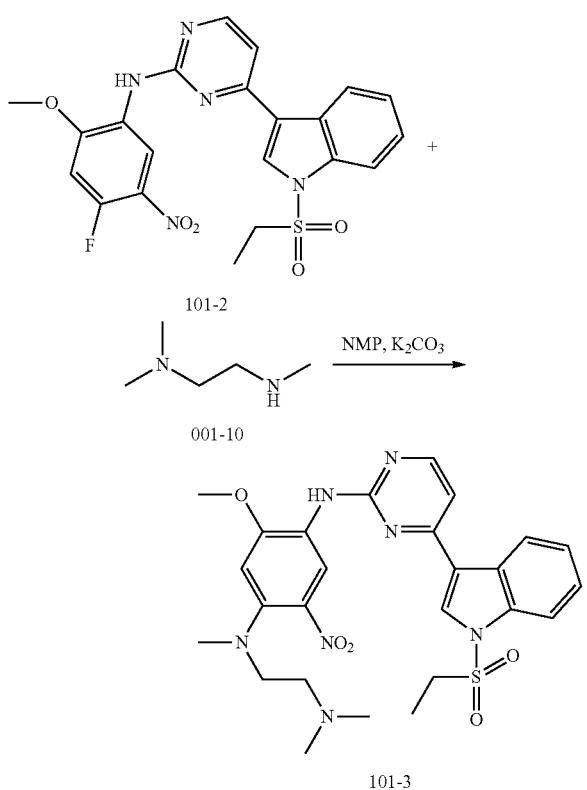

Under a nitrogen atmosphere, the intermediate 101-2 (2.1 g, 4.45 mmol) as a raw material was dissolved in 20 mL of NMP at room temperature in a 100 mL single-necked flask, followed by sequentially adding N,N,N'-trimethylethylenediamine (682 mg, 6.67 mmol) and anhydrous potassium carbonate (1.85 g, 13.4 mmol) into the reaction system. Next, the reaction system was heated to 30° C., and then carried out for 24 h. After detecting the reaction was completed, the reaction system was cooled to room temperature. The reaction mixture was poured into 200 mL of ice water to quench the reaction. A solid was precipitated and the reaction mixture was filtered under suction. The solid was collected and dried to give 2 g of the intermediate 101-3 as a red solid. LCMS: 554.

4. Synthesis of Intermediate 101-4

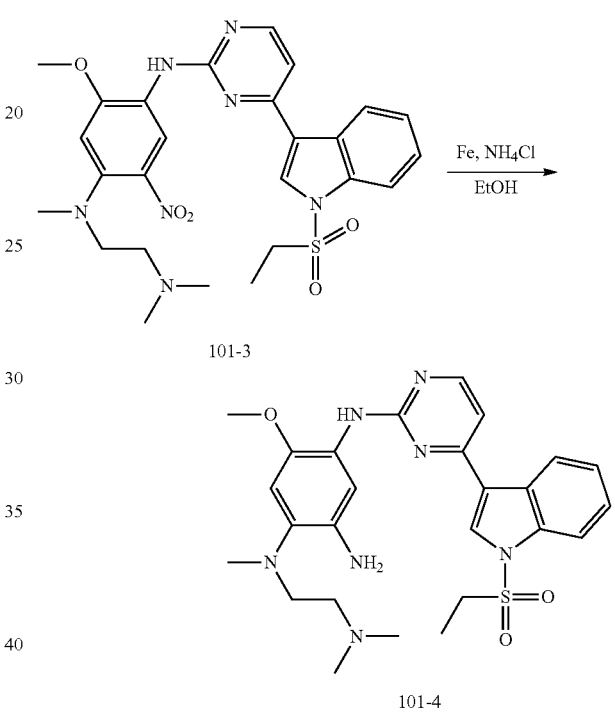

Under a nitrogen atmosphere, 30 mL of ethanol, 10 mL of water, the intermediate 101-3 (2.0 g, 3.36 mmol) as a raw material, iron powder (1.21 g, 21.61 mmol) and ammonium chloride (134 mL, 2.51 mmol) were sequentially added into a 100 mL single-necked flask at room temperature, followed by that the reaction was heated to 85° C. and carried out for 3 h. After detecting the reaction was completed, the reaction was cooled to room temperature. The resulting mixture was filtered by suction, and the filtrate was collected and concentrated to dryness. The resulting residue was purified by preparative HPLC (column: C18 silica gel; mobile phase: acetonitrile/water (0.05% trifluoroacetic acid); 35% acetonitrile to 50% acetonitrile; 15 min; 70 mL/min; detection wavelength: 254 nm). The product was collected, and the combined mixture was adjusted with a saturated solution of sodium bicarbonate to pH=8, extracted three times with 200 mL of methylene chloride. The organic was collected, combined, dried over anhydrous sodium sulfate and concentrated to dryness to give 1.3 g of the intermediate 101-4 (69%) as a green solid. LCMS: 524.

5. Synthesis of Compound 101

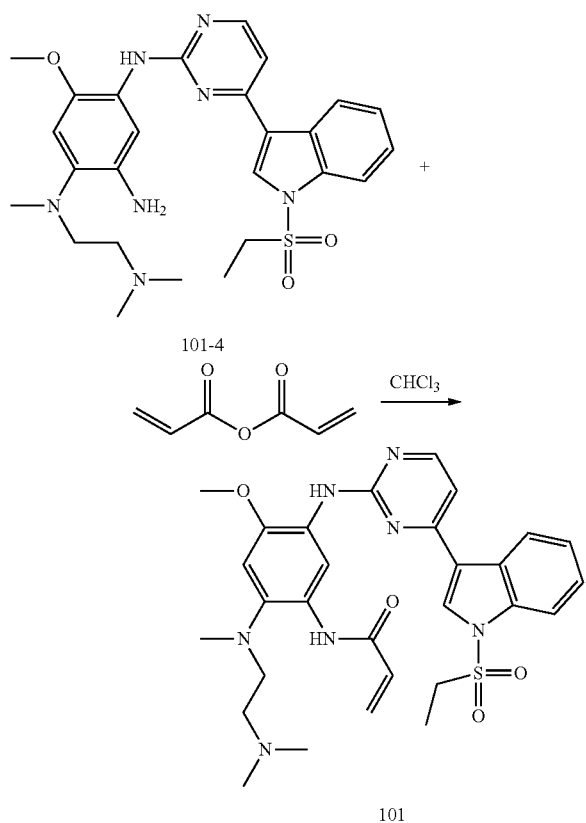

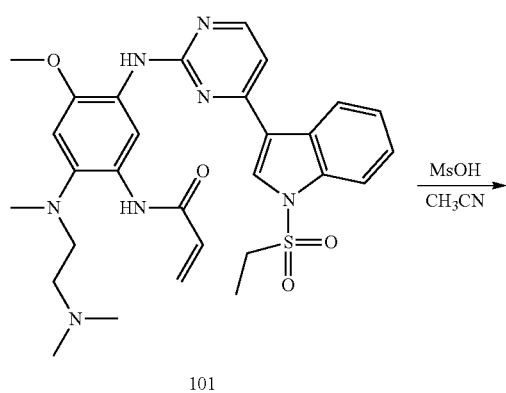

Under a nitrogen atmosphere, the intermediate 101-4 (400 mg, 0.76 mmol) as a raw material was dissolved in 10 mL of chloroform at room temperature in a 50 mL single-necked flask and acrylic anhydride (125 mg, 0.99 mmol) was added to the reaction system. Next, the reaction was carried out at room temperature for 2 h. After detecting the reaction was completed, the reaction system was quenched with 2 mL of ice water and concentrated to dryness. The resulting residue was purified by high pressure HPLC (column: Waters X-bridge C18, 19*150 mm; the mobile phase: water (0.05% ammonia)/acetonitrile, 40% acetonitrile to 85% acetonitrile, 9 min, 15 mL/min; detection wavelength: 254 nm). The product was collected and concentrated to dryness to give compound 101.

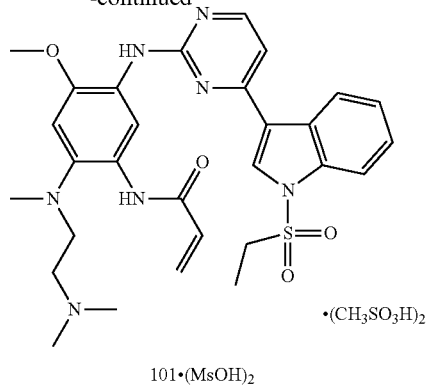

The compound 101 was dissolved in 2 mL of acetonitrile, methanesulfonic acid (2.0 eq) was added thereto and the reaction mixture was freeze dried to give 73.8 mg of methanesulfonate of the compound 101 (13%) as a yellow solid. LCMS (parent molecule) $C_{29}H_{35}S\ N_7O_4$: (ES, m/z): 578 [M+H]$^+$. $^1$H-NMR (methanesulfonate): (300 MHz, DMSO-D$_6$, ppm): δ 9.56 (s, 1H), 9.25 (br s, 1H), 8.65 (s, 1H), 8.48-8.41 (m, 2H), 8.31 (s, 1H), 7.91 (d, J=8.1 Hz, 1H), 7.59 (d, J=5.1 Hz, 1H), 7.47-7.42 (m, 2H), 7.05 (s, 1H), 6.71-6.61 (m, 1H), 6.326-6.26 (m, 1H), 5.81-5.77 (m, 1H), 3.85-3.81 (s, 3H), 3.78-3.73 (s, 2H), 3.32 (m, 4H), 2.83-2.82 (s, 6H), 2.65 (s, 3H), 2.27-2.50 (s, 6H), 1.08-1.23 (m, 3H).

Example 102

1. Synthesis of Intermediate 102-1

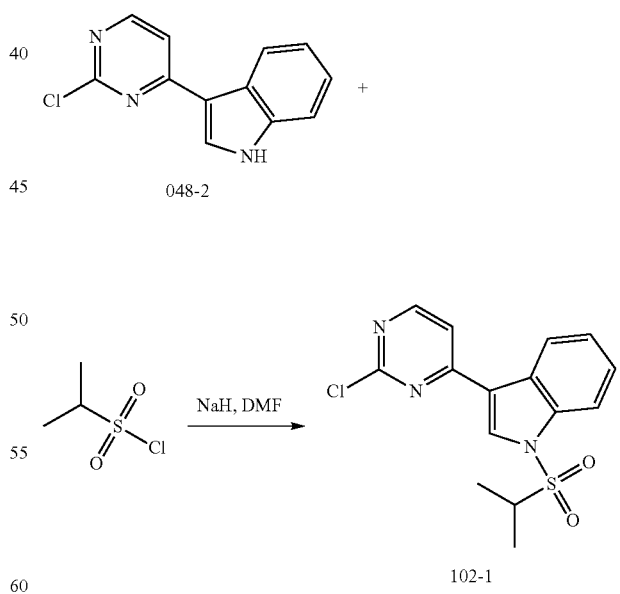

The reaction steps and conditions for the synthesis of compound 102-1 were the same as those in the first step of example 101, except that ethylsulfonyl chloride in example 101 was replaced with isopropylsulfonyl chloride. LCMS: 336.

2. Synthesis of Intermediate 102-2

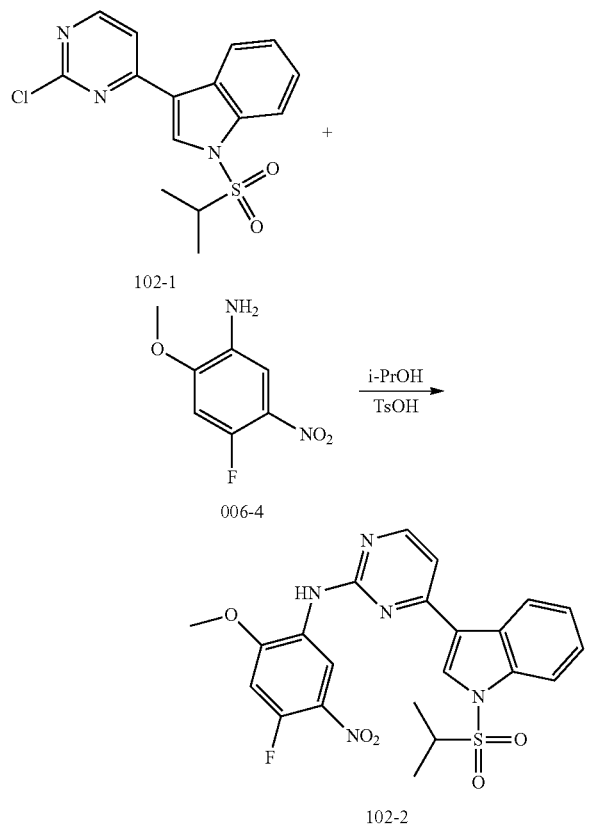

Under a nitrogen atmosphere, 20 mL of isopropyl alcohol, the intermediate 102-1 (2.0 g, 6.55 mmol), the intermediate 006-4 (1.2 g, 6.45 mmol) and p-toluenesulfonic acid (1.47 g, 8.52 mmol) were sequentially added into a 100 mL single-necked flask at room temperature. Next, the reaction was heated to 105° C. and carried out for 2 h. After detecting the reaction was completed, the reaction system was cooled to room temperature and quenched by adding 100 mL of ice water. The reaction mixture was filtered, and the solid was collected and dried to give 2.1 g of the intermediate 102-2 as a red solid. LCMS: 486.

3. Synthesis of Intermediate 102-3

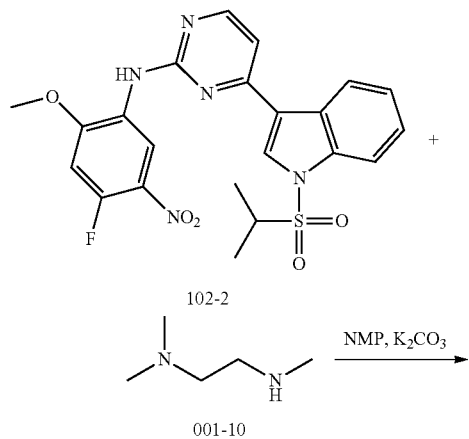

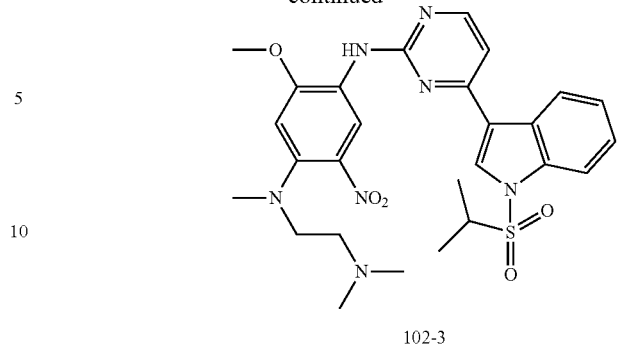

Under a nitrogen atmosphere, the intermediate 102-3 (2.1 g, 4.33 mmol) as a raw material was dissolved in 20 mL of NMP at room temperature in a 100 mL single-necked flask, followed by sequentially adding N,N,N'-trimethylethylene-diamine (662 mg, 6.48 mmol) and anhydrous potassium carbonate (1.85 g, 13.82 mmol) into the reaction system. Next, the reaction system was heated to 30° C., and then carried out for 24 h. After detecting the reaction was completed, the reaction system was cooled to room temperature. The reaction mixture was poured into 200 mL of ice water to quench the reaction. The reaction mixture was filtered and the solid was collected and dried to give 2 g of the intermediate 102-3 (81%) as a red solid. LCMS: 568.

4. Synthesis of Intermediate 102-4

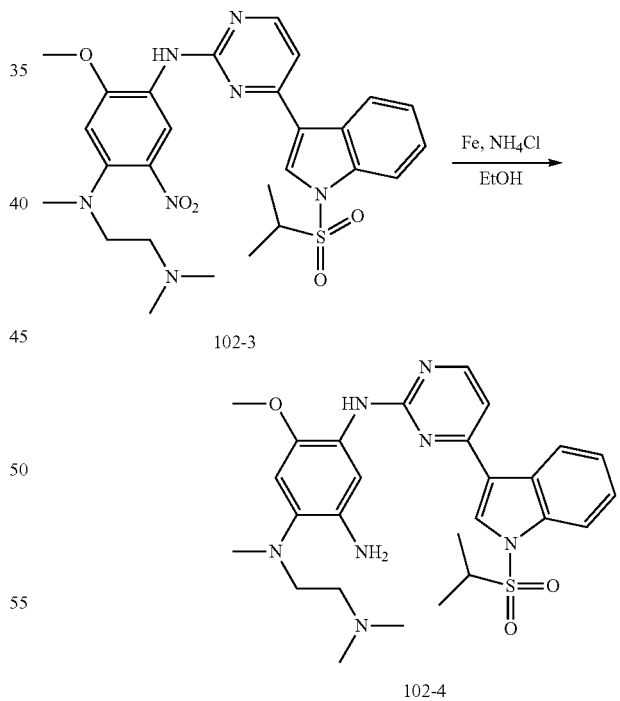

Under a nitrogen atmosphere, 30 mL of ethanol, 10 mL of water, the intermediate 102-3 (2.0 g, 3.52 mmol) as a raw material, iron powder (1.18 g, 21.1 mmol) and ammonium chloride (143 mL, 2.67 mmol) were sequentially added into a 100 mL single-necked flask at room temperature, followed by that the reaction was heated to 85° C. and carried out for 3 h. After detecting the reaction was completed, the reaction was cooled to room temperature. The resulting mixture was filtered by suction, and the filtrate was collected and concentrated to dryness. The resulting residue was purified by Comi-Flash-HPLC (column: C18 silica gel; mobile phase: acetonitrile/water (0.05% trifluoroacetic acid); 35% acetonitrile to 50% acetonitrile; 15 min; 70 mL/min; detection wavelength: 254 nm). The product was collected, and the combined mixture was adjusted with a saturated solution of sodium bicarbonate to pH=8, extracted three times with 200 mL of methylene chloride. The organic was collected, combined, dried over anhydrous sodium sulfate and concentrated to dryness to give 1.1 g of the intermediate 102-4 (58%) as a green solid. LCMS: 538.

5. Synthesis of Compound 102

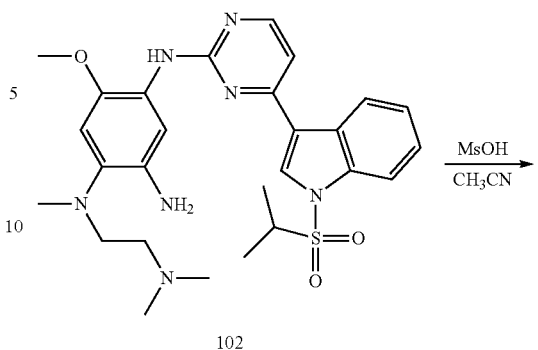

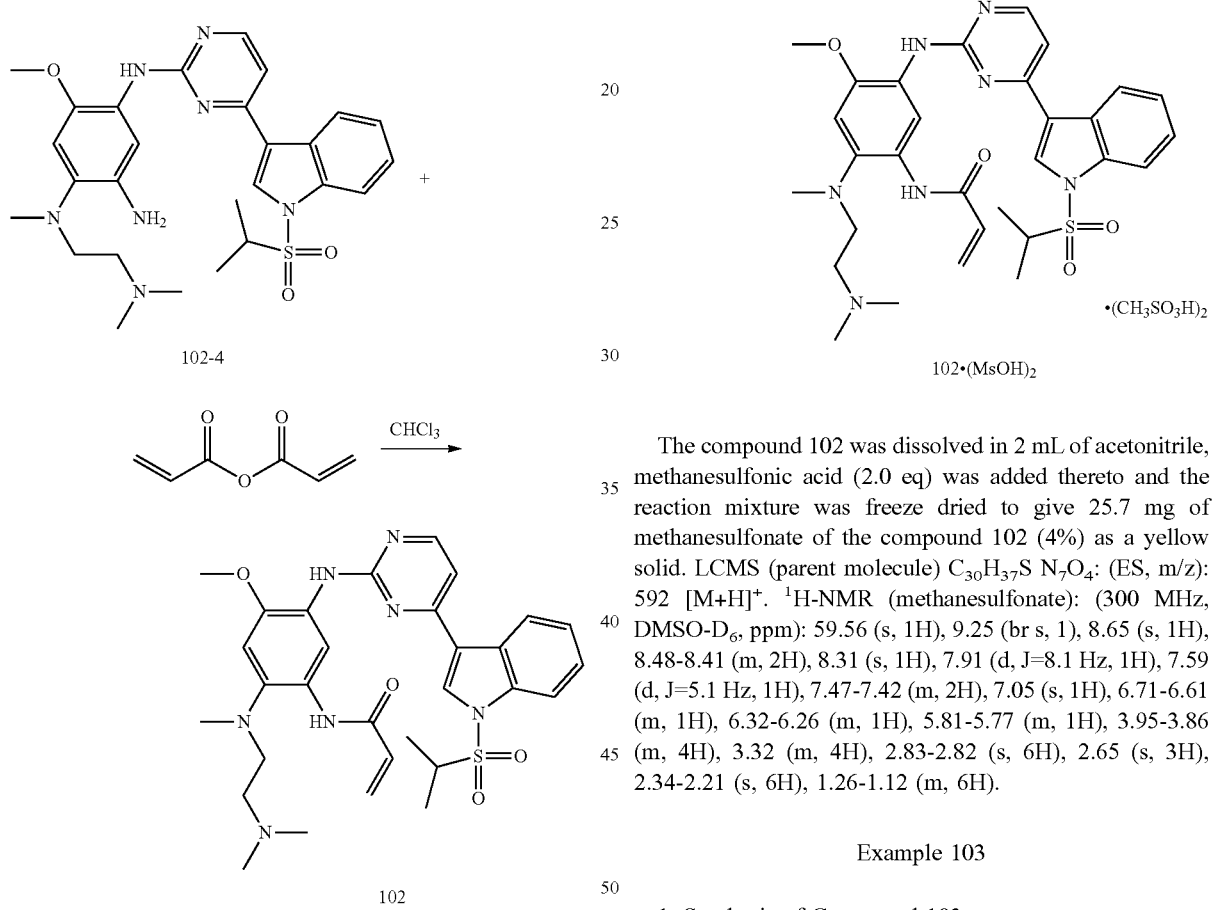

Under a nitrogen atmosphere, the intermediate 102-4 (400 mg, 0.74 mmol) as a raw material was dissolved in 10 mL of chloroform at room temperature in a 50 mL single-necked flask and acrylic anhydride (122 mg, 0.97 mmol) was added to the reaction system. Next, the reaction was carried out at room temperature for 2 h. After detecting the reaction was completed, the reaction system was quenched with 2 mL of ice water and concentrated to dryness. The resulting residue was purified by high pressure HPLC (column: Waters X-bridge C18, 19*150 mm; the mobile phase: 0.05% ammonia/acetonitrile, 40% acetonitrile to 85% acetonitrile, 9 min, 15 m/min; detection wavelength: 254 nm). The product was collected and concentrated to dryness to give compound 102.

The compound 102 was dissolved in 2 mL of acetonitrile, methanesulfonic acid (2.0 eq) was added thereto and the reaction mixture was freeze dried to give 25.7 mg of methanesulfonate of the compound 102 (4%) as a yellow solid. LCMS (parent molecule) $C_{30}H_{37}S\ N_7O_4$: (ES, m/z): 592 [M+H]$^+$. $^1$H-NMR (methanesulfonate): (300 MHz, DMSO-D$_6$, ppm): 59.56 (s, 1H), 9.25 (br s, 1), 8.65 (s, 1H), 8.48-8.41 (m, 2H), 8.31 (s, 1H), 7.91 (d, J=8.1 Hz, 1H), 7.59 (d, J=5.1 Hz, 1H), 7.47-7.42 (m, 2H), 7.05 (s, 1H), 6.71-6.61 (m, 1H), 6.32-6.26 (m, 1H), 5.81-5.77 (m, 1H), 3.95-3.86 (m, 4H), 3.32 (m, 4H), 2.83-2.82 (s, 6H), 2.65 (s, 3H), 2.34-2.21 (s, 6H), 1.26-1.12 (m, 6H).

Example 103

1. Synthesis of Compound 103

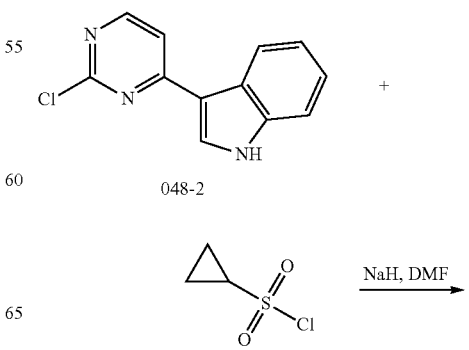

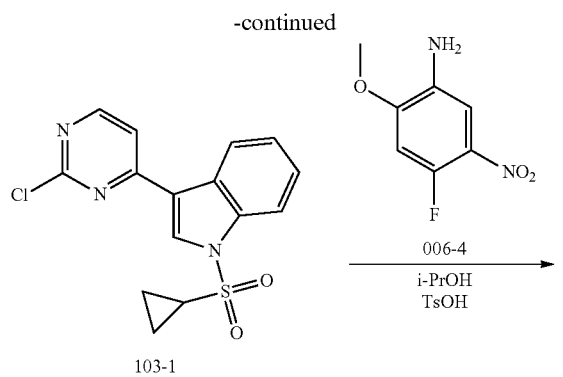
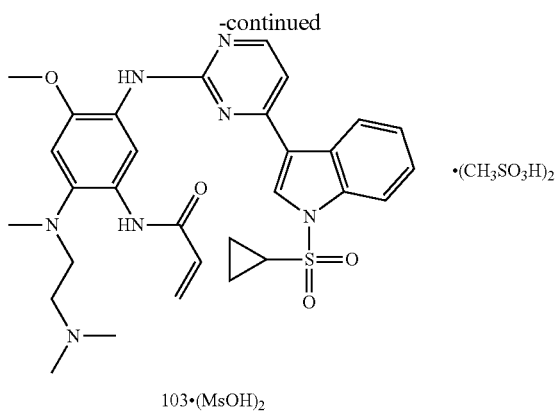
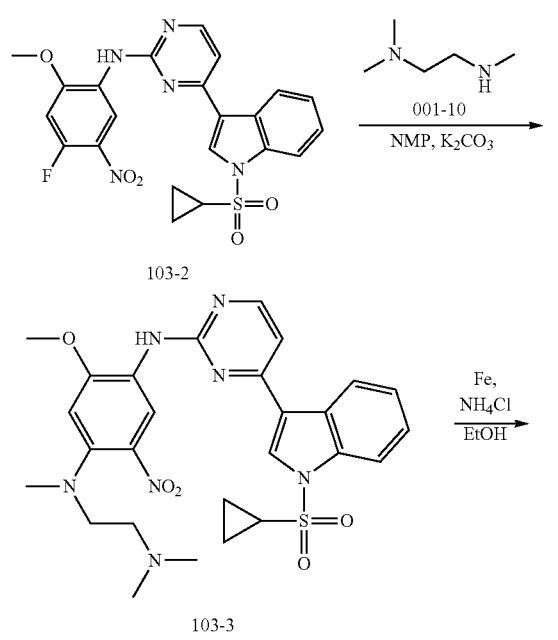
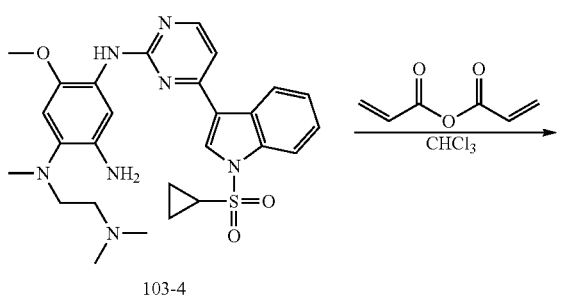
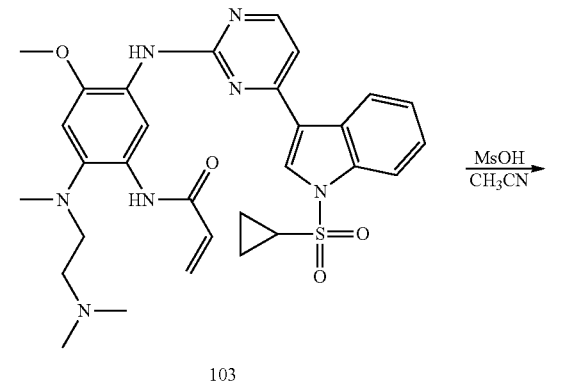
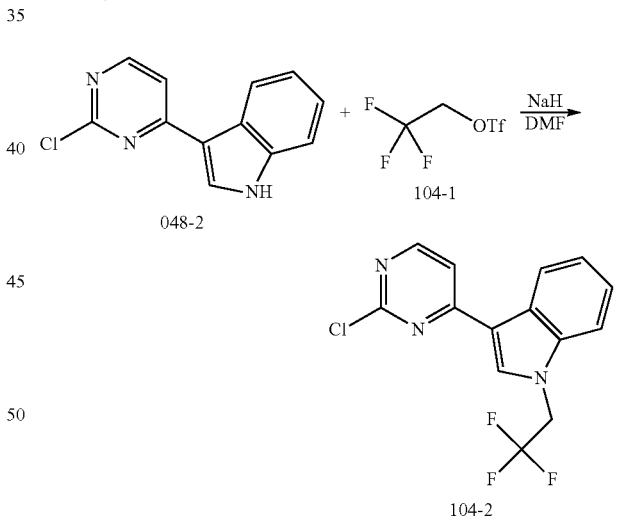

The reaction steps and conditions for the synthesis of compound 103 and its methanesulfonate were the same as those in the first to fifth steps of example 102, except that isopropylsulfonyl chloride in example 102 was replaced with the intermediate of cyclopropylsulfonyl chloride in the first step. LCMS (parent molecule) $C_{30}H_{37}SN_7O_4$: (ES, m/z): 590 [M+H]$^+$. $^1$H-NMR (methanesulfonate): (300 MHz, DMSO-D$_6$, ppm): δ 9.56 (s, 1H), 9.25 (br s, 1H), 8.72 (s, 1H), 8.43-8.41 (m, 2H), 8.31 (s, 1H), 7.96 (d, J=8.4 Hz, 1H), 7.61 (d, J=4.8 Hz, 1H), 7.47-7.31 (m, 2H), 7.05 (s, 1H), 6.72-6.63 (m, 1H), 6.28 (d, J 16.5 Hz, 1H), 5.78 (d, J=10.2 Hz, 1H), 3.86 (s, 3H), 3.41-3.20 (m, 5H), 2.82 (s, 6H), 2.66 (s, 3H), 2.18 (s, 6H), 1.36-1.23 (m, 2H), 1.16-1.05 (m, 2H).

Example 104

1. Synthesis of Intermediate 104-2

Under a nitrogen atmosphere, the intermediate 048-2 (3.0 g, 13 mmol) as a raw material was dissolved in 30 mL of N,N-dimethylformamide in a 100 mL three-necked flask at room temperature. The reaction system was cooled to 0° C. and sodium hydride (785 mg, 18.5 mmol) was added thereto in batches. Next, the reaction was carried out at 0° C. for 0.5 h, trifluoroethyltriflate 104-1 (3.65 g, 15 mmol) was added into the reaction system, followed by that the reaction was carried out at room temperature for 2 h. After detecting the reaction was completed, the reaction mixture was poured into 200 mL of ice water to quench the reaction. A red solid was precipitated, and the resulting mixture was filtrated, and the solid was collected and dried to dryness, to give 4.2 g of the intermediate 104-2 as a red solid. LCMS: 312.0.

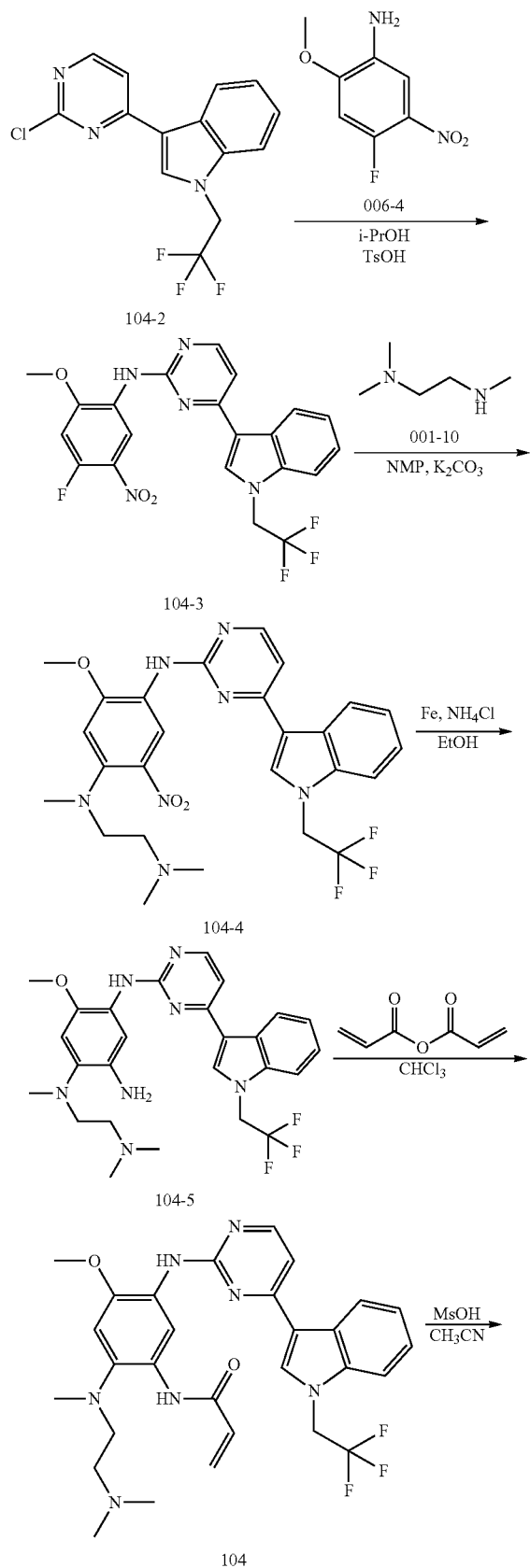

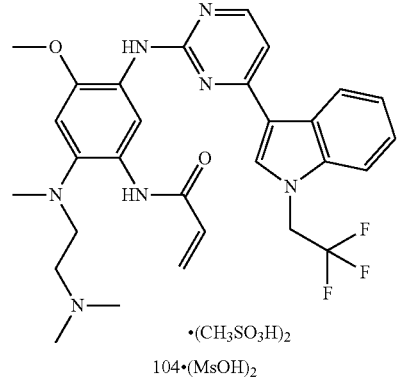 [SMILES: C=CC(=O)Nc1cc(Nc2nccc(-c3cn(CC(F)(F)F)c4ccccc34)n2)c(OC)cc1N(C)CCN(C)C]

The reaction steps and conditions for the synthesis of compound 104 and its methanesulfonate were the same as those in the second to fifth steps of example 101, except that the intermediate 101-1 in example 101 was replaced with the intermediate 104-2. LCMS (parent molecule) $C_{29}H_{32}F_3N_7O_2$: (ES, m/z): 568 [M+H]$^+$. $^1$H-NMR (methanesulfonate): (300 MHz, DMSO-D$_6$, ppm): δ 9.51 (s, 1H), 9.35-9.27 (br s, 2H), 8.76 (s, 1H), 8.45-8.30 (m, 3H), 7.78 (d, J=8.1 Hz, 1H), 7.44 (d, J=6.3 Hz, 1H), 7.36-7.31 (m, 1H), 7.23-7.21 (m, 1H), 7.08 (s, 1H), 6.76-6.67 (m, 1H), 6.29 (d, J=16.8 Hz, 1H), 5.80 (d, J=10.8 Hz, 1H), 5.42-5.33 (m, 2H), 3.87 (s, 3H), 3.50-3.33 (m, 4H), 2.83 (s, 6H), 2.68 (s, 3H), 2.50 (s, 6H).

Example 105

1. Synthesis of Intermediate 105-2

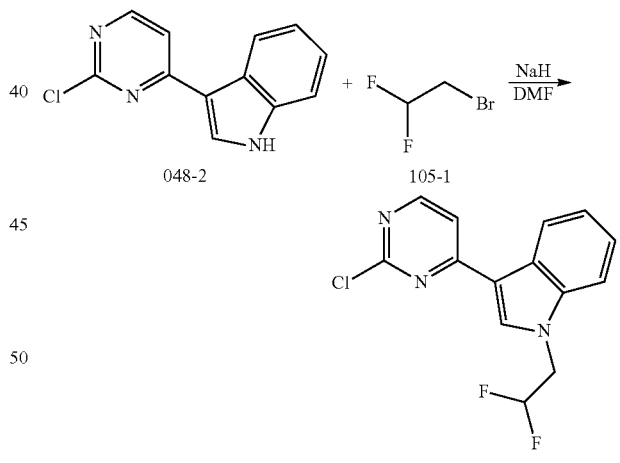

Under a nitrogen atmosphere, the intermediate 048-2 (4.0 g, 17.4 mmol) as a raw material was dissolved in 40 mL of N,N-dimethylformamide in a 100 mL three-necked flask at room temperature. The reaction system was cooled to 0° C. and sodium hydride (900 mg, 37.5 mmol) was added thereto in batches. Next, the reaction was carried out at 0° C. for 0.5 h, and 1,1-difluoro-2-bromoethane (4.8 g, 33.5 mmol) was added into the reaction system, followed by that the reaction was carried out at room temperature for 2 h. After detecting the reaction was completed, the reaction mixture was poured into 100 mL of ice water to quench the reaction. The resulting mixture was extracted twice with 100 mL of EA and the organic phases were combined and dried to dryness. The resulting residue was purified by silica gel column chromatography (the used eluent (PE:EA=10:1-5:1)), and the product was collected and concentrated to dryness so as to give 1.6 g of the intermediate 105-2 (31%) as a red solid. LCMS: 294.0.

2. Synthesis of Compound 105

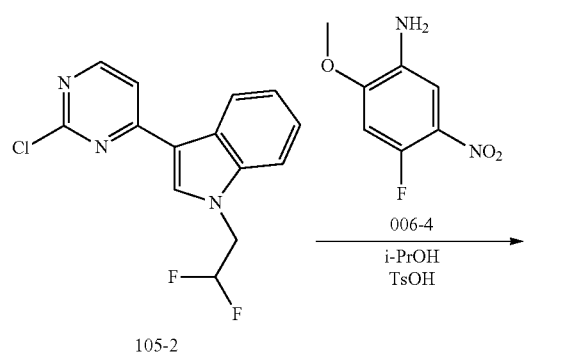

105-2

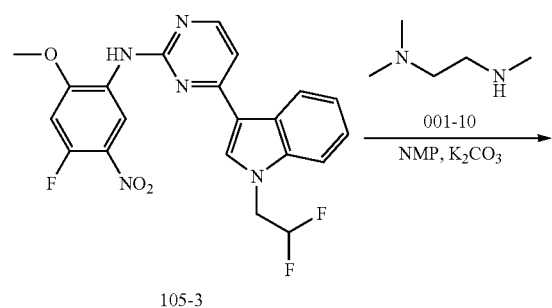

105-3

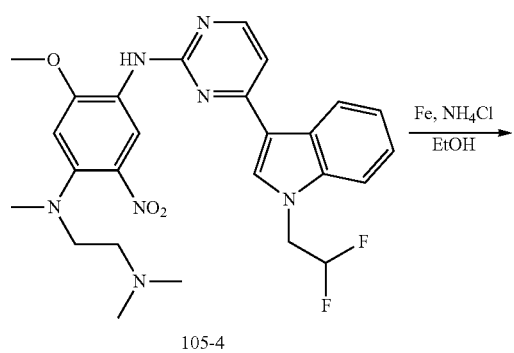

105-4

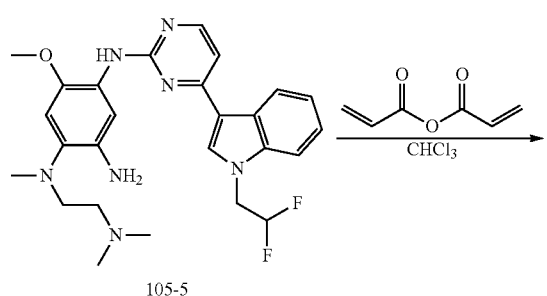

105-5

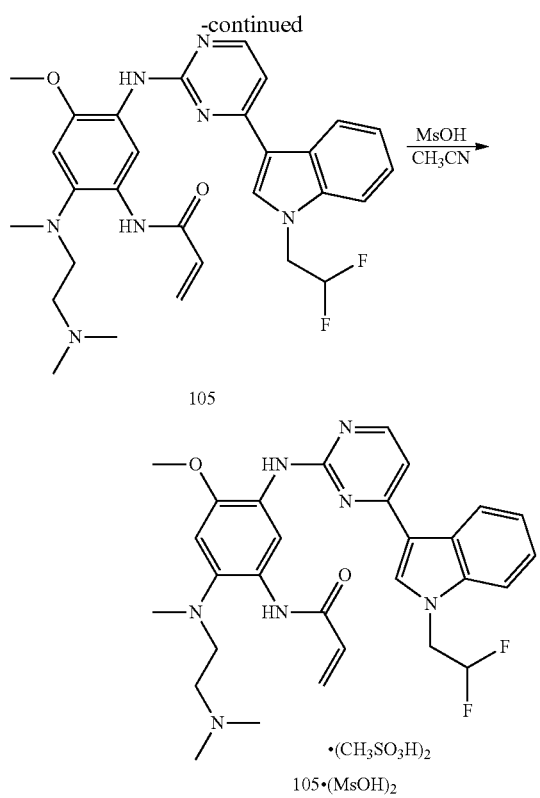

105

105·(MsOH)$_2$

The reaction steps and conditions for the synthesis of compound 105 and its methanesulfonate were the same as those in the second to fifth steps of example 101, except that the intermediate 101-1 in example 101 was replaced with the intermediate 105-2. LCMS (parent molecule) C$_{29}$H$_{33}$F$_2$N$_7$O$_2$: (ES, m/z): 550 [M+H]$^+$. $^1$H-NMR (methanesulfonate): (300 MHz, DMSO-D$_6$, ppm): δ 9.51 (s, 1H), 9.30 (br s, 2H), 8.77 (s, 1H), 8.37-8.29 (m, 3H), 7.71 (d, J=8.1 Hz, 1H), 7.45-7.43 (m, 1H), 7.33-7.26 (m, 1H), 7.25 (d, J=5.1 Hz, 1H), 7.09 (s, 1H), 6.77-6.71 (m, 1H), 6.50 (s, 1H), 6.28 (d, J=17.4 Hz, 1H), 5.79 (d, J=10.5 Hz, 1H), 4.92-4.81 (m, 2H), 3.94 (s, 3H), 3.34-3.31 (m, 4H), 2.83 (s, 6H), 2.68 (s, 3H), 2.50 (s, 6H).

Example 106

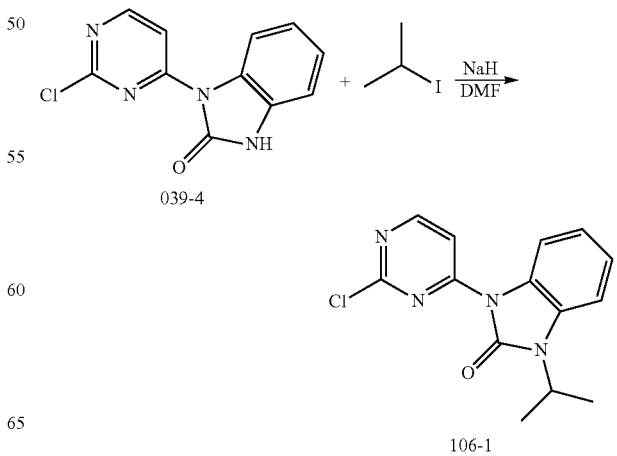

106-1

1. Synthesis of Intermediate 106-1

Under a nitrogen atmosphere, the intermediate 039-4 (5.0 g, 20.3 mmol) as a raw material was dissolved in 100 mL of anhydrous DMF in a 250 mL single-necked flask at room temperature. The reaction was cooled to 0° C., and sodium hydride (731 mg, 30.5 mmol) was added thereto in batches for 10 min. Next, the reaction was carried out at 0° C. for 1 h, and then iodoisopropane (5.18 g, 30.5 mmol) was added into the reaction system, and then the reaction was carried out at room temperature for overnight. After detecting the reaction was completed, the reaction system was quenched with 400 mL of ice water. The resulting mixture was extracted three times with 200 mL of dichloromethane. The organic phases were combined and washed three times with 600 mL of saturated brine. The organic phases were dried over anhydrous sodium sulfate and concentrated to dryness. The resulting residue was purified with silica gel column chromatography (eluent: EA/PE=1:10-1:5). The product was collected and concentrated to dryness so as to give 3.0 g of the intermediate 106-1 (51%) as a white solid. LCMS: 289.1.

2. Synthesis of Intermediate 106-2

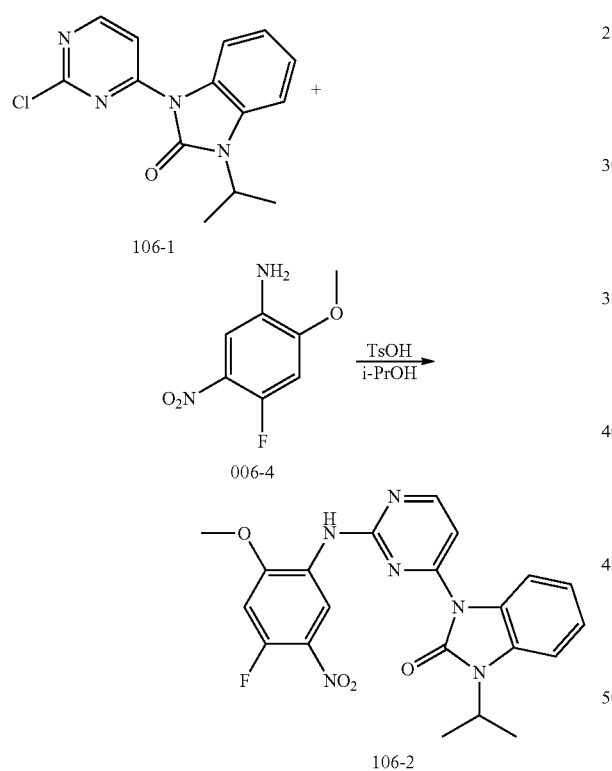

Under a nitrogen atmosphere, the intermediate 106-1 (1.5 g, 5.2 mmol) as a raw material was dissolved in 20 mL of isopropyl alcohol in a 100 mL single-necked flask at room temperature, then sequentially adding the intermediate 006-4 (969 mg, 5.20 mmol)) and p-toluenesulfonic acid (1.08 g, 6.24 mmol) into the reaction system. Next, the reaction was heated to 105° C. and carried out overnight. After detecting the reaction was completed, the reaction system was cooled to room temperature. The reaction mixture was filtered, and the filter cake was collected and rinsed three times with 10 mL of isopropanol. The resulting solid was dried to give 1.3 g of the intermediate 106-2 (57%) as a yellow solid. LCMS: 439.1.

3. Synthesis of Intermediate 106-3

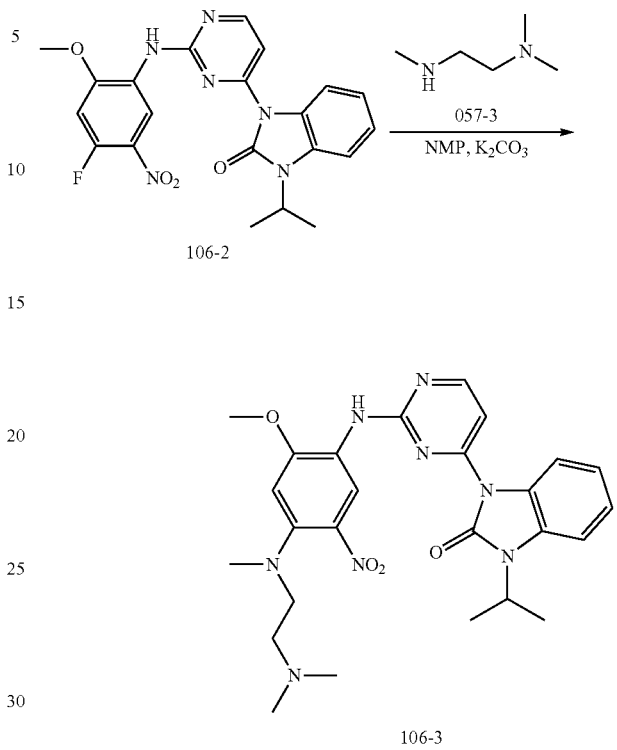

Under a nitrogen atmosphere, the intermediate 106-2 (1.3 g, 2.97 mmol) as a raw material was dissolved in 10 mL of NMP at room temperature in a 100 mL single-necked flask, followed by sequentially adding N,N,N'-trimethylethylenediamine (454 mg, 4.44 mmol) and anhydrous potassium carbonate (1.23 g, 8.82 mmol) into the reaction system. Next, the reaction system was heated to 100° C., and then carried out for 3 h. After detecting the reaction was completed, the reaction system was cooled to room temperature. The reaction mixture was poured into 500 mL of ice water to quench the reaction. The reaction mixture was filtered and the filter cake was collected and dried to give 1.4 g of the intermediate 106-3 (91%) as a red solid. LCMS: 521.3.

4. Synthesis of Intermediate 106-4

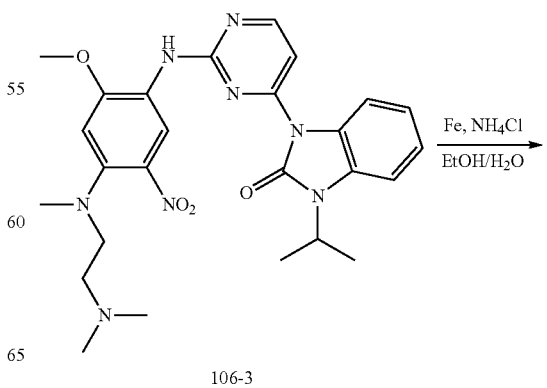

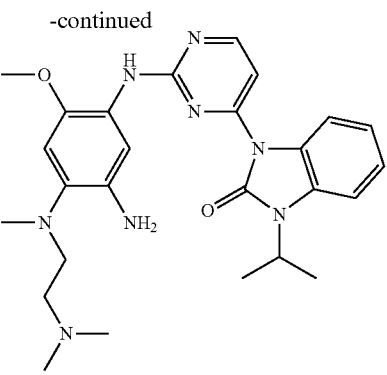

106-4

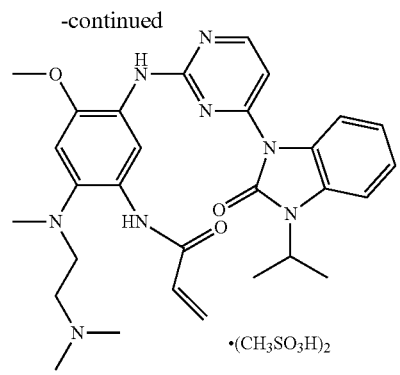

106·(MsOH)₂

Under a nitrogen atmosphere, 210 mL of ethanol, 70 mL of water, the intermediate 106-3 (1.4 g, 2.69 mmol) as a raw material, iron powder (905 mg, 16.2 mmol) and ammonium chloride (99.8 mL, 1.87 mmol) were sequentially added into a 500 mL single-necked flask at room temperature, followed by that the reaction was heated to 85° C. and carried out overnight. After detecting the reaction was completed, the reaction was cooled to room temperature. The resulting mixture was filtered by suction, and the filtrate was collected and concentrated to dryness. The resulting residue was purified by preparative Combi-Flash-HPLC (column: C18 silica gel; mobile phase: acetonitrile/water (0.05% trifluoroacetic acid); 35% acetonitrile to 50% acetonitrile; 15 min; 70 mL/min; detection wavelength: 254 nm). The resulting organic phases were concentrated to dryness, so as to give 1.1 g of the intermediate 106-4 (68%) as a yellow solid. LCMS: 521.3.

5. Synthesis of Compound 106

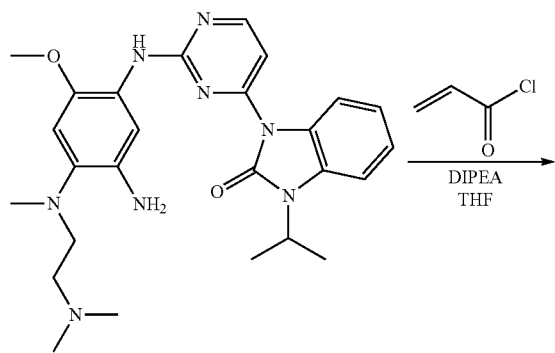

Under a nitrogen atmosphere, the intermediate 106-4 (604 mg, 1.00 mmol) as a raw material was dissolved in 10 mL of anhydrous tetrahydrofuran in a 100 mL three-necked flask at room temperature, followed by adding DIPEA (387 mg, 2.99 mmol). The reaction system was cooled to 0° C. and acryloyl chloride (90 mg, 0.99 mmol) was added thereto at 0° C. Next, the reaction was carried out at room temperature for 1 h. After detecting the reaction was completed, the reaction system was quenched with 50 mL of ice water. The resulting mixture was extracted three times with 100 mL of dichloromethane. The organic phases were combined, washed three times with 300 mL of saturated brine, and dried over anhydrous sodium sulfate and concentrated to dryness. The resulting residue was purified by high pressure preparative Prep-HPLC (column: Waters X-bridge RP18, 19*150 mm, 5 um; mobile phase: water (10 mM NH₄HCO₃+0.05% NH₃.H₂O)/acetonitrile, 60% acetonitrile to 75% acetonitrile, 8 min, 20 mL/min; detection wavelength: 254 nm). The resulting organic phases were concentrated to dryness to give the compound 106.

The compound 106 was dissolved in 10 mL of acetonitrile, methanesulfonic acid (2.0 eq) was added thereto and the resulting reaction mixture was freeze dried to give 85.0 mg of methanesulfonate of the compound 106 (12%) as a yellow solid. LCMS (parent molecule) $C_{29}H_{36}N_8O_3$: (ES, m/z): 545.3 [M+H]⁺. ¹H-NMR (methanesulfonate): (300 MHz, DMSO-D₆, ppm): δ 9.50 (br s, 2H), 9.30 (br s, 1H), 8.45 (d, J=6.3 Hz, 1H), 8.14 (br s, 1H), 8.10 (s, 1H), 7.85 (d, J=6.3 Hz, 1H), 7.41 (d, J=7.8 Hz, 1H), 7.21-7.16 (m, 1H), 7.00-6.95 (m, 1H), 6.74-6.65 (m, 1H), 6.30-6.24 (m, 1H), 5.87-5.76 (m, 1H), 4.73-4.64 (m, 1H), 3.83 (s, 3H), 3.33 (m, 4H), 2.83 (s, 3H), 2.82 (s, 3H), 2.73 (s, 3H), 2.38 (s, 6H), 1.50 (s, 3H), 1.48 (s, 3H).

Example 107

1. Synthesis of Intermediate 107-1

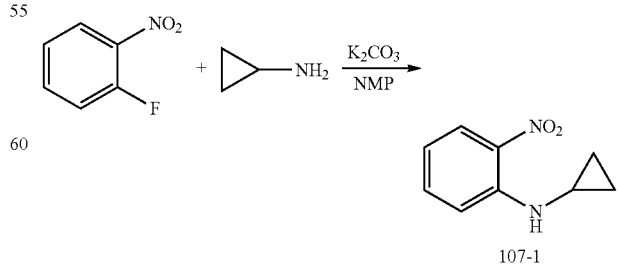

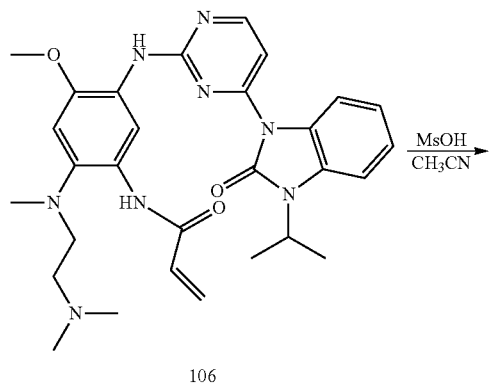

106

107-1

Under a nitrogen atmosphere, o-nitrofluorobenzene (15 g, 106 mmol) as a raw material was dissolved in 150 mL of NMP in a 500 mL single-necked flask at room temperature, followed by sequentially adding cyclopropylamine (9.10 g, 159 mmol), anhydrous potassium carbonate (44 g, 316 mmol) the reaction system. Next, the reaction was heated to 100° C. and carried out for 3 h. After detecting the reaction was completed, the reaction system was cooled to room temperature and the reaction mixture was poured into 150 mL ice water to quench the reaction. The reaction system was extracted three times with 150 mL of dichloromethane. The organic phases were combined, washed with 500 mL of saturated brine three times and dried over anhydrous sodium sulfate and concentrated to dryness to give 16 g of the intermediate 107-1 (84%) as a yellow oil. LCMS: 179.1.

2. Synthesis of Intermediate 107-2

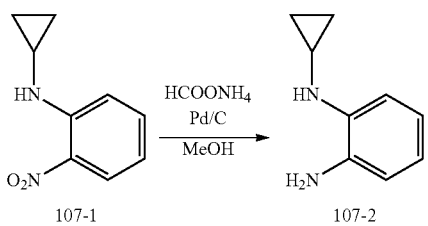 [SMILES: "MeOH" ; O=[N+]([O-])c1ccccc1NC1CC1 ; Nc1ccccc1NC1CC1]

Under a nitrogen atmosphere, the intermediate 107-1 (16 g, 89.8 mmol) as a raw material was dissolved in 160 mL of anhydrous methanol in a 500 mL single-necked flask at room temperature, and then Pd/C (16 g, 5% by weight) and ammonium formate (16 g, 254 mmol) were sequentially added to the reaction system, then the reaction was carried out at room temperature overnight. Next, after detecting the reaction was completed, the reaction mixture was filtered and the filtrate was collected and concentrated to dryness. The resulting residue was purified by silica gel column chromatography (eluent: EA/PE (1:10-1:5)), and the product was collected and concentrated to dryness to give 12 g of the intermediate 107-2 (90%) as a colorless oil. LCMS: 149.1.

3. Synthesis of Intermediate 107-3

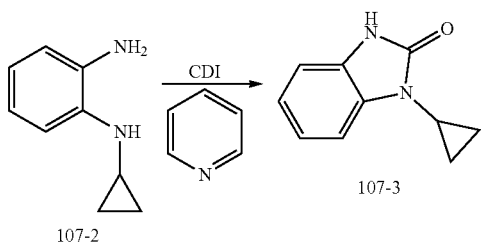

Under a nitrogen atmosphere, the intermediate 107-2 (8.0 g, 54.0 mmol) as a raw material was dissolved in 100 mL of anhydrous tetrahydrofuran at room temperature in a 250 mL single-necked flask, followed by sequentially adding carbonyldiimidazole CDI (19.7 g, 108 mmol) and pyridine (8.54 g, 108 mmol) into the reaction system. Next, the reaction system was heated to 65° C., and then carried out for 3 h. After detecting the reaction was completed, the reaction system was cooled to room temperature. The reaction mixture was poured into 100 mL of ice water to quench the reaction. The reaction system was washed with 300 mL of dichloromethane three times, and the organic phases were combined, washed with 300 mL of saturated brine three times, dried over anhydrous sodium sulfate and concentrated to dryness. The resulting residue was purified by silica gel column chromatography (eluent: EA/PE (1:10-1:5)), and the product was collected and concentrated to dryness to give 4.2 g of the intermediate 107-3 (45%) as a white solid. LCMS: 175.1.

4. Synthesis of Intermediate 107-4

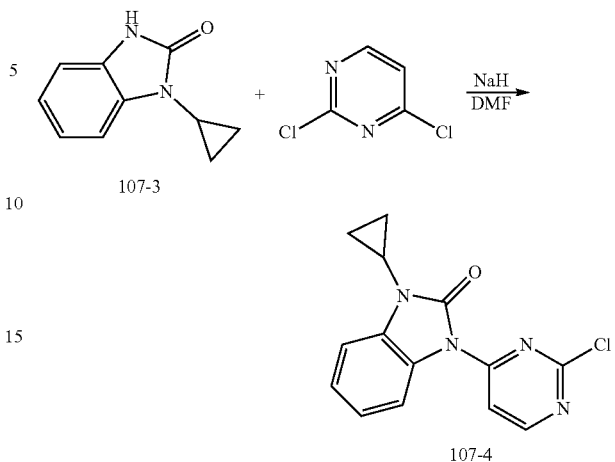

Under a nitrogen atmosphere, the intermediate 107-3 (4.2 g, 24.1 mmol) as a raw material was dissolved in 50 mL of anhydrous DMF in 250 mL of a three-necked flask, then the reaction was cooled to 0° C. and NaH (869 m& 36.2 mmol) was added in batches for 10 min. Next, the reaction was carried out at 0° C. for 1 h, and then 2,4-dichloropyrimidine (5.36 g, 36.0 mmol) was added and the reaction was carried out at room temperature overnight. Next day, after detecting the reaction was completed, the reaction system was quenched with 100 ML of ice water. The system was extracted with 100 mL of methylene chloride three times. The organic phases were combined, washed with 300 mL of saturated brine three times, dried over anhydrous sodium sulfate and concentrated to dryness. The resulting residue was purified by silica gel column chromatography (eluent: EA/PE=1:10-1:5) and the product was collected and concentrated to dryness to give 4 g of the intermediate 107-4 (58%) as a white solid. LCMS: 287.1.

5. Synthesis of Compound 107

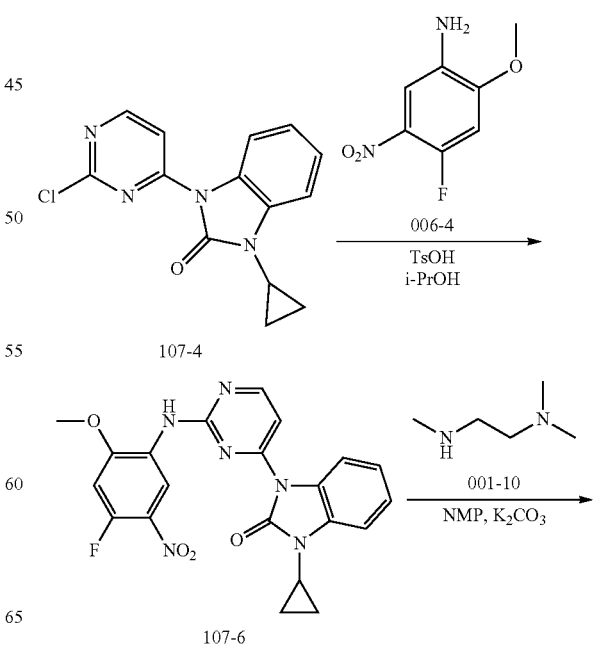

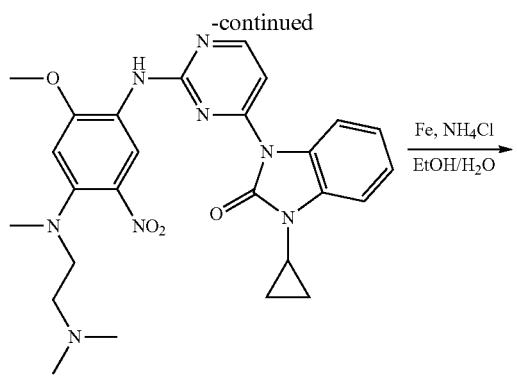

107-6

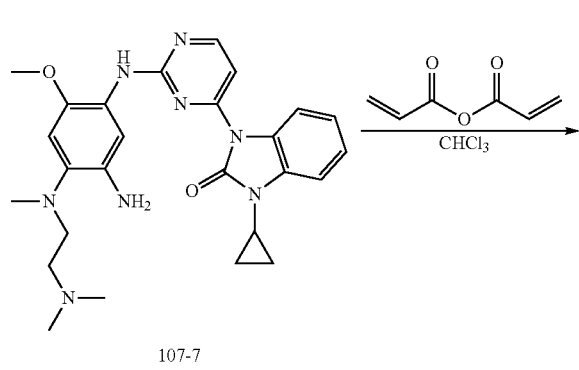

107-7

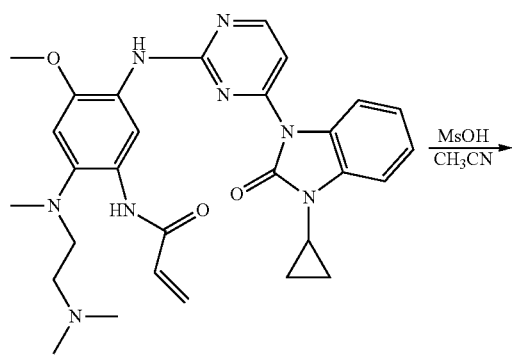

107

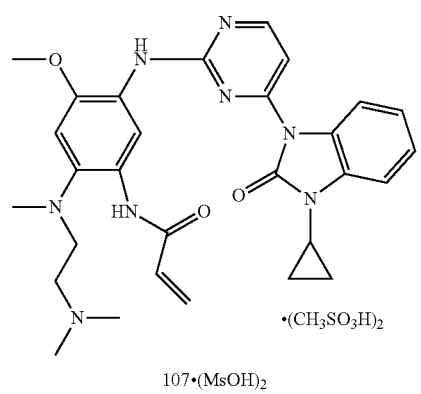

107·(MsOH)₂

The reaction steps and conditions for the synthesis of compound 107 and its methanesulfonate from the intermediate 107-4 were the same as those in the second to fifth steps of example 101, except that the intermediate 101-1 in example 101 was replaced with the intermediate 107-4. Data for compound 107: LCMS (parent molecule) $C_{29}H_{34}N_8O_3$: (ES, m/z): 543.3[M+H]⁺. ¹H-NMR (methanesulfonate): (300 MHz, DMSO-D₆, ppm): δ 9.49-9.26 (m, 3H), 8.44 (d, J=6.3 Hz, 1H), 8.10 (br s, 2H), 7.83-7.81 (m, 1H), 7.31-7.19 (m, 2H), 7.05-6.96 (m, 2H), 6.72-6.64 (m, 1H), 6.29-6.24 (m, 1H), 5.79-5.76 (m, 1H), 3.82 (s, 3H), 3.33 (m, 4H), 2.95-2.93 (m, 1H), 2.83 (s, 3H), 2.82 (s, 3H), 2.66 (s, 3H), 2.37 (s, 6H), 1.10-1.08 (m, 2H), 0.93 (m, 2H).

Example 108

1. Synthesis of Intermediate 108-1

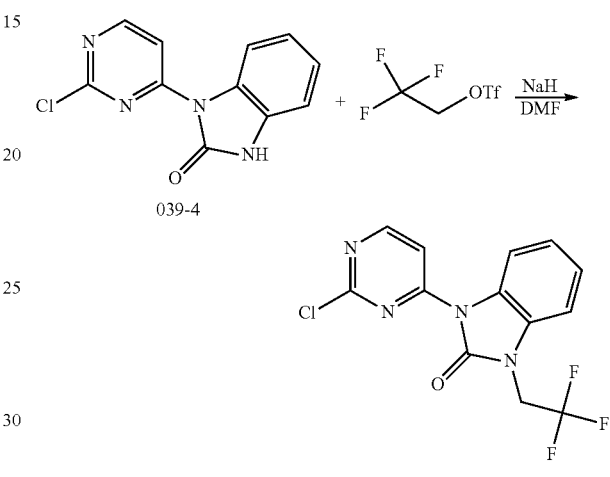

Under a nitrogen atmosphere, the intermediate 039-4 (3.0 g, 12 mmol) as a raw material was dissolved in 30 mL of N,N-dimethylformamide in a 100 mL three-necked flask at room temperature. The reaction system was cooled to 0° C. and sodium hydride (731 mg, 18.2 mmol) was added thereto in batches. Next, the reaction was carried out at 0° C. for 0.5 h, trifluoroethylmethanesulfonate (3.39 g, 14.6 mmol) was added into the reaction system, then the reaction was carried out at room temperature for 2 h. After detecting the reaction was completed, the reaction mixture was poured into 200 mL of ice water to quench the reaction. A red solid was precipitated, and the resulting mixture was filtrated, and the solid was collected and dried to dryness to give 3.5 g of the intermediate 108-1 as a red solid. LCMS: 329.0.

2. Synthesis of Compound 108

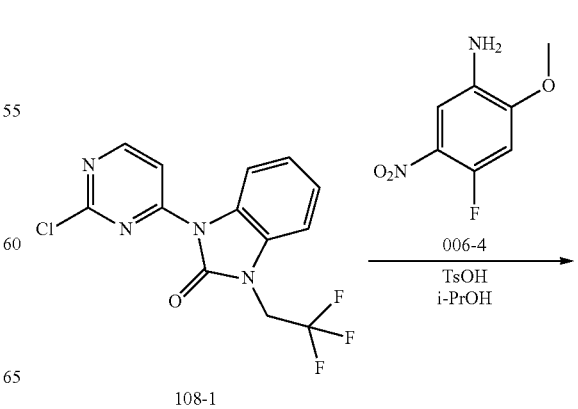

-continued

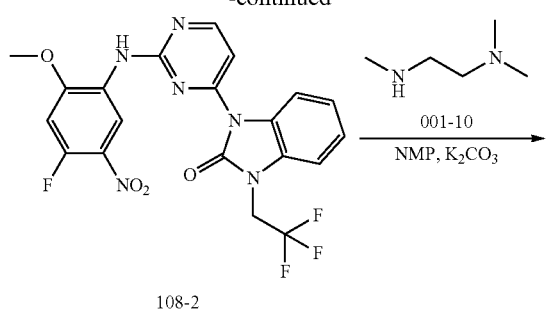

108-2

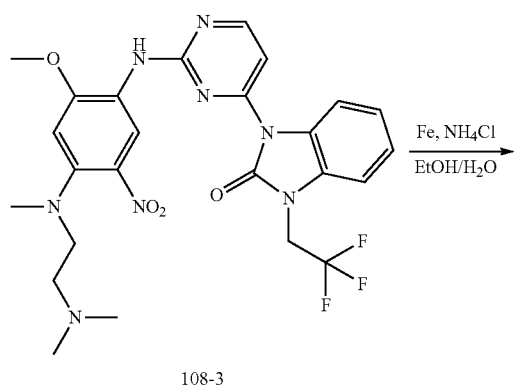

108-3

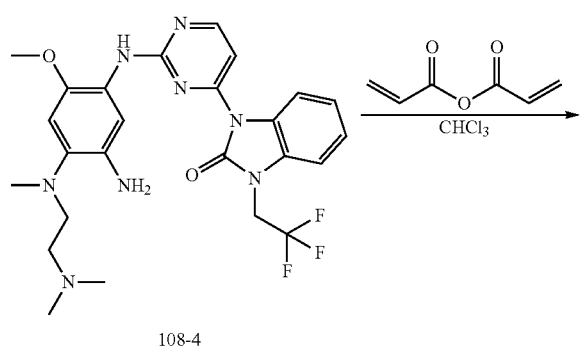

108-4

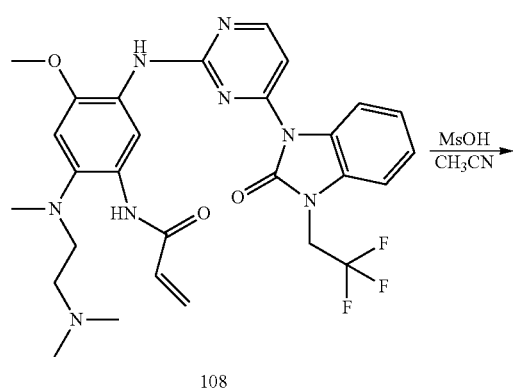

108

-continued

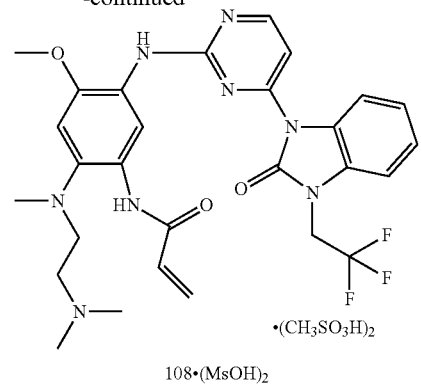

108·(MsOH)$_2$

The reaction steps and conditions for the synthesis of compound 108 and its methanesulfonate from the intermediate 108-1 were the same as those in the second to fifth steps of example 101, except that the intermediate 101-1 in example 101 was replaced with the intermediate 108-1. Data for compound 108: LCMS (parent molecule) $C_{28}H_{32}F_3N_8O_3$: (ES, m/z): 585.2 [M+H]$^+$. $^1$H-NMR (methanesulfonate): (300 MHz, DMSO-D$_6$, ppm): δ 9.50 (s, 1H), 9.25 (br s, 2H), 8.49 (d, J=6.0 Hz, 1H), 7.74 (d, J=6.0 Hz, 1H), 7.42-7.40 (m, 1H), 7.23-7.21 (m, 1H), 7.27-7.22 (m, 1H), 7.11-7.02 (m, 2H), 6.78-6.63 (m, 1H), 6.27 (d, J=17.1 Hz, 1H), 5.78 (d, J=10.5 Hz, 1H), 4.85 (s, 2H), 3.85 (s, 3H), 3.50-3.20 (m, 4H), 2.83-2.73 (m, 6H), 2.67 (s, 3H), 2.37 (s, 6H).

Example 109

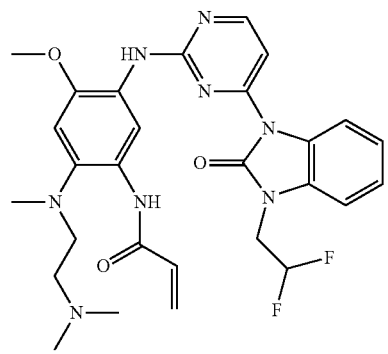 [SMILES: C=CC(=O)Nc1cc(Nc2nccc(-n3c(=O)n(CC(F)F)c4ccccc43)n2)c(OC)cc1N(C)CCN(C)C]

1. Synthesis of Intermediate 109-1

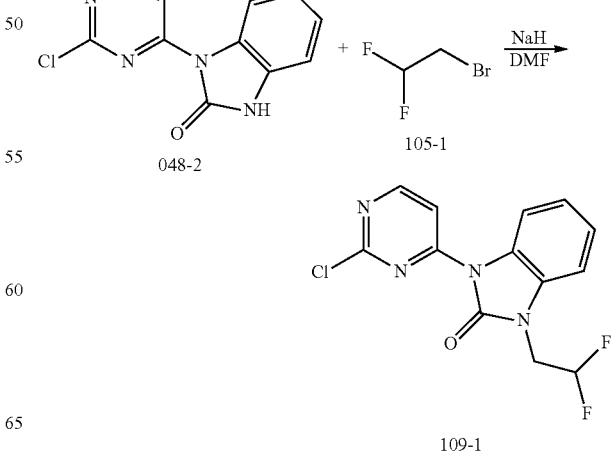

109-1

Under a nitrogen atmosphere, the intermediate 048-2 (3.0 g, 12.2 mmol) as a raw material was dissolved in 30 mL of N,N-dimethylformamide in a 100 mL three-necked flask at room temperature. The reaction system was cooled to 0° C. and sodium hydride (731 mg, 18.2 mmol) was added thereto in batches. Next, the reaction was carried out at 0° C. for 0.5 h, and 1,2-difluoro-2-bromoethane (3.48 g, 20.0 mmol) was added into the reaction system, then the reaction was carried out at room temperature for 2 h. After detecting the reaction was completed, the reaction mixture was poured into 100 mL of ice water to quench the reaction. The resulting mixture was extracted with 100 mL of ethyl acetate twice, the organic phases were combined and washed with 100 mL of saturated brine twice, dried and concentrated to dryness. The resulting residue was purified by silica gel column chromatography (eluent, EA:PE=0-20%), and the product fraction was collected, concentrated to dryness to give 1.23 g of the intermediate 109-1 (33%) as a red solid. LCMS: 311.0.

2. Synthesis of Compound 109

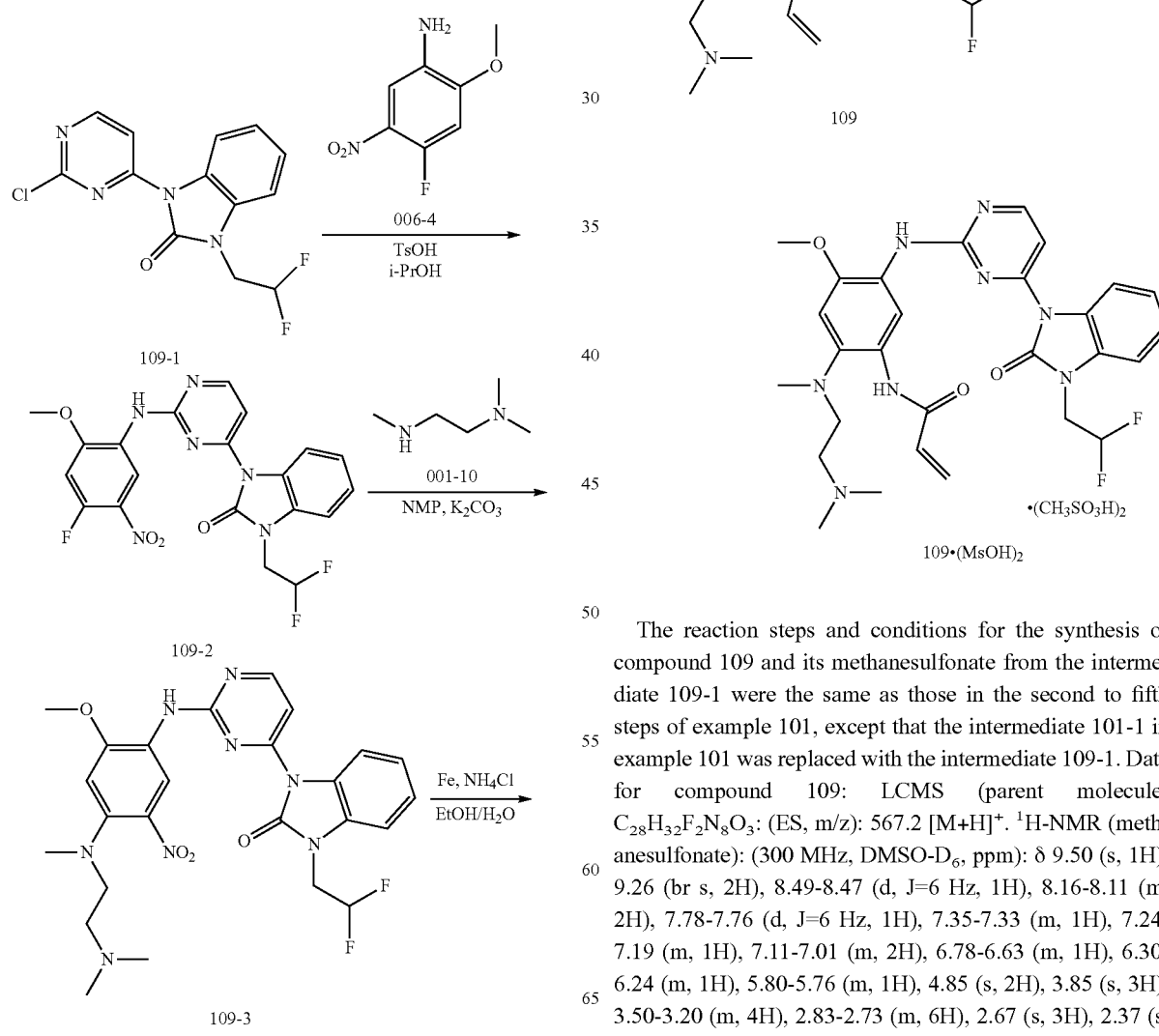
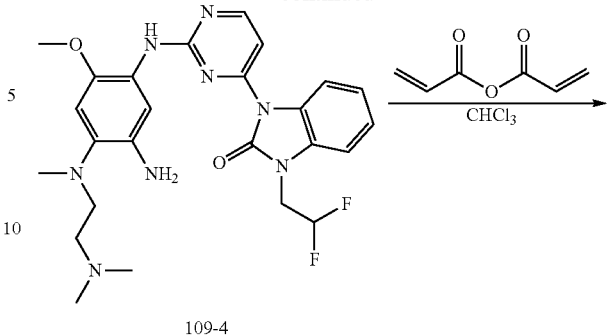
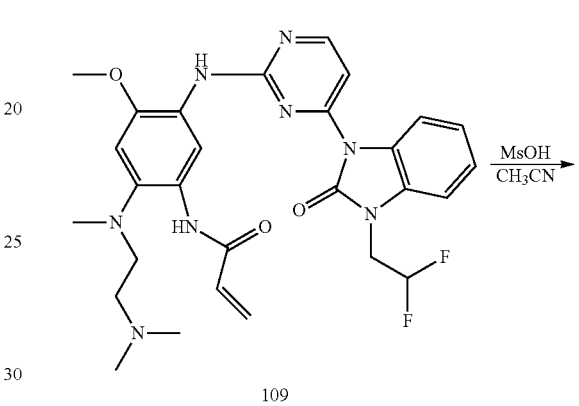
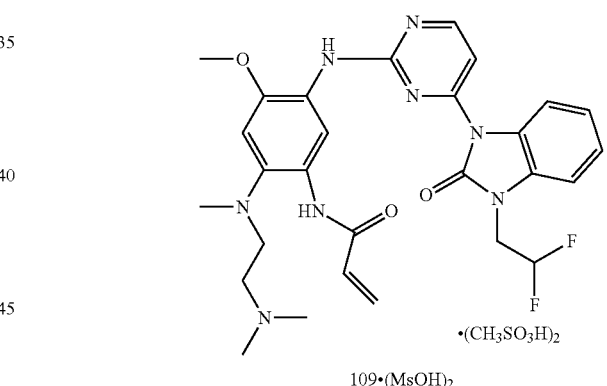

The reaction steps and conditions for the synthesis of compound 109 and its methanesulfonate from the intermediate 109-1 were the same as those in the second to fifth steps of example 101, except that the intermediate 101-1 in example 101 was replaced with the intermediate 109-1. Data for compound 109: LCMS (parent molecule) $C_{28}H_{32}F_2N_8O_3$: (ES, m/z): 567.2 [M+H]$^+$. $^1$H-NMR (methanesulfonate): (300 MHz, DMSO-D$_6$, ppm): δ 9.50 (s, 1H), 9.26 (br s, 2H), 8.49-8.47 (d, J=6 Hz, 1H), 8.16-8.11 (m, 2H), 7.78-7.76 (d, J=6 Hz, 1H), 7.35-7.33 (m, 1H), 7.24-7.19 (m, 1H), 7.11-7.01 (m, 2H), 6.78-6.63 (m, 1H), 6.30-6.24 (m, 1H), 5.80-5.76 (m, 1H), 4.85 (s, 2H), 3.85 (s, 3H), 3.50-3.20 (m, 4H), 2.83-2.73 (m, 6H), 2.67 (s, 3H), 2.37 (s, 6H).

Example 110

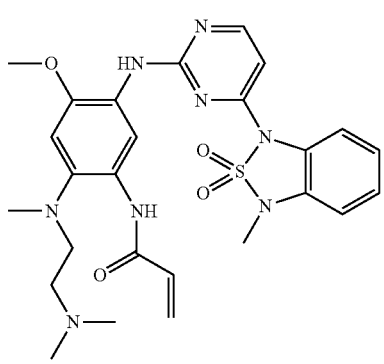 [SMILES: C=CC(=O)Nc1cc(Nc2nccc(N3c4ccccc4N(C)S3(=O)=O)n2)c(OC)cc1N(C)CCN(C)C]

1. Synthesis of Intermediate 110-1

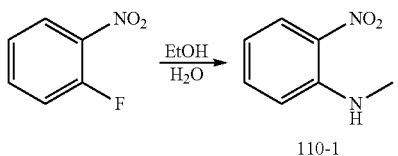

110-1

Under a nitrogen atmosphere, 2-nitrofluorobenzene (20 g, 141 mmol) as a raw material was dissolved in 500 mL of anhydrous ethanol in a 1000 mL of three-necked flask at room temperature, followed by adding methylamine hydrochloride (28.5 g, 422 mmol) and 50 mL of water into the reaction system. The reaction was raised to 100° C. and carried out overnight. Next day, after detecting the reaction was completed, the reaction system was cooled to room temperature, concentrated to dryness. The resulting residue was purified by silica gel column chromatography (eluent: PE:EA=5:1). The product was collected, concentrated to dryness to give 18.0 g of the intermediate 110-1 (83%) as a yellow solid. LCMS: 153.0.

2. Synthesis of Intermediate 110-2

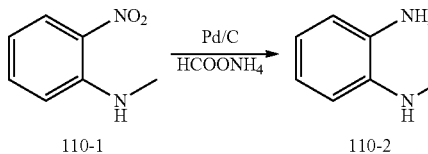

110-1          110-2

Under a nitrogen atmosphere, the intermediate 110-1 (15.0 g, 98.6 mmol) as a raw material was dissolved in in 500 mL of methanol in 1000 mL three-necked flask at room temperature, and palladium on carbon containing water (5.0 g, 9.86 mmol) and ammonium formate (30.0 g, 476 mmol) were sequentially added into the flask, then the reaction was carried out at room temperature for 2 h. After detecting the reaction was completed, the reaction system was filtered under suction; the filtrate was collected, concentrated to dryness. 200 mL of water was added into the residue, and the resulting mixture was extracted with 100 mL of dichloromethane three times. The organic phases were combined, dried over anhydrous sodium sulfate and concentrated to dryness to give 10.0 g of the intermediate 110-2 (83%) as a yellow solid. LCMS: 123.0.

3. Synthesis of Intermediate 110-3

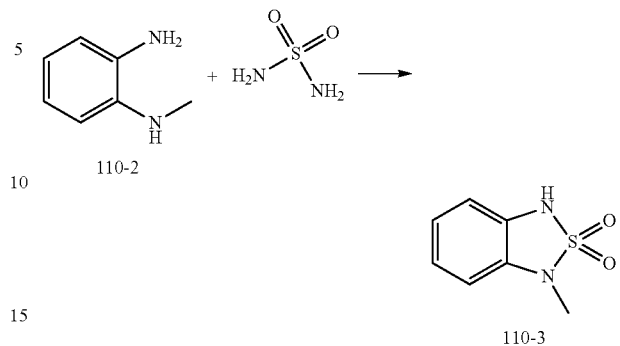

110-2

110-3

Under a nitrogen atmosphere, the intermediate 110-2 (10.0 g, 81.9 mmol) as a raw material was dissolved in 500 mL of pyridine in a 1000 mL three-necked flask at room temperature and sulfonamide (7.8 g, 81.2 mmol) was added to the reaction flask. After completion of the reaction, the reaction was heated to 120° C. and carried out for 1 hour. After detecting the reaction was completed, the reaction system was cooled to room temperature. The reaction mixture was concentrated to dryness. The resulting residue was purified by silica gel column chromatography (eluent: PE:EA=10:1-1:1), and then the resulting product was collected and concentrated to dryness to give 8.5 g of the intermediate 110-3 (56%) as a brown solid. LCMS: 185.0.

4. Synthesis of Intermediate 110-4

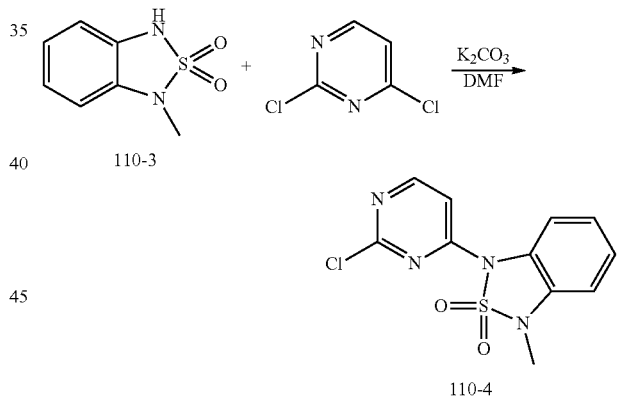

110-3

110-4

Under a nitrogen atmosphere, the intermediate 110-3 (3.2 g, 17.4 mmol) as a raw material was dissolved in 200 mL of anhydrous DMF in a 500 mL three-necked flask at room temperature, and then anhydrous potassium carbonate (6.8 g, 49.2 mmol) and 2,4-dichloropyrimidine (2.5 g, 16.8 mmol) were added to the reaction flask, then the reaction system was heated to 100° C. and maintained for overnight. Next day, after detecting the reaction was completed, the reaction was cooled to room temperature and 500 mL of ice water was added to quench the reaction. The reaction mixture was extracted with 200 mL of dichloromethane three times. The combined phases were combined, dried over anhydrous sodium sulfate and concentrated to dryness. The resulting residue was purified by silica gel column chromatography (eluent: PE:EA=10:1-1:1). The product was collected, concentrated to dryness to give 1.5 g of the intermediate 110-4 (29%) as a yellow solid. LCMS: 297.0.

5. Synthesis of Compound 110

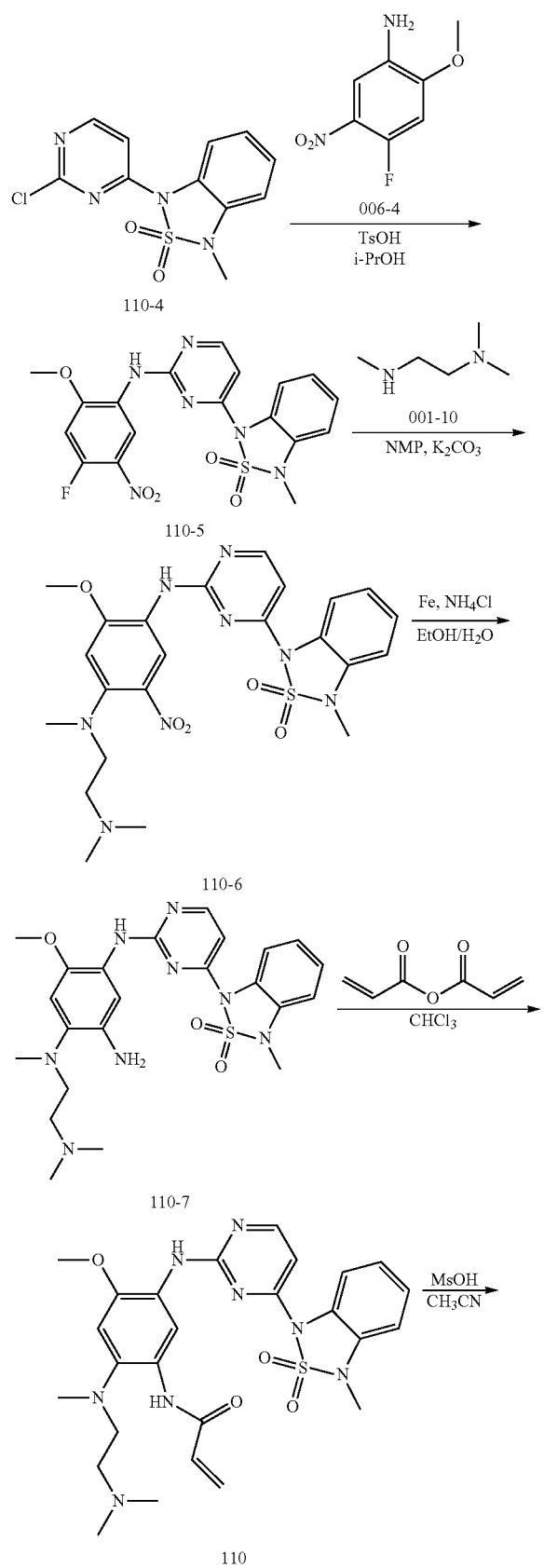

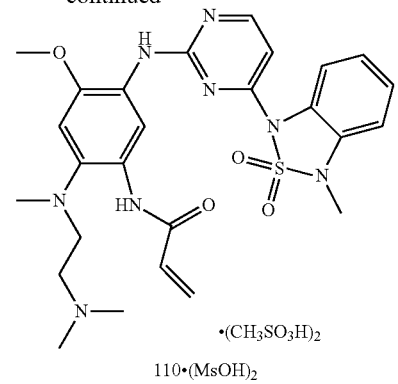

The reaction steps and conditions for the synthesis of compound 110 and its methanesulfonate from the intermediate 110-4 were the same as those in the second to fifth steps of example 101, except that the intermediate 110-1 in example 101 was replaced with the intermediate 110-4. Data for compound 110: LCMS (parent molecule) $C_{26}H_{32}N_8O_4S$: (ES, m/z): 553 [M+H]$^+$. $^1$H-NMR (methanesulfonate): (300 MHz, DMSO-D$_6$, ppm): 59.50 (s, 1H), 9.21 (br s, 1H), 8.99 (s, 1H), 8.46 (d, J=6 Hz, 1H), 8.09 (s, 1H), 7.86 (d, J=7.5 Hz, 1H), 7.20-7.16 (m, 2H), 7.01-6.89 (m, 3H), 6.70-6.60 (m, 1H), 6.28 (d, J=17.1 Hz, 1H), 5.78 (d, J=11.1 Hz, 1H), 3.83 (s, 3H), 3.33-3.29 (m, 7H), 2.82 (s, 3H), 2.80 (s, 3H), 2.73 (s, 3H), 2.15 (s, 6H).

Example 111

1. Synthesis of Intermediate 111-4

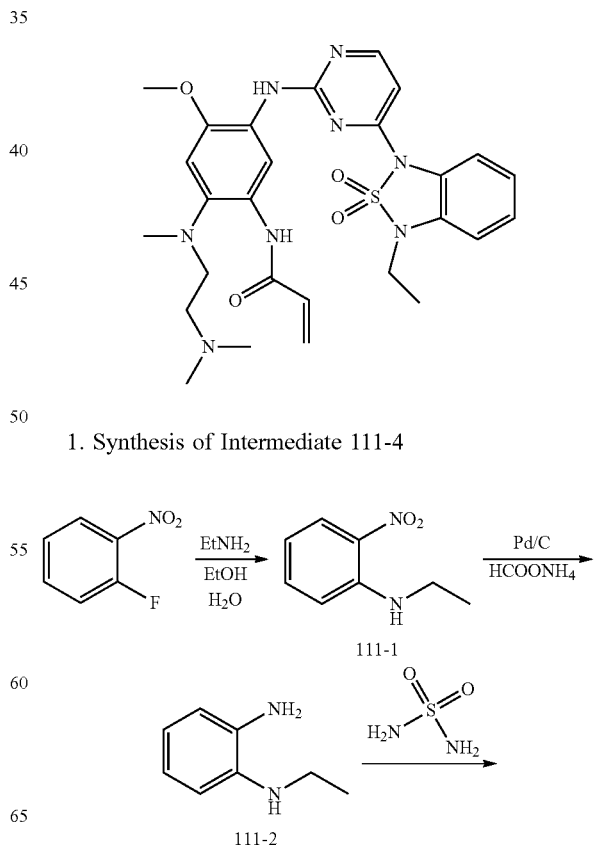

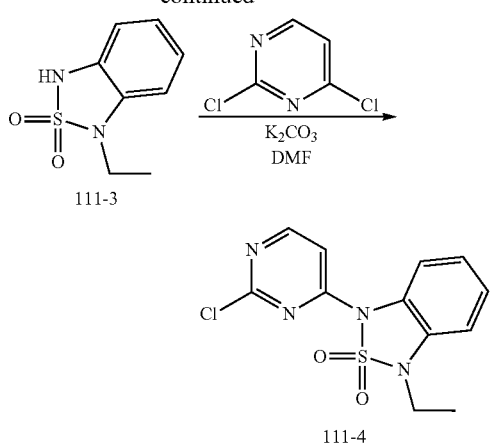

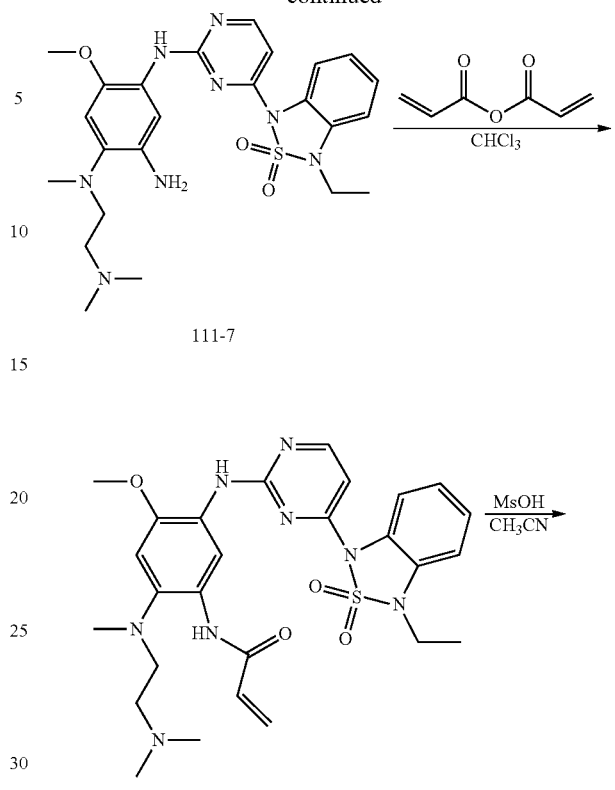

The reaction steps and conditions for the synthesis of the intermediate 111-4 from 2-nitrofluorobenzene as a raw material were the same as those in the first to fourth steps of example 110, except that methylamine in example 110 was replaced with ethylamine. LCMS for the intermediate 111-4: 311.0.

2. Synthesis of Compound 111

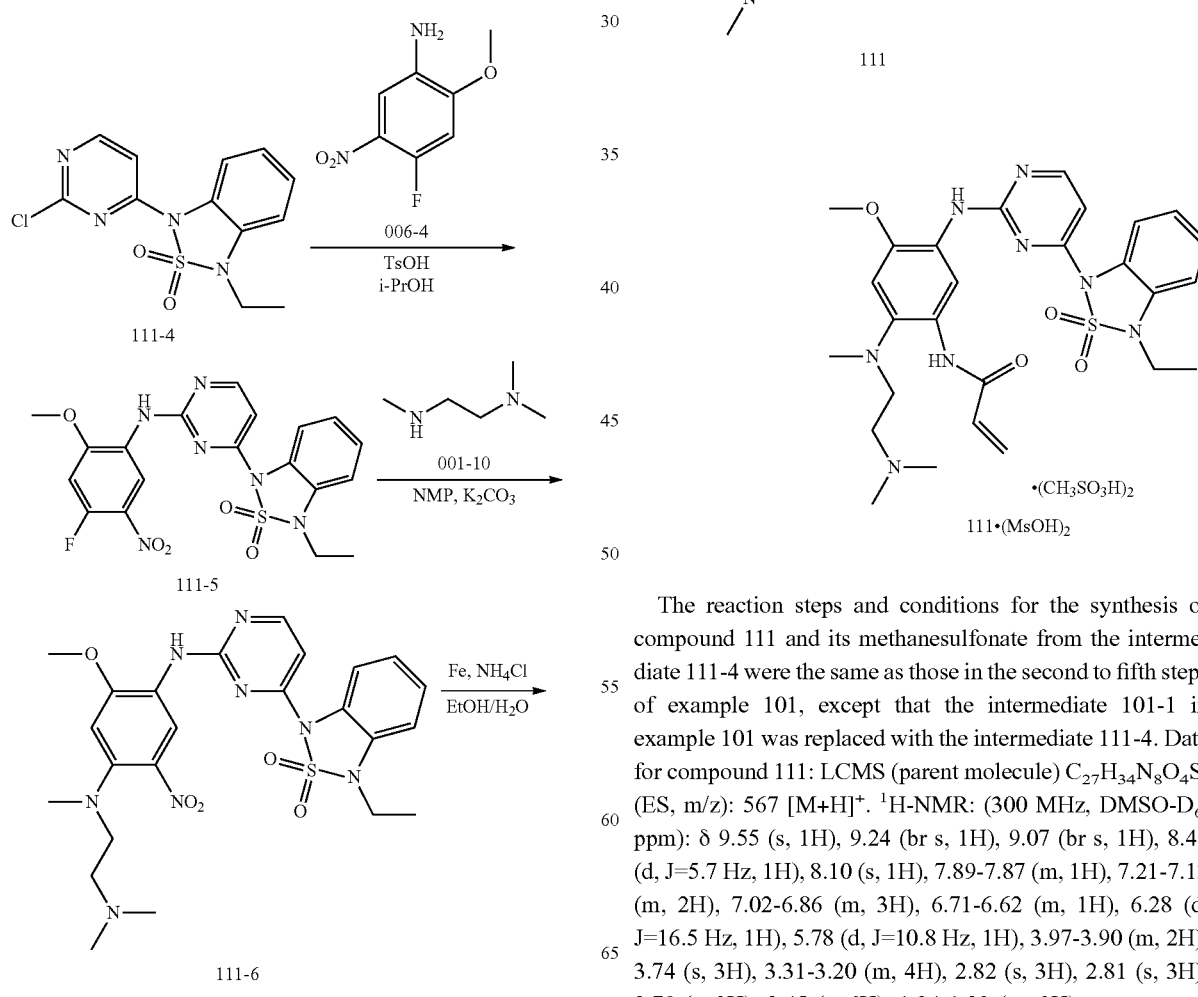

The reaction steps and conditions for the synthesis of compound 111 and its methanesulfonate from the intermediate 111-4 were the same as those in the second to fifth steps of example 101, except that the intermediate 101-1 in example 101 was replaced with the intermediate 111-4. Data for compound 111: LCMS (parent molecule) $C_{27}H_{34}N_8O_4S$: (ES, m/z): 567 [M+H]$^+$. $^1$H-NMR: (300 MHz, DMSO-D$_6$, ppm): δ 9.55 (s, 1H), 9.24 (br s, 1H), 9.07 (br s, 1H), 8.45 (d, J=5.7 Hz, 1H), 8.10 (s, 1H), 7.89-7.87 (m, 1H), 7.21-7.13 (m, 2H), 7.02-6.86 (m, 3H), 6.71-6.62 (m, 1H), 6.28 (d, J=16.5 Hz, 1H), 5.78 (d, J=10.8 Hz, 1H), 3.97-3.90 (m, 2H), 3.74 (s, 3H), 3.31-3.20 (m, 4H), 2.82 (s, 3H), 2.81 (s, 3H), 2.70 (s, 3H), 2.45 (s, 6H), 1.34-1.23 (m, 3H).

Example 112

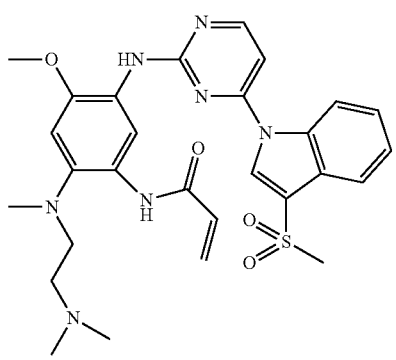 [SMILES: C=CC(=O)Nc1cc(Nc2nccc(-n3cc(S(C)(=O)=O)c4ccccc43)n2)c(OC)cc1N(C)CCN(C)C]

1. Synthesis of Intermediate 112-1

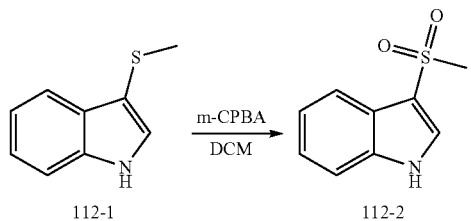

Under a nitrogen atmosphere, dimethyl sulfide (11 g, 177 mmol) was dissolved in 500 mL of methylene chloride in a 1000 mL of four-necked flask at room temperature. The reaction was cooled to 0° C., and N-chlorosuccinimide (23 g, 172 mmol) was added to the reaction system at 0° C. Next, the reaction system was cooled to −20° C. and the indole (20 g, 171 mmol) as a raw material was added to the reaction system. Then, the reaction mixture was heated to room temperature and the reaction was carried out for 1 hour. After the reaction was completed, the reaction mixture was concentrated to dryness and the resulting residue was dissolved in 200 mL of p-xylene, then the reaction system was heated to reflux for 30 minutes. After completion of the reaction, the reaction system was cooled to room temperature. The reaction mixture was concentrated to dryness and the residue was purified by silica gel column chromatography (eluent, EA/PE=1:30-1:5). The product was collected, and concentrated to dryness to give 11.0 g of the intermediate 112-1 (39%) as a yellow solid. LCMS: 163.2.

2. Synthesis of Intermediate 112-2

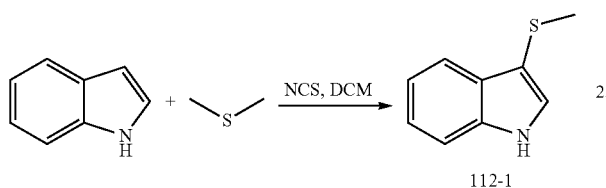

Under a nitrogen atmosphere, the intermediate 112-1 (10 g, 61.3 mmol) as a raw material was dissolved in 500 mL of dichloromethane in a 1000 mL four-necked flask, and m-chloroperbenzoic acid (m-CPBA) (26 g, 150.67 mmol) was added to the reaction system. Next, the reaction was carried out at room temperature overnight. After completion of the reaction, the reaction mixture was directly concentrated to dryness and the resulting residue was purified by silica gel column chromatography (eluent: EA:PE=1:10-1:3). The product was collected and concentrated to dryness to give 3.5 g of the intermediate 112-2 (29%) as a yellow solid. LCMS: 195.2.

3. Synthesis of Intermediate 112-3

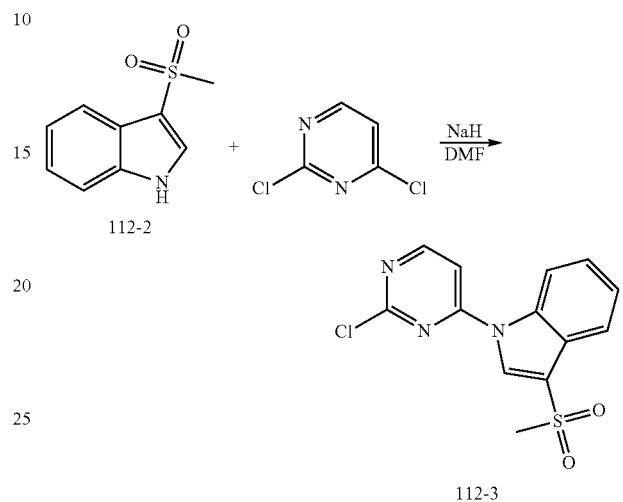

Under a nitrogen atmosphere, the intermediate 112-2 (3.5 g, 17.9 mmol) as a raw material was dissolved in 150 mL of anhydrous DMF in a 500 mL three-necked flask at room temperature. The reaction was cooled to 0° C. and sodium hydride (60%) (800 mg, 21 mmol) was added thereto in batches. Next, the reaction was performed for 10 min at 0° C. Next, 2,4-dicholopyrimidine (2.6 g, 20.1 mmol) was added into the reaction system, after that, the reaction was heated to room temperature and carried out for 2 h. After the reaction was completed, the reaction mixture was poured into 500 mL of ice water to quench the reaction. The resulting mixture was extracted with 200 mL of ethyl acetate three times. The organic phases were combined and washed with 200 mL of saturated brine once. The organic phases were dried over anhydrous sodium sulfate and concentrated to dryness. The resulting residue was purified with silica gel column chromatography (EA:PE=1:20-1:5). The organic phases were collected and concentrated to dryness to give 1.2 g of the intermediate 112-3 (22%) as a yellow solid. LCMS: 307.8.

4. Synthesis of Compound 112

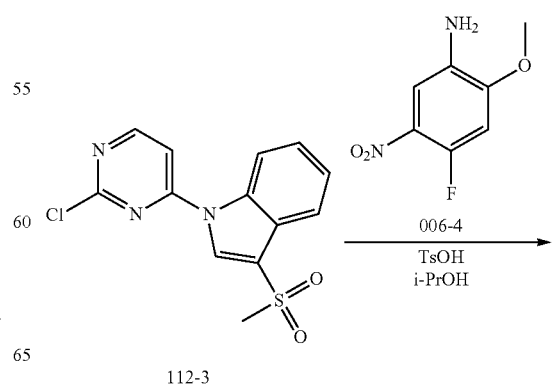

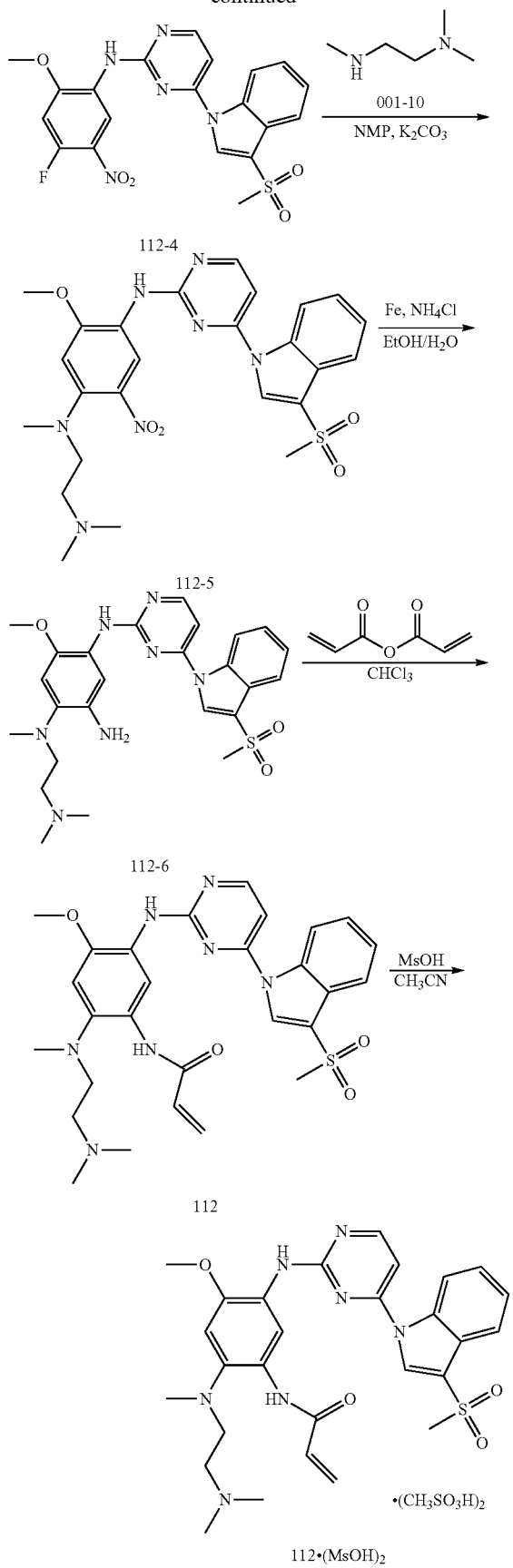

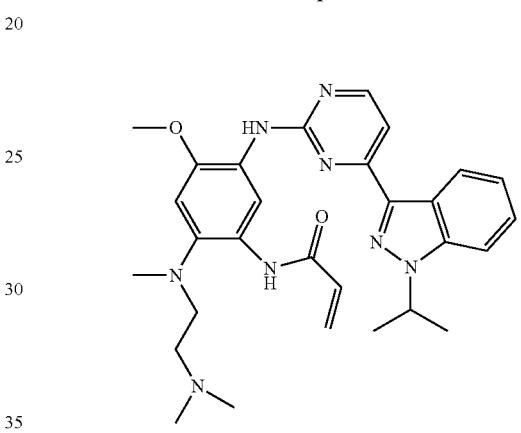

The reaction steps and conditions for the synthesis of compound 112 and its methanesulfonate from the intermediate 112-3 were the same as those in the second to fifth steps of example 101, except that the intermediate 101-1 in example 101 was replaced with the intermediate 112-3. Data for compound 112: LCMS (parent molecule) $C_{28}H_{33}N_7O_4S$: (ES, m/z): 564 $[M+H]^+$. $^1$H-NMR: (300 MHz, DMSO-$D_6$, ppm): δ 9.48 (s, 1H), 9.42 (s, 1H), 9.28 (br s, 1H), 8.75 (s, 1H), 8.68 (br s, 1H), 8.38-8.32 (m, 2H), 7.88-7.85 (m, 1H), 7.38-7.33 (m, 2H), 7.08 (s, 1H), 6.74-6.25 (m, 2H), 6.25 (d, J=17.1 Hz, 1H), 5.76 (d, J=11.1 Hz, 1H), 3.86 (s, 3H), 3.33-3.19 (m, 7H), 2.85-2.84 (m, 6H), 2.67 (s, 3H), 2.36 (s, 6H).

Example 113

1. Synthesis of Intermediate 113-1

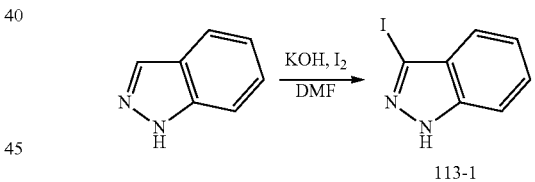

Under a nitrogen atmosphere, indazole (20 g, 169 mmol) as a raw material was dissolved in 500 mL of DMF at 1000 mL of a single-necked flask at room temperature, followed by sequentially adding iodine (43 g, 169 mmol) and potassium hydroxide (38 g, 677 mmol). Next, the reaction was carried out overnight. After detecting the reaction was completed, the reaction system was quenched with 300 mL of ice water. The resulting mixture was extracted with 300 mL of methylene chloride three times, and the organic phases were combined, washed with 300 mL of saturated brine three times and dried over anhydrous sodium sulfate and concentrated to dryness. The resulting residue was purified by silica gel column chromatography (eluent: EA/PE (1:10-1:5)), and the organic phase of the product was collected and concentrated to dryness to give 30% of the intermediate 113-1 (73%) as a white solid. LCMS: 244.9

2. Synthesis of Intermediate 113-2

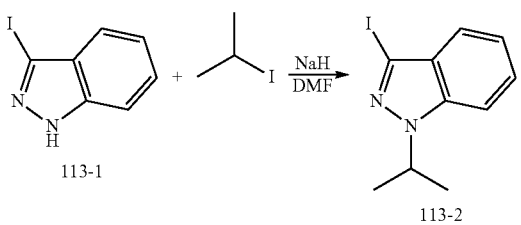

Under a nitrogen atmosphere, the intermediate 113-1 (15 g, 61.5 mmol) as a raw material was dissolved in 500 mL of anhydrous DMF in a 1000 mL three-necked flask at room temperature. The reaction system was cooled to 0° C. and sodium hydride (2.2 g, 92.2 mmol) was added thereto in batches for 10 min. Next, the reaction was carried out at 0° C. for 1 h, iodoisopropane (15.7 g, 92.4 mmol) was added into therein, followed by that the reaction was heated to 100° C. and carried out overnight. After detecting the reaction was completed, the reaction system was cooled to room temperature and quenched with 100 mL of ice water. The resulting mixture was extracted with 500 mL of dichloromethane three times, the organic phases were combined and washed with 100 mL of saturated brine three times, dried over anhydrous sodium sulfate and concentrated to dryness. The resulting residue was purified by silica gel column chromatography (eluent: EA:PE (1:10-1:5)), and the organic phases were collected, concentrated to dryness to give 13 g of the intermediate 113-2 (74%) as a yellow solid. LCMS: 287.0.

3. Synthesis of Intermediate 113-3

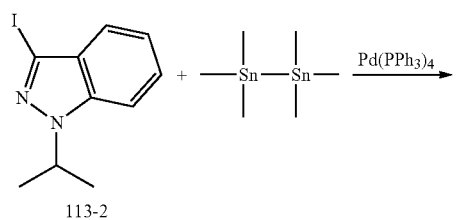

Under a nitrogen atmosphere, the intermediate 113-2 (3.0 g, 10.5 mmol) as a raw material was dissolved in 100 mL of 1,4-dioxane in 250 mL of a three-necked flask at room temperature, followed by sequentially adding hexamethylditin (4.15 g, 12.7 mmol) and tetrakis(triphenylphosphine)palladium (1.21 g, 1.05 mmol). Next, the reaction system was heated to 105° C. and carried out overnight. After detecting the reaction was completed, the reaction system was cooled to room temperature and the resulting mixture was used directly in the next step reaction.

4. Synthesis of Intermediate 113-4

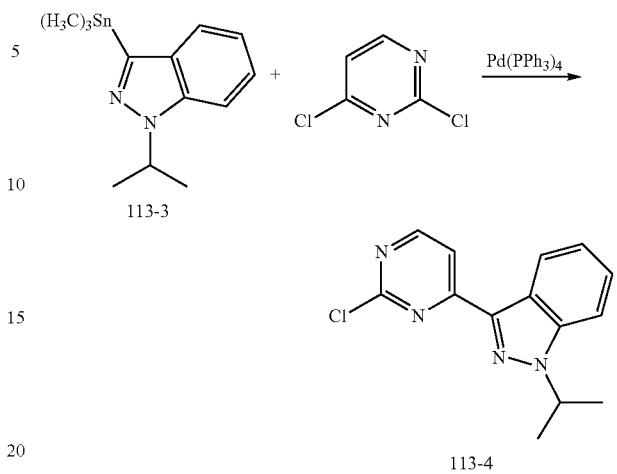

Under a nitrogen atmosphere, the reaction mixture (the intermediate 113-3) (3.40 g, 10.5 mmol) obtained in the previous step was dissolved in about 100 mL of solution of 1,4-dioxane in a 500 mL three-necked flask at room temperature, followed by sequentially adding 2,4-dichloropyrimidine (1.7 g, 11.4 mmol) and tetrakis(triphenylphsophine)palladium (1.21 g, 1.05 mmol). Next, the reaction system was heated to 105° C. overnight. After detecting the reaction was completed, the reaction system was cooled to room temperature and the reaction mixture was quenched with 200 mL of ice water. The resulting mixture was extracted with 200 mL of dichloromethane twice, then the organic phases were combined, washed with 400 mL of saturated brine three times, dried over anhydrous sodium sulfate, and concentrated to dryness. The resulting residue was purified by silica gel column chromatography (eluent: EA/PE (1:10-1:3)). The organic phases were collected and concentrated to dryness to give 1.9 g of the intermediate 113-4 (66%) as a white solid. LCMS: 273.1.

5. Synthesis of Compound 113

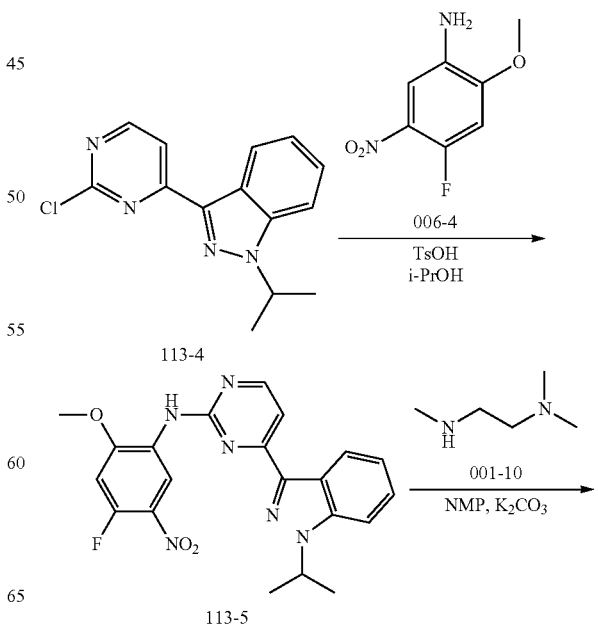

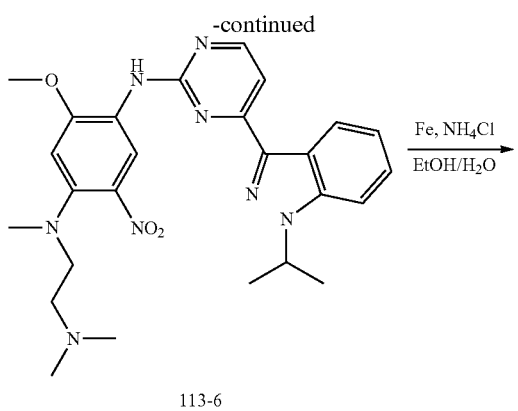

113-6

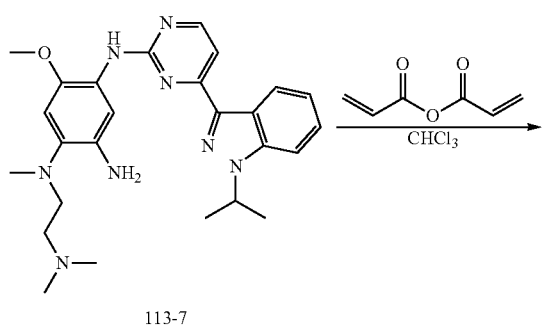

113-7

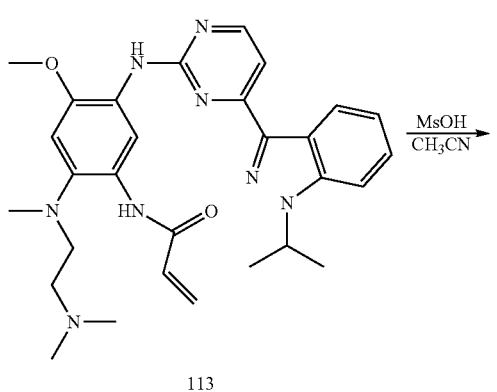

113

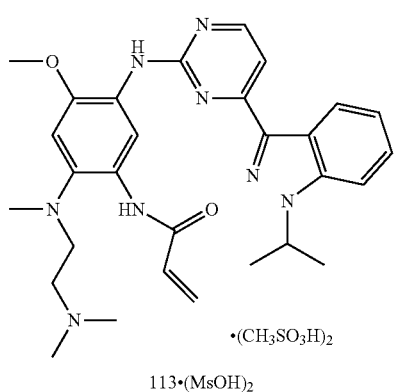

113·(MsOH)₂

The reaction steps and conditions for the synthesis of compound 113 and its methanesulfonate from the intermediate 113-4 were the same as those in the second to fifth steps of example 101, except that the intermediate 101-1 in example 101 was replaced with the intermediate 113-4. Data for compound 113: LCMS (parent molecule) $C_{29}H_{36}N_8O_2$: (ES, m/z): 529.3[M+H]⁺. ¹H-NMR (methanesulfonate): (300 MHz, DMSO-D₆, ppm): δ 9.59 (s, 1H), 9.26 (br s, 2H), 8.45 (d, J=5.7 Hz, 1H), 8.37 (br s, 1H), 8.30 (s, 1H), 7.84 (d, J=8.4 Hz, 1H), 7.57 (d, J=5.7 Hz, 1H), 7.48-7.43 (m, 1H), 7.24-7.19 (m, 1H), 7.06 (s, 1H), 6.72-6.64 (m, 1H), 6.28 (d, J=16.2 Hz, 1H), 5.78 (d, J=11.1 Hz, 1H), 5.20-5.11 (m, 1H), 3.87 (s, 3H), 3.32-3.45 (m, 4H), 2.84 (s, 3H), 2.83 (s, 3H), 2.67 (s, 3H), 2.36 (s, 6H), 1.58 (s, 3H), 1.55 (s, 3H).

Experimental Example 1

Experiment of Cell Growth Inhibition

The compounds that were preferentially targeted for EGFR targeting certain mutations and relatively weak in wild-type EGFR were identified by determining the growth of cells. The NCI-H1975 cell line is a human non-small cell lung cancer cell containing T790M and L858R EGFR mutations, and the cell is grown in RPMI-1640 medium (GIBCO) containing 10% fetal bovine serum (FBS). The LoVo cell line is a wild-type EGFR human colon adenocarcinoma cell, and is grown in F-12K medium (GIBCO) containing 10% FBS. NCI-H2073 cell line is a wild-type EGFR human non-small cell lung cancer cell and grown in ACL-4 medium containing 10% FBS. The growth rate of NCI-H1975, LoVo and NCI-H2073 cells was detected by Cell Titer-Glo luminescence activity assay (Promega # G7572).

Briefly, trypsin was used for digesting cells in the logarithmic growth phase. 96-well plates were seeded with 50,000 Lovo or NCI-H2073 cells, 2500-3000 NCI-H1975 cells per well and provided with blank control wells containing only nutrient solution without inoculated cell, and the plates were incubated in a humidified incubator with 5% CO₂ at 37° C. After 24 hours, the DMSO solution of the different compounds was diluted with a cell culture medium at 3.16 times per time to eight different concentrations from high to low levels. The concentration of test drug in NCI-H1975 cells was from 0.03 nM to 100 nM, and that in LoVo and NCI-H2073 cells was from 3 nM to 10 μM. The cell culture medium containing the different compounds was then added to a 96-well cell plate in which one cell control well comprising cell culture medium only containing DMSO was provided. After a drug treatment for 72 hours, the cell plates were removed from the incubator and allowed to stand at room temperature for 30 minutes. Next, Cell Titer-Glo reagent was added to the wells and the 96-well cell plate was shaken at room temperature for 10 minutes to induce cell lysis. The 96-well cell plate was placed on the bench for 2 minutes to stabilize the luminescence signal. Finally, the 96-well cell plate was placed in an EnVision Multi-labeled Microplate Reader (PerkinElmer), and the signal was read with an integral time of 0.5 seconds.

Percentage of cell growth inhibition %=(maximum signal−compound signal)/(maximum signal−minimum signal)*100%    Formula:

The maximal signal was obtained from the cell control well which were treated with the DMSO solution having no any compound;

The compound signal was obtained from the drug-treated cell wells to which the compound was added;

The minimum signal was obtained from a blank control well to which no cells and only nutrient solution was added.

The cell growth inhibition curve was calculated by Graph-Pad Prism V5.0 software and the compound concentration required to give a 50% inhibition was calculated based on this data, i.e., $IC_{50}$ of compounds.

The results are listed in Table 1 below.

TABLE 1

Results of compound activity

| Compound # or its salt # | NCI-H1975 $IC_{50}$ (nM) | Lovo $IC_{50}$ (nM) | NCI-H2073 $IC_{50}$ (nM) |
|---|---|---|---|
| 1. $(HCl)_n$ | 5.4 | 2257 | 230 |
| 2. $(MsOH)_3$ | 6.1 | 2297 | 474 |
| 3. $(MsOH)_2$ | 6.2 | 3086 | 295 |
| 4. $(MsOH)_3$ | 8.6 | 2573 | 500 |
| 5. $(MsOH)_3$ | 5.4 | 4230 | 335 |
| 6. $(HCl)_n$ | >100 | 4978 | |
| 7. $(MsOH)_3$ | 9.9 | 2168 | 760 |
| 8. MsOH | 113 | 1937 | 870 |
| 9. $(MsOH)_2$ | 13.0 | 2065 | 1130 |
| 10. $(MsOH)_3$ | >100 | 3019 | |
| 11. $(MsOH)_2$ | 35.4 | 1272 | |
| 12. $(MsOH)_2$ | 35.2 | 1718 | |
| 13. $(MsOH)_2$ | >100 | 444 | |
| 14. $(MsOH)_2$ | >100 | 481 | |
| 15. $(MsOH)_2$ | >100 | 333 | |
| 16. $(MsOH)_2$ | 82.2 | 569 | |
| 17. $(MsOH)_2$ | >100 | >10000 | |
| 18. $(MsOH)_3$ | 43.6 | 520 | |
| 19. MsOH | 48.5 | 955 | |
| 20. $(MsOH)_4$ | >100 | 267 | |
| 21. $(MsOH)_2$ | >100 | >10,000 | |
| 22 | 20.5 | >10,000 | >10000 |
| 23 | 90.8 | 2284 | |
| 24. $(MsOH)_3$ | >100 | 2579 | |
| 25. $(MsOH)_2$ | >100 | 5247 | |
| 26. $(MsOH)_2$ | >100 | 5128 | |
| 27. $(MsOH)_3$ | 84.0 | 1812 | |
| 28 | >100 | 538 | |
| 29. $(MsOH)_2$ | 13.0 | 2519 | 2520 |
| 30. $(MsOH)_2$ | >100 | 2551 | |
| 31. $(MsOH)_3$ | >100 | 846 | |
| 32. (MsOH) | >100 | >10000 | |
| 33. HCl | >100 | 1432 | |
| 34. $(MsOH)_3$ | 39.9 | 446 | |
| 35. $(MsOH)_3$ | 48.4 | 912 | |
| 36. $(MsOH)_3$ | 15.0 | 4328 | 410 |
| 37. $(MsOH)_3$ | 8.1 | 4658 | 260 |
| 38. $(HCl)_n$ | 8.2 | 2990 | 476 |
| 39. $(MsOH)_3$ | 0.8 | 3388 | 18 |
| 40. $(MsOH)_3$ | 1.3 | 6093 | 183 |
| 41. $(HCl)_n$ | 7.4 | >10000 | 340 |
| 42. $(HCl)_n$ | 7.1 | 7095 | 490 |
| 43. $(HCl)_n$ | 18.1 | 2171 | |
| 44. $(HCl)_n$ | 14.0 | 870 | 280 |
| 45. $(HCl)_n$ | >100 | 1090 | |
| 46. $(MsOH)_2$ | 155 | 1166 | |
| 47. $(MsOH)_2$ | 134 | 1625 | |
| 48. $(HCl)_n$ | 5.5 | 2344 | 435 |
| 49. $(HCl)_n$ | 0.7 | 2263 | 135 |
| 50. $(HCl)_n$ | 9.2 | >10000 | 290 |
| 51. $(HCl)_n$ | 2.6 | 1276 | 325 |
| 52. $(HCl)_n$ | 5.2 | 6103 | 220 |
| 53. $(HCl)_n$ | 14.0 | 2860 | 690 |
| 54. $(HCl)_n$ | 38.2 | 738 | |
| 55. $(HCl)_n$ | >100 | 3227 | |
| 56. $(HCl)_n$ | 36.0 | 4180 | >10000 |
| 57. $(HCl)_n$ | 8.2 | | 280 |
| 58. $(HCl)_n$ | 1.6 | | 116 |
| 59. $(HCl)_n$ | 1.3 | 4180 | 120 |
| 60. $(HCl)_n$ | 1.4 | 4070 | 110 |
| 61. $(HCl)_n$ | 1.5 | | 29 |
| 62. $(HCl)_n$ | 3.2 | | 270 |
| 63. $(HCl)_n$ | 4.8 | | 410 |
| 64. $(HCl)_n$ | 6.0 | | 310 |
| 65. $(MsOH)_2$ | 1.9 | | 151 |
| 66. $(MsOH)_3$ | 3.6 | | 201 |
| 67 | 81.7 | | 4098 |
| 68. $(MsOH)_2$ | 0.4 | | 43 |
| 69. $(MsOH)_3$ | 0.8 | | 63 |
| 70. $(MsOH)_2$ | 0.5 | | 46 |
| 71. $(MsOH)_2$ | 0.4 | | 64 |
| 72. $(MsOH)_3$ | 2.7 | | 282 |
| 73. $(MsOH)_2$ | 1.7 | | 179 |
| 74. $(MsOH)_3$ | 14.4 | | 463 |
| 76. $(MsOH)_2$ | 1.0 | | 56 |
| 101. $(MsOH)_2$ | 5.5 | | 193 |
| 102. $(MsOH)_2$ | 6.4 | | 170 |
| 103. $(MsOH)_2$ | 13.1 | | 300 |
| 104. $(MsOH)_2$ | 16.5 | | 977 |
| 105. $(MsOH)_2$ | 15.7 | | 543 |
| 106. $(MsOH)_2$ | 4.7 | | 155 |
| 107. $(MsOH)_2$ | 7.4 | | 185 |
| 108. $(MsOH)_2$ | 5.9 | | 253 |
| 109. $(MsOH)_2$ | 4.5 | | 268 |
| 110. $(MsOH)_2$ | 2.9 | | 103 |
| 111. $(MsOH)_2$ | 2.7 | | 49 |
| 112. $(MsOH)_2$ | 100 | | 5425 |
| 113. $(MsOH)_2$ | 26.5 | | 595 |

Experimental Example 2

Comparison of the concentration of the metabolite AZ5104 in rats' body plasma of the pyrimidine compounds according to the present invention and AZD9291

Briefly, AZD9291 or the compound 49. $(HCl)_n$ of Example 49 or the compound 104. $(MsOH)_2$ of Example 104 were administered intragastrically to 200-220 g of adult male rats at amount of 10 mg/kg. Each administration group had two to three rats. After administration, 150 μl of blood was extracted from the vein on the rat tail at different times (0.25, 0.5, 1, 2, 4, 6, 8, 12 and 24 hours), put in a tube with K2EDTA and placed immediately on ice. Then, the blood sample was centrifuged in centrifuge with a 4-degree at a speed of 2000 g for 15 minutes. The plasma was separated and placed in a small tube and stored in a refrigerator at −80° C. The concentration of parent drug and metabolite in plasma sample was analyzed by LC/MS.

The results are listed in Table 2 below.

TABLE 2

Comparison of the concentration of parent drug and metabolite AZ5104 in plasma sample of rats' body

| Compound # or its salt # | Parent drug AUC (hr * uM) | AZ5104 AUC (hr * uM) |
|---|---|---|
| AZD9291 | 0.64 | 0.02 |
| 49. $(HCl)_n$ | 0.91 | lower than the limit of quantification (BQL) |
| 104. $(MsOH)_2$ | 1.49 | lower than the limit of quantification (BQL) |

The invention claimed is:

1.

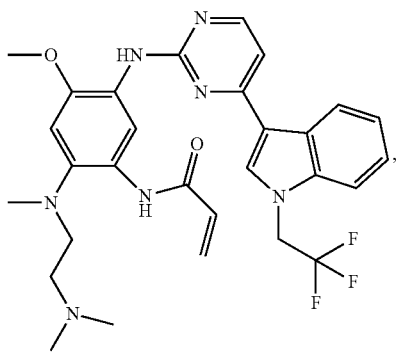 [SMILES: C=CC(=O)Nc1cc(Nc2nccc(-c3cn(CC(F)(F)F)c4ccccc34)n2)c(OC)cc1N(C)CCN(C)C]

or a pharmaceutically acceptable salt thereof.

2. A pharmaceutical composition comprising

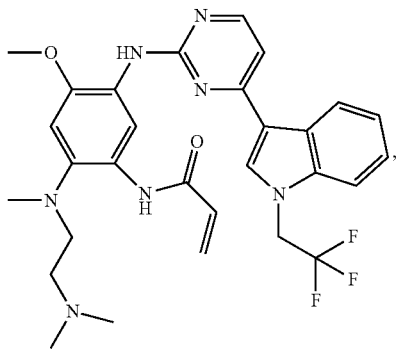 [SMILES: C=CC(=O)Nc1cc(Nc2nccc(-c3cn(CC(F)(F)F)c4ccccc34)n2)c(OC)cc1N(C)CCN(C)C]

or a pharmaceutically acceptable salt thereof.

3. A method of treating lung cancer in a subject in need thereof, comprising administering to the subject a therapeutically effective amount of the pharmaceutical composition of claim 2.

4. The method of claim 3, wherein the lung cancer is non-small cell lung cancer.

5. A method of treating lung cancer in a subject in need thereof, comprising administering to the subject a therapeutically effective amount of

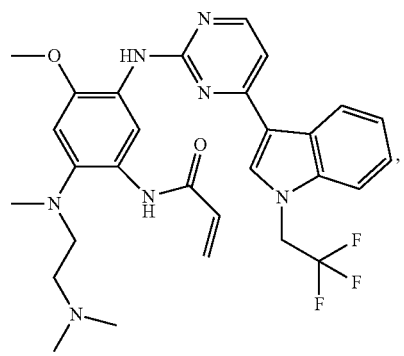 [SMILES: C=CC(=O)Nc1cc(Nc2nccc(-c3cn(CC(F)(F)F)c4ccccc34)n2)c(OC)cc1N(C)CCN(C)C]

or a pharmaceutically acceptable salt thereof.

6. The method of claim 5, wherein the lung cancer is non-small cell lung cancer.

* * * * *